US010610536B2

(12) United States Patent
Surber

(10) Patent No.: US 10,610,536 B2
(45) Date of Patent: *Apr. 7, 2020

(54) AEROSOL PIRFENIDONE AND PYRIDONE ANALOG COMPOUNDS AND USES THEREOF

(71) Applicant: Avalyn Pharma Inc., Seattle, WA (US)

(72) Inventor: Mark William Surber, San Diego, CA (US)

(73) Assignee: AVALYN PHARMA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,366

(22) Filed: Jul. 23, 2018

(65) Prior Publication Data

US 2018/0325917 A1 Nov. 15, 2018

Related U.S. Application Data

(60) Continuation of application No. 15/495,806, filed on Apr. 24, 2017, now Pat. No. 10,028,966, which is a
(Continued)

(51) Int. Cl.
| | |
|---|---|
| *A61K 31/573* | (2006.01) |
| *A61K 31/4418* | (2006.01) |
| *A61K 9/00* | (2006.01) |
| *A61K 47/02* | (2006.01) |
| *A61K 47/12* | (2006.01) |
| *A61M 11/00* | (2006.01) |
| *A61M 11/02* | (2006.01) |

(52) U.S. Cl.
CPC .......... *A61K 31/573* (2013.01); *A61K 9/0078* (2013.01); *A61K 31/4418* (2013.01); *A61K 47/02* (2013.01); *A61K 47/12* (2013.01); *A61M 11/001* (2014.02); *A61M 11/005* (2013.01); *A61M 11/02* (2013.01)

(58) Field of Classification Search
CPC ...... A61K 31/573; A61K 47/12; A61K 47/02; A61K 31/4418; A61K 9/0078; A61M 11/02; A61M 11/001; A61M 11/005
See application file for complete search history.

(56) References Cited

U.S. PATENT DOCUMENTS 10,028,966 B2 * 7/2018 Surber ............... A61K 31/4418

* cited by examiner

*Primary Examiner* — Aradhana Sasan
*Assistant Examiner* — Quanglong N Truong
(74) *Attorney, Agent, or Firm* — Kurt T. Mulville; VLP Law Group, LLP

(57) ABSTRACT

Disclosed herein are formulations of pirfenidone or pyridone analog compounds for aerosolization and use of such formulations for aerosol administration of pirfenidone or pyridone analog compounds for the prevention or treatment of various fibrotic and inflammatory diseases, including disease associated with the lung, heart, kidney, liver, eye and central nervous system. In some embodiments, pirfenidone or pyridone analog compound formulations and delivery options described herein allow for efficacious local delivery of pirfenidone or pyridone analog compound. Compositions include all formulations, kits, and device combinations described herein. Methods include inhalation procedures, indications and manufacturing processes for production and use of the compositions described.

13 Claims, 5 Drawing Sheets

| | Inhaled (mg RDD) | | | Oral (801 mg) | |
|---|---|---|---|---|---|
| | 2.5 | 50 | 120 | Fed | Fast |
| Lung Tissue Cmax (µg/g) | 3.9 | 70.3 | 168.7 | 3.9 | 7.8 |
| Lung Tissue AUC$_{0-18hrs}$ (µg*hr/g) | 1.7 | 33.2 | 79.8 | 30.8 | 33.9 |
| Plasma Cmax (µg/mL) | 0.4 | 7.9 | 18.0 | 7.8 | 15.7 |
| Plasma AUC$_{0-18hrs}$ (µg*hr/mL) | 1.1 | 23.0 | 55.1 | 55.1 | 69.7 |

Modeled human inhaled aerosol pirfenidone pharmacokinetics.

Related U.S. Application Data division of application No. 14/593,935, filed on Jan. 9, 2015, now Pat. No. 9,770,443.

(60) Provisional application No. 62/000,473, filed on May 19, 2014, provisional application No. 61/977,529, filed on Apr. 9, 2014, provisional application No. 61/951,686, filed on Mar. 12, 2014, provisional application No. 61/925,791, filed on Jan. 10, 2014.

FIG. 1. Modeled Nebulized Aerosol Administration to a Human.

FIG. 2. Modeled Nebulized Aerosol Administration to a Human – 50 mcg/gram target lung tissue Cmax and correlated lung tissue and plasma pharmacokinetics.

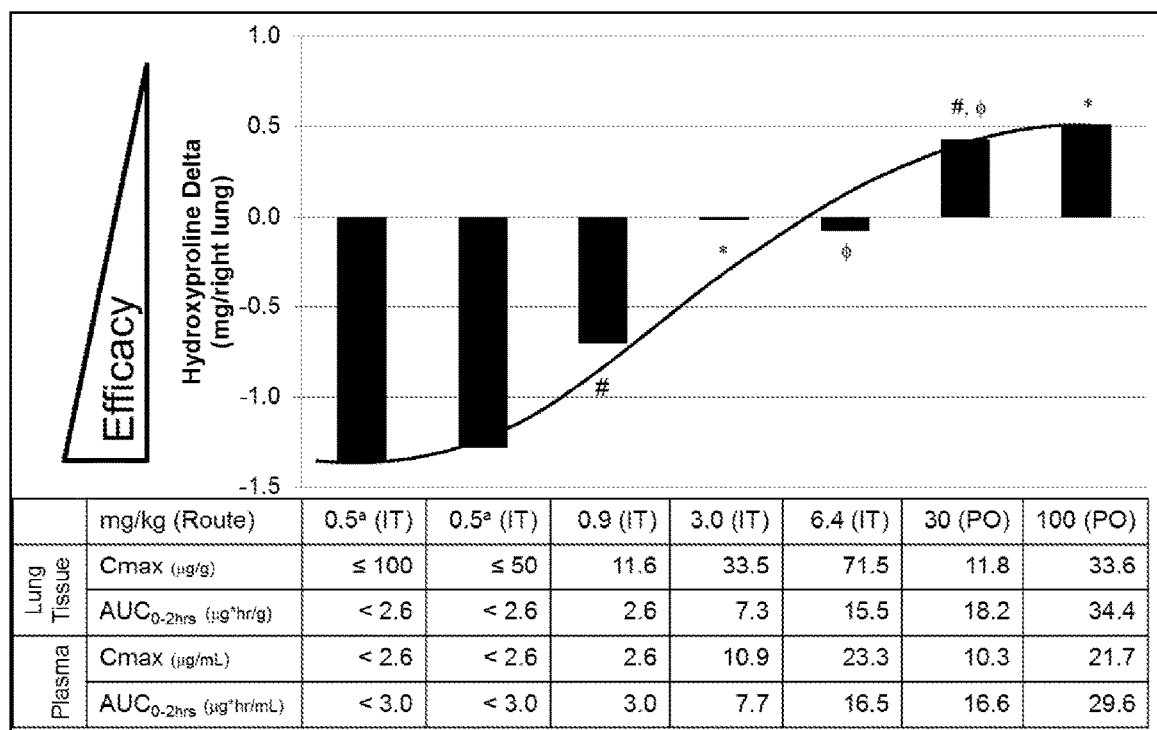
FIG. 3. Hydroxyproline results from bleomycin model of pulmonary fibrosis.

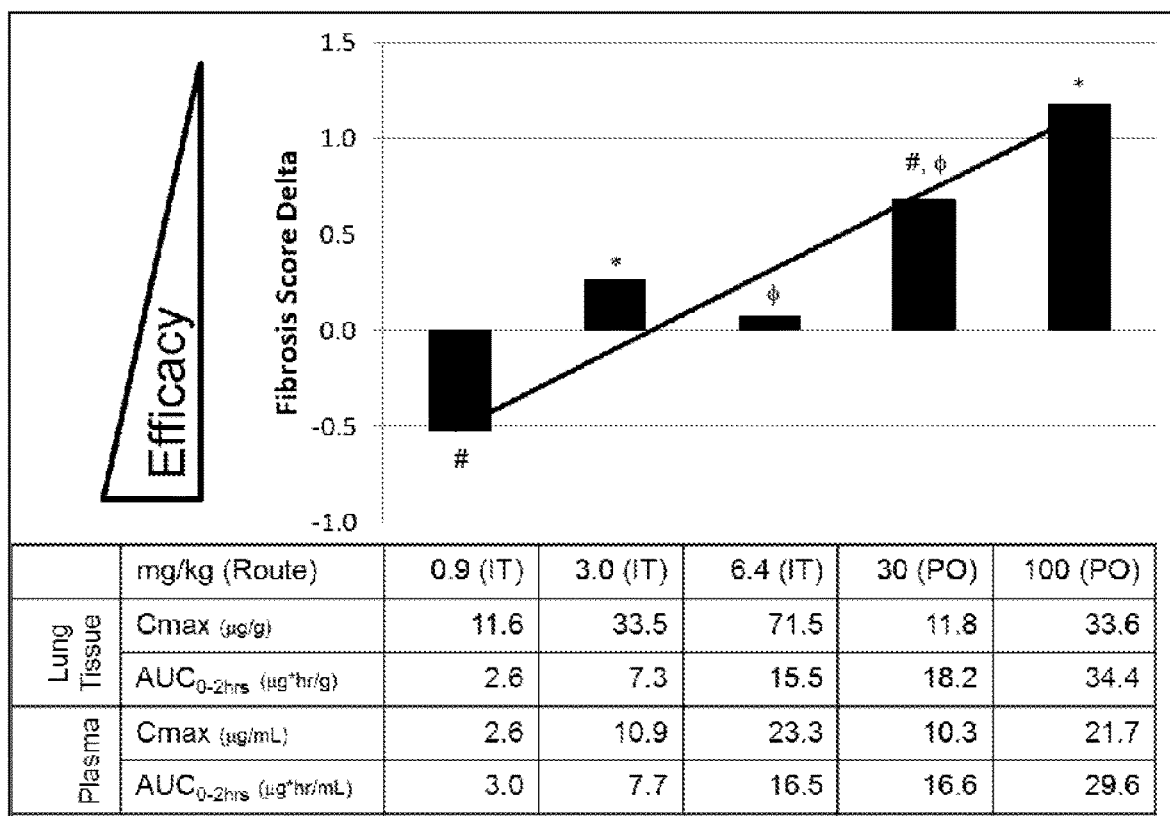
FIG. 4. Histopathology results from bleomycin model of pulmonary fibrosis.

|  |  | Inhaled (mg RDD) | | | Oral (801 mg) | |
|---|---|---|---|---|---|---|
|  |  | 2.5 | 50 | 120 | Fed | Fast |
| Lung Tissue | Cmax (µg/g) | 3.9 | 70.3 | 168.7 | 3.9 | 7.8 |
| Lung Tissue | $AUC_{0-18hrs}$ (µg*hr/g) | 1.7 | 33.2 | 79.8 | 30.8 | 33.9 |
| Plasma | Cmax (µg/mL) | 0.4 | 7.9 | 18.0 | 7.8 | 15.7 |
| Plasma | $AUC_{0-18hrs}$ (µg*hr/mL) | 1.1 | 23.0 | 55.1 | 55.1 | 69.7 |

FIG. 5. Modeled human inhaled aerosol pirfenidone pharmacokinetics.

AEROSOL PIRFENIDONE AND PYRIDONE ANALOG COMPOUNDS AND USES THEREOF

PRIORITY CLAIM

This application is a continuation of U.S. patent application Ser. No. 15/495,806, filed Apr. 24, 2017, which is a divisional of U.S. patent application Ser. No. 14/593,935, filed Jan. 9, 2015, which claims the benefit of priority from U.S. Provisional Application No. 61/925,791, filed on Jan. 10, 2014; U.S. Provisional Application No. 61/951,686, filed on Mar. 12, 2014; U.S. Provisional Application No. 61/977,529, filed on Apr. 9, 2014; U.S. Provisional Application No. 62/000,473, filed on May 19, 2014, and herein incorporated by reference in their entirety.

FIELD OF THE INVENTION

The present invention relates in its several embodiments to liquid, dry powder and metered-dose formulations for therapeutic inhaled delivery of pyridone compositions such as pirfenidone to desired anatomical sites, for treatment and/or prophylaxis of a variety of pulmonary, neurologic, cardiovascular and solid organ disease conditions.

BACKGROUND OF THE INVENTION

A number of undesirable pulmonary diseases such as interstitial lung disease (ILD; and sub-class diseases therein), chronic obstructive pulmonary disease (COPD; and sub-class diseases therein), asthma, and fibrotic indications of the kidney, heart and eye, the diseases are initiated from an external challenge. By non-limiting example, these effectors can include infection, cigarette smoking, environmental exposure, radiation exposure, surgical procedures and transplant rejection. However, other causes related to genetic disposition and the effects of aging may also be attributed. Described herein are compositions of pirfenidone or a pyridone analog compound that are suitable for inhalation delivery to the lungs and/or systemic compartment and methods of using such compositions.

SUMMARY

According to a certain embodiment of the present invention, there is provided a pirfenidone or pyridone analog compound formulation composition for oral pulmonary or intranasal inhalation delivery, comprising formulations for aerosol administration of pirfenidone or pyridone analog compounds for the prevention or treatment of various fibrotic and inflammatory diseases, including disease associated with the lung, heart, kidney, liver, eye and central nervous system.

In one aspect, described herein is a method for the treatment of lung disease in a mammal comprising administering a dose of pirfenidone or a pyridone analog compound by inhalation to the mammal in need thereof on a continuous dosing schedule. In some embodiments, the continuous dosing schedule includes administering a dose of pirfenidone or a pyridone analog compound daily, every other day, every third day, every fourth day, every fifth day, every sixth day, weekly, biweekly, monthly or bimonthly. In some embodiments, the dosing schedule, whether daily or less than daily, includes administering one, two, three, or more than three doses of pirfenidone or a pyridone analog compound on the days of dosing. In some embodiments, each inhaled dose of pirfenidone or a pyridone analog compound is administered with a nebulizer, a metered dose inhaler, or a dry powder inhaler. In some embodiments, each inhaled dose comprises an aqueous solution of pirfenidone or a pyridone analog compound. In some embodiments, each inhaled dose comprises from about 0.1 mL to about 6 mL of an aqueous solution of pirfenidone or a pyridone analog compound, wherein the concentration of pirfenidone or pyridone analog compound in the aqueous solution is from about 0.1 mg/mL and about 60 mg/mL and the osmolality of the of the aqueous solution is from about 50 mOsmol/kg to about 6000 mOsmol/kg. In some embodiments, the aqueous solution of each inhaled dose further comprises one or more additional ingredients selected from co-solvents, tonicity agents, sweeteners, surfactants, wetting agents, chelating agents, anti-oxidants, salts, and buffers. In some embodiments, the aqueous solution of each inhaled dose further comprises a citrate buffer or phosphate buffer, and one or more salts selected from the group consisting of sodium chloride, magnesium chloride, sodium bromide, magnesium bromide, calcium chloride and calcium bromide. In some embodiments, the aqueous solution of each inhaled dose comprises: water; pirfenidone or pyridone analog compound at a concentration from about 0.1 mg/mL to about 20 mg/mL; one or more salts, wherein the total amount of the one or more salts is from about 0.01% to about 2.0% by weight of the weight of aqueous solution; and optionally a phosphate buffer that maintains the pH of the solution from about pH 5.0 to about pH 8.0, or citrate buffer than maintains the pH of the solution from about 4.0 to about 7.0; and the osmolality of the of the aqueous solution is from about 50 mOsmol/kg to about 2000 mOsmol/kg. In some embodiments, each inhaled dose is administered with a liquid nebulizer. In some embodiments, the liquid nebulizer: (i) after administration of the inhaled dose, achieves lung deposition of at least 7% of the pirfenidone or pyridone analog compound administered to the mammal; (ii) provides a Geometric Standard Deviation (GSD) of emitted droplet size distribution of the aqueous solution of about 1.0 μm to about 2.5 μm; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 tam) of droplets emitted from the liquid nebulizer of at least about 30%; (v) provides an output rate of at least 0.1 mL/min; and/or (vi) provides at least about 25% of the aqueous solution to the mammal. In some embodiments, a) the lung tissue Cmax of pirfenidone or pyridone analog compound from each inhaled dose is at least equivalent to or greater than a lung tissue Cmax of up to 801 mg of an orally administered dosage of pirfenidone or pyridone analog compound; and/or b) the blood $AUC_{0-24}$ of pirfenidone or pyridone analog compound from each inhaled dose that is directly administered to the lungs of the mammal is less than or equivalent to the blood $AUC_{0-24}$ of up to 801 mg of an orally administered dosage of pirfenidone or pyridone analog compound. In some embodiments, the blood $AUC_{0-24}$ of pirfenidone or pyridone analog compound from each inhaled dose is less than the blood $AUC_{0-24}$ of up to 801 mg of an orally administered dosage of pirfenidone or pyridone analog compound. In some embodiments, the blood $AUC_{0-24}$ of pirfenidone or pyridone analog compound from each inhaled dose is less than 80%, less than 70%, less than 60%, less than 50%, less than 40%, less than 30%, less than 20%, less than 10%, less than 5%, less than 2.5%, less than 1.0%, less than 0.5%, less than 0.25%, less than 0.1%, less than 0.05%, less than 0.025% or less than 0.01% of the blood $AUC_{0-24}$ of up to 801 mg of an orally administered dosage of pirfenidone or pyridone analog compound. In some embodiments, the blood $AUC_{0-24}$ of pirfenidone or pyridone analog compound from each inhaled dose is between 0.01-90%, 0.01-80%, 0.01-70%, 0.01-60%, 0.01-50%, 0.01-40%, 0.01-30%, 0.01-20%, 0.01-10%, 0.01-5%, 0.01-2.5%, 0.01-1%, 0.01-0.1%, 5-90%, between 5-80%, between 5-70%, between 5-60%, between 5-50%, between 5-40%, between 5-30%, between 5-20%, between 5-10%, between 1-5%, between 1-10%, between 1-20%, between 1-30%, between 1-40%, between 1-50%, between 1-60%, between 1-70%, between 1-80%, or between 1-90% of the blood $AUC_{0-24}$ of up to 801 mg of an orally administered dosage of pirfenidone or pyridone analog compound. In some embodiments, wherein each inhaled dose is less than ½ of the up to 801 mg of an orally administered dosage of pirfenidone or pyridone analog compound. In some embodiments, wherein each inhaled dose is less than ½, ⅓, ¼, ⅕, ⅙, ⅛, 1/10, 1/20, 1/40, 1/50, 1/75, 1/100, 1/200, 1/300, or 1/400 of the up to 801 mg of an orally administered dosage of pirfenidone or pyridone analog compound. In some embodiments, the pirfenidone or a pyridone analog compound is administered at least once a week. In some embodiments, the pirfenidone or a pyridone analog compound is administered on a continuous daily dosing schedule. In some embodiments, the pirfenidone or a pyridone analog compound is administered once a day, twice a day, or three times a day. In some embodiments, the lung disease is idiopathic pulmonary fibrosis, lung cancer or pulmonary hypertension. In some embodiments, the lung disease is idiopathic pulmonary fibrosis. In some embodiments, the lung disease is pulmonary hypertension. In some embodiments, the lung disease is pulmonary hypertension secondary to interstitial lung disease. In some embodiments, the lung disease is cancer. In some embodiments, the lung disease is lung cancer. In some embodiments, the lung disease is lung cancer where in the therapeutic target is tumor stroma. In some embodiments, the lung disease is lung cancer and the treatment comprises inhibiting, reducing or slowing the growth of lung tumor stroma. In some embodiments, the method further comprises administration of one or more additional therapeutic agents to the mammal.

In another aspect, described herein is a method for the treatment of lung disease in a mammal comprising: administering a dose of pirfenidone or a pyridone analog compound by inhalation to the mammal in need thereof, wherein the blood $AUC_{0-24}$ of pirfenidone or pyridone analog compound from the inhaled dose is less than the blood $AUC_{0-24}$ of up to 801 mg of an orally administered dosage of pirfenidone or pyridone analog compound. In some embodiments, the blood $AUC_{0-24}$ of pirfenidone or pyridone analog compound from each inhaled dose is less than 80%, less than 70%, less than 60%, less than 50%, less than 40%, less than 30%, less than 20%, less than 10%, less than 5%, less than 2.5%, less than 1.0%, less than 0.5%, less than 0.25%, less than 0.1%, less than 0.05%, less than 0.025% or less than 0.01% of the blood $AUC_{0-24}$ of up to 801 mg of an orally administered dosage of pirfenidone or pyridone analog compound. In some embodiments, the blood $AUC_{0-24}$ of pirfenidone or pyridone analog compound from each inhaled dose is between 0.01-90%, 0.01-80%, 0.01-70%, 0.01-60%, 0.01-50%, 0.01-40%, 0.01-30%, 0.01-20%, 0.01-10%, 0.01-5%, 0.01-2.5%, 0.01-1%, 0.01-0.1%, 5-90%, between 5-80%, between 5-70%, between 5-60%, between 5-50%, between 5-40%, between 5-30%, between 5-20%, between 5-10%, between 1-5%, between 1-10%, between 1-20%, between 1-30%, between 1-40%, between 1-50%, between 1-60%, between 1-70%, between 1-80%, or between 1-90% of the blood $AUC_{0-24}$ of up to 801 mg of an orally administered dosage of pirfenidone or pyridone analog compound. In some embodiments, the inhaled dose of pirfenidone or pyridone analog compound is administered with a nebulizer, a metered dose inhaler, or a dry powder inhaler. In some embodiments, the inhaled dose comprises an aqueous solution of pirfenidone or a pyridone analog compound and the dose is administered with a liquid nebulizer. In some embodiments, each inhaled dose that is directly administered to the lungs of the mammal comprises from about 0.1 mL to about 6 mL of an aqueous solution of pirfenidone or a pyridone analog compound, wherein the concentration of pirfenidone or pyridone analog compound in the aqueous solution is from about 0.1 mg/mL and about 60 mg/mL and the osmolality of the of the aqueous solution is from about 50 mOsmol/kg to about 6000 mOsmol/kg. In some embodiments, the aqueous solution of each inhaled dose further comprises: one or more additional ingredients selected from co-solvents, tonicity agents, sweeteners, surfactants, wetting agents, chelating agents, anti-oxidants, salts, and buffers. In some embodiments, the aqueous solution of each inhaled dose further comprises: a citrate buffer or phosphate buffer, and one or more salts selected from the group consisting of sodium chloride, magnesium chloride, sodium bromide, magnesium bromide, calcium chloride and calcium bromide. In some embodiments, the aqueous solution of each inhaled dose comprises: water; pirfenidone or pyridone analog compound at a concentration from about 0.1 mg/mL to about 20 mg/mL; one or more salts, wherein the total amount of the one or more salts is from about 0.01% to about 2.0% by weight of the weight of aqueous solution; and optionally a phosphate buffer that maintains the pH of the solution from about pH 5.0 to about pH 8.0, or citrate buffer than maintains the pH of the solution from about 4.0 to about 7.0. In some embodiments, the inhaled dose of pirfenidone or a pyridone analog compound is administered on a continuous dosing schedule. In some embodiments, the lung disease is idiopathic pulmonary fibrosis, lung cancer or pulmonary hypertension. In some embodiments, the lung disease is idiopathic pulmonary fibrosis. In some embodiments, the lung disease is pulmonary hypertension. In some embodiments, the lung disease is pulmonary hypertension secondary to interstitial lung disease. In some embodiments, the lung disease is cancer. In some embodiments, the lung disease is lung cancer. In some embodiments, the lung disease is lung cancer where in the therapeutic target is tumor stroma. In some embodiments, the lung disease is lung cancer and the treatment comprises inhibiting, reducing or slowing the growth of lung tumor stroma. In some embodiments, the method further comprises administration of one or more additional therapeutic agents to the mammal.

In one aspect, described herein is an aqueous solution for nebulized inhalation administration comprising: water; pirfenidone, or a pyridone analog compound, at a concentration from about 0.1 mg/mL to about 20 mg/mL; sodium citrate; citric acid; sodium chloride; and sodium saccharin. In some embodiments, the aqueous solution comprises: water; pirfenidone, or a pyridone analog compound, at a concentration from about 1 mg/mL to about 20 mg/mL; sodium citrate; citric acid; sodium chloride; and sodium saccharin. In some embodiments, the aqueous solution comprises about 3.5 mM sodium citrate and about 1.5 mM citric acid. In some embodiments, the osmolality of the aqueous solution is from about 50 mOsmol/kg to about 1000 mOsmol/kg. In some embodiments, the osmolality of the aqueous solution is from about 50 mOsmol/kg to about 800 mOsmol/kg. In some embodiments, the osmolality of the aqueous solution is from about 50 mOsmol/kg to about 700 mOsmol/kg. In some embodiments, the osmolality of the aqueous solution is from about 100 mOsmol/kg to about 600 mOsmol/kg. In some embodiments, the aqueous solution comprises about 150 mM of sodium chloride. In some embodiments, the aqueous solution comprises about 0.1 mM to about 1 mM of sodium saccharin.

In one aspect, described herein is an aqueous solution for nebulized inhalation administration comprising: water; pirfenidone at a concentration from about 0.1 mg/mL to about 20 mg/mL; sodium citrate; citric acid; sodium chloride; and sodium saccharin; wherein the pH is about 4.0 to about 7.0. In some embodiments, the aqueous solution comprises: water; pirfenidone at a concentration from about 1 mg/mL to about 20 mg/mL; sodium citrate; citric acid; about 100-200 mM of sodium chloride; and sodium saccharin. In some embodiments, the sodium citrate concentration and the citric acid concentration is in a range of 1-10 mM and the aqueous solution has a pH of about 5-6, wherein the pH is optionally achieved by addition of acid or base. In some embodiments, the acid is hydrochloric acid. In some embodiments, the base is sodium hydroxide. In some embodiments, the aqueous solution comprises about 3.5 mM sodium citrate and about 1.5 mM citric acid. In some embodiments, the osmolality of the aqueous solution is from about 50 mOsmol/kg to about 1000 mOsmol/kg. In some embodiments, the aqueous solution comprises about 150 mM of sodium chloride. In some embodiments, the aqueous solution comprises about 0.1 mM to about 1 mM of sodium saccharin. In some embodiments, the pH of the aqueous solution is about 5.5; and the osmolality of the aqueous solution is from about 100 mOsmol/kg to about 500 mOsmol/kg. In some embodiments, the pH of the aqueous solution is about 5.5; and the osmolality of the aqueous solution is from about 200 mOsmol/kg to about 500 mOsmol/kg. In some embodiments, the pH of the aqueous solution is about 5.5; and the osmolality of the aqueous solution is from about 250 mOsmol/kg to about 500 mOsmol/kg.

In one aspect, described herein is an aqueous solution for nebulized inhalation administration consisting essentially of: water; pirfenidone at a concentration from about 0.1 mg/mL to about 20 mg/mL; sodium citrate; citric acid; sodium chloride; and sodium saccharin; wherein the pH is about 4.0 to about 7.0. In some embodiments, the aqueous solution consists essentially of: water; pirfenidone at a concentration from about 1 mg/mL to about 20 mg/mL; sodium citrate; citric acid; about 100-200 mM of sodium chloride; and sodium saccharin. In some embodiments, the sodium citrate concentration and the citric acid concentration is in a range of 1-10 mM and the aqueous solution has a pH of about 5-6, wherein the pH is optionally achieved by addition of acid or base. In some embodiments, the acid is hydrochloric acid. In some embodiments, the base is sodium hydroxide. In some embodiments, the aqueous solution comprises about 3.5 mM sodium citrate and about 1.5 mM citric acid. In some embodiments, the osmolality of the aqueous solution is from about 50 mOsmol/kg to about 1000 mOsmol/kg. In some embodiments, the concentration of sodium chloride in the aqueous solution is about 150 mM. In some embodiments, the concentration of sodium saccharin in the aqueous solution is about 0.1 mM to about 1 mM. In some embodiments, the pH of the aqueous solution is about 5.5; and the osmolality of the aqueous solution is from about 100 mOsmol/kg to about 500 mOsmol/kg. In some embodiments, the pH of the aqueous solution is about 5.5; and the osmolality of the aqueous solution is from about 200 mOsmol/kg to about 500 mOsmol/kg. In some embodiments, the pH of the aqueous solution is about 5.5; and the osmolality of the aqueous solution is from about 250 mOsmol/kg to about 500 mOsmol/kg.

In another aspect, described herein is a unit dosage adapted for use in a liquid nebulizer comprising from about 0.5 mL to about 6 mL of the aqueous solution described herein. In some embodiments, the liquid nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the lungs of the mammal. In some embodiments, the liquid nebulizer: (i) after administration of the inhaled dose, achieves lung deposition of at least 7% of the pirfenidone administered to the mammal; (ii) provides a Geometric Standard Deviation (GSD) of emitted droplet size distribution of the aqueous solution of about 1.0 μm to about 2.5 μm; (iii) provides droplets of the aqueous solution emitted with the high efficiency liquid with: a) a mass median aerodynamic diameter (MMAD) of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 μm) of droplets emitted from the liquid nebulizer of at least about 30%; (v) provides an output rate of at least 0.1 mL/min; and/or (vi) provides at least about 25% of the aqueous solution to the mammal.

In one aspect, described herein is a method of decreasing IL-113 levels in the lungs of a mammal diagnosed with pulmonary fibrosis comprising administering by inhalation the aqueous solution described herein to the mammal diagnosed with pulmonary fibrosis, wherein the administration of the aqueous solution to the mammal decreases IL-1β levels in the bronchial lavage fluid (BAL) of the mammal by at least 10%, 20%, 30%, or 40%. In some embodiments, the IL-1β levels in the bronchial lavage fluid (BAL) of the mammal are decreased by at least 30%. In some embodiments, the pulmonary fibrosis is idiopathic pulmonary fibrosis (IPF) or pulmonary fibrosis associated with systemic sclerosis. In some embodiments, the aqueous solution is administered by inhalation to the mammal in need thereof with a liquid nebulizer. In some embodiments, the liquid nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the lungs of the mammal. In some embodiments, the liquid nebulizer: (i) after administration of the inhaled dose, achieves lung deposition of at least 7% of the pirfenidone administered to the mammal; (ii) provides a Geometric Standard Deviation (GSD) of emitted droplet size distribution of the aqueous solution of about 1.0 μm to about 2.5 μm; (iii) provides droplets of the aqueous solution emitted with the high efficiency liquid with: a) a mass median aerodynamic diameter (MMAD) of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 μm) of droplets emitted from the liquid nebulizer of at least about 30%; (v) provides an output rate of at least 0.1 mL/min; and/or (vi) provides at least about 25% of the aqueous solution to the mammal. In some embodiments, the dose of the aqueous solution of pirfenidone is administered at least once a week. In some embodiments, the dose of the aqueous solution of pirfenidone is administered on a continuous daily dosing schedule. In some embodiments, the dose of the aqueous solution of pirfenidone is administered once a day, twice a day, three times a day, four times a day, five times a day, or six times a day. In some embodiments, each dose of the aqueous solution of pirfenidone is administered within 20 minutes. In some embodiments, the method further comprises administration of one or more additional therapeutic agents to the mammal.

In another aspect, described herein is a method for the treatment of lung disease in a mammal comprising: administering by inhalation a dose of the aqueous solution described herein to the mammal in need thereof on a continuous dosing schedule. In some embodiments, the lung disease is idiopathic pulmonary fibrosis, or pulmonary fibrosis associated with systemic sclerosis, radiation exposure or transplant, lung cancer or pulmonary hypertension. In some embodiments, the lung disease is lung cancer and the treatment comprises inhibiting, reducing or slowing the growth of lung tumor stroma. In some embodiments, the aqueous solution is administered by inhalation to the mammal in need thereof with a liquid nebulizer. In some embodiments, the liquid nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the lungs of the mammal. In some embodiments, the liquid nebulizer: (i) after administration of the inhaled dose, achieves lung deposition of at least 7% of the pirfenidone administered to the mammal; (ii) provides a Geometric Standard Deviation (GSD) of emitted droplet size distribution of the aqueous solution of about 1.0 µm to about 2.5 µm; (iii) provides droplets of the aqueous solution emitted with the high efficiency liquid with: a) a mass median aerodynamic diameter (MMAD) of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 μm) of droplets emitted from the liquid nebulizer of at least about 30%; (v) provides an output rate of at least 0.1 mL/min; and/or (vi) provides at least about 25% of the aqueous solution to the mammal. In some embodiments, the dose of the aqueous solution of pirfenidone is administered at least once a week. In some embodiments, the dose of the aqueous solution of pirfenidone is administered on a continuous daily dosing schedule. In some embodiments, the dose of the aqueous solution of pirfenidone is administered once a day, twice a day, three times a day, four times a day, five times a day, or six times a day. In some embodiments, each dose of the aqueous solution of pirfenidone is administered within 20 minutes. In some embodiments, the method further comprises administration of one or more additional therapeutic agents to the mammal.

In one aspect, described herein is an aqueous solution for nebulized inhalation administration comprising: water; pirfenidone, or a pyridone analog compound, at a concentration from about 0.1 mg/mL to about 20 mg/mL; wherein the osmolality of the aqueous solution is from about 50 mOsmol/kg to about 2000 mOsmol/kg. In some embodiments, the aqueous solution does not include any cosolvents and/or surfactants. In some embodiments, the solution further comprises one or more additional ingredients selected from buffers and salts. In some embodiments, the buffer is a citrate buffer or phosphate buffer; and the salt is sodium chloride or magnesium chloride, or sodium bromide or magnesium bromide, calcium chloride or calcium bromide. In some embodiments, the aqueous solution comprises: water; pirfenidone or pyridone analog compound at a concentration from about 1 mg/mL to about 20 mg/mL; wherein the total amount of the one or more salts is about 0.01% to about 2.0% v/v; and optionally a phosphate buffer that maintains the pH of the solution from about pH 6.0 to about pH 8.0, or citrate buffer than maintains the pH of the solution from about 4.0 to about 7.0. In some embodiments, the aqueous solution comprises: water; pirfenidone or pyridone analog compound at a concentration from about 5 mg/mL to about 18 mg/mL; wherein the total amount of the one or more salts is about 0.01% to about 2.0% v/v; and optionally a phosphate buffer that maintains the pH of the solution from about pH 6.0 to about pH 8.0, or citrate buffer than maintains the pH of the solution from about 4.0 to about 7.0; wherein the osmolality of the aqueous solution is from about 50 mOsmol/kg to about 2000 mOsmol/kg.

In the embodiments described herein, the inhaled doses are delivered <5, <4, <3, <2, <1 times a day, or less than daily. In some embodiments, the inhaled doses are delivered by nebulization using standard tidal breathing of continuous flow aerosol or breath actuated aerosol. In such embodiments of nebulized delivery, delivery times can be <20, <15, <10, <8, <6, <4, <2 or <1 minute. In some embodiments, the inhaled doses are delivered by inhalation of a dispersed dry powder aerosol using <10, <8, <6, <5, <4, <3, <2 or 1 breath of either a passive dispersion dry power inhaler or active dispersion dry powder inhaler. In some embodiments, the inhaled doses are delivered by inhalation of aerosol using <10, <8, <6, <5, <4, <3, <2 or 1 breath of a compressed gas metered dose inhaler with or without a spacer.

In one aspect, described herein is an aqueous solution for nebulized inhalation administration comprising: water; pirfenidone, or a pyridone analog compound, at a concentration from about 10 mg/mL to about 50 mg/mL; and one or more co-solvents. In another aspect, described herein is an aqueous solution for nebulized inhalation administration comprising: water; pirfenidone, or a pyridone analog compound, at a concentration from about 10 mg/mL to about 50 mg/mL; optionally one or more buffers to maintain the pH between about pH 4.0 to about pH 8.0; and one or more co-solvents. In some embodiments, the pH of the aqueous solution if from about pH 4.0 to about pH 8.0. In some embodiments, the pH of the aqueous solution if from about pH 6.0 to about pH 8.0. In some embodiments, described herein is an aqueous solution for nebulized inhalation administration comprising: water; pirfenidone, or a pyridone analog compound, at a concentration from about 0.1 mg/mL to about 60 mg/mL; and one or more co-solvents, wherein the osmolality of the aqueous solution is from about 50 mOsmol/kg to about 6000 mOsmol/kg. In some embodiments, pirfenidone, or a pyridone analog compound, is at a concentration from about 10 mg/mL to about 60 mg/mL. In some embodiments, pirfenidone, or a pyridone analog compound, is at a concentration from about 10 mg/mL to about 50 mg/mL. In some embodiments, pirfenidone, or a pyridone analog compound, is at a concentration from about 15 mg/mL to about 50 mg/mL. In some embodiments, pirfenidone, or a pyridone analog compound, is at a concentration from about 20 mg/mL to about 50 mg/mL. In some embodiments, pirfenidone, or a pyridone analog compound, is at a concentration from about 25 mg/mL to about 50 mg/mL. In some embodiments, pirfenidone, or a pyridone analog compound, is at a concentration from about 30 mg/mL to about 50 mg/mL. In some embodiments, the osmolality of the aqueous solution is from about 50 mOsmol/kg to about 6000 mOsmol/kg. In some embodiments, the osmolality of the aqueous solution is from about 50 mOsmol/kg to about 5000 mOsmol/kg. In some embodiments, the osmolality of the aqueous solution is from about 100 mOsmol/kg to about 5000 mOsmol/kg, from about 300 mOsmol/kg to about 5000 mOsmol/kg, from about 400 mOsmol/kg to about 5000 mOsmol/kg, from about 600 mOsmol/kg to about 5000 mOsmol/kg, from about 1000 mOsmol/kg to about 5000 mOsmol/kg, or from about 2000 mOsmol/kg to about 5000 mOsmol/kg. In some embodiments, the total concentration of co-solvents is from about 1% to about 40% v/v. In some embodiments, the total concentration of co-solvents is from about 1% to about 30% v/v. In some embodiments, the total concentration of co-solvents is from about 1% to about 25% v/v. In some embodiments, the one or more co-solvents are selected from ethanol, propylene glycol, and glycerol. In some embodiments, the one or more co-solvents are selected from ethanol, and propylene glycol. In some embodiments, the aqueous solution includes both ethanol and propylene glycol. In some embodiments, the solution further comprises one or more additional ingredients selected from surfactants, taste masking agents/sweeteners and salts. In some embodiments, the tastemaking agent/sweetener is saccharin, or salt thereof. In some embodiments, the solution further comprises one or more additional ingredients selected from surfactants and salts. In some embodiments, the surfactant is polysorbate 80 or cetylpyridinium bromide. In some embodiments, the salt is sodium chloride or magnesium chloride. In some embodiments, the surfactant is polysorbate 80 or cetylpyridinium bromide, and the salt is sodium chloride or magnesium chloride. In some embodiments, the aqueous solution includes one more buffers selected from a citrate buffer and a phosphate buffer. In some embodiments, the aqueous solution includes a phosphate buffer. In some embodiments, the aqueous solution includes a citrate buffer. In some embodiments, described herein is from about 0.5 mL to about 6 mL of the aqueous solution described herein.

In some embodiments, the solution further comprises one or more additional ingredients selected from surfactants, buffers and salts. In some embodiments, the surfactant is polysorbate 80 or cetylpyridinium bromide; the buffer is a citrate buffer or phosphate buffer; and the salt is sodium chloride or magnesium chloride.

In some embodiments, the aqueous solution comprises: water; pirfenidone or pyridone analog compound at a concentration from about 10 mg/mL to about 60 mg/mL; one or more co-solvents, wherein the total amount of the one or more co-solvents is about 1% to about 40% v/v, where the one or more co-solvents are selected from about 1% to about 25% v/v of ethanol, about 1% to about 25% v/v of propylene glycol, and about 1% to about 25% v/v of glycerol; and optionally a phosphate buffer that maintains the pH of the solution from about pH 6.0 to about pH 8.0.

In some embodiments, the aqueous solution comprises: water; pirfenidone or pyridone analog compound at a concentration from about 15 mg/mL to about 50 mg/mL; one or more co-solvents, wherein the total amount of the one or more co-solvents if about 1 to about 30% v/v, where the one or more co-solvents are selected from about 1% to about 10% v/v of ethanol, and about 1% to about 20% v/v of propylene glycol; and optionally a phosphate buffer that maintains the pH of the solution from about pH 6.0 to about pH 8.0; wherein the osmolality of the aqueous solution is from about 400 mOsmol/kg to about 6000 mOsmol/kg.

In some embodiments, the aqueous solution for nebulized inhalation administration described herein comprises: water; pirfenidone or pyridone analog compound at a concentration from about 10 mg/mL to about 50 mg/mL; optionally a phosphate buffer that maintains the pH of the solution from about pH 6.0 to about pH 8.0; one or more co-solvents selected from about 1% to about 25% v/v of ethanol and about 1% to about 25% v/v of propylene glycol, where the total amount of co-solvents is from 1% to 25% v/v. In some embodiments, the aqueous solution for nebulized inhalation administration described herein comprises: water; pirfenidone or pyridone analog compound at a concentration from about 10 mg/mL to about 50 mg/mL; optionally a phosphate buffer that maintains the pH of the solution from about pH 6.0 to about pH 8.0; about 8% v/v of ethanol; and about 16% v/v of propylene glycol. In some embodiments, the aqueous solution for nebulized inhalation administration described herein consists essentially of: water; pirfenidone or pyridone analog compound at a concentration from about 10 mg/mL to about 50 mg/mL; optionally a phosphate buffer that maintains the pH of the solution from about pH 6.0 to about pH 8.0; one or more co-solvents selected from about 1% to about 25% v/v of ethanol and about 1% to about 25% v/v of propylene glycol, where the total amount of co-solvents is from 1% to 25% v/v. In some embodiments, the aqueous solution for nebulized inhalation administration described herein consists essentially of: water; pirfenidone or pyridone analog compound at a concentration from about 10 mg/mL to about 50 mg/mL; optionally a phosphate buffer that maintains the pH of the solution from about pH 6.0 to about pH 8.0; about 8% v/v of ethanol; and about 16% v/v of propylene glycol. In some embodiments, described herein is from about 0.5 mL to about 6 mL of the aqueous solution described herein.

In some embodiments, described herein is a unit dosage adapted for use in a liquid nebulizer comprising from about 0.5 mL to about 6 mL of an aqueous solution of pirfenidone or a pyridone analog compound, wherein the concentration of pirfenidone or pyridone analog compound in the aqueous solution is from about 0.1 mg/mL to about 60 mg/mL. In some embodiments, the aqueous solution further comprises one or more additional ingredients selected from co-solvents, tonicity agents, sweeteners, surfactants, wetting agents, chelating agents, anti-oxidants, salts, and buffers; and the osmolality of the aqueous solution is from about 50 mOsmol/kg to about 6000 mOsmol/kg. In some embodiments, the aqueous solution further comprises: one or more co-solvents selected from ethanol, propylene glycol, and glycerol; and one or both of a citrate buffer or a phosphate buffer. In some embodiments, the aqueous solution comprises: pirfenidone or pyridone analog compound dissolved in water at a concentration from about 15 mg/mL to about 50 mg/mL; optionally a phosphate buffer that maintains the pH of the solution from about pH 6.0 to about pH 8.0; one or more co-solvents, wherein the total amount of the one or more co-solvents if about 1 to about 30% v/v, where the one or more co-solvents are selected from about 1% to about 10% v/v of ethanol, and about 1% to about 20% v/v of propylene glycol; wherein the osmolality of the aqueous solution is from about 400 mOsmol/kg to about 6000 mOsmol/kg. In some embodiments, the aqueous solution is as described herein.

In some embodiments, described herein is a kit comprising: a unit dosage of an aqueous solution of pirfenidone or pyridone analog as described herein in a container that is adapted for use in a liquid nebulizer.

In some embodiments, provided herein is an aqueous droplet of pirfenidone or pyridone analog compound, wherein the aqueous droplet has a diameter less than about 5.0 µm. In some embodiments, the aqueous droplet was produced from a liquid nebulizer and an aqueous solution of pirfenidone or pyridone analog compound. In some embodiments, the aqueous solution of pirfenidone or pyridone analog compound is as described herein. In some embodiments, the aqueous solution has concentration of pirfenidone or pyridone analog compound from about 0.1 mg/mL and about 60 mg/mL and an osmolality from about 50 mOsmol/kg to about 6000 mOsmol/kg. In some embodiments, the aqueous droplet is produced by a nebulizing an aqueous solution of pirfenidone or pyridone analog compound as described herein with a nebulizer. In some embodiments, the nebulizer is a liquid nebulizer. In some embodiments, the nebulizer is a high efficiency liquid nebulizer.

In some embodiments, provided herein is an aqueous aerosol comprising a plurality of aqueous droplets of pirfenidone or pyridone analog compound. In some embodiments, described herein is an aqueous aerosol comprising a plurality of aqueous droplets of pirfenidone or pyridone analog compound, wherein the plurality of aqueous droplets have a volumetric mean diameter (VMD), mass median aerodynamic diameter (MMAD), and/or mass median diameter (MMD) of less than about 5.0 µm. In some embodiments, the plurality of aqueous droplets was produced from a liquid nebulizer and an aqueous solution of pirfenidone or pyridone analog compound. In some embodiments, the aqueous solution has concentration of pirfenidone or pyridone analog compound from about 10 mg/mL and about 60 mg/mL and an osmolality from about 50 mOsmol/kg to about 6000 mOsmol/kg. In some embodiments, at least 30% of the aqueous droplets in the aerosol have a diameter less than about 5 µm. In some embodiments, the aqueous aerosol is produced by a nebulizing an aqueous solution of pirfenidone or pyridone analog compound as described herein with a nebulizer. In some embodiments, the nebulizer is a liquid nebulizer. In some embodiments, the nebulizer is a high efficiency liquid nebulizer.

In some embodiments, the nebulizer used in any of the methods described herein is a liquid nebulizer. In some embodiments, the nebulizer used in any of the methods described herein is a jet nebulizer, an ultrasonic nebulizer, a pulsating membrane nebulizer, a nebulizer comprising a vibrating mesh or plate with multiple apertures, or a nebulizer comprising a vibration generator and an aqueous chamber. In some embodiments, the nebulizer used in any of the methods described herein is a nebulizer comprising a vibrating mesh or plate with multiple apertures. In some embodiments, the liquid nebulizer: (i) achieves lung deposition of at least 7% of the pirfenidone or pyridone analog compound administered to the mammal; (ii) provides a Geometric Standard Deviation (GSD) of emitted droplet size distribution of the aqueous solution of about 1.0 µm to about 2.5 µm; (iii) provides: a) a mass median aerodynamic diameter (MMAD) of droplet size of the aqueous solution emitted with the high efficiency liquid nebulizer of about 1 µm to about 5 µm; b) a volumetric mean diameter (VMD) of about 1 jam to about 5 jam; and/or c) a mass median diameter (MMD) of about 1 jam to about 5 jam; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal.

In some embodiments, the liquid nebulizer is characterized as having at least two, at least three, at least four, at least five, or all six of (i), (ii), (iii), (iv), (v), (vi). In some embodiments, the liquid nebulizer: (i) achieves lung deposition of at least 5%, at least 6%, at least 7%, at least 8%, at least 9%, at least 10%, at least 12%, at least 14%, at least 16%, at least 18%, at least 20%, at least 25%, at least 30%, at least 35%, at least 40% at least 45%, at least 50%, at least 55%, at least 60%, at least 65%, at least 70%, at least 75%, or at least 80% of the pirfenidone or pyridone analog compound administered to the mammal. In some embodiments, the liquid nebulizer: (ii) provides a Geometric Standard Deviation (GSD) of emitted droplet size distribution of the aqueous solution of about 1.0 µm to about 2.5 µm, about 1.2 µm to about 2.3 µm, about 1.4 µm to about 2.1 µm, or about 1.5 µm to about 2.0 µm. In some embodiments, the liquid nebulizer: (iii) provides a) a mass median aerodynamic diameter (MMAD) of droplet size of the aqueous solution emitted with the high efficiency liquid nebulizer of about less than 5 m or about 1 m to about 5 µm; b) a volumetric mean diameter (VMD) of about less than 5 µm or about 1 µm to about 5 µm; and/or c) a mass median diameter (MMD) of about less than 5 µm or about 1 µm to about 5 µm. In some embodiments, the liquid nebulizer: (iv) provides a fine particle fraction (FPF=%≤5 microns) of droplets emitted from the liquid nebulizer of at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%. In some embodiments, the liquid nebulizer: (v) provides an output rate of at least 0.1 mL/min, of at least 0.2 mL/min, of at least 0.3 mL/min, of at least 0.4 mL/min, of at least 0.5 mL/min, of at least 0.6 mL/min, of at least 0.7 mL/min, of at least 0.8 mL/min, of at least 0.9 mL/min, of at least 1.0 mL/min, or less than about 1.0 mL/min. In some embodiments, the liquid nebulizer: (vi) provides at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 95%, of the aqueous solution to the mammal. In some embodiments, the liquid nebulizer provides an respirable delivered dose (RDD) of at least 5%, at least 6%, at least 7%, at least 8%, at least 10%, at least 12%, at least 16%, at least 20%, at least 24%, at least 28%, at least 32%, at least 36%, at least 40%, at least 45%, at least 50%, at least 55%, at least 60%, at least 65%, at least 70%, at least 75%, at least 80%, at least 85%, or at least 90%.

In some embodiments, described herein is a method for the treatment of lung disease in a mammal comprising: administering to mammal in need thereof an aqueous solution comprising pirfenidone or a pyridone analog compound with a liquid nebulizer. In some embodiments, described herein is a method for the treatment of lung disease in a mammal comprising: administering to mammal in need thereof an aqueous solution comprising pirfenidone or a pyridone analog compound with a liquid nebulizer; wherein the aqueous solution comprises water; pirfenidone, or a pyridone analog compound, at a concentration from about 0.1 mg/mL to about 60 mg/mL; and one or more co-solvents, wherein the osmolality of the aqueous solution is from about 50 mOsmol/kg to about 6000 mOsmol/kg. In some embodiments, the aqueous solution comprises water; pirfenidone or pyridone analog compound at a concentration from about 10 mg/mL to about 60 mg/mL; one or more co-solvents, wherein the total amount of the one or more co-solvents is about 1% to about 40% v/v, where the one or more co-solvents are selected from about 1% to about 25% v/v of ethanol, about 1% to about 25% v/v of propylene glycol, and about 1% to about 25% v/v of glycerol; and optionally a phosphate buffer that maintains the pH of the solution from about pH 6.0 to about pH 8.0. In some embodiments, the aqueous solution comprises water; pirfenidone or pyridone analog compound at a concentration from about 15 mg/mL to about 50 mg/mL; one or more co-solvents, wherein the total amount of the one or more co-solvents if about 1 to about 30% v/v, where the one or more co-solvents are selected from about 1% to about 10% v/v of ethanol, and about 1% to about 20% v/v of propylene glycol; and optionally a phosphate buffer that maintains the pH of the solution from about pH 6.0 to about pH 8.0; wherein the osmolality of the aqueous solution is from about 400 mOsmol/kg to about 6000 mOsmol/kg. In some embodiments, the nebulizer is a jet nebulizer, an ultrasonic nebulizer, a pulsating membrane nebulizer, a nebulizer comprising a vibrating mesh or plate with multiple apertures, or a nebulizer comprising a vibration generator and an aqueous chamber. In some embodiments, the liquid nebulizer: (i) achieves lung deposition of at least 7% of the pirfenidone or pyridone analog compound administered to the mammal; (ii) provides a Geometric Standard Deviation (GSD) of emitted droplet size distribution of the aqueous solution of about 1.0 μm to about 2.5 m; (iii) provides: a) a mass median aerodynamic diameter (MMAD) of droplet size of the aqueous solution emitted with the high efficiency liquid nebulizer of about 1 μm to about 5 μm; b) a volumetric mean diameter (VMD) of about 1 μm to about 5 μm; and/or c) a mass median diameter (MMD) of about 1 μm to about 5 μm; (iv) provides a fine particle fraction (FPF=%≤5 microns) of droplets emitted from the liquid nebulizer of at least about 30%; (v) provides an output rate of at least 0.1 mL/min; and/or (vi) provides at least about 25% of the aqueous solution to the mammal. In some embodiments, the mammal is a human. In some embodiments, the lung disease is lung fibrosis and the mammal is a human. In some embodiments, the lung disease is idiopathic pulmonary fibrosis and the mammal is a human. In some embodiments, the lung disease is pulmonary hypertension and the mammal is a human. In some embodiments, the lung disease is Type 1, 2, 3, 4 and 5 Pulmonary Hypertension and the mammal is a human. In some embodiments, the lung disease is cancer and the mammal is a human. In some embodiments, the lung cancer is small cell lung cancer and the mammal is a human. In some embodiments, the lung cancer is non-small cell lung cancer and the mammal is a human. In some embodiments, the pulmonary cancer is large cell carcinoma and the mammal is a human. In some embodiments, the pulmonary cancer is mesothelioma and the mammal is a human. In some embodiments, the pulmonary cancer is lung carcinoid tumors or bronchial cardinoids and the mammal is a human. In some embodiments, the pulmonary cancer is secondary lung cancer resulting from metastatic disease and the mammal is a human. In some embodiments, the pulmonary cancer is bronchioloalveolar carcinoma and the mammal is a human. In some embodiments, the pulmonary cancer is sarcoma and the mammal is a human. In some embodiments, the pulmonary cancer is a lymphoma and the mammal is a human. In some embodiments, the liquid nebulizer delivers from about 0.1 mg to about 360 mg of pirfenidone or pyridone analog compound to the lungs of the mammal in less than about 20 minutes with mass median diameter (MMAD) particles sizes from about 1 to about 5 micron.

In some embodiments, the lung tissue Cmax and/or AUC of pirfenidone or pyridone analog compound that is obtained after a single administration of the aqueous solution to the mammal with a liquid nebulizer is about the same or greater than the lung tissue Cmax and/or AUC of pirfenidone or pyridone analog compound that is obtained after a single dose of orally administered pirfenidone or pyridone analog compound at a dose that is from about 80% to about 120% of the dose administered with the liquid nebulizer; and/or the plasma Cmax and/or AUC of pirfenidone or pyridone analog compound that is obtained after a single administration of the aqueous solution to the mammal with a liquid nebulizer is at least 10% or greater than the plasma Cmax and/or AUC of pirfenidone or pyridone analog compound that is obtained after a single dose of orally administered pirfenidone or pyridone analog compound at a dose that is from about 80% to about 120% of the dose administered with the liquid nebulizer. In some embodiments, the lung tissue Cmax of pirfenidone or pyridone analog compound that is obtained after a single administration of the aqueous solution to the mammal with a liquid nebulizer is greater than the lung tissue Cmax of pirfenidone or pyridone analog compound that is obtained after a single dose of orally administered pirfenidone or pyridone analog compound at a dose that is from about 80% to about 120% of the dose administered with the liquid nebulizer. In some embodiments, the lung tissue AUC of pirfenidone or pyridone analog compound that is obtained after a single administration of the aqueous solution to the mammal with a liquid nebulizer is greater than the lung tissue AUC of pirfenidone or pyridone analog compound that is obtained after a single dose of orally administered pirfenidone or pyridone analog compound at a dose that is from about 80% to about 120% of the dose administered with the liquid nebulizer. In some embodiments, the plasma Cmax of pirfenidone or pyridone analog compound that is obtained after a single administration of the aqueous solution to the mammal with a liquid nebulizer is at least 10% or greater than the plasma Cmax of pirfenidone or pyridone analog compound that is obtained after a single dose of orally administered pirfenidone or pyridone analog compound at a dose that is from about 80% to about 120% of the dose administered with the liquid nebulizer. In some embodiments, the plasma AUC of pirfenidone or pyridone analog compound that is obtained after a single administration of the aqueous solution to the mammal with a liquid nebulizer is at least 10% or greater than the plasma AUC of pirfenidone or pyridone analog compound that is obtained after a single dose of orally administered pirfenidone or pyridone analog compound at a dose that is from about 80% to about 120% of the dose administered with the liquid nebulizer.

In some embodiments, the liquid nebulizer delivers from about 0.1 mg to about 360 mg of pirfenidone or pyridone analog compound to the lungs of the mammal in less than about 20 minutes with mass median diameter (MMAD) particles sizes from about 1 to about 5 micron.

In some embodiments, administration with the liquid nebulizer does not include an initial dose-escalation period.

In some embodiments, described herein is a method of reducing the risk of gastrointestinal (GI) adverse events in the treatment of a human with pirfenidone or pyridone analog compound, comprising: administering to the human in need thereof a nebulized aqueous solution comprising pirfenidone or a pyridone analog compound with a liquid nebulizer; wherein the aqueous solution comprises water; pirfenidone, or a pyridone analog compound, at a concentration from about 0.1 mg/mL to about 60 mg/mL; and one or more co-solvents, wherein the osmolality of the aqueous solution is from about 50 mOsmol/kg to about 6000 mOsmol/kg. In some embodiments, the aqueous solution comprises water; pirfenidone or pyridone analog compound at a concentration from about 10 mg/mL to about 60 mg/mL; one or more co-solvents, wherein the total amount of the one or more co-solvents is about 1% to about 40% v/v, where the one or more co-solvents are selected from about 1% to about 25% v/v of ethanol, about 1% to about 25% v/v of propylene glycol, and about 1% to about 25% v/v of glycerol; and optionally a phosphate buffer that maintains the pH of the solution from about pH 6.0 to about pH 8.0.

In some embodiments, the aqueous solution comprises water; pirfenidone or pyridone analog compound at a concentration from about 15 mg/mL to about 50 mg/mL; one or more co-solvents, wherein the total amount of the one or more co-solvents if about 1 to about 30% v/v, where the one or more co-solvents are selected from about 1% to about 10% v/v of ethanol, and about 1% to about 20% v/v of propylene glycol; and optionally a phosphate buffer that maintains the pH of the solution from about pH 6.0 to about pH 8.0; wherein the osmolality of the aqueous solution is from about 400 mOsmol/kg to about 6000 mOsmol/kg. In some embodiments, the pirfenidone or pyridone analog is administered to treat lung disease in the human. In some embodiments, lung disease is idiopathic pulmonary fibrosis.

In some embodiments, the liquid nebulizer delivers about 0.1 mg to about 360 mg of prifenidone or pyridone analog compound to the lungs in less than about 20 minutes with mass median diameter (MMAD) particles sizes from about 1 to about 5 micron.

In some embodiments, administration with the liquid nebulizer does not include an initial dose-escalation period.

In some embodiments, about 0.5 mL to about 6 mL of the aqueous solution is administered to the mammal with a liquid nebulizer, the solution having a concentration of pirfenidone or pyridone analog compound from about 0.1 mg/mL to about 60 mg/mL and the osmolality of the aqueous solution is from about 50 mOsmol/kg to about 5000 mOsmol/kg; and the liquid nebulizer is a nebulizer comprising a vibrating mesh or plate with multiple apertures.

In some embodiments, the liquid nebulizer delivers about 0.1 mg to about 360 mg of prifenidone or pyridone analog compound to the lungs in less than about 20 minutes with mass median diameter (MMAD) particles sizes from about 1 to about 5 micron. In some embodiments, the aqueous solution has a pH from about 4.0 to about 8.0 and an osmolality from about 400 mOsmol/kg to about 5000 mOsmol/kg.

In some embodiments, described herein is an inhalation system for administration of pirfenidone or pyridone analog compound to the respiratory tract of a human, the system comprising: (a) about 0.5 mL to about 6 mL of an aqueous solution of pirfenidone or pyridone analog compound; and (b) a high efficiency liquid nebulizer. In some embodiments, the aqueous solution is any of the aqueous solutions described herein. In some embodiments, the concentration of pirfenidone or pyridone analog compound in the aqueous solution is from about 0.1 mg/mL and about 60 mg/mL and the osmolality of the aqueous solution is from about 400 mOsmol/kg to about 6000 mOsmol/kg. In some embodiments, the aqueous solution comprises: water; pirfenidone, or a pyridone analog compound, at a concentration from about 10 mg/mL to about 50 mg/mL; optionally a phosphate buffer that maintains the pH of the solution from about pH 6.0 to about pH 8.0; about 1% to about 8% of ethanol; and/or about 2% to about 16% of propylene glycol. In some embodiments, the aqueous solution is as described herein.

In one aspect, described herein is a method of achieving a lung tissue Cmax of pirfenidone or pyridone analog compound that is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times a Cmax of up to 801 mg of an orally administered dosage of pirfenidone or pyridone analog compound, the method comprising nebulizing an aqueous solution comprising pirfenidone or pyridone analog compound and administering the nebulized aqueous solution to a human. In some embodiments, described herein is a method of achieving a lung tissue Cmax of pirfenidone or pyridone analog compound that is at least equivalent to or greater than a Cmax of up to 801 mg of an orally administered dosage of pirfenidone or pyridone analog compound, the method comprising nebulizing an aqueous solution comprising pirfenidone or pyridone analog compound and administering the nebulized aqueous solution to a human.

In one aspect, described herein is a method of achieving a lung tissue $AUC_{0-24}$ of pirfenidone or pyridone analog compound that is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times $AUC_{0-24}$ of up to 801 mg of an orally administered dosage of pirfenidone or pyridone analog compound, the method comprising nebulizing an aqueous solution comprising pirfenidone or pyridone analog compound and administering the nebulized aqueous solution to a human. In some embodiments, described herein is a method of achieving a lung tissue $AUC_{0-24}$ of pirfenidone or pyridone analog compound that is at least equivalent to or greater than $AUC_{0-24}$ of up to 801 mg of an orally administered dosage of pirfenidone or pyridone analog compound, the method comprising nebulizing an aqueous solution comprising pirfenidone or pyridone analog compound and administering the nebulized aqueous solution to a human.

In one aspect, described herein is a method of administering pirfenidone or a pyridone analog compound to a human, comprising administering a nebulized aqueous solution containing the pirfenidone or pyridone analog, wherein the lung tissue Cmax achieved with the nebulized solution is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times the lung tissue Cmax achieved with an orally administered pirfenidone or pyridone analog compound dosage that is from 80% to 120% of the dose amount of pirfenidone that is administered by nebulization.

In one aspect, described herein is a method of administering pirfenidone or a pyridone analog compound to a human, comprising administering a nebulized aqueous solution containing the pirfenidone or pyridone analog, wherein the lung tissue Cmax achieved with the nebulized solution is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times the lung tissue Cmax achieved with an orally administered pirfenidone or pyridone analog compound dosage that is from 80% to 120% of the dosage of pirfenidone or pyridone analog compound in the nebulized aqueous solution of pirfenidone or pyridone analog compound. In some embodiments, described herein is a method of administering pirfenidone or a pyridone analog compound to a human, comprising administering a nebulized aqueous solution containing the pirfenidone or pyridone analog, wherein the lung tissue Cmax achieved with the nebulized solution is at least equivalent to or greater than the lung tissue Cmax achieved with an orally administered pirfenidone or pyridone analog compound dosage that is from 80% to 120% of the dosage of pirfenidone or pyridone analog compound in the nebulized aqueous solution of pirfenidone or pyridone analog compound that is administered.

In some embodiments, described herein is a method of administering pirfenidone or a pyridone analog compound to a human, comprising administering a nebulized aqueous solution containing the pirfenidone or pyridone analog, wherein the plasma $AUC_{0-24}$ achieved with the nebulized solution is at least 10% or greater than the plasma $AUC_{0-24}$ achieved with an orally administered pirfenidone or pyridone analog compound dosage that is from 80% to 120% of the dosage of pirfenidone or pyridone analog compound in the nebulized aqueous solution of pirfenidone or pyridone analog compound that is administered.

In one aspect, described herein is a method of administering pirfenidone or a pyridone analog compound to a human, comprising administering a nebulized aqueous solution containing the pirfenidone or pyridone analog, wherein the lung tissue $AUC_{0-24}$ achieved with the nebulized solution is at least 1.5 times, at least 2 times, at least 3 times, at least 4 times, at least 5 times, at least 6 times, at least 1.5 times, at least 1.5 times, at least 1.5 times, at least 1.5 times, at least 7 times, at least 8 times, at least 9 times, at least 10 times, at least 1.5-20 times, at least 1.5-15 times, at least 1.5-10 times, at least 1.5-5 times, or at least 1.5-3 times the lung tissue $AUC_{0-24}$ achieved with an orally administered pirfenidone or pyridone analog compound dosage that is from 80% to 120% of the dosage of pirfenidone or pyridone analog compound in the nebulized aqueous solution of pirfenidone or pyridone analog compound. In some embodiments, described herein is a method of administering pirfenidone or a pyridone analog compound to a human, comprising administering a nebulized aqueous solution containing the pirfenidone or pyridone analog, wherein the lung tissue $AUC_{0-24}$ achieved with the nebulized solution is at least 1.5 times the lung tissue $AUC_{0-24}$ achieved with an orally administered pirfenidone or pyridone analog compound dosage that is from 80% to 120% of the dosage of pirfenidone or pyridone analog compound in the nebulized aqueous solution of pirfenidone or pyridone analog compound.

In one aspect, provided herein is a method of improving the pharmacokinetic profile obtained in a human following a single oral dose administration of pirfenidone or pyridone analog. In some embodiments, the pirfenidone or pyridone analog is administered to the human to treat lung disease. In some embodiments, the lung disease is lung fibrosis. In some embodiments, the lung disease is idiopathic pulmonary fibrosis. In some embodiments, the single oral dose comprises up to about 801 mg of pirfenidone or pyridone analog compound. In some embodiments, the method of improving the pharmacokinetic profile comprises the step of administering pirfenidone or pyridone analog by inhalation. In some embodiments, the pharmacokinetic profile comprises the lung tissue pharmacokinetic profile. In some embodiments, the pharmacokinetic profile comprises the lung tissue pharmacokinetic profile and/or plasma pharmacokinetic profile. In some embodiments, the pirfenidone or pyridone analog is administered as an aqueous solution with a liquid nebulizer. In some embodiments, the aqueous solution of pirfenidone or pyridone analog is as described herein. In some embodiments, the method of improving the pharmacokinetic profile further comprises a comparison of the pharmacokinetic parameters following inhalation administration to the same parameters obtained following oral administration. In some embodiments, the improvement in pharmacokinetic profile is substantially the same as depicted in FIG. 1. In some embodiments, the initial improvement in pharmacokinetic profile is substantially the same as depicted in FIG. 1, but the pulmonary half-life is extended providing longer pulmonary residence time. In some embodiments, a prolonged improvement in pharmacokinetic profile is obtained by repeated and frequent administrations of the aqueous solution of pirfenidone or pyridone analog as described herein by inhalation. In some embodiments, repeated administration of pirfenidone or pyridone analog by inhalation provides more frequent direct lung exposure benefiting the human through repeat high Cmax levels. In some embodiments, the inhaled pirfenidone or pyridone analog doses are administered once a day, twice a day, three times a day, four time a day, every other day, twice a week, three times a week, four times a week, five times a week, six times a week, seven times a week, or any combination thereof. In some embodiments, the improvement in pharmacokinetic profile is substantially the same as depicted in FIG. 2. In some embodiments, the initial improvement in pharmacokinetic profile is substantially the same as depicted in FIG. 2, but the pulmonary half-life is extended providing longer pulmonary residence time. In some embodiments, a prolonged improvement in pharmacokinetic profile is obtained by repeated and frequent administrations of the aqueous solution of pirfenidone or pyridone analog as described herein by inhalation. In some embodiments, repeated administration of pirfenidone or pyridone analog by inhalation provides more frequent direct lung exposure benefiting the human through repeat high Cmax levels. In some embodiments, the inhaled pirfenidone or pyridone analog doses are administered once a day, twice a day, three times a day, four time a day, every other day, twice a week, three times a week, four times a week, five times a week, six times a week, seven times a week, or any combination thereof. In some embodiments, the improvement in pharmacokinetic profile is substantially the same as depicted in FIG. 5. In some embodiments, the initial improvement in pharmacokinetic profile is substantially the same as depicted in FIG. 5, but the pulmonary half-life is extended providing longer pulmonary residence time. In some embodiments, a prolonged improvement in pharmacokinetic profile is obtained by repeated and frequent administrations of the aqueous solution of pirfenidone or pyridone analog as described herein by inhalation. In some embodiments, repeated administration of pirfenidone or pyridone analog by inhalation provides more frequent direct lung exposure benefiting the human through repeat high Cmax levels. In some embodiments, the inhaled pirfenidone or pyridone analog doses are administered once a day, twice a day, three times a day, four time a day, every other day, twice a week, three times a week, four times a week, five times a week, six times a week, seven times a week, or any combination thereof.

In some embodiments, described herein is a pharmaceutical composition for pulmonary delivery, comprising a solution of pirfenidone or pyridone analog having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the composition comprises a taste masking agent. In some embodiments, the taste masking agent is selected from the group consisting of lactose, sucrose, dextrose, saccharin, aspartame, sucrulose, ascorbate and citrate. In some embodiments, the composition comprises a mucolytic agent suitable for pulmonary delivery. In some embodiments, the composition comprises a second anti-fibrotic agent suitable for pulmonary delivery. In some embodiments, the composition comprises a second anti-inflammatory agent suitable for pulmonary delivery.

In some embodiments, described herein is a pharmaceutical composition for pulmonary delivery, comprising a solution of pirfenidone or pyridone analog and a taste masking agent, wherein the solution has an osmolality greater than about 100 mOsmol/kg, and a pH greater than about 4.0. In some embodiments, the pirfenidone or pyridone analog concentration is greater than about 34 mcg/mL. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the composition comprises a taste masking agent. In some embodiments, the taste masking agent is selected from the group consisting of lactose, sucrose, dextrose, saccharin, aspartame, sucrulose, ascorbate and citrate. In some embodiments, the composition comprises a mucolytic agent suitable for pulmonary delivery. In some embodiments, the composition comprises a second anti-fibrotic agent suitable for pulmonary delivery. In some embodiments, the composition comprises a second anti-inflammatory agent suitable for pulmonary delivery.

In some embodiments, described herein is a sterile, single-use container comprising from about 0.1 mL to about 20 mL of a solution of pirfenidone or pyridone analog having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the container further comprises a taste masking agent. In some embodiments, the taste masking agent is selected from the group consisting of lactose, sucrose, dextrose, saccharin, aspartame, sucrulose, ascorbate and citrate. In some embodiments, the container further comprises a mucolytic agent suitable for pulmonary delivery. In some embodiments, the container further comprises a second anti-fibrotic agent suitable for pulmonary delivery. In some embodiments, the container further comprises a second anti-inflammatory agent suitable for pulmonary delivery.

In one aspect, described herein is a method to treat a pulmonary disease comprising inhaling an aerosol of pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the method further comprises administering a second anti-fibrotic agent suitable for pulmonary delivery. In some embodiments, the method further comprises administering a second anti-inflammatory agent suitable for pulmonary delivery. In some embodiments, the pulmonary disease is interstitial lung disease. In some embodiments, the interstitial lung disease is idiopathic pulmonary fibrosis. In some embodiments, the interstitial lung disease is radiation-therapy-induced pulmonary fibrosis. In some embodiments, the pulmonary disease is chronic obstructive pulmonary disease. In some embodiments, the pulmonary disease is chronic bronchitis. In some embodiments, the pulmonary disease is asthma. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In some embodiments, described herein is a pharmaceutical composition for pulmonary delivery, comprising a solution of pirfenidone or pyridone analog and a taste masking agent, wherein the solution has an osmolality greater than about 50 mOsmol/kg, and a pH greater than about 4.0. In some embodiments, the pirfenidone or pyridone analog concentration is greater than about 34 mcg/mL. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 50 mOsmol/kg to about 2000 mOsmol/kg. In some embodiments, the composition comprises a taste masking agent. In some embodiments, the taste masking agent is selected from the group consisting of lactose, sucrose, dextrose, saccharin, aspartame, sucrulose, ascorbate and citrate. In some embodiments, the composition comprises a mucolytic agent suitable for pulmonary delivery. In some embodiments, the composition comprises a second anti-fibrotic agent suitable for pulmonary delivery. In some embodiments, the composition comprises a second anti-inflammatory agent suitable for pulmonary delivery. In some embodiments, the composition comprises a second anti-cancer agent suitable for pulmonary delivery. In some embodiments, the composition comprises a second anti-pulmonary hypertension agent suitable for pulmonary delivery.

In one aspect, described herein is a method to treat a pulmonary disease comprising inhaling an aerosol of pirfenidone or pyridone analog solution having a concentration greater than about 34 mcg/mL, having an osmolality greater than about 50 mOsmol/kg, and having a pH greater than about 4.0. In some embodiments, the pirfenidone or pyridone analog concentration is greater than about 0.1 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 50 mOsmol/kg to about 2000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the method further comprises administering a second anti-fibrotic agent suitable for pulmonary delivery. In some embodiments, the method further comprises administering a second anti-inflammatory agent suitable for pulmonary delivery. In some embodiments, the pulmonary disease is interstitial lung disease and the mammal is a human. In some embodiments, the interstitial lung disease is idiopathic pulmonary fibrosis and the mammal is a human. In some embodiments, the interstitial lung disease is radiation-therapy-induced pulmonary fibrosis and the mammal is a human. In some embodiments, the pulmonary disease is chronic obstructive pulmonary disease and the mammal is a human. In some embodiments, the pulmonary disease is chronic bronchitis and the mammal is a human. In some embodiments, the pulmonary disease is asthma and the mammal is a human. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In one aspect, described herein is a method to treat a pulmonary disease comprising inhaling an aerosol of pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 0.1 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 50 mOsmol/kg to about 2000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the method further comprises administering a second anti-fibrotic or anti-cancer, anti-pulmonary hypertension or anti-infective agent suitable for pulmonary delivery. In some embodiments, the method further comprises administering a second anti-inflammatory agent suitable for pulmonary delivery. In some embodiments, the composition may be co-administered with a second anti-fibrotic or anti-cancer, anti-pulmonary hypertension or anti-infective agent suitable for pulmonary delivery. In some embodiments, the composition co-administered a second anti-inflammatory agent suitable for pulmonary delivery. In some embodiments, the method further comprises administering a second anti-fibrotic agent suitable for pulmonary delivery. In some embodiments, the method further comprises administering a second anti-inflammatory agent suitable for pulmonary delivery. In some embodiments, the pulmonary disease is lung cancer. In some embodiments, the lung cancer is small cell lung cancer. In some embodiments, the lung cancer is non-small cell lung cancer. In some embodiments, the pulmonary cancer is large cell carcinoma. In some embodiments, the pulmonary cancer is mesothelioma. In some embodiments, the pulmonary cancer is lung carcinoid tumors or bronchial cardinoids. In some embodiments, the pulmonary cancer is secondary lung cancer resulting from metastatic disease. In some embodiments, the pulmonary cancer is bronchioloalveolar carcinoma. In some embodiments, the pulmonary cancer may be sarcoma. In some embodiments, the pulmonary cancer is may be a lymphoma. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In one aspect, described herein is a method to treat a pulmonary disease comprising inhaling an aerosol of pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 0.1 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 50 mOsmol/kg to about 2000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the method further comprises administering a second anti-fibrotic or anti-cancer, anti-pulmonary hypertension or anti-infective agent suitable for pulmonary delivery. In some embodiments, the method further comprises administering a second anti-inflammatory agent suitable for pulmonary delivery. In some embodiments, the composition may be co-administered with a second anti-fibrotic or anti-cancer, anti-pulmonary hypertension or anti-infective agent suitable for pulmonary delivery. In some embodiments, the composition co-administered a second anti-inflammatory agent suitable for pulmonary delivery. In some embodiments, the method further comprises administering a second anti-fibrotic agent suitable for pulmonary delivery. In some embodiments, the method further comprises administering a second anti-inflammatory agent suitable for pulmonary delivery. In some embodiments, the pulmonary disease is pulmonary hypertension. In some embodiments, the pulmonary hypertension is Type 1. In some embodiments, the pulmonary hypertension is Type 2. In some embodiments, the pulmonary hypertension is Type 3. In some embodiments, the pulmonary hypertension is Type 4. In some embodiments, the pulmonary hypertension is Type 5. In some embodiments, the pulmonary hypertension is secondary to pulmonary fibrosis. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In one aspect, described herein is a method to administer an anti-fibrotic agent to lungs of a patient, comprising: introducing in a nebulizer a pirfenidone or pyridone analog solution having a concentration greater than about 34 mcg/mL, having an osmolality greater than about 100 mOsmol/kg, and having a pH greater than about 4.0. In another aspect, described herein is a method to administer an anti-inflammatory agent to lungs of a patient, comprising: introducing in a nebulizer a pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the mucolytic agent is inhaled separately from the pirfenidone or pyridone analog solution. In some embodiments, the method further comprises administering a second anti-fibrotic agent suitable for pulmonary delivery. In some embodiments, the method further comprises administering a second anti-inflammatory agent suitable for pulmonary delivery.

In one aspect, described herein is a method to treat an extrapulmonary disease target comprising inhaling an aerosol of pirfenidone or pyridone analog solution having a concentration greater than about 34 mcg/mL, having an osmolality greater than about 100 mOsmol/kg, and having a pH greater than about 4.0 for the purpose of absorbing into the pulmonary vasculature and exposing downstream disease targets to delivered pirfenidone or pyridone analog. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the pirfenidone or pyridone analog solution has a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for pulmonary delivery. In some embodiments, the mucolytic agent is inhaled separately from the pirfenidone or pyridone analog solution. In some embodiments, the method further comprises administering a second anti-fibrotic agent suitable for pulmonary delivery. In some embodiments, the method further comprises administering a second anti-inflammatory agent suitable for pulmonary delivery. In some embodiments, the extrapulmonary disease target is the heart. In some embodiments, the extrapulmonary disease target is the kidney. In some embodiments, the extrapulmonary disease target is the liver.

In any of the methods described herein using an aerosol or nebulizer to deliver a pirfenidone or pyridone analog compound to the lungs, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 17 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In one aspect, described herein is a method to treat a neurologic disease comprising intranasal inhalation of an aerosol of pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the aerosol further comprises a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for intranasal delivery. In some embodiments, the method further comprises administering a second anti-fibrotic agent suitable for intranasal delivery. In some embodiments, the method further comprises administering a second anti-inflammatory agent suitable for intranasal delivery. In some embodiments, the neurologic disease is multiple sclerosis. In some embodiments, the aerosol comprises particles having a mean aerodynamic diameter from about 1 micron to about 20 microns. In some embodiments, the aerosol has a mean particle size from about 1 microns to about 20 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths.

In some embodiments, described herein is a method to administer an anti-demylination agent to nasal cavity of a patient, comprising: introducing in a nebulizer a pirfenidone or pyridone analog solution having a concentration greater than about 34 mcg/mL, having an osmolality greater than about 100 mOsmol/kg, and having a pH greater than about 4.0. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the solution further comprises a taste masking agent. In some embodiments, the taste masking agent is selected from the group consisting of lactose, sucrose, dextrose, saccharin, aspartame, sucrulose, ascorbate and citrate. In some embodiments, the method further comprises administering a mucolytic agent suitable for intranasal delivery. In some embodiments, the mucolytic agent is inhaled separately from the pirfenidone or pyridone analog solution. In some embodiments, the method further comprises administering a second agent suitable for intranasal delivery.

In any of the methods described herein involving introducing in a nebulizer a pirfenidone or pyridone analog solution, the method involves a step of opening a sterile single-use container containing between about 0.5 mL to about 10 mL of a solution of pirfenidone or pyridone analog solution for introduction into a nebulizer.

In any of the methods described herein involving a nebulizer, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the aerosol comprises particles having a mean aerodynamic diameter from about 1 micron to about 20 microns. In some embodiments, the aerosol has a mean particle size from about 1 microns to about 20 microns volumetric mean diameter and a particle size geometric standard deviation of less than or equal to 3 microns. In some embodiments, the inhaling step delivers a dose of a least 6.8 mcg pirfenidone or pyridone analog. In some embodiments, the inhaling step delivers a dose of a least 340 mcg pirfenidone or pyridone analog. In some embodiments, the inhaling step delivers a dose of a least 740 mcg pirfenidone or pyridone analog. In some embodiments, the inhaling step delivers a dose of a least 1.7 mg pirfenidone or pyridone analog. In some embodiments, the inhaling step delivers a dose of a least 93 mg pirfenidone or pyridone analog. In some embodiments, the inhaling step delivers a dose of a least 463 mg pirfenidone or pyridone analog. In some embodiments, the inhaling step is performed in less than about 20 minutes. In some embodiments, the inhaling step is performed in less than about 10 minutes. In some embodiments, the inhaling step is performed in less than about 7.5 minutes. In some embodiments, the inhaling step is performed in less than about 5 minutes. In some embodiments, the inhaling step is performed in less than about 2.5 minutes. In some embodiments, the inhaling step is performed in less than about 1.5 minutes. In some embodiments, the inhaling step is performed in less than about 30 seconds. In some embodiments, the inhaling step is performed in less than about 5 breaths. In some embodiments, the inhaling step is performed in less than about 3 breaths. In some embodiments, the inhaling step is performed in one breath.

In one aspect, provided herein is a kit comprising: a pharmaceutical composition comprising a pirfenidone or pyridone analog solution in a sterile container, wherein the pirfenidone or pyridone analog solution has a concentration greater than about 34 mcg/mL, an osmolality greater than about 100 mOsmol/kg, and a pH greater than about 4.0, and a nebulizer adapted to aerosolize the pirfenidone or pyridone analog solution for delivery to the middle to lower respiratory tract through oral inhalation. In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the solution further comprises a taste masking agent. In some embodiments, the taste masking agent is selected from the group consisting of lactose, sucrose, dextrose, saccharin, aspartame, sucrulose, ascorbate and citrate. In some embodiments, the kit further comprises a mucolytic agent suitable for pulmonary delivery. In some embodiments, the kit further comprises a second anti-fibrotic agent suitable for pulmonary delivery. In some embodiments, the kit further comprises a second anti-inflammatory agent suitable for pulmonary delivery.

In another aspect, provided herein is a kit comprising: a pharmaceutical composition comprising a pirfenidone or pyridone analog solution in a sterile container, wherein the pirfenidone or pyridone analog solution has a concentration greater than about 34 mcg/mL, an osmolality greater than about 100 mOsmol/kg, and a pH greater than about 4.0, and a nebulizer adapted to aerosolize the pirfenidone or pyridone analog solution for delivery to the nasal cavity through intranasal inhalation.

In some embodiments, the pirfenidone or pyridone analog concentration is greater than about 1.72 mg/mL. In some embodiments, the pirfenidone or pyridone analog concentration is greater than about 86 mg/mL. In some embodiments, the pirfenidone or pyridone analog solution has a permeant ion concentration from about 30 mM to about 300 mM. In some embodiments, the permeant ion is chloride or bromide. In some embodiments, the pirfenidone or pyridone analog solution has a pH from about 4.0 to about 8.0. In some embodiments, the pirfenidone or pyridone analog solution has an osmolality from about 100 mOsmol/kg to about 1000 mOsmol/kg. In some embodiments, the pirfenidone or pyridone analog solution has an osmolality from about 50 mOsmol/kg to about 5000 mOsmol/kg. In some embodiments, the solution further comprises a taste masking agent. In some embodiments, the taste masking agent is selected from the group consisting of lactose, sucrose, dextrose, saccharin, aspartame, sucrulose, ascorbate and citrate. In some embodiments, the kit further comprises a mucolytic agent suitable for intranasal delivery. In some embodiments, the kit further comprises a second anti-fibrotic agent suitable for intranasal delivery. In some embodiments, the kit further comprises a second anti-inflammatory agent suitable for intranasal delivery.

In one aspect, described herein is a method for treating lung disease, comprising administering pirfenidone or pyridone analog to a middle to lower respiratory tract of a subject having or suspected of having interstitial lung disease through oral inhalation of an aerosol comprising pirfenidone or pyridone analog, wherein the disease is selected from interstitial lung disease, including idiopathic pulmonary fibrosis and radiation therapy-induced fibrosis; chronic obstructive pulmonary disease; and asthma. In some embodiments, the subject is identified as having interstitial lung disease. In some embodiments, the subject is identified as having idiopathic pulmonary fibrosis. In some embodiments, the subject is identified as having radiation therapy-induced pulmonary fibrosis. In some embodiments, the subject is identified as having chronic obstructive pulmonary disease. In some embodiments, the subject is identified as having chronic bronchitis. In some embodiments, the subject is identified as having asthma. In some embodiments, the subject is a subject being mechanically ventilated.

A method for treating extrapulmonary disease, comprising administering pirfenidone or pyridone analog to a middle to lower respiratory tract of a subject having or suspected of having extrapulmonary fibrosis, inflammatory and/or toxicity-related diseases through oral inhalation of an aerosol comprising pirfenidone or pyridone analog for purposes of pulmonary vascular absorption and delivery to extrapulmonary diseased tissues, wherein the disease is selected from cardiac fibrosis, kidney fibrosis, hepatic fibrosis, kidney toxicity and heart toxicity. In some embodiments, the subject is identified as having cardiac fibrosis. In some embodiments, the subject is identified as having kidney fibrosis. In some embodiments, the subject is identified as having hepatic fibrosis. In some embodiments, the subject is identified as having kidney toxicity. In some embodiments, the subject is identified as having heart toxicity. In some embodiments, the subject is a subject being mechanically ventilated.

In one aspect, described herein is a method for treating neurologic disease, comprising administering pirfenidone or pyridone analog to the nasal cavity of a subject having or suspected of having neurologic disease through intranasal inhalation of an aerosol comprising pirfenidone or pyridone analog for purposes of nasal vascular absorption and delivery to central nervous system, wherein the disease is multiple sclerosis. In some embodiments, the subject is identified as having multiple sclerosis. In some embodiments, the subject is a subject being mechanically ventilated.

In one aspect, described herein is a pharmaceutical composition for pulmonary delivery, comprising a dry powder containing pirfenidone or pyridone analog having a dosage content greater than about 1%. In some embodiments, the pirfenidone or pyridone analog dose content is greater than about 6.8 mcg. In some embodiments, the pirfenidone or pyridone analog content is greater than about 340 mcg. In some embodiments, the pirfenidone or pyridone analog content is greater than about 17 mg. In some embodiments, the pirfenidone or pyridone analog content is greater than about 463 mg. In some embodiments, the powder further comprises a blending agent. In some embodiments, the blending agent is selected from the group consisting of lactose.

In one aspect, described herein is a pharmaceutical composition for pulmonary delivery, comprising a dry powder containing pirfenidone or pyridone analog having a dosage content greater than about 1%. In yet another aspect, described herein is a sterile, single-use container comprising from about 0.5 mg to about 100 mg dry powder containing pirfenidone or pyridone analog having a dosage content greater than about 1%. In a further aspect, described is a method to treat a pulmonary disease comprising inhalation of a dry powder aerosol containing pirfenidone or pyridone dosage content greater than about 1%. In some embodiments, the pirfenidone or pyridone analog dose content is greater than about 6.8 mcg. In some embodiments, the pirfenidone or pyridone analog content is greater than about 340 mcg. In some embodiments, the pirfenidone or pyridone analog content is greater than about 17 mg. In some embodiments, the pirfenidone or pyridone analog content is greater than about 463 mg. In some embodiments, the dry powder further comprises a blending agent. In some embodiments, the blending agent is lactose. In some embodiments, the pulmonary disease is interstitial lung disease. In some embodiments, the interstitial lung disease is idiopathic pulmonary fibrosis. In some embodiments, the interstitial lung disease is radiation-therapy-induced pulmonary fibrosis. In some embodiments, the pulmonary disease is chronic obstructive pulmonary disease. In some embodiments, the pulmonary disease is chronic bronchitis. In some embodiments, the pulmonary disease is asthma. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the inhaling step delivers a dose of a least 6.8 mcg pirfenidone or pyidone analog. In some embodiments, the inhaling step delivers a dose of a least 340 mcg pirfenidone or pyidone analog. In some embodiments, the inhaling step delivers a dose of a least 740 mcg pirfenidone or pyidone analog. In some embodiments, the inhaling step delivers a dose of a least 1.7 mg pirfenidone or pyidone analog. In some embodiments, the inhaling step delivers a dose of a least 93 mg pirfenidone or pyidone analog. In some embodiments, the inhaling step delivers a dose of a least 463 mg pirfenidone or pyidone analog. In some embodiments, the inhaling step is performed in less than about 5 breaths. In some embodiments, the inhaling step is performed in less than about 3 breaths. In some embodiments, the inhaling step is performed in less than about 2 breaths. In some embodiments, the inhaling step is performed in one breath.

In one aspect, provided herein is a method to administer an anti-fibrotic agent to lungs of a subject, comprising: introducing in a dry powder inhaler a pirfenidone or pyridone analog dry powder formulation having a dosage content greater than about 1%. In another aspect, provided herein is a method to administer an anti-inflammatory agent to lungs of a subject, comprising: introducing in a dry powder inhaler a pirfenidone or pyridone analog dry powder formulation having a dosage content greater than about 1%. In yet another aspect, provided herein is a method to treat an extrapulmonary disease target comprising inhalation of a dry powder aerosol containing pirfenidone or pyridone dosage content greater than about 1%. In some embodiments, the extrapulmonary disease target is the heart. In some embodiments, the extrapulmonary disease target is the kidney. In some embodiments, the extrapulmonary disease target is the liver. In yet another aspect, provided herein is a method to treat a neurologic disease comprising intranasal inhalation of a dry powder aerosol containing pirfenidone or pyridone dosage content greater than about 1%. In some embodiments, the neurologic disease is multiple sclerosis. In yet another aspect, provided herein is a method to administer an anti-demylination agent to nasal cavity of a subject, comprising: introducing in a dry powder inhaler a pirfenidone or pyridone analog dry powder formulation having a dosage content greater than about 1%. In some embodiments, the pirfenidone or pyridone analog dose content is greater than about 6.8 mcg. In some embodiments, the pirfenidone or pyridone analog content is greater than about 340 mcg. In some embodiments, the pirfenidone or pyridone analog content is greater than about 17 mg. In some embodiments, the pirfenidone or pyridone analog content is greater than about 463 mg. In some embodiments, the dry powder comprises a blending agent. In some embodiments, the blending agent is lactose. In some embodiments, the aerosol comprises particles having a mean aerodynamic diameter from about 1 micron to about 5 microns. In some embodiments, the aerosol has a mean particle size from about 1 microns to about 5 microns volumetric mean diameter and a particle size geometric standard deviation of less than or equal to 3 microns. In some embodiments, the aerosol comprises particles having a mean aerodynamic diameter from about 1 micron to about 20 microns. In some embodiments, the aerosol has a mean particle size from about 1 microns to about 20 microns volumetric mean diameter and a particle size geometric standard deviation of less than or equal to 3 microns. In some embodiments, the inhaling step delivers a dose of a least 6.8 mcg pirfenidone or pyidone analog. In some embodiments, the inhaling step delivers a dose of a least 340 mcg pirfenidone or pyidone analog. In some embodiments, the inhaling step delivers a dose of a least 740 mcg pirfenidone or pyidone analog. In some embodiments, the inhaling step delivers a dose of a least 1.7 mg pirfenidone or pyidone analog. In some embodiments, the inhaling step delivers a dose of a least 17 mg pirfenidone or pyidone analog. In some embodiments, the inhaling step delivers a dose of a least 93 mg pirfenidone or pyidone analog. In some embodiments, the inhaling step delivers a dose of a least 463 mg pirfenidone or pyidone analog. In some embodiments, the inhaling step is performed in less than about 5 breaths. In some embodiments, the inhaling step is performed in less than about 3 breaths. In some embodiments, the inhaling step is performed in less than about 2 breaths. In some embodiments, the inhaling step is performed in one breath. In some embodiments, the method further comprises the step of opening a single-use dry powder container holding between about 0.5 mg to about 10 mg dry powder formulation containing pirfenidone or pyridone analog for introduction into a dry powder inhaler.

In one aspect, described herein is a kit comprising: a pharmaceutical composition comprising a dry powder pirfenidone or pyridone analog formulation in a container, wherein the pirfenidone or pyridone analog dosage content is greater than about 1%; and a dry powder inhaler adapted to aerosolize the pirfenidone or pyridone analog dry powder formulation for delivery to the middle to lower respiratory tract through oral inhalation. In another aspect, described herein is a kit comprising: a pharmaceutical composition comprising a dry powder pirfenidone or pyridone analog formulation in a container, wherein the pirfenidone or pyridone analog dosage content is greater than about 1%, and a dry powder inhaler adapted to aerosolize the pirfenidone or pyridone analog dry powder formulation for delivery to the nasal cavity through intranasal inhalation. In some embodiments, the pirfenidone or pyridone analog dose content is greater than about 6.8 mcg. In some embodiments, the pirfenidone or pyridone analog content is greater than about 340 mcg. In some embodiments, the pirfenidone or pyridone analog content is greater than about 17 mg. In some embodiments, the pirfenidone or pyridone analog content is greater than about 463 mg. In some embodiments, the powder further comprises a blending agent. In some embodiments, the blending agent is lactose.

In one aspect, described herein is a method for treating lung disease, comprising administering pirfenidone or pyridone analog to a middle to lower respiratory tract of a subject having or suspected of having interstitial lung disease through oral inhalation of an aerosol comprising pirfenidone or pyridone analog, wherein the disease is selected from interstitial lung disease, including idiopathic pulmonary fibrosis and radiation therapy-induced fibrosis; chronic obstructive pulmonary disease; and asthma. In some embodiments, the subject is identified as having interstitial lung disease. In some embodiments, the subject is identified as having idiopathic pulmonary fibrosis. In some embodiments, the subject is identified as having radiation therapy-induced pulmonary fibrosis. In some embodiments, the subject is identified as having chronic obstructive pulmonary disease. In some embodiments, the subject is identified as having chronic bronchitis. In some embodiments, the subject is identified as having asthma. In some embodiments, the subject is a subject being mechanically ventilated.

In one aspect, described herein is a method for treating lung disease, comprising administering pirfenidone or pyridone analog to a middle to lower respiratory tract of a subject having or suspected of having pulmonary disease through oral inhalation of an aerosol comprising pirfenidone or pyridone analog, wherein the pulmonary disease is cancer. In some embodiments, the therapeutic target for said pulmonary cancer is tumor stroma. In some embodiments, the subject is a subject being mechanically ventilated.

In one aspect, described herein is a method for treating lung disease, comprising administering pirfenidone or pyridone analog to a middle to lower respiratory tract of a subject having or suspected of having pulmonary disease through oral inhalation of an aerosol comprising pirfenidone or pyridone analog, wherein the pulmonary disease is pulmonary hypertension. In some embodiments, the subject is a subject being mechanically ventilated.

In one aspect, described herein is a method for treating extrapulmonary disease, comprising administering pirfenidone or pyridone analog to a middle to lower respiratory tract of a subject having or suspected of having extrapulmonary fibrosis, inflammatory and/or toxicity-related diseases through oral inhalation of an aerosol comprising pirfenidone or pyridone analog for purposes of pulmonary vascular absorption and delivery to extrapulmonary diseased tissues, wherein the disease is selected from cardiac fibrosis, kidney fibrosis, hepatic fibrosis, kidney toxicity and heart toxicity.

In some embodiments, the subject is identified as having cardiac fibrosis. In some embodiments, the subject is identified as having kidney fibrosis. In some embodiments, the subject is identified as having hepatic fibrosis. In some embodiments, the subject is identified as having kidney toxicity. In some embodiments, the subject is identified as having heart toxicity. In some embodiments, the subject is a subject being mechanically ventilated.

In one aspect, described herein is a method for treating neurologic disease, comprising administering pirfenidone or pyridone analog to the nasal cavity of a subject having or suspected of having neurologic disease through intranasal inhalation of an aerosol comprising pirfenidone or pyridone analog for purposes of nasal vascular absorption and delivery to central nervous system, wherein the disease is multiple sclerosis. In some embodiments, the subject is identified as having multiple sclerosis. In some embodiments, the subject is a subject being mechanically ventilated.

In one aspect, described herein is a method of administering pirfenidone or pyridone analog to treat a patient with idiopathic pulmonary fibrosis (IPF), wherein the patient avoids abnormal liver function exhibited by a grade 2 or higher abnormality following oral administration in one or more biomarkers of liver function after pirfenidone or pyridone analog administration, comprising administering to said patient pirfenidone or pyridone analog at doses less than 300 mg per day. In some embodiments, "Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN. In some embodiments, the pirfenidone or pyridone analog is delivered to the patient by oral inhalation or intranasal inhalation. In some embodiments, said one or more biomarkers of liver function is selected from the group consisting of alanine transaminase, aspartate transaminase, bilirubin, and alkaline phosphatase. In some embodiments, the method further comprises the step of measuring one or more biomarkers of liver function. In some embodiments, the blood Cmax following administration of pirfenidone or pyridone analog is less than 10 mcg/mL. In some embodiments, the blood Cmax following administration of pirfenidone or pyridone analog is greater than 10 mcg/mL.

In one aspect, described herein is a method of administering pirfenidone or pyridone analog to treat a patient with idiopathic pulmonary fibrosis (IPF), wherein the patient avoids the incidence of photosensitivity reaction observed following oral administration, comprising administering to said patient pirfenidone or pyridone analog at doses less than 360 mg per day. In some embodiments, the pirfenidone or pyridone analog is delivered to the patient by oral inhalation or intranasal inhalation. In some embodiments, the incidence of photosensitivity reaction adverse events is less than about 12%. In some embodiments, the blood Cmax following administration of pirfenidone or pyridone analog is less than 10 mcg/mL. In some embodiments, the blood Cmax following administration of pirfenidone or pyridone analog is greater than 10 mcg/mL.

In one aspect, described herein is a method of administering pirfenidone or pyridone analog to treat a patient with idiopathic pulmonary fibrosis (IPF), wherein the patient avoids the incidence of phototoxicity observed following oral administration, comprising administering to said patient pirfenidone or pyridone analog at doses less than 360 mg per day. In some embodiments, the pirfenidone or pyridone analog is delivered to the patient by oral inhalation or intranasal inhalation. In some embodiments, the incidence of photosensitivity reaction adverse events is less than about 12%. In some embodiments, the blood Cmax following administration of pirfenidone or pyridone analog is less than 10 mcg/mL. In some embodiments, the blood Cmax following administration of pirfenidone or pyridone analog is greater than 10 mcg/mL.

In one aspect, described herein is a method of administering pirfenidone or pyridone analog to treat a patient with idiopathic pulmonary fibrosis (IPF), wherein the patient avoids the incidence of gastrointestinal adverse events observed following oral administration, by delivering pirfenidone or pyridone analog directly to the lung by oral inhalation or intranasal inhalation. In some embodiments, gastrointestinal adverse events observed following oral administration of pirfenidone or pyridone analog include, but are not limited to any one or more of the following: dyspepsia, nausea, diarrhea, gastroesophageal reflux disease (GERD) and vomiting. In some embodiments, less than 360 mg per day of pirfenidone or pyridone analog is delivered to the patient by inhalation. In some embodiments, less than 1000 mg, less than 900 mg, less 600 mg, or less than 300 mg per day of pirfenidone or pyridone analog is delivered to the patient by inhalation. In some embodiments, less than 300 mg per day of pirfenidone or pyridone analog is delivered per dose to the patient by inhalation. In some embodiments, pirfenidone or pyridone analog is delivered by inhalation once per day, twice per day, three time a day, or four time a day.

In some embodiments, up to about 360 mg of pirfenidone or pyridone analog is delivered to the patient by inhalation per dose. In some embodiments, about 1 mg to about 360 mg, about 10 mg to about 360 mg, about 20 mg to about 360 mg, about 30 mg to about 360 mg, about 40 mg to about 360 mg, about 50 mg to about 360 mg, about 60 mg to about 70 mg, about 80 mg to about 360 mg, about 90 mg to about 360 mg, about 100 mg to about 360 mg, about 120 mg to about 360 mg, about 140 mg to about 360 mg, about 160 mg to about 360 mg, about 180 mg to about 360 mg, or about 200 mg to about 360 mg, of pirfenidone or pyridone analog is delivered to the patient by inhalation per dose. In some embodiments, pirfenidone or pyridone analog is delivered by inhalation once per day, twice per day, three time a day, or four time a day.

In one aspect, described herein is a pharmaceutical composition comprising a therapeutically effective amount of an inhaled agent, wherein the agent is pirfenidone or pyridone analog, wherein the agent is in a particle less than 5 microns in mass mean aerodynamic diameter or less than 10 microns volumetric mean diameter wherein the composition, upon inhalation, delivers a dose to the lung greater than 1 mcg pirfenidone or pyridone analog compound per gram of adult human lung tissue.

In one aspect, described herein is a pharmaceutical composition for aerosol delivery to the lung, comprising a solution of pirfenidone or pyridone analog containing a divalent cation. In some embodiments, the divalent cation is selected from the group consisting of calcium, iron, magnesium, and beryllium. In some embodiments, the ratio of pirfenidone or pyridone analog to divalent cation is within the molar range of 1 to about 0.1 to 10, in unit increments of about 0.01. By example, 1 to about 10, 1 to about 9, 1 to about 8, 1 to about 7, 1 to about 6, 1 to about 5, 1 to about 4, 1 to about 3, 1 to about 2, 1 to about 1.5, 1 to about 1, 1 to about 0.75, 1 to about 0.5, 1 to about 0.25, and 1 to about 0.1. In some embodiments, the active pharmaceutical ingredient is pirfenidone or pyridone analog concentration is between 0.1 mg/mL and 50 mg/mL in unit increments of about 0.01 mg/mL composition. By example, about 0.1 mg/mL, about 0.5 mg/mL, about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 15 mg/mL, about 20 mg/mL, about 25 mg/mL, about 30 mg/mL, about 30 mg/mL, about 35 mg/mL, about 40 mg/mL, about 45 mg/mL, about 50 mg/mL, about 55 mg/mL, and about 60 mg/mL. In some embodiments, the active pharmaceutical ingredient is not a salt of pirfenidone or pyridone analog. In some embodiments, the composition is a stable, water-soluble formulation. In some embodiments, the osmolality is greater than about 50 mOsmol/kg composition in unit increments of about 1 mOsmol/kg. By example, greater than about 50 mOsmol/kg, about 100 mOsmol/kg, about 150 mOsmol/kg, about 200 mOsmol/kg, about 250 mOsmol/kg, about 300 mOsmol/kg, about 350 mOsmol/kg, about 400 mOsmol/kg, about 450 mOsmol/kg, about 500 mOsmol/kg, about 550 mOsmol/kg, about 600 mOsmol/kg, about 650 mOsmol/kg, about 700 mOsmol/kg, about 750 mOsmol/kg, about 800 mOsmol/kg, about 850 mOsmol/kg, about 900 mOsmol/kg, about 950 mOsmol/kg, about 1000 mOsmol/kg, greater than about 1500 mOsmol/kg, about 2000 mOsmol/kg, about 2500 mOsmol/kg, greater than about 3000 mOsmol/kg, about 3500 mOsmol/kg, about 4000 mOsmol/kg, greater than about 4500 mOsmol/kg, about 5000 mOsmol/kg, about 5500 mOsmol/kg, about 6000 mOsmol/kg, or greater than about 6000 mOsmol/kg. In some embodiments, the pH is greater than about 3.0 in pH unit increments of about 0.1. By example, a pH of about 3, a pH of about 3.5, a pH of about 4, a pH of about 4.5, a pH of about 5, a pH of about 5.5, a pH of about 6, a pH of about 6.5, a pH of about 7, a pH of about 7.5, a pH of about 8, a pH of about 8.5, a pH of about 9, a pH of about 9.5, a pH of about 10 a pH of about 10.5, and a pH of about 11. In some embodiments, the pH is balanced by the inclusion of an organic buffer selected from the group consisting of citric acid, citrate, malic acid, malate, pyridine, formic acid, formate, piperazine, succinic acid, succinate, histidine, maleate, bis-tris, pyrophosphate, phosphoric acid, phosphate, PIPES, ACES, MES, cacodylic acid, carbonic acid, carbonate, ADA (N-(2-Acetamido)-2-iminodiacetic acid). In some embodiments, the pirfenidone or pyridone analog solution contains a permeant ion concentration. In some embodiments, the permeant ion is selected from the group consisting of bromine, chloride, and lithium. In some embodiments, the permeant ion concentration is from about 30 mM to about 300 mM in about 0.1 mM increments. By example, about 30 mM, about 40 mM, about 50 mM, about 60 mM, about 70 mM, about 80 mM, about 90 mM, about 100 mm, about 150 mM, about 200 mM, about 250 mM, and about 300 mM. In some embodiments, the composition further comprises a taste masking agent. In some embodiments, the taste masking agent is selected from the group consisting of lactose, sucrose, dextrose, saccharin, aspartame, sucrulose, ascorbate, multivalent cation and citrate. In some embodiments, the taste masking agent concentration is from 0.01 mM to about 50 mM in about 0.01 mM increments. By examples, about 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, and about 50 mM.

In some embodiments, the formulations described herein are filled into a primary package. In some embodiments, primary packaging material is taken from the group consisting of glass or plastic, wherein plastic materials may be selected from the group consisting of low-density polyethylene (LDPE), high-density polypropylene (HDPP), or high-density polyethylene (HDPE). In some embodiments, the primary packaging consists of a vial, syringe or ampoule. In some embodiments, the composition is protected from light.

In some embodiments, the compositions described herein are formulated under or to result in conditions of reduced oxygen. In some embodiments, oxygen is reduced by sparging the formulation diluent prior to addition of the active pharmaceutical ingredient. Sparging gases may be selected from the group consisting of carbon dioxide, argon or nitrogen. In some embodiments, oxygen is reduced by sparging the formulation diluent after addition of the active pharmaceutical ingredient. Sparging gases may be selected from the group consisting of carbon dioxide, argon or nitrogen. In some embodiments, oxygen exposure is reduced by replacing the ambient gas headspace of the formulation container with an inert gas. Inert gases may be selected from the group consisting of argon or nitrogen.

In some embodiments, oxygen exposure is reduced by replacing the ambient gas headspace of the primary packaging container with an inert gas. Inert gases may be selected from the group consisting of argon or nitrogen.

In some embodiments, oxygen exposure is reduced by inserting the primary packaging into a gas-impermeable secondary packaging container.

In some embodiments, oxygen exposure is reduced by replacing the ambient gas headspace of the secondary packaging with an inert gas. Inert gases may be selected from the group consisting of argon or nitrogen.

In some embodiments, the aerosol for delivery to the lungs of a mammal described herein contains a fine particle fraction between 10 and 100% with increment units of 1%. By example, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. In some embodiments, the fine particle dose is between about 0.1 mg to about 360 mgs pirfenidone or pyridone analog, in 0.1 mg increments. By example, about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 25 mg, about 30 mg, about 35 mg, about 40 mg, about 45 mg, about 50 mg, about 60 mg, about 70 mg, about 80 mg, about 90 mg, about 100 mg, about 150 mg, about 200 mg, about 220 mg, about 240 mg, about 260 mg, about 280 mg, about 300 mg, about 320 mg, about 340 mg, or about 360 mg.

In some embodiments, the compositions further comprise a mucolytic agent suitable for pulmonary delivery. In some embodiments, the compositions further comprise a second anti-fibrotic agent suitable for pulmonary delivery. In some embodiments, the compositions further comprise a second anti-inflammatory agent suitable for pulmonary delivery.

These and other aspects of the invention will be evident upon reference to the following detailed description. All of the U.S. patents, U.S. patent application publications, U.S. patent applications, foreign patents, foreign patent applications and non-patent publications referred to in this specification, are incorporated herein by reference in their entirety, as if each was incorporated individually. Aspects of the invention can be modified, if necessary, to employ concepts of the various patents, applications and publications to provide yet further embodiments of the invention.

BRIEF DESCRIPTION OF THE FIGURES

FIG. 1 shows a modeled nebulized aerosol administration of pirfenidone and oral administration of pirfenidone to a human subject. Model incorporates scaled pharmacokinetics from Example 6.

FIG. 2. Modeled Nebulized Aerosol Administration to a Human—50 mcg/gram target lung tissue Cmax and correlated lung tissue and plasma pharmacokinetics. Model incorporates scaled pharmacokinetics from Examples 6 and 7.

FIG. 3. Hydroxyproline results from bleomycin model of pulmonary fibrosis. Demonstrates pirfenidone U-shaped dose response. Also indicates that small dose, direct-lung aerosol delivery enables pirfenidone anti-fibrotic efficacy within limitations of the AUC-dependent, U-shaped dose response. Hydroxyrproline delta values were obtained by first subtracting sham results, and then subtracting that value from the bleomycin-only control. Obtained p-values: #=0.012 (same lung Cmax), *=0.084 (same lung Cmax), and 1=0.075 (same plasma AUC); a. Trivdei et al, Nanotechnology. 23(50):505101, 2012.

FIG. 4. Histopathology (fibrosis score) results from bleomycin model of pulmonary fibrosis. Demonstrates pirfenidone U-shaped dose response. Also indicates that small dose, direct-lung aerosol delivery enables pirfenidone anti-fibrotic efficacy within limitations of the AUC-dependent, U-shaped dose response. Fibrosis score delta values were obtained by first subtracting sham results, and then subtracting that value from the bleomycin-only control. Obtained p-values: #=0.007 (same lung Cmax), *=0.042 (same lung Cmax), and 4=0.143 (same plasma AUC).

FIG. 5. Modeled human inhaled aerosol pirfenidone pharmacokinetics. Demonstrates that aerosol inhalation enables a broad pirfenidone therapeutic range within the limitations of the pirfenidone U-shaped dose response. Model incorporates scaled pharmacokinetics from Example 8. Inhalation offers a broad therapeutic range within limitations of the pirfenidone U-shaped dose response. Compared to the 801 mg oral pirfenidone dose (taken with food; Rubino et al., Pulm Pharmacol Ther. 22(4):279-85, 2009), a 120 mg pirfenidone RDD inhaled over 5 minutes results in an equivalent plasma AUC and 43-fold greater lung tissue Cmax; a 50 mg pirfenidone RDD inhaled over 5 minutes results in a 2.4-fold lower plasma AUC and 18-fold greater lung tissue Cmax; and a 2.5 mg pirfenidone RDD inhaled over 1 minute results in a 50-fold lower plasma AUC and equivalent lung tissue Cmax. Upper panel inset illustrates pirfenidone pharmacokinetics between 0-10 mcg/gram human lung tissue pirfenidone and 0-4 hours.

DETAILED DESCRIPTION

A number of undesirable pulmonary diseases such as interstitial lung disease (ILD; and sub-class diseases therein), chronic obstructive pulmonary disease (COPD; and sub-class diseases therein), asthma, and fibrotic indications of the lungs, kidney, heart and eye, are initiated from an external challenge. By non-limiting example, these effectors can include infection, cigarette smoking, environmental exposure, radiation exposure, surgical procedures and transplant rejection. However, other causes related to genetic disposition and the effects of aging may also be attributed.

In epithelium, scarring serves a valuable healing role following injury. However, epithelium tissue may become progressively scarred following more chronic and or repeated injuries resulting in abnormal function. In the case of idiopathic pulmonary fibrosis (IPF; and other subclasses of ILD), if a sufficient proportion of the lung becomes scarred respiratory failure can occur. In any case, progressive scarring may result from a recurrent series of insults to different regions of the organ or a failure to halt the repair process after the injury has healed. In such cases the scarring process becomes uncontrolled and deregulated. In some forms of fibrosing disease scarring remains localized to a limited region, but in others it can affect a more diffuse and extensive area resulting in direct or associated organ failure.

In neurologic disease, inflammatory destruction of myelin (demylination) is considered the initial event in diseases such as multiple sclerosis. Demyelination causes scarring and hardening (sclerosis) of nerve tissue in the spinal cord, brain, and optic nerves. Demyelination slows conduction of nerve impulses, which results in weakness, numbness, pain, and vision loss.

In epithelial injury, epithelial cells are triggered to release several pro-fibrotic mediators, including the potent fibroblast growth factors transforming growth factor-beta (TGF-beta), tumor necrosis factor (TNF), endothelin, cytokines, metalloproteinases and the coagulation mediator tissue factor. Importantly, the triggered epithelial cell becomes vulnerable to apoptosis, and together with an apparent inability to restore the epithelial cell layer are the most fundamental abnormalities in fibrotic disease. In the case of demylination, abnormal TNF expression or activity is considered a primary cause of multiple sclerosis and other neurologic disorders, such as rheumatoid disease.

In conditions such as pulmonary, kidney, cardiac and ocular fibrosis, multiple sclerosis and rheumatoid disease, physiological responses characterized by control of pro-inflammatory and pro-fibrotic factors with pyridone analogs, such as pirfenidone may be beneficial to attenuate and/or reverse fibrosis and demyelination. Therapeutic strategies exploiting such pyridone analog and/or pirfenidone effects in these and other indications are contemplated herein.

TNF-alpha is expressed in asthmatic airways and may play a key role in amplifying asthmatic inflammation through the activation of NF-kappaB, AP-1 and other transcription factors. IgE receptor activation induces TNF-alpha release from human lung tissue and upregulates eosinophil TNF mRNA levels. TNF-alpha causes transient bronchial hyper-responsiveness likely through a muscarinic receptor expression-mediated response.

TNF-alpha is also believed to play a central role in the pathophysiology of COPD. It is produced by alveolar macrophages, neutrophils, T cells, mast cells and epithelial cells following contact with different pollutants including cigarette smoke. TNF-alpha has been shown in animal models to induce pathological features associated with COPD, such as an inflammatory cell infiltrate into the lungs, pulmonary fibrosis and emphysema. Intriguingly, TNF-alpha levels in sputum increase significantly during acute exacerbations of COPD.

The mechanism of action for pyridone analogs, such as pirfenidone is believed to be both anti-inflammatory and anti-fibrotic. Pirfenidone inhibits synthesis and release of pro-inflammatory cytokines and reduces the accumulation of inflammatory cells in response to various stimuli. Pirfenidone also attenuates fibroblast proliferation, production of fibrosis associated proteins and cytokines, and the increased biosynthesis and accumulation of extracellular matrix in response to cytokine growth factors such as TGF-beta and platelet-derived growth factor (PDGF).

In in vitro cell-based assays, pirfenidone suppressed the proliferation of fibroblasts; inhibited lipopolysaccharide (LPS)-stimulated release of PDGF, tumor necrosis factor alpha (TNF-alpha), and TGF-beta1; and inhibited collagen synthesis. Depending on the assay conditions, these in vitro activities were evident at pirfenidone concentrations of about 30 microM to about 10 mM (about 5.5 mcg/mL to about 1.85 mg/mL). Given that the oral Cmax of pirfenidone in IPF patients is about 42 microM in the recommended fed-state to about 84 microM in the fasting-state (or about 7.9 mcg/mL to about 15.7 mcg/mL, respectively), these same activities may be promoted in vivo, albeit in the lower range of observed efficacy.

Oral administration of pirfenidone to LPS-challenged mice resulted in dose-dependent decreased mortality, reduced serum levels of the pro-inflammatory cytokines TNF-alpha, interleukin (IL-12) and interferon gamma, and increased serum levels of the anti-inflammatory cytokine, IL-10. Pirfenidone treatment also prevented LPS-related hemorrhagic necrosis and apoptosis in the liver, and suppressed increases in TGF-beta.

In vitro studies suggest that pirfenidone may also suppress fibrogenesis through selective inhibition of p38 mitogen-activated protein kinase (MAPK). These observations have been associated with an attenuation of TGF-beta-induced collagen synthesis. The parallel observation that silencing p38 may also restore sensitivity to coriticosteroids in COPD is also promising for this and other disease populations. Unfortunately, compounds that inhibit p38 MAPK have also proven toxic and have been withdrawn from the clinical setting. These compounds have each employed oral administration.

In rat, hamster, and mouse models of bleomycin-induced lung fibrosis, prophylactic administration of pirfenidone reduced pulmonary fibrosis assessed by both histopathological analysis and quantitative determination of collagen content. Pirfenidone treatment also reduced pulmonary edema and pulmonary levels of TGF-beta, basic fibroblast growth factor (bFGF), and various pro-inflammatory cytokines.

In rat, pirfenidone decreased collagen production and deposition in hepatic fibrosis, reversed cardiac and renal fibrosis, and attenuated the increase in diastolic stiffness of diabetic hearts from streptozotocin-treated animals without normalizing cardiac contractility or renal function. In DOCA-salt hypertensive rats, pirfenidone also reversed and prevented cardiac remodeling, and reversed and prevented increased cardiac stiffness without reversing the increased vascular responses to noradrenaline.

Human studies have shown some clinical anti-inflammatory and anti-fibrotic benefit of oral pirfenidone. Phototoxicity, gastrointestinal disorders and abnormal liver function test values may result in human populations following oral administration of pirfenidone. As a consequence patient dosing must be closely monitored. In Phase 3 clinical studies with orally administered pirfenidone, initial dose escalation was required to establish gastrointestinal tolerance. However, dose levels are also limited during or following escalation due to occurrence of nausea, rash, dyspepsia, dizziness, vomiting, photosensitivity reaction, anorexia, and elevated AST and ALT serum transaminases. In some cases, oral administration of pirfenidone may result in dose de-escalation or discontinuation of pirfenidone administration.

In addition to required pirfenidone dose escalation to establish gastrointestinal tolerance, dose de-escalation and the use of food has been employed to enable oral administration to individuals unable to achieve tolerance and would otherwise be removed from therapy, for example, dose de-escalation of up to and greater than 50%. Further, clinical studies utilizing the use of food to enable dose tolerability may also be attempted. In both cases, the plasma Cmax is reduced dose-proportionately. More specifically, the fed-state results in about a 50% reduction in Cmax, about a seven-fold increase in Tmax and a reduction in overall exposure of 10-15%. Both fed and fasted state resulted in a plasma half-life of about 2.5 hours. While this approach may reduce gastrointestinal-related adverse events, the lack of clinically-significant efficacy in recent orally-administered clinical studies may have been influenced by these approaches.

Based upon clinical observations and adverse events as well as observed toxicities, oral pirfenidone therapy is limited to doses up to about 1800 mg/day to about 2400 mg/day (from 600 mg TID or 801 mg TID, respectively). Thus, while pirfenidone exhibits a wide range of non-human efficacy, human adverse events and toxicities have limited oral dosing to the lower end of this range.

Regulatory risk-benefit analysis between observed efficacy and associated adverse events of orally administered pirfenidone has led to concerns that these doses do not provide sufficient efficacy to warrant the safety risk; even in a terminal population of unmet clinical need. Provided herein in certain embodiments, is a method of administering an equivalent or increased pirfenidone or pyridone analog dose directly to the disease site (e.g., inhalation delivery to the lung) would provide equivalent or improved efficacy over oral routes. In certain embodiments, these doses require less administered drug. In certain embodiments, this approach of administering pirfenidone by inhalation may also benefit from reduced systemic exposure and an increased safety margin when compared to oral administration of pirfenidone. Described herein are compositions of pirfenidone or a pyridone analog compound that are suitable for delivery to a mammal by inhalation and methods of using such compositions.

It is unclear from the existing data whether pirfenidone anti-inflammatory or anti-fibrotic mechanism or mechanisms of action are driven by Cmax or exposure (area under the curve, AUC). In some embodiments, low to moderately-observed clinical efficacy may be associated with pirfenidone plasma levels about or greater than 5 mcg/mL, exposures (AUC0-infinity) about or greater than 50 mg·hr/L, and/or a plasma elimination rate of about 2.5 hours.

In some embodiments, intravenous or oral administration of pirfenidone may result in lung epithelial lining fluid (ELF) levels comparable to that observed in plasma, and thus, in some embodiments, clinically-measured plasma Cmax of about or greater than 5 mcg/mL are directly associated with low to moderately-observed clinical pulmonary efficacy. In some embodiments, plasma levels of pirfendione resulting from oral administration are associated with lower efficacy, and thus is some embodiments the resultant ELF and lung tissue levels are also associated with lower efficacy. In other embodiments, intravenous or oral administration of pirfenidone may result in lung epithelial lining fluid (ELF) levels less than that observed as efficacious from the plasma. In some embodiments, ELF levels corresponding with oral or intravenous-delivered, plasma-observed efficacious levels may be 0.1 mcg/mL to about 5 mcg/mL. In some embodiments, ELF levels corresponding with plasma-observed efficacious levels may be 0.1 mcg/mL to about 1 mcg/mL. In some embodiments, ELF levels corresponding with oral or intravenous-delivered, plasma-observed efficacious levels may be 0.5 mcg/mL to about 5 mcg/mL. In some embodiments, ELF levels corresponding with oral or intravenous-delivered, plasma-observed efficacious levels may be 0.3 mcg/mL to about 3 mcg/mL. In some embodiments, direct administration of pirfenidone to the lung, results in delivery of about or greater than 5 mcg pirfenidone to one mL ELF, and may result in equivalent pulmonary efficacy without elevated systemic levels associated with adverse events and toxicities observed with administration. By non-limiting example, this may be accomplished by oral or intranasal inhaled delivery of aerosolized pirfenidone or pyridone analog to the lung providing about or greater than 0.1 mcg/mL, for example greater than about 0.2 mcg/mL, 0.4 mcg/mL, 0.6 mcg/mL, 0.8 mcg/mL, 1.0 mcg/mL, 2 mcg/mL, 3 mcg/mL, 4 mcg/mL, 5 mcg/mL, 6 mcg/mL, 7 mcg/mL, 8 mcg/mL, 9 mcg/mL, or greater than 10 mcg/mL of pirfenidone or pyridone analog to the ELF. Once in the ELF, pirfenidone or pyridone analog will in some embodiments penetrate lung tissue resulting in between about 0.004 mcg and 0.7 mcg pirfenidone or pyridone analog to one gram lung tissue (about 0.1 mcg/mL in about 25 mL ELF to about 5 mcg/mL in about 75 mL ELF, about 600 grams adult human lung tissue weight).

In some embodiments, pirfenidone may readily equilibrate between the plasma and lung, and/or other organs. In some embodiments, organ pirfenidone levels may also mimic that of plasma, such as for example, the lung, heart, kidney or nervous system. In some embodiments, delivery of about or greater than 0.004 mcg to 0.7 mcg pirfenidone to one gram tissue may provide a similar therapeutic benefit to other organs. In some embodiments, providing additional pirfenidone or pyridone analog may provide additional efficacy. In some embodiments, this may be accomplished by inhalation (i.e. oral inhalation or intranasal inhalation) delivery of aerosolized pirfenidone or pyridone analog to the lung. In some embodiments, pirfenidone or pyridone analog delivered to the lung may, in some embodiments, become readily available to the heart. In some embodiments, providing about 0.1 mcg/mL to about 5 mcg/mL ELF or 0.004 mcg/gram to about 0.7 mcg/gram lung tissue pirfenidone or pyridone analog pyridone analog to the ELF or 0.2 to 0.7 mcg/gram lung tissue pirfenidone or pyridine analog may result in a similar efficacious dose to the heart in the absence of elevated systemic adverse events or toxicities observed with oral dosing. In some embodiments, intranasal inhalation or oral inhalation delivery of aerosolized pirfenidone or pyridone analog to the lung may result in efficacious delivery of pirfenidone or pyridone analog to the liver. In some embodiments, pirfenidone or pyridone analog delivered to the lung will become available to the liver. In some embodiments, providing about 0.1 mcg/mL to about 5 mcg/mL ELF or 0.004 mcg/gram to about 0.7 mcg/gram lung tissue pirfenidone or pyridone analog pyridone analog may result in a similar efficacious dose to the liver in the absence of elevated systemic adverse events or toxicities observed with oral dosing. In some embodiments, intranasal or oral inhalation delivery of aerosolized pirfenidone or pyridone analog to the lung may result in efficacious delivery of pirfenidone or pyridone analog to the kidney. In some embodiments, pirfenidone or pyridone analog delivered to the lung will become available to the kidney. In some embodiments, providing about 0.1 mcg/mL to about 5 mcg/mL ELF or 0.004 mcg/gram to about 0.7 mcg/gram lung tissue pirfenidone or pyridone analog pyridone analog may result in a similar efficacious dose to the kidney in the absence of elevated systemic adverse events or toxicities observed with oral dosing. In some embodiments, intranasal inhalation delivery of aerosolized pirfenidone or pyridone analog to the nasal cavity may result in efficacious delivery of pirfenidone or pyridone analog to the central nervous system (CNS). In some embodiments, inhalation delivery of pirfenidone or pyridone analog to the nasal cavity will become readily available to the CNS. In some embodiments, providing a nasal cavity-delivered dose equivalent to about 0.1 mcg/mL to about 5 mcg/mL ELF or 0.004 mcg/gram to about 0.7 mcg/gram lung tissue pirfenidone or pyridone analog may result in similar efficacy in the CNS in the absence elevated systemic adverse events or toxicities observed with oral dosing.

In some embodiments, topical delivery of aerosolized, liquid or cream pirfenidone or pyridone analog to a site of desired effect providing about 0.004 mcg/gram to about 0.7 mcg/gram tissue weight may result in a similar efficacious dose in the absence of systemic adverse events or toxicities. In some embodiments, topical delivery of aerosolized, liquid or cream pirfenidone or pyridone analog to damaged skin epithelium may prevent or reverse scarring, fibrosis and/or inflammation. This damage could be the result of infection, burn, surgery, acute of chronic injury (such as bed soars), or other event. In some embodiments, topical delivery of liquid or dry powder pirfenidone or pyridone analog to the bladder may prevent scarring, fibrosis and/or inflammation associated with bladder infection, bladder cancer, in-dwelling catheter or other event. In some embodiments, topical delivery of liquid pirfenidone or pyridone analog to the eye may prevent development of post-operative fibrosis in the conjunctiva and/or episclera following glaucoma surgery.

In some embodiments, injection delivery of liquid pirfenidone or pyridone analog to a site of desired effect providing about 0.004 mcg/gram to about 0.7 mcg/gram tissue weight pirfenidone or pyridone analog may result in a similar efficacious dose in the absence of systemic adverse events or toxicities. In some embodiments, injection delivery of liquid pirfenidone or pyridone analog to skeletal joints may prevent scarring, fibrosis and/or inflammation associated with autoimmune diseases, arthritis, rheumatoid arthritis, infection or other event.

In some embodiments, in addition to Cmax, and in additional embodiments, pirfenidone exposure (AUC) to the disease site may also be critical for efficacy. In some embodiments, plasma AUC0-infinity about or greater than 50 mg·hr/L is also associated with pulmonary efficacy. In some embodiments, partial or ready equilibrium of pirfenidone between the plasma and lung ELF and between the plasma and lung tissue, in some embodiments, may provide that AUC may also be mimicked in the lung. In other embodiments, lung ELF and tissue AUC may be less.

In some embodiments, individually or in combination Cmax, AUC and/or half-life are required for efficacy, and thus in some embodiments are provided a conservative model with all three parameters (Cmax, AUC and half-life) required for efficacy. In some embodiments, and by non-limiting example, direct inhalation delivery of about 0.1 mcg to about 5 mcg pirfenidone or pyridone analog to one mL lung ELF, providing an ELF AUC0-infinity about 1.0 mg·hr/L or about 50 mg·hr/L, and maintaining these levels for the same period of time as that delivered via the oral route are equivalently efficacious. Similarly, in other embodiments, direct inhalation delivery of about or greater than 0.2004 to 0.7 mcg pirfenidone or pyridone analog to one gram lung tissue, provides a tissue AUC0-infinity less than to equivalent or substantially equivalent to that of the plasma following oral delivery, and in further embodiments, maintaining these levels for the same period of time as that delivered via the oral route is equivalently efficacious. In some embodiments, the following assumptions and theoretical calculations are described for inhalation therapy:

ELF Delivery Assumptions:
1. The total volume of human ELF is 25 mL;
2. The inhaled route of administration is dependent upon a respirable delivered dose (RDD); RDD is the fraction of drug inhaled in aerosol particles less than 5 microns in diameter;
3. RDD of typical dry powder, liquid nebulization or meter-dose inhalation devices ranges from 10% to 70%. In some embodiments, higher and lower efficiency devices with RDDs greater than 70% and less than 10% are contemplated.
4. Plasma pirfenidone or pyridone analog half-life following oral administration is around 2.5 hours. In some embodiments, intestinal absorption affects this vule but for exemplary purposes of this model the lung ELF pirfenidone half-life following inhalation delivery is assumed to be one-half that following oral administration (e.g. 2.5 hours/2=1.25 hours). Half-life values may be supported by measurements indicating intravenous administration of pirfenidone results in a lung ELF half-life of around one-half that following oral administration;
5. In some embodiments, a lung ELF level of 5 mcg/mL may be the lower limit of efficacy; and
6. 801 mg oral pirfenidone results in a plasma level at or greater than 5 mcg/mL for 4 hours (human-measured value). For purposes of comparing routes, this model will assume lung ELF pirfenidone levels following oral administration remain at or above 5 mcg/mL lung ELF for the same duration as plasma.

Exemplary ELF Calculations:
1. Mcg pirfenidone delivered to 25 mL ELF to make 5 mcg/mL=125 mcg;
2. Based upon an RDD efficiency of 30%, the unit dose required is 416 mcg (125 mcg/0.3=416 mcg);
3. Based upon an RDD efficiency of 50%, the unit dose required is 250 mcg (125 mcg/0.5=250 mcg);
4. Based upon an RDD efficiency of 70%, the unit dose required is 179 mcg (125 mcg/0.7=179 mcg); and Compensating to maintain at or above these levels for 3.2 half lives of 1.25 hours each (4 hours at or above 5 mcg/mL with a lung half-life of 1.25 hours=3.2 half lives):
5. For an RDD efficiency of 30%, the unit dose required to maintain the lower limit of clinically-observed efficacy (in this case 416 mcg) for 3.2 half lives is 3994 mcg;
6. For an RDD efficiency of 50%, the unit dose required to maintain the lower limit of clinically-observed efficacy (in this case 250 mcg) for 3.2 half lives 2400 mcg; and
7. For an RDD efficiency of 70%, the unit dose required to maintain the lower limit of clinically-observed efficacy (in this case 179 mcg) for 3.2 half lives 1718 mcg.

By non-limiting example, based upon the above assumptions and in certain embodiments, a dose of approximately 4 mg in a device delivering pirfenidone or pyridone analog with 30% efficiency may result in lung ELF levels at or above 5 mcg/mL for the same duration as that obtained following 801 mg administered orally. Moreover, while the minimally efficacious pirfenidone dose may be maintained for this duration, local pirfenidone levels may also exhibit significantly higher ELF Cmax levels providing improved efficacy. In some embodiments, delivery of 4 mg pirfenidone or pyridone analog with a 30% efficiency device may result in a lung ELF Cmax up to about 48 mcg/mL (4 mg×30%=1.2 mg. 1.2 mg/25 mL ELF=48 mcg/mL). In some embodiments, based upon the above assumptions a dose of approximately 66 mg in a device delivering pirfenidone or pyridone analog with 70% efficiency may result in a lung ELF Cmax up to 1.85 mg/mL (66 mg×70%=46.2 mg. 46.2 mg/25 mL ELF=1.85 mg/mL). In some embodiments, based upon the above assumptions a dose of approximately 154 mg in a device delivering pirfenidone or pyridone analog with 30% efficiency may also result in a lung ELF Cmax up to 1.85 mg/mL (154 mg×30%=46.2 mg. 46.2 mg/25 mL ELF=1.85 mg/mL). In some embodiments, based upon the above assumptions a dose of approximately 12 mg in a device delivering pirfenidone or pyridone analog with 70% efficiency may result in a lung ELF Cmax up to 336 mcg/mL (12 mg×70%=8.4 mg. 8.4 mg/25 mL ELF=336 mcg/mL). In some embodiments, based upon the above assumptions a dose of approximately 28 mg in a device delivering pirfenidone or pyridone analog with 30% efficiency may also result in a lung ELF Cmax up to 336 mcg/mL (28 mg×30%=8.4 mg. 8.4 mg/25 mL ELF=336 mcg/mL). In some embodiments, this dose may result in maintaining at or above the 5 mcg/mL minimally efficacious dose for about 6 half-lifes, or about 15 hours. In some embodiments, the embodiments described for inhalation therapy provide beneficial efficacy through an increased Cmax and maintaining drug exposure at or above the 5 mcg/mL minimal efficacy range for a longer duration than that currently limited by oral dosing. In some embodiments, prolonged exposure may enable a reduced dosing interval (by example once-a-day or twice-a-day versus the current three times a day oral dosing regimen). In some embodiments, while delivery is directly to the lung, these doses may result in very low systemic plasma levels (e.g. around 2 mcg/mL pirfenidone). In some embodiments, although about 28 mg pirfenidone or pyridone analog delivered with a 30% efficiency aerosol device may initially result in elevated levels in vasculature and tissues immediately downstream of the lung (or nasal cavity), the dilute systemic plasma concentration may be around 1.7 mcg/mL (28 mg×30%=8.4 mg. 8.4 mg/5 L total body blood=1.7 mcg/mL). In some embodiments, delivery of about 46 mg pirfenidone or pyridone analog may result in a dilute systemic plasma concentration of about 9.3 mcg/mL.

One of skill in the art will recognize from the discussions herein that doses calculated in the above model will change if the actual measured lung ELF half-life of pirfenidone or pyridone analog elimination changes. If the half-life is shorter, more administered pirfenidone or pyridone analog will be required to maintain the lung ELF concentration above that considered the minimal efficacious level. Additional increases in administered pirfenidone or pyridone analog may be desired to further improve efficacy. Further, in addition to delivering desired lung tissue Cmax and AUC, oral inhaled or intranasal inhaled delivery of aerosol pirfenidone or pyridone analog may also serve an efficient route for systemic delivery. In some embodiments, dosing schemes are contemplated that enable inhaled delivery of pirfenidone or pyridone analog to initially achieve desired lung tissue Cmax and AUC, with plasma half-life slower than that of the lung ELF, and targeting the delivery of specific plasma concentrations may in turn prolong lung ELF-pirfenidone or pyridone analog exposure.

Exemplary Lung Tissue Delivery Assumptions:
1. The total wet weight of the adult human lung is about 685 to 1,050 grams (for calculations, conservatively about 1,000 grams);
2. The adult human lung blood volume is about 450 mL;
3. The tissue weight of the adult human lung is conservatively 1,050 grams wet weight minus 450 mL blood weight (assuming density of 1.0), equals 600 grams;
4. In some embodiments, following intravenous push of pirfenidone to a mouse:
   plasma pirfenidone Tmax is equivalent to lung Tmax
   40 mg/kg intravenous dose results in plasma Cmax of about 55 mcg/mL and a lung Cmax of 30 mcg/gram wet tissue
   Conservatively, blood makes up about 40% of the wet lung weight. Given that the plasma and lung Tmax are, in some embodiments, equivalent, it follows that much of the 30 mcg/g pirfenidone measured in the wet lung is due to the presence of blood. Conservatively, if blood makes up about 40% of the wet lung weight, then 40% of the plasma Cmax (or 55 mcg/mL×40%) is about 22 mcg/gram pirfenidone in the measured lung weight is due to blood. Taking the difference between the wet lung Cmax and this number (or 30 mcg/g minus 22 mcg/g), about 8 mcg/g is in the lung tissue.
   a measured wet lung half-life that is about 45% longer than the plasma half-life may be considered. Taking the argument above that about 40% of the wet lung pirfenidone is in the blood, the actual lung tissue half-life is much greater then 45% longer than plasma;
5. From the above observations and calculations that 55 mcg/mL plasma Cmax results in a lung tissue Cmax of about 8 mcg/gram, the following comparison to humans can be made:
   Taking an early assumption, the lower end of human efficacy is 5 mcg/mL plasma pirfenidone.
   Assuming the above ratio (55 mcg/mL plasma results in 8 mcg/gram lung tissue) is true for humans, 5 mcg/mL divided by 55 mcg/mL is about 9.1%. 9.1% of 8 mcg/gram is about 0.7 mcg/gram.
   Taken together, 5 mcg/mL plasma pirfenidone may result in 0.7 mcg/gram lung tissue pirfenidone. Thus, about 0.7 mcg/gram lung tissue pirfenidone is the lower end of efficacy.
6. The inhaled route of administration is dependent upon a respirable delivered dose (RDD). The RDD is the fraction of drug inhaled in aerosol particles less than 5 microns in diameter;
7. RDD of typical dry powder, liquid nebulization or meter-dose inhalation devices ranges from 10% to 70%. Higher and lower efficiency devices with RDDs greater than 70% and less than 10% also exist;
8. As discussed above, lung tissue pirfenidone half-life is much longer than the intravenously delivered plasma pirfenidone half-life (by as much or greater than 2-4×). Plasma pirfenidone half-life following oral administration is around 2.5 hours. However, continued intestinal absorption affects this number and hence is much longer than that following intravenous delivery. Therefore, for purposes of this model the lung tissue pirfenidone half-life following inhalation delivery will be considered equivalent to that following oral administration (e.g. 2.5 hours);
9. From the above observations and calculations, the lower limit of efficacy in lung tissue is 8 mcg/gram; and
10. Incorporating that 801 mg oral pirfenidone results in a human plasma level at or greater than 5 mcg/mL for 4 hours and that 5 mcg/mL plasma results in 0.7 mcg/gram lung tissue pirfenidone, what is delivered by oral or intranasal inhalation must be at or above 0.7 mcg/gram lung tissue pirfenidone for at least 4 hours for equivalent lung fibrosis efficacy to the oral dose.

Exemplary Lung Tissue Calculations:
1. Mcg pirfenidone delivered to 1000 grams wet lung tissue (blood plus lung tissue) to make 0.7 mcg/gram=700 mcg;
2. Based upon an RDD efficiency of 30%, the unit dose required is 2,333 mcg (700 mcg/0.3=2,333 mcg);
3. Based upon an RDD efficiency of 50%, the unit dose required is 1,400 mcg (700 mcg/0.5=1,400 mcg);
4. Based upon an RDD efficiency of 70%, the unit dose required is 1,000 mcg (700 mcg/0.7=1,000 mcg); and Compensating to maintain at or above these levels for 2 half lives of 2.5 hours each (4 hours at or above 0.7 mcg/gram wet lung tissue with a lung half-life of 2.5 hours=1.6 half lives):

5. For an RDD efficiency of 30%, the unit dose required to match the lower limit of clinically-observed oral route efficacy (in this case 2,333 mcg) for 1.6 half lives is 3,733 mcg;
6. For an RDD efficiency of 50%, the unit dose required to match the lower limit of clinically-observed oral route efficacy (in this case 1,400 mcg) for 1.6 half lives 2,240 mcg; and 7. For an RDD efficiency of 70%, the unit dose required to match the lower limit of clinically-observed oral route efficacy (in this case 1,000 mcg) for 1.6 half lives 1,600 mcg.

By non-limiting example, based upon the above assumptions a dose of approximately 3.7 mg in a device delivering pirfenidone or pyridone analog with 30% efficiency may result in wet lung tissue levels at or above 0.7 mcg/gram for the same duration as that obtained following 801 mg administered orally. Moreover, while the minimally efficacious pirfenidone dose is maintained for this duration, local pirfenidone levels may exhibit significantly higher wet lung tissue Cmax levels providing improved efficacy. By non-limiting example, delivery of 3.7 mg pirfenidone or pyridone analog with a 30% efficiency device may result in a wet lung tissue Cmax up to about 1.1 mcg/gram (3.7 mg×30%=1.1 mg. 1.1 mg/1,050 grams wet lung weight=1.1 mcg/gram). This number is near about 1.5-fold higher than that delivered following oral delivery. By another non-limiting example, based upon the above assumptions a dose of approximately 50 mg in a device delivering pirfenidone or pyridone analog with 30% efficiency may result in a wet lung tissue Cmax up to 14.3 mcg/mL (50 mg×30%=15 mg. 15 mg/1,050 grams wet lung weight=14.3 mcg/gram), or about 20-fold higher than that delivered following oral delivery. Under this scenario, this dose may result in maintaining at or above the 0.7 mcg/gram wet lung tissue minimally efficacious dose for at least about 5 half-lifes, or about 12.5 hours; compared to 4 hours following 801 mg oral dose administration. Similarly, by another non-limiting example, based upon the above assumptions a dose of approximately 15 mg in a device delivering pirfenidone or pyridone analog with 70% efficiency may result in a wet lung tissue Cmax up to 10 mcg/mL (15 mg×70%=10.5 mg. 10.5 mg/1,050 grams wet lung weight=10 mcg/gram), or about 14-fold higher than that delivered following oral delivery. Under this scenario, this dose may result in maintaining at or above the 0.7 mcg/gram wet lung tissue minimally efficacious dose for about 4.5 half-lifes, or at least about 11 hours; compared to 4 hours following 801 mg oral dose administration. Such duration over 0.7 mcg/gram lung tissue may permit twice a day dosing (BID). Similarly, by another non-limiting example, based upon the above assumptions a dose of approximately 75 mg in a device delivering pirfenidone or pyridone analog with 70% efficiency may result in a wet lung tissue Cmax up to 50 mcg/mL (75 mg×70%=52.5 mg. 52.5 mg/1,050 grams wet lung weight=50 mcg/gram), or about 71-fold higher than that delivered following oral delivery. Under this scenario, this dose may result in maintaining at or above the 0.7 mcg/gram wet lung tissue minimally efficacious dose for at least about 6 half-lifes, or about 15 hours; compared to 4 hours following 801 mg oral dose administration. Such duration over 0.7 mcg/gram lung tissue may permit BID dosing. Similarly, by another non-limiting example, based upon the above assumptions a dose of approximately 15 mg in a device delivering pirfenidone or pyridone analog with 30% efficiency may result in a wet lung tissue Cmax up to 4.3 mcg/mL (15 mg×30%=4.5 mg. 4.5 mg/1,050 grams wet lung weight=4.3 mcg/gram), or about 6-fold higher than that delivered following oral delivery. Under this scenario, this dose may result in maintaining at or above the 0.7 mcg/gram wet lung tissue minimally efficacious dose for at least about 3 half-lifes, or about 7.5 hours; compared to 4 hours following 801 mg oral dose administration. Similarly, by another non-limiting example, based upon the above assumptions a dose of approximately 75 mg in a device delivering pirfenidone or pyridone analog with 30% efficiency may result in a wet lung tissue Cmax up to 21 mcg/mL (75 mg×30%=22.5 mg. 52.5 mg/1,050 grams wet lung weight=21 mcg/gram), or about 31-fold higher than that delivered following oral delivery. Under this scenario, this dose may result in maintaining at or above the 0.7 mcg/gram wet lung tissue minimally efficacious dose for at least about 5 half-lifes, or about 12.5 hours; compared to 4 hours following 801 mg oral dose administration. Such duration over 0.7 mcg/gram lung tissue may permit BID dosing. Similarly, by another non-limiting example, based upon the above assumptions a dose of approximately 15 mg in a device delivering pirfenidone or pyridone analog with 10% efficiency may result in a wet lung tissue Cmax up to 1.4 mcg/mL (15 mg×10%=1.5 mg. 1.5 mg/1,050 grams wet lung weight=1.4 mcg/gram), or about 2-fold higher than that delivered following oral delivery. Under this scenario, this dose may result in maintaining at or above the 0.7 mcg/gram wet lung tissue minimally efficacious dose for about 1 half-lifes, or at least about 2.5 hours; compared to 4 hours following 801 mg oral dose administration. Similarly, by another non-limiting example, based upon the above assumptions a dose of approximately 75 mg in a device delivering pirfenidone or pyridone analog with 10% efficiency may result in a wet lung tissue Cmax up to 21 mcg/mL (75 mg×10%=7.5 mg. 7.5 mg/1,050 grams wet lung weight=7.1 mcg/gram), or about 10-fold higher than that delivered following oral delivery. Under this scenario, this dose may result in maintaining at or above the 0.7 mcg/gram wet lung tissue minimally efficacious dose for about 3.5 half-lifes, or at least about 8.8 hours; compared to 4 hours following 801 mg oral dose administration. Such duration over 0.7 mcg/gram lung tissue may permit TID dosing. Such an approach could benefit efficacy through an increased Cmax and maintaining drug exposure at or above the 0.7 mcg/gram wet lung tissue minimal efficacy range for a longer duration than that currently limited by oral dosing. Such prolonged exposure may enable a reduced dosing interval (by example once-a-day or twice-a-day versus the current three times a day oral dosing regimen). Moreover, while this approach delivers directly to the lung, using the above non-limiting examples these doses may result in reduced systemic plasma levels (e.g. Cmax from less than 0.6 mcg/mL pirfenidone from a 4.5 mg delivered dose to 5,000 mL blood to less than 2 mcg/mL pirfenidone from a 15 mg delivered dose to less than 10 mcg/mL from a 75 mg dose).

Doses calculated in the above model will change considerably if the actual measured lung tissue half-life of pirfenidone or pyridone analog elimination changes. If the half-life is faster, more inhaled pirfenidone or pyridone analog will be required to maintain the lung tissue concentration above that considered the minimal efficacious level. Additional increases in inhaled pirfenidone or pyridone analog may be desired to further improve efficacy. Further, in addition to delivering desired lung tissue Cmax and AUC, inhaled delivery of aerosol pirfenidone or pyridone analog may also serve an efficient route for systemic delivery. In some embodiments, dosing schemes are contemplated that enable inhaled delivery of pirfenidone or pyridone analog to initially achieve desired lung tissue Cmax and AUC, and as plasma half-life is predicted to be slower than that of the lung tissue, targeting the delivery of specific plasma concentrations may in turn prolong lung tissue-pirfenidone or pyridone analog exposure.

As scarring is irreversible, IPF efficacy is the act of protecting native lung tissue against invading fibrosis.

Therefore, maintaining regular efficacious drug levels in unaffected tissue is critical for improved patient survival. Clinical and nonclinical studies have suggested pirfenidone efficacy is dose-responsive ranging from slowed-disease progression to improvement. Unfortunately, substantial gastrointestinal (GI) side effects and systemic toxicity have forced an approved oral dose that is limited to the lower end of this range. Complicating matters, recommendations for dose-absorbing food and frequent triggering of dose-reduction/discontinuation protocols addressing these issues further reduce lung dose and interrupt required maintenance therapy of this otherwise promising drug. Inhalation delivery of aerosol pirfenidone or pyridone analog directly to the lung will reduce or eliminate these safety or tolerability limitations associated with the oral route of delivery.

Oral pirfenidone efficacy has been moderately demonstrated in human clinical studies and the data suggests that this effect increases with higher doses. Unfortunately, significant side effects and toxicity have limited the oral dose to the lower end of this efficacy range (Esbriet approved up to 2403 mg/d). Jeopardizing this already low efficacy dose, the Esbriet prescription requires an initial dose-escalation scheme and recommended administration with food to acquire minimal GI tolerance and an acceptable side-effect/toxicity profile (range up to three 267 mg capsules, or 801 mg three times a day (TID)). Unfortunately, not all patients reach this recommended dose and food further reduces bioavailability (food reduces Cmax and AUC~50% and ~20%, respectively). Further, elevated liver enzyme levels and skin photoreactivity initiate a physician-guided dose-reduction and stoppage protocol that in Phase 3 studies permitted up to a 50% dose reduction before discontinuation (in these studies between 48% and 67% of patient doses were reduced). As chronic lung tissue dosing of effective drug levels is critical for maintenance protection against invading fibrosis, it is likely that oral pirfenidone prescription and practice result in sub-efficacious dosing of this otherwise promising drug; a hypothesis that may in part explain the moderate efficacy observed in Phase 3 studies.

For oral administration in the context of treatment of pulmonary fibrosis high oral doses are required to achieve plasma levels required for efficacious lung tissue exposure. However, gastrointestinal side-effects and systemic toxicities have limited the approved oral dose to a level restricted to the low end of the efficacy and dose-response curve. In one embodiment, inhaled pirfenidone or pyridone analog improves pirfenidone treatment effectiveness through increased lung dose and improved compliance. In one embodiment, inhalation of pirfenidone or pyridone analog (e.g. with a nebulizer) delivers pirfenidone or pyridone analog directly to the lung and whole-body dilution of the delivered dose is minimized. In some embodiments, inhalation of pirfenidone reduces or eliminates GI exposure and/or systemic toxicities that are common with oral administration of pirfenidone or pyridone analog. In some embodiments, inhalation delivery of pirfenidone or pyridone analog provided herein provides higher lung tissue levels of pirfenidone than is possible through oral administration. In some embodiments, inhalation delivery of pirfenidone or pyridone analog serves as an efficient means of delivering pirfenidone or pyridone analog to the systemic compartment. In some embodiments, inhalation delivery of pirfenidone or pyridone analog provides Cmax and AUC benefits over the oral route. In some embodiments, inhalation delivery of pirfenidone or pyridone analog provides Cmax and AUC benefits over the oral route, wherein plasma re-circulated, aerosol-delivered pirfenidone or pyridone analog maintains these beneficial properties. In some embodiments, the methods described herein may be used to treat patients diagnosed with mild-to-moderate IPF. In some embodiments, the methods described herein may be used to treat patients diagnosed with mild-to-severe IPF. In some embodiments, the methods described herein may be used to treat patients diagnosed with mild-to-moderate IPF without the need to initially dose-escalate the patient. In some embodiments, the methods described herein may be used to treat patients diagnosed with mild-to-severe IPF without the need to initially dose-escalate the patient. In some embodiments, the methods described herein may be used to treat patients diagnosed with mild-to-moderate IPF without the need to monitor and dose-reduce or stop therapy due to gastrointestinal, phototoxic or liver enzyme-associated adverse events. In some embodiments, the methods described herein may be used to treat patients diagnosed with mild-to-severe IPF without the need to monitor and dose-reduce or stop therapy due to gastrointestinal, phototoxic or liver enzyme-associated adverse events. In some embodiments, the methods described herein may be used to provide a prophylactic therapy to patients diagnosed with mild-to-moderate IPF. In some embodiments, the methods described herein may be used to provide a prophylactic therapy to patients diagnosed with mild-to-severe IPF. In some embodiments, the methods described herein may be used to provide a prophylactic therapy to patients with mild-to-moderate IPF without the need to initially dose-escalate the patient. In some embodiments, the methods described herein may be used provide a prophylactic therapy to patients diagnosed with mild-to-severe IPF without the need to initially dose-escalate the patient. In some embodiments, the methods described herein may be used to provide a prophylactic therapy to patients diagnosed with mild-to-moderate IPF without the need to monitor and dose-reduce or stop therapy due to gastrointestinal, phototoxic or liver enzyme-associated adverse events. In some embodiments, the methods described herein may be used to provide a prophylactic therapy to patients diagnosed with mild-to-severe IPF without the need to monitor and dose-reduce or stop therapy due to gastrointestinal, phototoxic or liver enzyme-associated adverse events. In some embodiments, the methods described herein may be used to slow disease progression of patients diagnosed with mild-to-moderate IPF without the need to initially dose-escalate the patient. In some embodiments, the methods described herein may be used to slow disease progression of patients diagnosed with mild-to-severe IPF without the need to initially dose-escalate the patient. In some embodiments, the methods described herein may be used to slow disease progression of patients diagnosed with mild-to-moderate IPF without the need to monitor and dose-reduce or stop therapy due to gastrointestinal, phototoxic or liver enzyme-associated adverse events. In some embodiments, the methods described herein may be used to slow disease progression of patients diagnosed with mild-to-severe IPF without the need to monitor and dose-reduce or stop therapy due to gastrointestinal, phototoxic or liver enzyme-associated adverse events. By non-limiting example, clincal end points of IPF efficacy include reduced decline in forced vital capacity (FVC), reduced decline in distance walked over a six-minute interval (six-minute walk test; 6MWT), slowed decline in carbon monoxide diffusion capacity (DLCO), improved progression-free survival (PFS), reduced mortality and monitoring changes in biomarkers such as MMP7, and CCL18. In some embodiments, a comparison of oral and inhaled aerosol properties that may be observed is shown in Table A.

TABLE A

Advantages of inhaling pirfenidone

| Oral Pirfenidone | Inhaled Pirfenidone |
|---|---|
| High oral dose = minimally-effective lung levels | Lower inhaled dose = superior lung levels |
| Oral route = significant GI side effects | Inhaled route = no/reduced GI side effects |
| High dose = toxicity | Lower dose = reduced toxicity |
| Low efficacy: | High efficacy: |
| 1. Pirfenidone is a low potency drug. The oral route requires a very high dose to deliver sufficient lung levels. Significant GI side effects and to a lesser extent systemic toxicities limit the oral dose to the lower end of the efficacy and dose-response curve. | 1. Inhaled route permits use of smaller pirfenidone doses to deliver superior initial pirfenidone lung tissue Cmax and AUC in the absence of GI side-effects. In some embodiments, inhaled administration also serves as non-oral route for systemic delivery; enabling sufficient circulating plasma pirfenidone levels to extend the duration of superior efficacy. |
| 2. Initial dose escalation required to obtain maximum-tolerated maintenance dose. Due to poor tolerability, this maintenance dose is often set below the approved dose level | 2. Good tolerability permits establishing the maintenance dose a the approved level |
| 3. Continued intolerability and safety concerns reduce adherence to maintenance therapy Dose reduced and interrupted Recommended food absorbs drug Side effects and toxicity trigger dose reduction/stoppage protocols | 3. Strong adherence to maintenance therapy Dose and chronic therapy maintained Inhaled drug unaffected by food Safe & well-tolerated; no need for special protocols |

In some embodiments the methods described herein provide for delivery of high concentration, readily bioavailable pirfenidone or pyridone analog compound which in turn provides improved efficacy over pirfenidone or pyridone analog compound administered by the oral route or by inhalation of a slow-dissolving or otherwise slowly bioavailable compound formulation. In some embodiments, such slow-dissolving or otherwise slowly bioavailable compound formulations for inhalation include, but are not limited to a dry powder formulation, a liposomal formulation, a nano-suspension formulation, or a micro-suspension formulation. In some embodiments, the aqueous solutions of pirfenidone or pyridone analog described and contemplated herein for administration by inhalation are completely homogeneous and soluble.

In some embodiments, an obstacle to patient compliance with oral pirfenidone therapy is GI intolerability. Pirfenidone blood levels may also be important has they have been implicated in other observed toxicities. Thus, factors contributing to increased blood levels must be considered. For the oral route of administration, toxicity and GI intolerability have limited the dose to 801 mg three times a day. While elevated liver enzymes, photosensitivity reaction and phototoxicity occur at this dose, they occur with higher frequency and greater severity with higher doses. Secondly, pirfenidone is primarily metabolised by CYP1A2. In vitro metabolism studies with hepatic microsomes indicate that approximately 48% of pirfenidone is metabolised via CYP1A2 with other CYP isoenzymes including CYP2C9, 2C19, 2D6, and 2E1 each contributing less than 13%. Thus, inhibiting these enzyme systems results in elevated pirfenidone blood levels, resulting in increased incidence and severity of toxicity. To this end, items such as grapefruit juice, fluvoxamine and other inhibitors of CYP1A2 should be avoided during oral treatment with pirfenidone.

Oral administration of pirfenidoen is contraindicated in patients with concomitant use of fluvoxamine. Fluvoxamine should be discontinued prior to the initiation of Esbriet therapy and avoided during Esbriet therapy due to the reduced clearance of pirfenidone. Other therapies that are inhibitors of both CYP1A2 and one or more other CYP isoenzymes involved in the metabolism of pirfenidone (e.g. CYP2C9, 2C19, and 2D6) should also be avoided during pirfenidone treatment.

Also for the oral administration, special care should also be exercised if CYP1A2 inhibitors are being used concomitantly with potent inhibitors of one or more other CYP isoenzymes involved in the metabolism of pirfenidone such as CYP2C9 (e.g amiodarone, fluconazole), 2C19 (e.g. chloramphenicol) and 2D6 (e.g. fluoxetine, paroxetine).

The oral product should be used with caution in patients treated with other moderate or strong inhibitors of CYP1A2 (e.g. ciprofloxacin, amiodarone, propafenone).

As many products effecting CYP enzymes are useful to fibrosis patients, permitting their use would be beneficial. While the oral route is already at the maximum permissible dose (which provides only moderate efficacy), any inhibition of the enzymes described above elevates pirfenidone blood levels and increases the rate and severity of the toxic events described herein. In some embodiments oral inhalation and intranasal inhalation delivery of pirfenidone or pyridone analogs can achieve effective tissue levels with much less drug than that required by the oral product, and in some embodiments result in blood levels are significantly lower and consequences associated with CYP enzyme inhibitory properties described herein are removed. In some embodiments, use of these CYP inhibitory enzyme products currently contraindicated with the oral medicine may be administered with pirfenidone or pyridone analog.

The primary metabolite of pirfenidone is 5-carboxy-pirfenidone. Following oral or intravenous administration, this metabolite appears quickly at high concentrations in blood. 5-carboxy-pirfenidone does not appear to have anti-fibrotic or anti-inflammatory activity, its high blood levels occur at the loss of pirfenidone blood concentrations. Thus, while the oral product is dosed at the highest possible level, once pirfenidone enters the blood it is rapidly metabolized to a non-active species further reducing the drugs potential to achieve sufficient lung levels required for substantial efficacy. In some embodiments, because oral inhalation and intranasal inhalation delivery of pirfenidone or pyridone analogs can achieve effective lung tissue levels directly, extra-lung metabolism is minimized.

In some embodiments, administration of pirfenidone or pyridone analog compound by inhalation has reduced gastroinstestinal side-effects when compared to oral administration. In some embodiments, the reduced gastroinstestinal side-effects with administration by inhalation avoids the need for initial dose-escalation. In some embodiments, administration of pirfenidone or pyridone analog by inhalation avoids or substantially avoids the gastrointestinal tract and therefore effects observed with oral administration of pirfenidone or pyridone analog compound will be minimized or not present. In some embodiments, the lack of food effects with administration by inhalation will allow for full dose delivery.

In some embodiments, pharmaceutical compositions described herein are used in the treatment of lung disease in mammal. In some embodiments, the pharmaceutical compositions described herein are administered to a mammal by oral inhalation or intranasal inhalation methods for the purpose of treating lung disease in the mammal. In some embodiments, lung disease includes, but is not limited to, asthma, chronic obstructive pulmonary disease (COPD), pulmonary fibrosis, idiopathic pulmonary fibrosis, radiation induced fibrosis, silicosis, asbestos induced pulmonary or pleural fibrosis, acute lung injury, acute respiratory distress syndrome (ARDS), sarcoidosis, usual interstitial pneumonia (UIP), cystic fibrosis, Chronic lymphocytic leukemia (CLL)-associated fibrosis, Hamman-Rich syndrome, Caplan syndrome, coal worker's pneumoconiosis, cryptogenic fibrosing alveolitis, obliterative bronchiolitis, chronic bronchitis, emphysema, pneumonitis, Wegner's granulamatosis, lung scleroderma, silicosis, interstitial lung disease, asbestos induced pulmonary and/or pleural fibrosis. In some embodiments, lung disease is lung fibrosis (i.e. pulmonary fibrosis). In some embodiments, lung disease is idiopathic pulmonary fibrosis.

Pulmonary Fibrosis

In some embodiments, the compositions and methods described herein can treat or slow down the progression of or prevent pulmonary fibrosis. In some embodiments, pulmonary fibrosis includes interstitial pulmonary fibrosis. This group of disorders is characterized by scarring of deep lung tissue, leading to shortness of breath and loss of functional alveoli, thus limiting oxygen exchange. Etiologies include inhalation of inorganic and organic dusts, gases, fumes and vapors, use of medications, exposure to radiation, and development of disorders such as hypersensitivity pneumonitis, coal worker's pneumoconiosis, radiation, chemotherapy, transplant rejection, silicosis, byssinosis and genetic factors IPF as described herein refers to "idiopathic pulmonary fibrosis" and is in some embodiments a chronic disease that manifests over several years and is characterized by scar tissue within the lungs, in the absence of known provocation. Exercise-induced breathlessness and chronic dry cough may be the prominent symptoms. IPF belongs to a family of lung disorders known as the interstitial lung diseases (ILD) or, more accurately, the diffuse parenchymal lung diseases. Within this broad category of diffuse lung diseases, IPF belongs to the subgroup known as idiopathic interstitial pneumonia (IIP). There are seven distinct IIPs, differentiated by specific clinical features and pathological patterns. IPF is the most common form of IIP. It is associated with the pathologic pattern known as usual interstitial pneumonia (UIP); for that reason, IPF is often referred to as IPF/UIP. IPF is usually fatal, with an average survival of approximately three years from the time of diagnosis. There is no single test for diagnosing pulmonary fibrosis; several different tests including chest x-ray, pulmonary function test, exercise testing, bronchoscopy and lung biopsy are used in conjunction with the methods described herein.

Idiopathic pulmonary fibrosis (also known as cryptogenic fibrosing alveolitis) is the most common form of interstitial lung disease, and may be characterized by chronic progressive pulmonary parenchymal fibrosis. It is a progressive clinical syndrome with unknown etiology; the outcome is frequently fatal as no effective therapy exists. In some embodiments, pirfenidone inhibits fibroblast proliferation and differentiation related to collagen synthesis, inhibits the production and activity of TGF-beta, reduces production of fibronectin and connective tissue growth factor, inhibits TNF-alpha and I-CAM, increase production of IL-10, and/or reduces levels of platelet-derived growth factor (PDGF) A and B in bleomycin-induced lung fibrosis. The pirfenidone methods and compositions described herein may provide tolerability and usefulness in patients with advanced idiopathic pulmonary fibrosis and other lung diseases. In some embodiments, pirfenidone methods and compositions described herein may provide tolerability and usefulness in patients with mild to moderate idiopathic pulmonary fibrosis. In some embodiments, increased patient survival, enhanced vital capacity, reduced episodes of acute exacerbation (compared to placebo), and/or slowed disease progression are observed following pirfenidone treatment. In some embodiments inhaled delivery of pirfenidone or pyridone analog may be an effective means to prevent, manage or treat idiopathic pulmonary fibrosis or other pulmonary fibrotic diseases.

The term "pulmonary fibrosis", includes all interstitial lung disease associated with fibrosis. In some embodiments, pulmonary fibrosis includes the term "idiopathic pulmonary fibrosis" or "IPF". In some embodiments, pulmonary fibrosis, by non-limiting example, may result from inhalation of inorganic and organic dusts, gases, fumes and vapors, use of medications, exposure to radiation or radiation therapy, and development of disorders such as hypersensitivity pneumonitis, coal worker's pneumoconiosis, chemotherapy, transplant rejection, silicosis, byssinosis and genetic factors.

Exemplary lung diseases for the treatment or prevention using the methods described herein include, but are not limited, idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), sarcoidosis, scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced).

Inflammasome and Fibrosis

The innate immune response comprising the inflammasomes is one of the first lines of defense against tissue damage and pathogen invasion. The inflammasome mediates the activation and recruitment of inflammatory cells to the site of danger through the release of proinflammatory factors. The inflammasomes are capable of recognizing endogenous and exogenous alarm signals arising from intracellular or extracellular stressors. Endogenous stressors that are known to activate the inflammasome include specific chemical alarm signals, such as uric acid, ATP, potassium efflux from the cell and the newly identified endogenous peptide, acALY18. Exogenous stressors include pathogen-associated molecular patterns derived from a diverse range of conserved molecular motifs that are unique to bacteria, viruses and parasites, from exogenous chemicals or ultraviolet light. During inflammasome activation apoptosis speck-like protein containing a caspase activation and recruitment domain (CARD) (ASC) moves from the nucleus and assembles into the inflammasome complex recruiting procaspase-1. The resulting association of these proteins causes the cleavage and activation of caspase-1. Once caspase-1 is activated, it is then able to cleave a number of key pro-inflammatory cytokines, such as IL-1β3 and IL-18.

The NLRP3 inflammasome is the most extensively studied inflammasome and this inflammasome is capable of sensing a wide variety of alarm signals from endogenous and exogenous sources. It has been shown that the assembly of the NLRP3 inflammasome requires the presence of reactive oxygen species and the positional interaction between the endoplasmic reticulum and mitochondria. Quiescent NLRP3 is localized to the endoplasmic reticulum. However, once the inflammasome is activated both NLRP3 and ASC redistribute to the perinuclear region of the cell where they co-localize with the endoplasmic reticulum and mitochondrial organelles.

Assembly and activation of the inflammasome complex leads to the cleavage of caspase-1 (IL-1β converting enzyme/ICE) in a process that is tightly regulated. The active form of caspase-1 is able to cleave a wide variety of protein precursors that do not contain a secretion signaling sequence in a manner that appears to occur through an endoplasmic reticulum/Golgi-independent pathway that is now thought to involve autophagy. In addition to autophagy regulating the secretion of IL-1β, it also appears that autophagy may regulate the activation of the inflammasome. It has been shown that ASC is secreted from activated myofibroblasts at a higher rate than quiescent fibroblasts and other cells, suggesting that the inflammasome is secreted in a process that regulates its own activation. Furthermore, once activated, caspase-1 also induces its own secretion, possibly by the same autophagic mechanism, and we believe that this may also further regulate the cleavage of proteins that are processed by caspase-1.

IL-1β and IL-18 belong to the IL-1 family of proteins are processed into mature biologically active proteins when caspase-1 is activated. These proteins then become available for secretion. Numerous other proteins are also processed by caspase-1 and many of these proteins are involved in inflammation, the cytoskeleton of the cell and other functions.

Depending on the initiating mechanism, activation of the inflammasome can run a well-defined course, with resolution of inflammation and healing of the injury, or be continuous, resulting in chronic disease or fibrosis. It is speculated that in acute disease, the injury is able to be completely resolved, with clearance of the initiating signal, whereas in chronic disease leading to fibrosis the resulting pathogen or irritant is unable to be cleared, leading to continuous inflammasome activation and IL-1β and IL-18 processing.

The role of IL-1β in fibrosis and wound healing is apparent and studies have elucidated some of the downstream mechanisms that result in the induction of collagen. IL-1β can directly stimulate collagen secretion by fibroblasts in a dose-dependent manner and the transient over-expression of IL-1β by airway epithelial cells increases TGFβ1 and collagen deposition in the lung.

The transient expression of IL-1β is important for normal wound healing. However, chronic expression of IL-1β appears to mediate fibrosis. In normal wound healing, IL-1β secretion is found to peak at day 1 and declines during days 3-7 post-injury. Employing a deep incisional wound-healing model, mice deficient in the IL-1 receptor had improved wound healing, with less fibrosis and more collagenolytic activity. The wound fluids contained less TGFβ1, IL-6 and vascular endothelial growth factor, and wild-type wounds following Anakinra (IL-1 receptor antagonist) treatment contained less fibrosis, suggesting that IL-1 signaling is profibrotic.

Short-term IL-1β and TGFβ1 exposure (minutes) in proximal tubular cells inhibited the phosphorylation of Smad3, and this in turn inhibited downstream TGFβ1 signaling. In contrast, long exposure (24 h) of proximal tubular cells to IL-1β and TGFβ1 increased Smad3 phosphorylation, further enhancing TGFβ1 signaling. Other cells also exhibit similar responses to IL-1β, and exposure of microvascular endothelial cells to IL-1β was found to promote the permanent transformation of these cells into myofibroblasts.

IL-18 mRNA is constitutively expressed with low endogenous levels of protein in normal skin. Upon injury, the mRNA is rapidly translated into protein. Like IL-1β, IL-18 protein in wounded skin is transient and peaks at days 5-7. Immediately after wounding, there is a rapid decrease in IL-18 mRNA in the skin, but this returns to normal levels by day 13, once re-epithelialization is complete. In wound healing, IL-18 induces TGFβ1 and can induce IFNγ secretion by inflammatory cells. Interestingly, the inhibition of IFNγ signaling results in improved wound healing compared to wild-type mice, suggesting that IFNγ is required for balanced wound healing and that its absence may promote fibrosis.

The involvement of the inflammasome in fibrotic diseases is being elucidated. However, many studies to date have focused on inflammasome activation in inflammatory cells, rather than the activation of the inflammasome in stromal cells or parenchymal cells. Activation of the inflammasome appears to be involved in many chronic idiopathic diseases in addition to being involved in pathogen recognition or the recognition of cellular alarm signals (alarmins). It is speculated that fibrosis could be dependent on a number of factors, including the initiating events leading to inflammasome activation, the specifically activated inflammasome or inflammasome combination, the genetic variations that affect the response of the target cell to the activated inflammasome, inflammasome by-products, such as IL-1β and IL-18, the level of cytokine secreted from the cell, the cell type in which the inflammasome is activated (inflammatory cells versus stromal or parenchymal cells) or the duration of the activation of the inflammasome.

Even though stromal cells are not immune cells, activation of these cells is capable of inducing cytokine secretion that promotes downstream recruitment of inflammatory cells, and this can occur by inflammasome activation. Fibroblasts have not been considered central to the immune response, neither have they been considered to be immunologically relevant in infections. However, they can become activated to release of chemokines and cytokines for the recruitment of monocytes and neutrophils to sites when the skin has been breached or infected by a pathogen. Fibroblasts may be considered a sentinel cell that respond to bacterial products and cellular alarm signals due to tissue damage. Inflammasome activation induces the differentiation of quiescent fibroblasts to myofibroblasts. From this, continuous inflammasome dysregulation that promotes myofibroblast differentiation may be a key factor in excessive extracellular matrix accumulation and resulting organ failure. In contrast, in normal wound healing, inflammasome signalling is tightly regulated and, once the wound is closed, the myofibroblasts undergo apoptosis, limiting collagen secretion.

Many studies corroborate the role of the NLRP3 inflammasome in driving collagen deposition in the tissues and the activation of caspase-1 in wound healing: 1. In mice deficient in ASC protein had attenuated responses to the profibrotic compound, bleomycin; 2. In mice deficient in the IL-1 receptor there were also abrogated responses to bleomycin; 3. Direct administration of recombinant IL-1β into the lungs of wild-type mice, resulted in marked increase in tissue destruction with inflammation and collagen deposition; and 4. Inhibition of IL-1 signaling with the IL-1 receptor antagonist (Anakinra) limited fibrosis and was more effective than the administration of IL-1β-neutralizing antibodies.

In further studies it was found that uric acid was released into the lung parenchyma when bleomycin was instilled into the lungs. Uric acid is soluble in the cytosol of the cell. However, when it is released by injured cells it precipitates, forming monosodium urate crystals that are microscopic in size, and these crystals stimulate an immune response. It was speculated that the localized increase in uric acid resulted in the deposition of crystals that cause membrane damage to cells, resulting in the activation of NLRP3 inflammasome and subsequent release of IL-1β. It was further demonstrated that the signaling mediated by uric acid was dependent on the IL-1 receptor and the NLRP3 inflammasome, and suggested that an autocrine signaling loop mediating resulting fibrosis. Utilizing the caspase-1 deficient mouse, it was demonstrated that caspase-1 was necessary for the profibrotic effect of bleomycin.

Hepatic stellate cells are able to differentiate into myofibroblasts and up-regulate collagen secretion. Activated hepatic stellate cells can phagocytose pathogen and cellular debris, present antigen, express α-smooth muscle actin stress fibers, and migrate. It has been shown that monosodium urate crystals activated the inflammasome, leading to liver fibrosis. Together, these findings further suggested that the inflammasome is an important signaling pathway central to fibrotic diseases. In addition, it was shown that progression liver fibrosis was mediated by IL-1α and IL-1β, peaking on day 1, whereas collagen and α-smooth muscle actin peaked at day 3.

It has been shown that fibrosis in the autoimmune disease systemic sclerosis (SSc; scleroderma) is dependent on the inflammasome. It was shown that collagen secretion by myofibroblasts could be abrogated if caspase-1 was inhibited and, by inhibiting caspase-1, IL-1β and IL-18 were also inhibited. These data suggest that the release of IL-1β and IL-18 in SSc is mediated by an inflammasome activation that is dependent on caspase-1, and that this process is driving fibrosis. Furthermore, the pathogenic cell that drives the increased collagen synthesis in the skin and organs, the myofibroblast, could be phenotypically altered by inhibiting caspase-1. Specifically, α-smooth muscle actin stress fibers were thinner and contained less protein when caspase-1 signaling was inhibited. No change in α-smooth muscle actin expression was observed in quiescent fibroblasts and f-actin expression was unaffected by caspase-1 inactivation. These findings were further recapitulated in NLRP3- and ASC-deficient mice in a model of dermal fibrosis. The induction of dermal fibrosis with subcutaneous injections of bleomycin was inhibited in the knockout mice, as was pulmonary fibrosis. These findings suggest that active caspase-1 regulates SSc fibrosis and suggests that there may be autocrine signaling mediated by IL-1β and/or IL-18 that promotes the profibrotic phenotype in these patients.

Recently it was found that stimulation of cardiac fibroblasts, but not cardiomyocytes, with conditions mimicking hypoxia and reoxygenation stimulated the inflammasome and that this could lead to fibrosis. Under these conditions, reactive oxygen species and potassium efflux were the driving forces behind inflammasome activation. ASC-deficient mice had attenuated responses to ischaemia-reperfusion and reduced numbers of infiltrating macrophages and neutrophils. This study provides further evidence that fibroblasts may act as sentinel cells capable of sensing danger signals that are a result of ischaemia and reperfusion, causing an enhanced inflammatory response in the heart and inciting the deposition of collagens.

Endoplasmic Reticulum Stress and Fibrosis

The endoplasmic reticulum (ER) is a specialized cellular organelle that functions as the site for folding of proteins destined for several cellular compartments or the extracellular milieu. The ER also serves as a site for the biosynthesis for steroids, cholesterol and other lipids, and for the storage and cytosolic release of calcium. In addition, the ER can activate several signaling pathways collectively called the unfolded protein response (UPR) when it sustains stress that challenges its function. In eukaryotic cells, three ER-resident transmembrane proteins are crucial for sensing ER stress and transducing signals during the UPR: inositol-requiring enzyme 1 (IRE1), double-stranded RNA-activated protein kinase-(PKR)-like eukaryotic initiation factor 2α kinase (PERK) and the activating transcription factor-6 (ATF6). During transient and mild ER stress, the UPR restores ER homeostasis by adaptive mechanisms, including the expansion of ER size, enhanced protein folding capacity, suppression of protein synthesis through transcriptional and translational controls, and degradation of unfolded or misfolded proteins. However, if the stress is persistent and strong, the UPR activates mitochondria-dependent or mitochondria-independent apoptotic pathways. UPR signaling pathways are also involved in the activation of NF-κB, the major transcription factor regulating inflammatory processes. All three UPR pathways induced by the ER sensors IRE1α and PERK, and ATF6 potentially contribute to NF-κB activation during ER stress. During UPR activation the ER-resident IRE1α activates NF-κB through the IκB kinase (IKK) complex recruited by the formation of a complex between IRE1α and TRAF2. The kinase activity of IRE1α phosphorylates IKK, leading to degradation of I-κB and subsequent activation of NF-κB. PERK-induced phosphorylation of a subunit of the eukaryotic initiation factor 2-alpha (eIF2α) decreases the level of IκB protein by repression of I-κB translation, facilitating the nuclear translocation of NF-κB to regulate the transcription of target genes. In addition to these mechanisms, NF-κB may be activated by calcium-mediated ROS production during ER stress. Taken together, NF-κB activation associated with ER stress participates in the priming step of IL-1β production and inflammasome activation.

Kidney Fibrosis

In some embodiments, the compositions and methods described herein can treat or slow down the progression of or prevent kidney fibrosis. Kidney fibrosis may develop as a result of chronic infection, obstruction of the ureter by calculi, malignant hypertension, radiation therapy, transplant rejection, severe diabetic conditions, or chronic exposure to heavy metals. In addition, idiopathic glomerulosclerosis and renal interstitial fibrosis have been reported in children and adults. Kidney fibrosis correlates well with the overall loss of renal function. Studies have shown that oral pirfenidone provides protective effect against heavy metal challenge and fibrosis reversal following diabetic challenge in rats. Additionally, the antifibrotic action of pirfenidone in renal fibrosis following partial nephrectomy in rats has also been shown. Moreover, clinical studies administering oral pirfenidone have shown slowed renal function decline in focal segmental glomeruloschlerosis patients. In some embodiments, because the kidneys vasculature is immediately downstream of the lung, inhaled delivery of pirfenidone or pyridone analog may be an effective means to prevent, manage or treat kidney fibrosis resulting from various medical conditions or procedures without exposing the systemic compartment to otherwise toxic drug levels associated with oral administration.

The term "kidney fibrosis" by non-limiting example relates to remodeling associated with or resulting chronic infection, obstruction of the ureter by calculi, malignant hypertension, radiation therapy, transplant rejection, severe diabetic conditions or chronic exposure to heavy metals. In some embodiments, kidney fibrosis correlates well with the overall loss of renal function.

Heart and Kidney Toxicity

In some embodiments, the compositions and methods described herein can treat or slow down the progression of or prevent heart and/or kidney toxicity. Chemotherapeutic agents have toxic effects upon multiple organ during therapy. By non-limiting example doxorubicin has a broad spectrum of therapeutic activity against various tumors. However, its clinical use is limited by its undesirable systemic toxicity, especially in the heart and kidney. Treatment with pirfenidone reduced the severity of doxorubicin-induced toxicity as assessed by reduced mortality, diminished volume of recovered fluid in the abdominal cavity, and severity of cardiac and renal lesions at both the biochemical and morphological levels. In some embodiments, because the heart and kidney vasculature are immediately downstream of the lung, inhaled delivery of pirfenidone or pyridone analog may be an effective means to prevent, manage or treat chemotherapy-induced cardiac and/or renal inflammation without exposing the systemic compartment to otherwise toxic drug levels associated with oral administration. In some embodiments, inhaled delivery of pirfenidone or pyridone analog compound is used in the treatment of heart toxicity and/or kidney toxicity associated with chemotherapy or other therapeutic agents in a human.

The term "heart toxicity" by non-limiting example may be associated with or caused by exposure to chemotherapeutic agents having toxic effects. By non-limiting example doxorubicin has a broad spectrum of therapeutic activity against various tumors. However, its clinical use is limited by its undesirable systemic toxicity, especially in the heart and kidney.

The term "kidney toxicity" by non-limiting example may be associated with or caused by exposure to chemotherapeutic agents having toxic effects. By non-limiting example doxorubicin has a broad spectrum of therapeutic activity against various tumors. However, its clinical use is limited by its undesirable systemic toxicity, especially in the heart and kidney.

Cardiac Fibrosis

In some embodiments, the compositions and methods described herein can treat or slow down the progression of or prevent cardiac fibrosis. Cardiac remodeling as in chronic hypertension involves myocyte hypertrophy as well as fibrosis, an increased and non-uniform deposition of extracellular matrix proteins. The extracellular matrix connects myocytes, aligns contractile elements, prevents overextending and disruption of myocytes, transmits force and provides tensile strength to prevent rupture. Fibrosis occurs in many models of hypertension leading to an increased diastolic stiffness, a reduction in cardiac function and an increased risk of arrhythmias. If fibrosis rather than myocyte hypertrophy is the critical factor in impaired cardiovascular function, then reversal of cardiac fibrosis by itself may return cardiac function towards normal. Since collagen deposition is a dynamic process, appropriate pharmacological intervention could selectively reverse existing fibrosis and prevent further fibrosis and thereby improve function, even if the increased systolic blood pressure was unchanged.

Treatment of DOCA-salt hypertensive rats with pirfenidone reversed and prevented fibrosis. Suggesting that pirfenidone or pyridone analog therapy may be an effective means to attenuate cardiac fibrosis associated with chronic hypertension and also the functional impairment of the heart in hypertensive humans. Moreover, the reversal of fibrosis following pirfenidone treatment of streptozotocin-diabetic rats was also shown (Miric et al., 2001). Together, and because the heart vasculature are immediately downstream of the lung, inhaled delivery of pirfenidone or pyridone analog may be an effective means to prevent, manage or treat cardiac fibrosis resulting from various medical conditions or procedures, including by non-limiting example viral or bacterial infection, surgery, Duchenne muscular dystrophy, radiation, chemotherapy, and transplant rejection.

The term "cardiac fibrosis" by non-limiting example relates to remodeling associated with or resulting from viral or bacterial infection, surgery, Duchenne muscular dystrophy, radiation therapy, chemotherapy, transplant rejection and chronic hypertension where myocyte hypertrophy as well as fibrosis is involved and an increased and non-uniform deposition of extracellular matrix proteins occurs. Fibrosis occurs in many models of hypertension leading to an increased diastolic stiffness, a reduction in cardiac function, an increased risk of arrhythmias and impaired cardiovascular function.

Hepatic Fibrosis

In some embodiments, the compositions and methods described herein can treat or slow down the progression of or prevent hepatic fibrosis. Hepatic fibrosis occurs consequence of severe liver damage in patients with chronic liver disease, caused by non-limiting example persistent viral hepatitis, alcohol overload and autoimmune. Hepatic fibrosis involves an abnormal accumulation of extracellular matrix components, particularly collagens. Hepatic stellate cells are non-parenchymal liver cells residing in the perisinusoidal space. These cells have been shown to be the major cellular source of extracellular matrix in hepatic fibrosis. Studies have shown that oral pirfenidone provides protective effect against dimethylnitrosamine-induced hepatic fibrosis in preventing weight loss, suppressed loss in liver weight, suppressed induction of hepatic fibrosis determined by histological evaluation and reduced hepatic hydroxyproline levels. Expression of mRNA for type I collagen and transforming growth factor-beta in the liver were also suppressed by pirfenidone treatment. Additionally, clinical studies administering oral pirfenidone have shown decreased fibrosis and improved quality of life in Hepatitis C viral-related liver disease patients. Together, and because the liver vasculature is downstream of the lung, these results suggest that inhaled delivery of pirfenidone or pyridone analog may be an effective means to prevent, manage or treat hepatic fibrosis resulting from various medical conditions or procedures without exposing the systemic compartment to otherwise toxic drug levels associated with oral administration.

The term "hepatic fibrosis" by non-limiting example may be associated with or caused by severe liver damage in patients with chronic liver disease, caused by non-limiting example persistent viral hepatitis, alcohol overload and autoimmune diseases. Hepatic fibrosis involves an abnormal accumulation of extracellular matrix components, particularly collagens. Hepatic stellate cells are non-parenchymal liver cells residing in the perisinusoidal space.

Multiple Sclerosis

In some embodiments, the compositions and methods described herein can treat or slow down the progression of or prevent multiple sclerosis. Multiple sclerosis is a demyelinating disorder that is characterized by neurological deficits attributable to demyelinating lesions and progressive axonal loss in the white matter. The evidence that TNF-alpha plays a pivotal role in the pathogenesis of multiple sclerosis led to evaluation of pirfenidone in this indication. In a clinical study, oral pirfenidone improved the Scripps Neurological Rating Scale scores over placebo. Further, pirfenidone reduced the incidence of relapses and was associated with a marked improvement in bladder dysfunction. Together, and because the central nervous system vasculature is immediately downstream of the lung, these results suggest that inhaled delivery of pirfenidone or pyridone analog may be an effective means to prevent, manage or treat multiple sclerosis without exposing the systemic compartment to otherwise toxic drug levels associated with oral administration.

The term "multiple sclerosis" is a demyelinating disorder that is characterized by neurological deficits attributable to demyelinating lesions and progressive axonal loss in the white matter.

Chronic Obstructive Pulmonary Disease (COPD)

In some embodiments, the compositions and methods described herein can treat or slow down the progression of or prevent COPD. Oxidants and oxidative stress due to, by non-limiting example, cigarette smoking promote lung inflammation, which is mediated, at least in part, by activation of the transcription factors nuclear factor (NF)-κB and activator protein (AP)-1. These coordinate the expression of several genes thought to be important in COPD, such as interleukin (IL)-8 and TNFα. These pro-inflammatory cytokines and chemokines, together with IL-1β, strongly activate the p38 subgroup of mitogen-activated protein kinases (MAPKs), a family of signal transduction enzymes that also include extracellular signal-regulated kinases (ERK) and c-jun NH2-terminal kinases (JNK). JNK and p38 members are activated mainly by cytokines implicated in inflammation and apoptosis. Within the MAPK family, both the JNK and the p38 subgroups are involved in mediating pro-inflammatory responses, though p38 seems to play a prominent role in COPD. Pirfenidone has been shown to inhibit both TNF-alpha and p38-gamma MAPK. Moreover, silencing p38-gamma MAPK has been demonstrated to have potential to restore COPD sensitivity to corticosteroids (Mercado et al., 2007). In some embodiments, inhaled delivery of pirfenidone or pyridone analog compound is used in the treatment of COPD in a human. In some embodiments, inhaled delivery of pirfenidone or pyridone analog may be an effective means to prevent, manage or treat COPD or associated illness without exposing the systemic compartment to otherwise toxic drug levels associated with oral administration. Moreover, inhaled delivery of pirfenidone or pyridone analog may serve as conjunctive therapy with corticosteroids to restore their usefulness in this indication.

The term "chronic obstructive pulmonary disease" or "COPD" by non-limiting example may be associated with or caused by exposure to tobacco smoke and preexisting asthma. COPD describes a wide range of airway disorders that range from simple chronic bronchitis (smokers cough) to the more severe chronic obstructive bronchitis. The addition of episodes of airway hyper-reactivity to the above syndrome establishes the diagnosis of chronic asthmatic bronchitis. Chronic obstructive pulmonary disease includes, but is not limited to, chronic bronchitis, emphysema, and/or pulmonary hypertension.

Asthma

In some embodiments, the compositions and methods described herein can treat or slow down the progression of or prevent asthma. TNF-alpha has been shown to be a highly pro-inflammatory cytokine in asthma, as it upregulates adhesion molecules, increases mucin secretion, and promotes airway remodeling. TNF-alpha is produced by a large number of cells in the airways, including mast cells, smooth muscle cells, epithelial cells, monocytes, and macrophages. This cytokine has been shown to be relevant and increased in patients with asthma. Clinical studies using anti-TNF-alpha therapy have produced encouraging results. In one set of studies using a soluble form of recombinant human TNF-alpha receptor (etanercept) the medication improved FEV1 and improved quality of life. Another clinical study administering an anti-TNF-alpha antibody reduced asthma exacerbation (infliximab). However, because of concerns associated with adverse events future investigation of these therapies in asthma is unlikely. Because pirfenidone has been shown to inhibit TNF-alpha, inhaled delivery of pirfenidone or pyridone analog may be an effective means to manage or treat asthma or associated illness without exposing the systemic compartment to otherwise toxic drug levels associated with oral administration. In some embodiments, inhaled delivery of pirfenidone or pyridone analog compound is used in the treatment of asthma in a human. Moreover, inhaled delivery of pirfenidone or pyridone analog may serve as conjunctive therapy with corticosteroids to restore their usefulness in asthma patients exhibiting steroid resistance.

The term "asthma" is associated with or caused by environmental and genetic factors. Asthma is a common chronic inflammatory disease of the airways characterized by variable and recurring symptoms, reversible airflow obstruction, and bronchospasm. Symptoms include wheezing, coughing, chest tightness, and shortness of breath. The term asthma may be used with one or more adjectives to indicate cause. Non-limiting examples of asthma include, but are not limited to, allergic asthma, non-allergic asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, occupational asthma, steroid-resistant asthma, or seasonal asthma.

Lung Inflammation

In some embodiments, the compositions and methods described herein can treat or slow down the progression of or prevent lung inflammation. Pirfenidone therapy has shown to have anti-inflammatory effects in addition to anti-fibrotic effects. In some embodiments, pirfenidone or pyridone analog compound is administered to a human to treat lung inflammation. Lung inflammation is associated with or contributes to the symptoms of bronchitis, asthma, lung fibrosis, chronic obstructive pulmonary disorder (COPD), and pneumonitis.

Glaucoma Surgery Post-Operative Fibrosis

The success of glaucoma filtration surgery is dependent on the degree of post-operative wound healing and the amount of scar tissue formation. Bleb failure occurs as fibroblasts proliferate and migrate toward the wound, eventually causing scarring and closure of the fistula tract. This frequently leads to poor postoperative intraocular pressure control with subsequent progressive optic nerve damage. The use of adjunctive antifibrotic agents such as 5-fluorouracil and mitomycin C has significantly improved the success rate of filtration surgery. However, because of their nonspecific mechanisms of action, these agents can cause widespread cell death and apoptosis, resulting in potentially sight-threatening complications such as severe postoperative hypotony, bleb leaks, and endophthalmitis. Thus, alternative antifibrotic agents are needed. For this purpose, the antifibrotic agent pirfenidone or pyridone analog may prove beneficial.

Cancer

Lung cancer mortality is high, and annual lung cancer deaths equal prostate, breast, colon, and rectum cancers combined. Despite the advancement in knowledge on molecular mechanisms and the introduction of multiple new therapeutic lung cancer agents, the dismal 5-year survival rate (11-15%) remains relatively unaltered. This reflects the limited available knowledge on factors promoting oncogenic transformation to and proliferation of malignant cells.

Until recent years, the principal focus in cancer research has mostly been the malignant cell itself. As a consequence, today, there is a significant discrepancy between the vast knowledge about cancer biology generated in experimental settings and the translation of this knowledge into information that can be used in clinical decision making. Understanding the nature of the tumor environment today may be equally important for future cancer therapies as understanding cancer genetics per se. Cancers are not simply autonomous neoplastic cells but also composed of fibroblasts, immune cells, endothelial cells, and specialized mesenchymal cells. These different cell types in the stromal environment can be recruited by malignant cells to support tumor growth and facilitate metastatic dissemination.

Although the "seed and soil" hypothesis was presented more than a century ago, we are now starting to comprehend the complex crosstalk between the tumor cells (the "seeds") and the tumor-growing microenvironment (the "soil"). We now know that tumor growth is not determined only by malignant cells, because interactions between cancer cells and the stromal compartment have major impacts on cancer growth and progression. Aggressive malignant cells are clever at exploiting the tumor microenvironment: tumor cells can (1) reside in the stroma and transform it, (2) alter the surrounding connective tissue, and (3) modify the metabolism of resident cells, thus yielding a stroma, which is permissive rather than defensive.

Beyond overcoming the microenvironmental control by the host, key characteristics of cancer cells is their ability to invade the tissue and metastasize distantly. For invasion and metastasis, the concerted interactions between fibroblasts, immune cells, and angiogenic cells and factors are essential.

The tumor stroma basically consists of (1) the nonmalignant cells of the tumor such as CAFs, specialized mesenchymal cell types distinctive to each tissue environment, innate and adaptive immune cells, and vasculature with endothelial cells and pericytes and (2) the extracellular matrix (ECM) consisting of structural proteins (collagen and elastin), specialized proteins (fibrilin, fibronectin, and elastin), and proteoglycans. Angiogenesis is central for cancer cell growth and survival and has hitherto been the most successful among stromal targets in anticancer therapy. Initiation of angiogenesis requires matrix metalloproteinase (MMP) induction leading to degradation of the basement membrane, sprouting of endothelial cells, and regulation of pericyte attachment. However, CAFs play an important role in synchronizing these events through the expression of numerous ECM molecules and growth factors, including transforming growth factor (TGF)-$\beta$, vascular endothelial growth factor (VEGF), and fibroblast growth factor (FGF2).

The normal tissue stroma is essential for maintenance and integrity of epithelial tissues and contains a multitude of cells that collaborate to sustain normal tissue homeostasis. There is a continuous and bilateral molecular crosstalk between normal epithelial cells and cells of the stromal compartment, mediated through direct cell-cell contacts or by secreted molecules. Thus, minor changes in one compartment may cause dramatic alterations in the whole system.

A similarity exists between stroma from wounds and tumors, because both entities had active angiogenesis and numerous proliferating fibroblasts secreting a complex ECM, all on a background of fibrin deposition. Consequently, the tumor stroma has been commonly referred to as activated or reactive stroma.

A genetic alteration during cancer development, leading to a malignant cell, will consequently change the stromal host compartment to establish a permissive and supportive environment for the cancer cell. During early stages of tumor development and invasion, the basement membrane is degraded, and the activated stroma, containing fibroblasts, inflammatory infiltrates, and newly formed capillaries, comes into direct contact with the tumor cells. The basement membrane matrix also modifies cytokine interactions between cancer cells and fibroblasts. These cancer-induced alterations in the stroma will contribute to cancer invasion. Animal studies have shown that both wounding and activated stroma provides oncogenic signals to facilitate tumorigenesis. Although normal stroma in most organs contains a minimal number of fibroblasts in association with physiologic ECM, the activated stroma is associated with more ECM-producing fibroblasts, enhanced vascularity, and increased ECM production. This formation of a specific tumor stroma type at sites of active tumor cell invasion is considered an integral part of the tumor invasion and has been termed as tumor stromatogenesis.

The expansion of the tumor stroma with a proliferation of fibroblasts and dense deposition of ECM is termed a desmoplastic reaction. It is secondary to malignant growth and can be separated from alveolar collapse, which do not show neither activated fibroblasts nor the dense collagen/ECM. Morphologically this is termed desmoplasia and was initially conceived as a defense mechanism to prevent tumor growth, but data have shown that in established tumors, this process, quite oppositely, participates in several aspects of tumor progression, such as angiogenesis, migration, invasion, and metastasis. The latter studies show that fibroblasts and tumor cells can enhance local tissue growth and cancer progression through secreting ECM and degrading components of ECM within the tumor stroma. This is in part related to the release of substances sequestered in the ECM, such as VEGF, and cleavage of products from ECM proteins as a response to secretion of carcinoma-associated MMPs.

Profibrotic growth factors, released by cancer cells, such as TGF-β, platelet-derived growth factor (PDGF), and FGF2 govern the volume and composition of the tumor stroma as they are all key mediators of fibroblast activation and tissue fibrosis. PDGF and FGF2 play significant roles in angiogenesis as well.

In tumors, activated fibroblasts are termed as peritumoral fibroblasts or carcinoma-associated fibroblasts (CAFs). CAFs, like activated fibroblasts, are highly heterogeneous and believed to derive from the same sources as activated fibroblasts. The main progenitor seems to be the locally residing fibroblast, but they may also derive from pericytes and smooth muscle cells from the vasculature, from bone marrow-derived mesenchymal cells, or by epithelial or endothelial mesenchymal transition. The term CAF is rather ambiguous because of the various origins from which these cells are derived, as is the difference between activated fibroblasts and CAFs. There are increasing evidence for epigenetic and possibly genetic distinctions between CAFs and normal fibroblasts. CAFs can be recognized by their expression of α-smooth muscle actin, but due to heterogeneity α-smooth muscle actin expression alone will not identify all CAFs. Hence, other used CAF markers are fibroblast-specific protein 1, fibroblast activation protein (FAP), and PDGF receptor (PDGFR) α/β.

In response to tumor growth, fibroblasts are activated mainly by TGF-β, chemokines such as monocyte chemotactic protein 1, and ECM-degrading agents such as MMPs. Although normal fibroblasts in several in vitro studies have demonstrated an inhibitory effect on cancer progression, today, there is solid evidence for a cancer-promoting role of CAFs. In breast carcinomas, as much as 80% of stromal fibroblasts are considered to have this activated phenotype (CAFs).

CAFs promote malignant growth, angiogenesis, invasion, and metastasis. The roles of CAFS and their potential as targets for cancer therapy have been studied in xenografts models, and evidence from translational studies has revealed a prognostic significance of CAFs in several carcinoma types.

In the setting of tumor growth, CAFs are activated and highly synthetic, secreting, for example, collagen type I and IV, extra domain A-fibronectin, heparin sulfate proteoglucans, secreted protein acidic and rich in cysteine, tenascin-C, connective tissue growth factors, MMPs, and plasminogen activators. In addition to secreting growth factors and cytokines, which affect cell motility, CAFs are an important source for ECM-degrading proteases such as MMPs that play several important roles in tumorigenesis. Through degradation of ECM, MMPs can, depending on substrate, promote tumor growth, invasion, angiogenesis, recruitment of inflammatory cells, and metastasis. Besides, a number of proinflammatory cytokines seem to be activated by MMPs.

After injection of B16M melanoma cells in mice, the formation of liver metastases was associated with an early activation of stellate cells (fibroblast-like) in the liver, as these seemed important for creating a metastatic niche and promoting angiogenesis. MMPs have also been linked to tumor angiogenesis in various in vivo models. CAFs, when coinjected into mice, facilitated the invasiveness of otherwise noninvasive cancer cells. Furthermore, xenografts containing CAFs apparently grow faster than xenografts infused with normal fibroblasts.

At CAF recruitment and accumulation in the tumor stroma, these cells will actively communicate with cancer cells, epithelial cells, endothelial cells, pericytes, and inflammatory cells through secretion of several growth factors, cytokines, and chemokines. CAFs provide potent oncogenic molecules such as TGF-β and hepatocyte growth factor (HGF).

TGF-β is a pleiotropic growth factor expressed by both cancer and stromal cells. TGF-β is, in the normal and premalignant cells, a suppressor of tumorigenesis, but as cancer cells progress, the antiproliferative effect is lost, and instead, TGF-β promotes tumorigenesis by inducing differentiation into an invasive phenotype. TGF-β may also instigate cancer progression through escape from immunosurveillance, and increased expression of TGF-β correlate strongly with the accumulation of fibrotic desmoplastic tissue and cancer progression. Recently, a small molecule inhibitor of TGF-β receptor type I was reported to inhibit the production of connective tissue growth factor by hepatocellular carcinoma (HCC) cells, resulting in reduced stromal component of the HCCs. Inhibition of the TGF-β receptor aborted the crosstalk between HCCs and CAFs and consequently avoided tumor proliferation, invasion, and metastasis. HGF belongs to the plasminogen family and is tethered to ECM in a precursor form. It binds to the high-affinity receptor c-met, and overexpression or constant oncogenic c-Met signaling lead to proliferation, invasion, and metastasis.

PDGFs are regulators of fibroblasts and pericytes and play important roles in tumor progression. It is a chemotactic and growth factor for mesenchymal and endothelial cells. It has a limited autocrine role in tumor cell replication, but is a potential player, in a paracrine fashion, and in tumor stroma development. It induces the proliferation of activated fibroblasts and possibly recruits CAFs indirectly by stimulation of TGF-β release from macrophages.

A tumor cannot develop without the parallel expansion of a tumor stroma. Although we still do not comprehend the exact mechanisms regulating fibroblast activation and their accumulation in cancer, the available evidence points to the possibility that the tumor stroma or CAFs may be candidate targets for cancer treatment.

CAFs and MMPs have been considered two of the key regulators of epithelial-derived tumors representing potential new targets for integrative therapies, affecting both the transformed and nontransformed components of the tumor environment. As commented earlier, the experience with MMP inhibitors have so far been unsuccessful. Evidence that CAFs are epigenetically and possibly also genetically distinct from normal fibroblasts is beginning to define these cells as potential targets for anticancer therapy. FAP, expressed in more than 90% of epithelial carcinomas, emerged early as a promising candidate for targeting CAFs, and the potential therapeutic benefit of its inhibition was reviewed recently. In preclinical studies, abrogation of FAP attenuates tumor growth and significantly enhance tumor tissue uptake of anticancer drugs. In a phase I study, where patients with FAP-positive advanced carcinomas (colorectal cancer and NSCLC) were treated with FAP-antibody, the antibody bound specifically to tumor sites, but no objective responses were observed.

The consistent and repeated findings of cancer cells that readily undergo invasion and metastasis in response to TGF-β have pointed to the need of novel anticancer agents targeting the oncogenic activities of TGF-β. A large number of anti-TGF-β antibodies and TGF-β-receptor I kinases have been tested preclinically during the past decade. Because of the lack of success, targeting of the TGF-β signaling system still remains elusive. It should be noted that both protumoral and antitumoral effects have been assigned to TGF-β, and the multifunctional nature of TGF-β apparently represents the greatest barrier to effectively target this ligand, its receptor, or downstream effectors.

Pulmonary Hypertension

Pulmonary arterial hypertension (PAH) is a life-threatening disease characterized by a marked and sustained elevation of pulmonary artery pressure. The disease results in right ventricular failure and death. Current therapeutic approaches for the treatment of chronic pulmonary hypertension mainly provide symptomatic relief, as well as some improvement of prognosis. Although postulated for all treatments, evidence for direct antiproliferative effects of most approaches is missing. In addition, the use of most of the currently applied agents is hampered by either undesired side effects or inconvenient drug administration routes. Pathological changes in hypertensive pulmonary arteries include endothelial injury, proliferation, and hypercontraction of vascular smooth muscle cells (SMCs).

The World Health Organization divides pulmonary hypertension (PH) into five groups. These groups are organized based on the cause of the condition and treatment options. In all groups, the average pressure in the pulmonary arteries is 25 mmHg or higher. The pressure in normal pulmonary arteries is 8-20 mmHg at rest. (Note that group 1 is called pulmonary arterial hypertension (PAH) and groups 2 through 5 are called pulmonary hypertension. However, together all groups are called pulmonary hypertension.) Group 1 Pulmonary Arterial Hypertension includes PAH that has no known cause; PAH that's inherited; PAH that's caused by drugs or toxins, such as street drugs and certain diet medicines; PAH that's caused by conditions such as: Connective tissue diseases, HIV infection, Liver disease, Congenital heart disease. This is heart disease that's present at birth, Sickle cell disease, Schistosomiasis. This is an infection caused by a parasite. Schistosomiasis is one of the most common causes of PAH in many parts of the world; and PAH that is caused by conditions that affect the veins and small blood vessels of the lungs. Group 2 Pulmonary Hypertension includes PH with left heart disease. Conditions that affect the left side of the heart, such as mitral valve disease or long-term high blood pressure, can cause left heart disease and PH. Left heart disease is likely the most common cause of PH. Group 3 Pulmonary Hypertension includes PH associated with lung diseases, such as COPD (chronic obstructive pulmonary disease) and interstitial lung diseases. Interstitial lung diseases cause scarring of the lung tissue. Group 3 also includes PH associated with sleep-related breathing disorders, such as sleep apnea. Group 4 Pulmonary Hypertension includes PH caused by blood clots in the lungs or blood clotting disorders. Group 5 Pulmonary Hypertension includes PH caused by various other diseases or conditions. Examples include: Blood disorders, such as polycythemia vera and essential thrombocythemia, Systemic disorders, such as sarcoidosis and vasculitis. Systemic disorders involve many of the body's organs, Metabolic disorders, such as thyroid disease and glycogen storage disease. (In glycogen storage disease, the body's cells don't use a form of glucose properly), and Other conditions, such as tumors that press on the pulmonary arteries and kidney disease.

Several growth factors have been implicated in the abnormal proliferation and migration of SMCs, including PDGF, basic FGF (bFGF), and EGF. In vitro studies established that PDGF acts as a potent mitogen and chemoattractant for SMCs. Active PDGF is built up by polypeptides (A and B chain) that form homo- or heterodimers and stimulate α and β cell surface receptors. Recently, two additional PDGF genes were identified, encoding PDGF-C and PDGF-D polypeptides. The PDGF receptors (PDGFRs) belong to a family of transmembrane receptor tyrosine kinases (RTKs) and are supposed to be held together by the bivalent PDGF ligands. This complex of dimeric receptor and PDGF results in an autophosphorylation of the RTK and an increase in kinase activity.

Both receptors activate the major signaling transduction pathways, including Ras/MAPK, PI3K, and phospholipase Cγ. Recently, upregulation of both PDGFRα and PDGFRβ has been shown in lambs with chronic intrauterine pulmonary hypertension. Pulmonary PDGF-A or PDGF-B mRNA, however, did not differ between pulmonary hypertensive and control animals. In lung biopsies from patients with severe pulmonary arterial hypertension (PAH), PDGF-A chain expression was significantly increased.

PDGF-A and PDGF-B mRNA synthesis and steady-state levels of PDGF-A and PDGF-B mRNAs and PDGF isoforms are elevated in bleomycin-treated lungs. Pirfenidone has been observed to suppress PDGF-A and PDGF-B levels, perhaps via a posttranscriptional or translational mechanism resulting in decreased PDGF-A and PDGF-B protein. Further, pirfenidone has been observed to reduce bleomycin-induced lung fibrosis by downregulating the expression of PDGF-A as well as of PDGF-B proteins.

As altered PDGF signaling plays an important role in the course of PAH, pirfenidone or pyridone analog may also have a positive effect on hemodynamics and pulmonary vascular remodeling in PAH and serve as an anti-remodeling therapy for this disease.

The present invention provides, in several embodiments as herein disclosed, compositions and methods for pirfenidone and pyridone analog compound formulations that offer unprecedented advantages with respect to localized delivery of pirfenidone or pyridone analog in a manner that permits both rapid and sustained availability of therapeutically useful pirfenidone or pyridone analog levels to one or more desired tissues.

In certain preferred embodiments, and as described in greater detail below, delivery of the pirfenidone or pyridone analog compound formulation is to the respiratory tract tissues in mammalian subjects, for example, via the respiratory airways to middle airways and/or pulmonary beds (e.g., alveolar capillary beds) in human patients. According to certain particularly preferred embodiments, delivery to these regions of the lung may be achieved by inhalation therapy of a pirfenidone or pyridone analog compound formulation as described herein.

These and related embodiments will usefully provide therapeutic and/or prophylactic benefit, by making therapeutically effective pirfenidone or pyridone analog available to a desired tissue promptly upon administration, while with the same administration event also offering time periods of surprisingly sustained duration during which locally delivered pirfenidone or pyridone analog is available for a prolonged therapeutic effect.

The compositions and methods disclosed herein provide for such rapid and sustained localized delivery of a pirfenidone or pirfenidone or pyridone analog pyridone analog compound to a wide variety of tissues. Contemplated are embodiments for the treatment of numerous clinically significant conditions including pulmonary fibrosis, chronic obstructive pulmonary disease (COPD), asthma, cystic fibrosis, cardiac fibrosis, transplantation (e.g., lung, liver, kidney, heart, etc.), vascular grafts, and/or other conditions such as multiple sclerosis for which rapid and sustained bioavailable pirfenidone or pyridone analog therapy may be indicated.

Various embodiments thus provide compositions and methods for optimal prophylactic and therapeutic activity in prevention and treatment of pulmonary fibrosis in human and/or veterinary subjects using aerosol administration, and through the delivery of high-concentration (or dry formulation), sustained-release active drug exposure directly to the affected tissue. Specifically, and in certain preferred embodiments, concentrated doses are delivered of a pirfenidone or pyridone analog.

Without wishing to be bound by theory, according to certain of these and related embodiments as described in greater detail herein, a pirfenidone or pyridone analog is provided in a formulation having components that are selected to deliver an efficacious dose of pirfenidone or pyridone analog following aerosolization of a liquid, dry powder or metered-dose formulation providing rapid and sustained localized delivery of pirfenidone or pyridone analog to the site of desired effect.

According to certain related embodiments, regulation of the total amount of dissolved solutes in a pirfenidone or pyridone analog compound formulation is believed, according to non-limiting theory, to result in aqueous pirfenidone or pyridone analog compound formulations having therapeutically beneficial properties, including the properties of nebulized liquid particles formed from aqueous solutions of such formulations. Additionally, and as disclosed herein, it has been discovered that within the parameters provided herein as pertain to pirfenidone or pyridone analog compound concentration, pH, and total solute concentration, tolerability of formulations at or near the upper portion of the total solute concentration range can be increased by inclusion of a taste-masking agent as provided herein.

An unexpected observation is that exposure of inhaled pirfenidone to the lung surface results in depletion of essential lung-surface cations and increased propensity for acute toxicity. The apparent mechanism for this depletion is pirfenidone's ability to chelate ions such as iron(III) in a ratio of three pirfenidone molecules per on iron(III) ion. Chelation of iron(III) occurs at about one-half the chelation strength of EDTA. One method to prevent lung-surface ion depletion is to formulation prifenidone with a multivalent ion. By non-limiting example, such multi-valent cations may include iron(II), iron(III), calcium, magnesium, etc. By non-limiting example, formulation of pirfenidone was found to chelate magnesium at a ratio of two pirfenidone molecules to one magnesium ion. Thus, formulation of between about two and ten pirfenidone molecules with one magnesium molecule results in filling or saturating the chelation capacity of pirfenidone and reduces pirfenidone's to deplete lung-surface cations. Coupling this solution with the need to adjust formulation osmolality and permeant ion content, the salt form of multivalent ion may also be beneficial. By non-limiting example, using magnesium chloride to formulate pirfenidone reduces pirfenidone's ability to deplete essential lung-surface cations, contributes to adjusting the formulations osmolality and serves to provide the formulation a chloride permeant ion. In certain such embodiments, for example, a pirfenidone or pyridone analog compound formulation that comprises pirfenidone or a pyridone analog alone or formulated with excipients dissolved in a simple aqueous solution that may be aerosolized and injected or inhaled to the nasal or pulmonary compartment. Such a formulation may contain a multivalent cation and/or be buffered to a pH from about 4.0 to about 11.0, more preferably from about pH 4.0 to about pH 8.0, at a concentration of at least 34 mcg/mL to about 463 mg/mL, and having a total osmolality at least 100 mOsmol/kg to about 6000 mOsmol/kg, or 300 to about 5000 mOsmol/kg. Such a simple aqueous formulation may further comprise a taste-masking agent thereby to become tolerable for inhalation administration (i.e., to overcome undesirable taste or irritative properties that would otherwise preclude effective therapeutic administration). Hence and as described in greater detail herein, regulation of formulation conditions with respect to pH, buffer type, pirfenidone or pyridone analog concentration, total osmolality and potential taste-masking agent, provides certain therapeutic and other advantages.

In certain such embodiments, for example, a pirfenidone or pyridone analog compound formulation that comprises pirfenidone or a pyridone analog in a dry powder formulation alone or formulated with an excipient, such as a multivalent cation providing improved stability and/or dispersion properties, such that at least 0.1 mg to about 100 mg may be dispersed and injected or inhaled to the nasal or pulmonary compartment. Hence and as described in greater detail herein, regulation of formulation conditions with respect to dispersion excipient, pirfenidone or pyridone analog stability (including, by non-limiting example polymorph, amorphic content and water content), pirfenidone or pyridone analog amount and potential taste-masking agent, provides certain therapeutic and other advantages.

In certain such embodiments, for example, a pirfenidone or pyridone analog compound formulation that comprises pirfenidone or a pyridone analog in a pressurized meter-dose inhaler configuration providing improved stability and/or aerosol properties, such that at least 0.1 mg to about 100 mg may be aerosolized and injected or inhaled to the nasal or pulmonary compartment. Hence and as described in greater detail herein, regulation of formulation conditions with respect to propellant, suitable pressurized metered-dose inhaler canister, pirfenidone or pyridone analog stability provides certain therapeutic and other advantages.

In certain preferred embodiments, a pirfenidone or pyridone analog compound formulation or salts thereof may serve as prodrugs, sustained-release or active substances in the presently disclosed formulations and compositions and may be delivered, under conditions and for a time sufficient to produce maximum concentrations of sustained-release or active drug to the respiratory tract (including pulmonary beds, nasal and sinus cavities), and other non-oral topical compartments including, but not limited to the skin, rectum, vagina, urethra, urinary bladder, eye, and ear. As disclosed herein, certain particularly preferred embodiments relate to administration, via oral and/or nasal inhalation, of a pirfenidone or pyridone analog compound to the lower respiratory tract, in other words, to the lungs or pulmonary compartment (e.g., respiratory bronchioles, alveolar ducts, and/or alveoli), as may be effected by such "pulmonary delivery" to provide effective amounts of the pirfenidone or pyridone analog compound to the pulmonary compartment and/or to other tissues and organs as may be reached via the circulatory system subsequent to such pulmonary delivery of the pirfenidone or pyridone analog compound to the pulmonary vasculature.

Because different drug products are known to have varying efficacies depending on the dose, form, concentration and delivery profile, certain presently disclosed embodiments provide specific formulation and delivery parameters that produce anti-inflammatory, anti-fibrotic, anti-demylination and/or tissue-remodeling results that are prophylactic or therapeutically significant. These and related embodiments thus preferably include a pirfenidone or pyridone analog compound such as pirfenidone or pyridone analog alone or a salt thereof. As noted above, however, the invention is not intended to be so limited and may relate, according to particularly preferred embodiments, to pirfenidone or a salt thereof. Other contemplated embodiments may relate to another pyridone analog compound such as those disclosed herein.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory, anti-fibrotic or tissue-remodeling benefits, for instance, to prevent, manage or treat patients with pulmonary fibrosis.

Because different drug products are known to vary in efficacy depending on the dose, form, concentration and delivery profile, the presently disclosed embodiments provide specific formulation and delivery parameters that produce protection against and treatment for pulmonary fibrosis associated, by non-limiting example with infection, radiation therapy, chemotherapy, inhalation of environmental pollutants (e.g. dust, vapors, fumes, and inorganic and organic fibers), hypersensitivities, silicosis, byssinosis, genetic factors and transplant rejection.

These and related applications are also contemplated for use in the diseased lung, sinus, nasal cavity, heart, kidney, liver, nervous system and associated vasculature. The pirfenidone or pyridone analog compound formulations and methods described herein may be used with commercially available inhalation devices, or with other devices for aerosol therapeutic product administration.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory, anti-fibrotic or tissue-remodeling benefits, for instance, to prevent, manage or treat cardiac fibrosis in human and/or veterinary subjects. Such embodiments provide for direct and high concentration delivery of the pirfenidone or pyridone analog compound to the pulmonary vasculature immediately upstream of the left atrium and hence, to the coronary arterial system with interlumenal atrial and ventricular exposure.

Because different drug products are known to vary in efficacy depending on the dose, form, concentration and delivery profile, the presently disclosed embodiments provide specific formulation and delivery parameters that produce protection against and treatment for cardiac fibrosis associated, by non-limiting example with infection, surgery, radiation therapy, chemotherapy and transplant rejection.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory, anti-fibrotic or tissue-remodeling benefits, for instance, to prevent, manage or treat kidney fibrosis. Such embodiments provide for direct and high concentration delivery of the pirfenidone or pyridone analog compound to the pulmonary vasculature immediately upstream of the left atrium, left ventical and hence, to the kidney vasculature.

Because different drug products are known to vary in efficacy depending on the dose, form, concentration and delivery profile, the presently disclosed embodiments provide specific formulation and delivery parameters that produce protection against and treatment for kidney fibrosis associated, by non-limiting example with infection, ureter calculi, malignant hypertension, radiation therapy, diabetes, exposure to heavy metals, chemotherapy and transplant rejection.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory benefits, for instance, to prevent, manage or treat heart or kidney toxicity. Such embodiments provide for direct and high concentration delivery of the pirfenidone or pyridone analog compound to the pulmonary vasculature immediately upstream of the left atrium, left ventical, and hence, to the heart and kidney vasculature.

Because different drug products are known to vary in efficacy depending on the dose, form, concentration and delivery profile, the presently disclosed embodiments provide specific formulation and delivery parameters that produce protection against and treatment for heart or kidney toxicity associated, by non-limiting example with chemotherapy.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory, anti-fibrotic or tissue-remodeling benefits, for instance, to prevent, manage or treat hepatic fibrosis. Such embodiments provide for direct and high concentration delivery of the pirfenidone or pyridone analog compound to the pulmonary vasculature immediately upstream of the left atrium, left ventical and hence, to the hepatic vasculature.

Because different drug products are known to vary in efficacy depending on the dose, form, concentration and delivery profile, the presently disclosed embodiments provide specific formulation and delivery parameters that produce protection against and treatment for hepatic fibrosis associated, by non-limiting example with hepatic infection, hepatitis, alcohol overload, autoimmune disease, radiation therapy, chemotherapy and transplant rejection.

As a non-limiting example, in a preferred embodiment, a pyridone analog compound as provided herein (e.g., pirfenidone) formulated to permit mist, gas-liquid suspension or liquid nebulized, dry powder and/or metered-dose nasal-injected or inhaled, or orally-inhaled aerosol administration to supply effective concentrations or amounts conferring desired anti-inflammatory and/or anti-demylination benefits, for instance, to prevent, manage or treat multiple sclerosis. If by oral inhalation, such embodiments provide for direct and high concentration delivery of the pirfenidone or pyridone analog compound to the pulmonary vasculature immediately upstream of the left atrium, left ventical and hence, to the central nervous system. If by nasal injection or nasal inhalation, such embodiments provide for direct and high concentration delivery of the pirfenidone or pyridone analog compound to the nasal and sinus vasculature immediately upstream of the central nervous system.

Because different drug products are known to vary in efficacy depending on the dose, form, concentration and delivery profile, the presently disclosed embodiments provide specific formulation and delivery parameters that produce protection against and treatment for multiple sclerosis associated.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory, anti-fibrotic or tissue-remodeling benefits, for instance, to prevent, manage or treat patients with diseases associated with chronic obstructive pulmonary disease (COPD), including emphysema and chronic bronchitis.

Because different drug products are known to vary in efficacy depending on the dose, form, concentration and delivery profile, the presently disclosed embodiments provide specific formulation and delivery parameters that produce protection against and treatment for COPD associated, by non-limiting example with exposure to pipe, cigar and cigarette smoke, secondhand smoke, air pollution, and chemical fumes or dust, and/or alpha-1 antitrypsin deficiency.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-inflammatory benefits, for instance, to prevent, manage or treat patients with asthma.

Because different drug products are known to vary in efficacy depending on the dose, form, concentration and delivery profile, the presently disclosed embodiments provide specific formulation and delivery parameters that produce protection against and treatment for asthma associated, by non-limiting example with exercise, genetics, airborne allergens, inhaled irritants such as pipe, cigar and cigarette smoke, and childhood respiratory infection.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts conferring desired anti-fibrotic, anti-inflammatory or tissue-remodeling benefits, for instance, to prevent, manage or treat patients with cystic fibrosis. Such embodiments may include co-formulation or co-administration of a pyridone analog compound with an antibiotic, steroid, hyperosmolar solution, DNAse or other mucus thinning agent, or other agent.

Because different drug products are known to vary in efficacy depending on the dose, form, concentration and delivery profile, the presently disclosed embodiments provide specific formulation and delivery parameters that produce protection against and treatment for cystic fibrosis.

For the applications described herein, liquid nebulized, dry powder or metered-dose aerosol pirfenidone or pyridone analog compound (or salt thereof) may be co-administered, administered sequentially or prepared in a fixed combination with an antimicrobial (e.g. tobramycin and/or other aminoglycoside such as amikacin, aztreonam and/or other beta or mono-bactam, ciprofloxacin, levofloxacin and/or other, fluoroquinolones, azithromycin and/or other macrolides or ketolides, tetracycline and/or other tetracyclines, quinupristin and/or other streptogramins, linezolid and/or other oxazolidinones, vancomycin and/or other glycopeptides, and chloramphenicol and/or other phenicols, and colisitin and/or other polymyxins), bronchodilator (e.g. beta-2 agonists and muscarinic antagonists), corticosteroids (e.g. salmeterol, fluticasone and budesonide), glucocorticoids (e.g. prednisone), Cromolyn, Nedocromil, Leukotriene modifiers (e.g. montelukast, zafirlukast and zileuton) hyperosmolar solution, DNAse or other mucus thinning agent, interferon gamma, cyclophosphamide, colchicine, N-acetylcysteine, azathioprine, bromhexine, endothelin receptor antagonist (e.g. bosentan and ambrisentan), PDE5 inhibitor (e.g. sildenafil, vardenafil and tadalafil), PDE4 inhibitor (e.g. roflumilast, cilomilast, oglemilast, tetomilast and SB256066), prostinoid (e.g. epoprostenol, iloprost and treprostinin), nitric oxide or nitric oxide-donating compound, IL-13 blocker, IL-10 blocker, CTGF-specific antibody, CCN2 inhibitors, angiotensin-converting enzyme inhibitors, angiotensin receptor antagonists, PDGF inhibitors, PPAR antagonist, imatinib, CCL2-specific antibody, CXCR2 antagonist, triple growth factor kinase inhibitor, anticoagulant, TNF blocker, tetracycline or tetracycline derivative, 5-lipoxygenase inhibitor, pituitary hormone inhibitor, TGF-beta-neutralizing antibody, copper chelator, angiotensin II receptor antagonist, chemokine inhibitor, NF-kappaB inhibitor, NF-kappaB antisense oligonucleotide, IKK-1 and -2 inhibitor (e.g. imidazoquinoxaline or derivative, and quinazoline or derivative), JNK2 and/or p38 MAPK inhibitor (e.g. pyridylimidazolbutyn-I-ol, SB856553, SB681323, diaryl urea or derivative, and indole-5-carboxamide), PI3K inhibitor, LTB4 inhibitor, antioxidant (e.g. Mn-pentaazatetracyclohexacosatriene, M40419, N-acetyl-L-cysteine, Mucomyst, Fluimucil, Nacystelyn, Erdosteine, Ebeselen, thioredoxin, glutathione peroxidase memetrics, Curcumin C3 complex, Resveratrol and analogs, Tempol, catalytic antioxidants, and OxSODrol), TNF scavenger (e.g. infliximab, ethercept, adalumimab, PEG-sTNFR 1, afelimomab, and antisense TNF-alpha oligonucleotide), Interferon beta-1a (Avonex, Betaseron, or Rebif), glatiramer acetate (Copaxone), mitoxantrone (Novantrone), natalizumab (Tysabri), Methotrexate, azathioprine (Imuran), intravenous immunoglobulin (IVIg), cyclophosphamide (Cytoxan), lioresal (Baclofen), tizanidine (Zanaflex), benzodiazepine, cholinergic medications, antidepressants and amantadine.

As shown as a promising approach to treat cancer and pulmonary arterial hypertension, to enable "cocktail therapy" or "cocktail prophylaxis" in fibrotic disease, more specifically idiopathic pulmonary fibrosis and other pulmonary fibrotic disease, methods to administer pirfenidone or pyridone analog as either co-administered, administered sequentially, or co-prescribed (such that medicines are requested by a prescribing physician to be taken in some sequence as combination therapy to treat the same disease) with agents targeting cancer, fibrotic or inflammatory disease are described. By non-limiting example, pirfenidone or pyridone analog is administered either in fixed combination, co-administered, administered sequentially, or co-prescribed with the monoclonal GS-6624 (formerly known as AB0024), analog or another antibody targeting LOXL2 protein associated with connective tissue biogenesis to reduce inflammation, tumor stroma and/or fibrosis. By another non-limiting example, pirfenidone or pyridone analog is administered either in fixed combination, co-administered, administered sequentially, or co-prescribed with IW001 (Type V collagen), analog or other collagen targeting immunogenic tolerance to reduce inflammation, tumor stroma and/or fibrosis. By another non-limiting example, pirfenidone or pyridone analog is administered either in fixed combination, co-administered, administered sequentially, or co-prescribed with PRM-151 (recombinant pentraxin-2), analog or other molecule targeting regulation of the injury response to reduce inflammation, tumor stroma and/or fibrosis. By another non-limiting example, pirfenidone or pyridone analog is administered either in fixed combination, co-administered, adminstered sequentially, or co-prescribed with CC-930 (Jun kinase inhibitor), analog or other Jun kinase inhibitor to reduce the inflammatory response. By another non-limiting example, pirfenidone or pyridone analog is administered either in fixed combination, co-administered, adminstered sequentially, or co-prescribed with imatinib (a.k.a. Gleeve or Glivec (tyrosin kinase inhibitor)), analog or other tyrosine inhibitor to inhibit lung fibroblast-myofibroblast transformation and proliferation as well as extracellular matrix production and tumor stroma formation/maintenance through inhibition of PDFG and transforming growth factor (TGF)-13 signaling. By another non-limiting example, pirfenidone or pyridone analog is administered either in fixed combination, co-administered, adminstered sequentially, or co-prescribed with STX-100 (monoclonal antibody targeting integrin alpha-v beta-6), analog or other antibody targeting integrin alpha-v beta-6 or other integrin to reduce tumor stroma and/or fibrosis. By another non-limiting example, pirfenidone or pyridone analog is administered either in fixed combination, co-administered, adminstered sequentially, or co-prescribed with QAX576 (monoclonal antibody targeting interleukin 13 [IL-13]), analog or other antibody targeting IL-13 to reduce tumor stroma and/or inflammation. By another non-limiting example, pirfenidone or pyridone analog is administered either in fixed combination, co-administered, adminstered sequentially, or co-prescribed with FG-3019 (monoclonal antibody targeting connective tissue growth factor [CTGF]), analog or other antibody targeting CTGF to reduce tumor stroma and/or fibrosis. By another non-limiting example, pirfenidone or pyridone analog is administered either in fixed combination, co-administered, adminstered sequentially, or co-prescribed with CNTO-888 (a monoclonal antibody targeting chemokine [C—C motif] ligand 2 [CCL2]), analog or other antibody targeting CCL2 to reduce tumor stroma and/or fibrosis. By another non-limiting example, pirfenidone or pyridone analog is administered either in fixed combination, co-administered, adminstered sequentially, or co-prescribed with Esbriet, Pirespa or Pirfenex (trade names for pirfenidone), or analog targeting inflammation, tumor stroma and/or fibrosis. By another non-limiting example, pirfenidone or pyridone analog is administered either in fixed combination, co-administered, adminstered sequentially, or co-prescribed with BIBF-1120 (also known as Vargatef; a triple kinase inhibitor targeting vascular endothelial growth factor [VEGF], platelet-derived growth factor [PDGF] and fibroblast growth factor [FGF]), analog or other triple kinase inhibitor to reduce fibrosis, tumor stroma and/or inflammation.

As with administration of pirfenidone, oral and parenteral routes of administration (by non-limiting example, intravenous and subcutaneous) of other compounds, molecules and antibodies targeting the reduction of inflammation, tumor stroma and/or fibrosis is often associated with, by non-limiting example, adverse reactions such as gastrointestinal side effects, liver, kidney, skin, cardiovascular or other toxicities. As described herein for pirfenidone or pyridone analogs, the benefits of oral or intranasal inhalation directly to the lung or tissues immediately downstream of the nasal and/or pulmonary compartments will also benefit these compounds. Therefore, by non-limiting example, the monoclonal GS-6624 (formerly known as AB0024), analog or another antibody targeting LOXL2 protein associated with connective tissue biogenesis to reduce inflammation, tumor stroma and/or fibrosis may be administered by oral or intranasal inhalation for direct delivery to the lung or tissues immediately downstream of the nasal or pulmonary compartments. By another non-limiting example, PRM-151 (recombinant pentraxin-2), analog or other molecule targeting regulation of the injury response to reduce inflammation and/or fibrosis may be administered by oral or intranasal inhalation for direct delivery to the lung or tissues immediately downstream of the nasal or pulmonary compartments. By another non-limiting example, CC-930 (Jun kinase inhibitor), analog or other Jun kinase inhibitor to reduce tumor stroma and/or the inflammatory response may be administered by oral or intranasal inhalation for direct delivery to the lung or tissues immediately downstream of the nasal or pulmonary compartments. By another non-limiting example, imatinib (a.k.a. Gleeve or Glivec (tyrosin kinase inhibitor)), analog or other tyrosine inhibitor to inhibit lung fibroblast-myofibroblast transformation and proliferation as well as extracellular matrix production and tumor stroma formation/maintenance through inhibition of PDFG and transforming growth factor (TGF)-β signaling may be administered by oral or intranasal inhalation for direct delivery to the lung or tissues immediately downstream of the nasal or pulmonary compartments. By another non-limiting example, STX-100 (monoclonal antibody targeting integrin alpha-v beta-6), analog or other antibody targeting integrin alpha-v beta-6 or other integrin to reduce tumor stroma and/or fibrosis may be administered by oral or intranasal inhalation for direct delivery to the lung or tissues immediately downstream of the nasal or pulmonary compartments. By another non-limiting example, QAX576 (monoclonal antibody targeting interleukin 13 [IL-13]), analog or other antibody targeting IL-13 to reduce tumor stroma and/or inflammation may be administered by oral or intranasal inhalation for direct delivery to the lung or tissues immediately downstream of the nasal or pulmonary compartments. By another non-limiting example, FG-3019 (monoclonal antibody targeting connective tissue growth factor [CTGF]), analog or other antibody targeting CTGF to reduce tumor stroma and/or fibrosis may be administered by oral or intranasal inhalation for direct delivery to the lung or tissues immediately downstream of the nasal or pulmonary compartments. By another non-limiting example, CNTO-888 (a monoclonal antibody targeting chemokine [C—C motif] ligand 2 [CCL2]), analog or other antibody targeting CCL2 to reduce tumor stroma and/or fibrosis may be administered by oral or intranasal inhalation for direct delivery to the lung or tissues immediately downstream of the nasal or pulmonary compartments. By another non-limiting example, BIBF-1120 (also known as Vargatef; a triple kinase inhibitor targeting vascular endothelial growth factor [VEGF], platelet-derived growth factor [PDGF] and fibroblast growth factor [FGF]), analog or other triple kinase inhibitor to reduce tumor stroma and/or fibrosis and/or inflammation may be administered by oral or intranasal inhalation for direct delivery to the lung or tissues immediately downstream of the nasal or pulmonary compartments.

As shown as a promising approach to treat cancer and pulmonary arterial hypertension, to enable "cocktail therapy" or "cocktail prophylaxis" in pulmonary hypertension secondary to fibrotic disease, more specifically Type 3 Pulmonary Hypertension, methods to administer pirfenidone or pyridone analog as either co-administered, adminstered sequentially, or co-prescribed (such that medicines are requested by a prescribing physician to be taken in some sequence as combination therapy to treat the same disease) with agents targeting pulmonary hypertension, fibrotic or inflammatory disease are described. By non-limiting example, pirfenidone or pyridone analog is administered either in fixed combination, co-administered, adminstered sequentially, or co-prescribed with the monoclonal GS-6624 (formerly known as AB0024), analog or another antibody targeting LOXL2 protein associated with connective tissue biogenesis to reduce inflammation, pulmonary hypertension and/or fibrosis. By another non-limiting example, pirfenidone or pyridone analog is administered either in fixed combination, co-administered, adminstered sequentially, or co-prescribed with IW001 (Type V collagen), analog or other collagen targeting immunogenic tolerance to reduce inflammation, pulmonary hypertension and/or fibrosis. By another non-limiting example, pirfenidone or pyridone analog is administered either in fixed combination, co-administered, adminstered sequentially, or co-prescribed with PRM-151 (recombinant pentraxin-2), analog or other molecule targeting regulation of the injury response to reduce inflammation, pulmonary hypertension and/or fibrosis. By another non-limiting example, pirfenidone or pyridone analog is administered either in fixed combination, co-administered, adminstered sequentially, or co-prescribed with CC-930 (Jun kinase inhibitor), analog or other Jun kinase inhibitor to reduce the inflammatory response. By another non-limiting example, pirfenidone or pyridone analog is administered either in fixed combination, co-administered, adminstered sequentially, or co-prescribed with imatinib (a.k.a. Gleeve or Glivec (tyrosin kinase inhibitor)), analog or other tyrosine inhibitor to inhibit lung fibroblast-myofibroblast transformation and proliferation as well as extracellular matrix production and pulmonary hypertension formation/maintenance through inhibition of PDFG and transforming growth factor (TGF)-β signaling. By another non-limiting example, pirfenidone or pyridone analog is administered either in fixed combination, co-administered, adminstered sequentially, or co-prescribed with STX-100 (monoclonal antibody targeting integrin alpha-v beta-6), analog or other antibody targeting integrin alpha-v beta-6 or other integrin to reduce pulmonary hypertension and/or fibrosis. By another non-limiting example, pirfenidone or pyridone analog is administered either in fixed combination, co-administered, adminstered sequentially, or co-prescribed with QAX576 (monoclonal antibody targeting interleukin 13 [IL-13]), analog or other antibody targeting IL-13 to reduce pulmonary hypertension and/or inflammation. By another non-limiting example, pirfenidone or pyridone analog is administered either in fixed combination, co-administered, adminstered sequentially, or co-prescribed with FG-3019 (monoclonal antibody targeting connective tissue growth factor [CTGF]), analog or other antibody targeting CTGF to reduce pulmonary hypertension and/or fibrosis. By another non-limiting example, pirfenidone or pyridone analog is administered either in fixed combination, co-administered, adminstered sequentially, or co-prescribed with CNTO-888 (a monoclonal antibody targeting chemokine [C—C motif] ligand 2 [CCL2]), analog or other antibody targeting CCL2 to reduce pulmonary hypertension and/or fibrosis. By another non-limiting example, pirfenidone or pyridone analog is administered either in fixed combination, co-administered, adminstered sequentially, or co-prescribed with Esbriet, Pirespa or Pirfenex (trade names for pirfenidone), or analog targeting inflammation, pulmonary hypertension and/or fibrosis. By another non-limiting example, pirfenidone or pyridone analog is administered either in fixed combination, co-administered, adminstered sequentially, or co-prescribed with BIBF-1120 (also known as Vargatef; a triple kinase inhibitor targeting vascular endothelial growth factor [VEGF], platelet-derived growth factor [PDGF] and fibroblast growth factor [FGF]), analog or other triple kinase inhibitor to reduce fibrosis, pulmonary hypertension and/or inflammation. By another non-limiting example, pirfenidone or pyridone analog is administered either in fixed combination, co-administered, adminstered sequentially, or co-prescribed with an endothelin receptor antagonist (e.g., bosentan or ambrisentan) to treat pulmonary hypertension in association with cancer, tumor stroma or fibrosis. By another non-limiting example, pirfenidone or pyridone analog is administered either in fixed combination, co-administered, adminstered sequentially, or co-prescribed with a PDE5 inhibitor (e.g. sildenafil, vardenafil and tadalafil) to treat pulmonary hypertension in association with cancer, tumor stroma or fibrosis. By another non-limiting example, pirfenidone or pyridone analog is administered either in fixed combination, co-administered, adminstered sequentially, or co-prescribed with a prostinoid (e.g. epoprostenol, iloprost and treprostinin) to treat pulmonary hypertension in association with cancer, tumor stroma or fibrosis. By another non-limiting example, pirfenidone or pyridone analog is administered either in fixed combination, co-administered, adminstered sequentially, or co-prescribed with a nitric oxide or nitric oxide-donating compound (e.g., nitrate, nitrite or inhaled nitrite) to treat pulmonary hypertension in association with cancer, tumor stroma or fibrosis.

As with administration of pirfenidone, oral and parenteral routes of administration (by non-limiting example, intravenous and subcutaneous) of other compounds, molecules and antibodies targeting the reduction of inflammation, pulmonary hypertension and/or fibrosis is often associated with, by non-limiting example, adverse reactions such as gastrointestinal side effects, liver, kidney, skin, cardiovascular or other toxicities. As described herein for pirfenidone or pyridone analogs, the benefits of oral or intranasal inhalation directly to the lung or tissues immediately downstream of the nasal and/or pulmonary compartments will also benefit these compounds. Therefore, by non-limiting example, the monoclonal GS-6624 (formerly known as AB0024), analog or another antibody targeting LOXL2 protein associated with connective tissue biogenesis to reduce inflammation, pulmonary hypertension and/or fibrosis may be adminstered by oral or intranasal inhalation for direct delivery to the lung or tissues immediately downstream of the nasal or pulmonary compartments. By another non-limiting example, PRM-151 (recombinant pentraxin-2), analog or other molecule targeting regulation of the injury response to reduce inflammation, pulmonary hypertension and/or fibrosis may be administered by oral or intranasal inhalation for direct delivery to the lung or tissues immediately downstream of the nasal or pulmonary compartments. By another non-limiting example, CC-930 (Jun kinase inhibitor), analog or other Jun kinase inhibitor to reduce pulmonary hypertension and/or the inflammatory response may be administered by oral or intranasal inhalation for direct delivery to the lung or tissues immediately downstream of the nasal or pulmonary compartments. By another non-limiting example, imatinib (a.k.a. Gleeve or Glivec (tyrosin kinase inhibitor)), analog or other tyrosine inhibitor to inhibit lung fibroblast-myofibroblast transformation and proliferation as well as extracellular matrix production and pulmonary hypertension through inhibition of PDFG and transforming growth factor (TGF)-β signaling may be administered by oral or intranasal inhalation for direct delivery to the lung or tissues immediately downstream of the nasal or pulmonary compartments. By another non-limiting example, STX-100 (monoclonal antibody targeting integrin alpha-v beta-6), analog or other antibody targeting integrin alpha-v beta-6 or other integrin to reduce pulmonary hypertension and/or fibrosis may be administered by oral or intranasal inhalation for direct delivery to the lung or tissues immediately downstream of the nasal or pulmonary compartments. By another non-limiting example, QAX576 (monoclonal antibody targeting interleukin 13 [IL-13]), analog or other antibody targeting IL-13 to reduce pulmonary hypertension and/or inflammation may be administered by oral or intranasal inhalation for direct delivery to the lung or tissues immediately downstream of the nasal or pulmonary compartments. By another non-limiting example, FG-3019 (monoclonal antibody targeting connective tissue growth factor [CTGF]), analog or other antibody targeting CTGF to reduce pulmonary hypertension and/or fibrosis may be administered by oral or intranasal inhalation for direct delivery to the lung or tissues immediately downstream of the nasal or pulmonary compartments. By another non-limiting example, CNTO-888 (a monoclonal antibody targeting chemokine [C—C motif] ligand 2 [CCL2]), analog or other antibody targeting CCL2 to reduce pulmonary hypertension and/or fibrosis may be administered by oral or intranasal inhalation for direct delivery to the lung or tissues immediately downstream of the nasal or pulmonary compartments. By another non-limiting example, BIBF-1120 (also known as Vargatef; a triple kinase inhibitor targeting vascular endothelial growth factor [VEGF], platelet-derived growth factor [PDGF] and fibroblast growth factor [FGF]), analog or other triple kinase inhibitor to reduce pulmonary hypertension and/or fibrosis and/or inflammation may be administered by oral or intranasal inhalation for direct delivery to the lung or tissues immediately downstream of the nasal or pulmonary compartments. By another non-limiting example, an endothelin receptor antagonist (e.g., bosentan or ambrisentan) to treat pulmonary hypertension in association with cancer, tumor stroma or fibrosis. By another non-limiting example, a PDE5 inhibitor (e.g. sildenafil, vardenafil and tadalafil) to treat pulmonary hypertension in association with cancer, tumor stroma or fibrosis. By another non-limiting example, a prostinoid (e.g. epoprostenol, iloprost and treprostinin) to treat pulmonary hypertension in association with cancer, tumor stroma or fibrosis. By another non-limiting example, a nitric oxide or nitric oxide-donating compound (e.g., nitrate, nitrite or inhaled nitrite) to treat pulmonary hypertension in association with cancer, tumor stroma or fibrosis.

As shown as a promising approach to treat cancer and pulmonary arterial hypertension, to enable "cocktail therapy" or "cocktail prophylaxis" in cancer, more specifically lung cancer, methods to administer pirfenidone or pyridone analog as either co-administered, administered sequentially, or co-prescribed (such that medicines are requested by a prescribing physician to be taken in some sequence as combination therapy to treat the same disease) with agents targeting cancer are described. Anti-cancer agents may include gefitinib (Iressa, also known as ZD1839). Gefitinib is a selective inhibitor of epidermal growth factor receptor's (EGFR) tyrosine kinase domain. The target protein (EGFR) is a family of receptors which includes Her1(erb-B1), Her2(erb-B2), and Her 3(erb-B3). EGFR is overexpressed in the cells of certain types of human carcinomas—for example in lung and breast cancers. This leads to inappropriate activation of the anti-apoptotic Ras signalling cascade, eventually leading to uncontrolled cell proliferation. Research on gefitinib-sensitive non-small cell lung cancers has shown that a mutation in the EGFR tyrosine kinase domain is responsible for activating anti-apoptotic pathways. These mutations tend to confer increased sensitivity to tyrosine kinase inhibitors such as gefitinib and erlotinib. Of the types of non-small cell lung cancer histologies, adenocarcinoma is the type that most often harbors these mutations. These mutations are more commonly seen in Asians, women, and non-smokers (who also tend to more often have adenocarcinoma). Gefitinib inhibits EGFR tyrosine kinase by binding to the adenosine triphosphate (ATP)-binding site of the enzyme. Thus the function of the EGFR tyrosine kinase in activating the anti-apoptotic Ras signal transduction cascade is inhibited, and malignant cells are inhibited. While gefitinib has yet to be proven to be effective in other cancers, there is potential for its use in the treatment of other cancers where EGFR overexpression is involved. As gefitinib is a selective chemotherapeutic agent, its tolerability profile is better than previous cytotoxic agents. Adverse drug reactions (ADRs) are acceptable for a potentially fatal disease. Acne-like rash is reported very commonly. Other common adverse effects include: diarrhoea, nausea, vomiting, anorexia, stomatitis, dehydration, skin reactions, paronychia, asymptomatic elevations of liver enzymes, asthenia, conjunctivitis, blepharitis. Infrequent adverse effects include: interstitial lung disease, corneal erosion, aberrant eyelash and hair growth.

Another anti-cancer agent is Erlotinib (also known as Tarceva). Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor. For the signal to be transmitted, two EGFR molecules need to come together to form a homodimer. These then use the molecule of ATP to trans-phosphorylate each other on tyrosine residues, which generates phosphotyrosine residues, recruiting the phosphotyrosine-binding proteins to EGFR to assemble protein complexes that transduce signal cascades to the nucleus or activate other cellular biochemical processes. By inhibiting the ATP, formation of phosphotyrosine residues in EGFR is not possible and the signal cascades are not initiated. Erlotinib has shown a survival benefit in the treatment of lung cancer. Erlotinib is approved for the treatment of locally advanced or metastatic non-small cell lung cancer that has failed at least one prior chemotherapy regimen. It is also approved in combination with gemcitabine for treatment of locally advanced, unresectable, or metastatic pancreatic cancer. In lung cancer, erlotinib has been shown to be effective in patients with or without EGFR mutations, but appears to be more effective in the group of patients with EGFR mutations. The response rate among EGFR mutation positive patients is approximately 60%. Patients who are non-smokers, and light former smokers, with adenocarcinoma or subtypes like BAC are more likely to have EGFR mutations, but mutations can occur in all types of patients. EGFR positive patients are generally KRAS negative. Erlotinib has recently been shown to be a potent inhibitor of JAK2V617F activity. JAK2V617F is a mutant of tyrosine kinase JAK2, is found in most patients with polycythemia vera (PV) and a substantial proportion of patients with idiopathic myelofibrosis or essential thrombocythemia. The study suggests that erlotinib may be used for treatment of JAK2V617F-positive PV and other myeloproliferative disorder. Rash occurs in the majority of patients. This resembles acne and primarily involves the face and neck. It is self-limited and resolves in the majority of cases, even with continued use. Interestingly, some clinical studies have indicated a correlation between the severity of the skin reactions and increased survival though this has not been quantitatively assessed. Cutaneous rash may be a surrogate marker of clinical benefit. Other side effects include diarrhea, loss of appetite, fatigue, rarely, interstitial pneumonitis, which is characterized by cough and increased dyspnea. This may be severe and must be considered among those patients whose breathing acutely worsens. It has also been suggested that erlotinib can cause hearing loss. Rare side effects include serious gastrointestinal tract, skin, and ocular disorders. In addition, some people prescribed erlotinib have developed serious or fatal gastrointestinal tract perforations; "bullous, blistering, and exfoliative skin conditions, some fatal; and serious eye problems such as corneal lesions. Some of the cases, including ones which resulted in death, were suggestive of Stevens-Johnson syndrome/toxic epidermal necrolysis. Erlotinib is mainly metabolized by the liver enzyme CYP3A4. Compounds which induce this enzyme (i.e. stimulate its production), such as St John's wort, can lower erlotinib concentrations, while inhibitors can increase concentrations. As with other ATP competitive small molecule tyrosine kinase inhibitors, such as imatinib in CML, patients rapidly develop resistance. In the case of erlotinib this typically occurs 8-12 months from the start of treatment. Over 50% of resistance is caused by a mutation in the ATP binding pocket of the EGFR kinase domain involving substitution of a small polar threonine residue with a large nonpolar methionine residue (T790M). While proponents of the 'gatekeeper' mutation hypothesis suggest this mutation prevents the binding of erlotinib through steric hindrance, research suggests that T790M confers an increase in ATP binding affinity reducing the inhibitory effect of erlotinib. Approximately 20% of drug resistance is caused by amplification of the hepatocyte growth factor receptor, which drives ERBB3 dependent activation of PI3K. Other cases of resistance can involve numerous mutations, including recruitment of a mutated IGF-1 receptor to homodimerize with EGFR so forming a heterodimer. This allows activation of the downstream effectors of EGFR even in the presence of an EGFR inhibitor. Some IGR-1R inhibitors are in various stages of development (based either around TKIs such as AG1024 or AG538 or pyrrolo[2,3-d]-pyrimidine derivatives such as NVP-AEW541). The monoclonal antibody figitumumab which targets the IGF-1R is currently undergoing clinical trials. Another cause of resistance can be inactivating mutations of the PTEN tumor suppressor which allow increased activation of Akt independent of stimulation by EGFR. The most promising approach to combating resistance is likely to be combination therapy. Commencing treatment with a number of different therapeutic agents with differing modes of action is thought to provide the best defense against development of T790M and other resistance conferring mutations.

Another anti-cancer agent is Bortezomib (originally codenamed PS-341; marketed as Velcade and Bortecad). Bortezomib is the first therapeutic proteasome inhibitor to be tested in humans. It is approved in the U.S. for treating relapsed multiple myeloma and mantle cell lymphoma. In multiple myeloma, complete clinical responses have been obtained in patients with otherwise refractory or rapidly advancing disease. Bortezomib was originally synthesized as MG-341. After promising preclinical results, the drug (PS-341) was tested in a small Phase I clinical trial on patients with multiple myeloma cancer. Bortezomib (Velcade) is approved for use in multiple myeloma. Another commercially available bortezomib product—Bortenat, reportedly contains substantially more active entity than declared, potentially and even more resulting in increased toxicity. Moreover, Bortenat has some other chemical and formulation deviations from the registered ethic product Velcade, with unclear clinical impact. The boron atom in bortezomib binds the catalytic site of the 26S proteasome with high affinity and specificity. In normal cells, the proteasome regulates protein expression and function by degradation of ubiquitylated proteins, and also cleanses the cell of abnormal or misfolded proteins. Clinical and preclinical data support a role in maintaining the immortal phenotype of myeloma cells, and cell-culture and xenograft data support a similar function in solid tumor cancers. While multiple mechanisms are likely to be involved, proteasome inhibition may prevent degradation of pro-apoptotic factors, permitting activation of programmed cell death in neoplastic cells dependent upon suppression of pro-apoptotic pathways. Recently, it was found that bortezomib caused a rapid and dramatic change in the levels of intracellular peptides that are produced by the proteasome. Some intracellular peptides have been shown to be biologically active, and so the effect of bortezomib on the levels of intracellular peptides may contribute to the biological and/or side effects of the drug. Bortezomib is rapidly cleared following intravenous administration. Peak concentrations are reached at about 30 minutes. Drug levels can no longer be measured after an hour. Pharmacodynamics are measured by measuring proteasome inhibition in peripheral blood mononuclear cells. The much greater sensitivity of myeloma cell lines and mantle cell lines to proteasome inhibition compared with normal peripheral blood mononuclear cells and most other cancer cell lines is poorly understood. Bortezomib is associated with peripheral neuropathy in 30% of patients; occasionally, it can be painful. This can be worse in patients with pre-existing neuropathy. In addition, myelosuppression causing neutropenia and thrombocytopenia can also occur and be dose-limiting. However, these side effects are usually mild relative to bone marrow transplantation and other treatment options for patients with advanced disease. Bortezomib is associated with a high rate of shingles, although prophylactic acyclovir can reduce the risk of this. Gastro-intestinal effects and asthenia are the most common adverse events. The established the efficacy of bortezomib is 1.3 mg/m2 (with or without dexamethasone) administered by intravenous bolus on days 1, 4, 8, and 11 of a 21-day cycle for a maximum of eight cycles in heavily pretreated patients with relapsed/refractory multiple myeloma. The demonstrated superiority of bortezomib is 1.3 mg/m2 over a high-dose dexamethasone regimen (by example median TTP 6.2 vs 3.5 months, and 1-year survival 80% vs. 66%). Laboratory studies and clinical trials are investigating whether it might be possible to further increase the anticancer potency of bortezomib by combining it with novel types of other pharmacologic agents. For example, clinical trials have indicated that the addition of thalidomide, lenalidomide, inhibitors of vascular endothelial growth factor (VEGF), or arsenic trioxide might be beneficial. In laboratory studies, it was found that bortezomib killed multiple myeloma cells more efficiently when combined, for example, with histone deacetylase inhibitors, thapsigargin, or celecoxib. There is preclinical evidence that bortezomib is synergistic with Reolysin in pancreatic cancer. However, the therapeutic efficacy and safety of any of these latter combinations has not yet been evaluated in cancer patients.

Another family of anti-cancer agent are Janus kinase inhibitors. Also known as JAK inhibitors, these are a type of medication that functions by inhibiting the activity of one or more of the Janus kinase family of enzymes (JAK1, JAK2, JAK3, TYK2), thereby interfering with the JAK-STAT signaling pathway. These inhibitors have therapeutic application in the treatment of cancer and inflammatory diseases. Cytokines play key roles in controlling cell growth and the immune response. Many cytokines function by binding to and activating type I and type II cytokine receptors. These receptors in turn rely on the Janus kinase (JAK) family of enzymes for signal transduction. Hence drugs that inhibit the activity of these Janus kinases block cytokine signaling. More specifically, Janus kinases phosphorylate activated cytokine receptors. These phosphorylated receptor in turn recruit STAT transcription factors which modulate gene transcription. The first JAK inhibitor to reach clinical trials was tofacitinib. Tofacitinib is a specific inhibitor of JAK3 (IC50=2 nM) thereby blocking the activity of IL-2, IL-4, IL-15 and IL-21. Hence Th2 cell differentiation is blocked and therefore tofacitinib is effective in treating allergic diseases. Tofacitinib to a lesser extent also inhibits JAK1 (IC50=100 nM) and JAK2 (IC50=20 nM) which in turn blocks IFN-γ and IL-6 signaling and consequently Th1 cell differentiation. Examples of JAK inhibitors include: Ruxolitinib against JAK1/JAK2 for psoriasis, myelofibrosis, and rheumatoid arthritis; Tofacitinib (tasocitinib; CP-690550) against JAK3 for psoriasis and rheumatoid arthritis; Baricitinib (LY3009104, INCB28050) against JAK1/JAK2 for rheumatoid arthritis; CYT387 against JAK2 for myeloproliferative disorders; Lestaurtinib against JAK2, for acute myelogenous leukemia (AML); Pacritinib (SB1518) against JAK2 for relapsed lymphoma and advanced myeloid malignancies, chronic idiopathic myelofibrosis (CIMF); and TG101348 against JAK2 for myelofibrosis.

Another family of anti-cancer agent is ALK inhibitors. ALK inhibitors are potential anti-cancer drugs that act on tumors with variations of anaplastic lymphoma kinase (ALK) such as an EML4-ALK translocation. About 7% of Non-small cell lung carcinomas (NSCLC) have EML4-ALK translocations. Examples of ALK inhibitors include: Crizotinib (trade name Xalkori) is approved for NSCLC; AP26113 is at the preclinical stage; and LDK378 is developed by Novartis as the second-generation ALK inhibitor. NPM-ALK is a different variation/fusion of ALK that drives anaplastic large-cell lymphomas (ALCLs) and is the target of other ALK inhibitors. Crizotinib has an aminopyridine structure, and functions as a protein kinase inhibitor by competitive binding within the ATP-binding pocket of target kinases. About 4% of patients with non-small cell lung carcinoma have a chromosomal rearrangement that generates a fusion gene between EML4 ('echinoderm microtubule-associated protein-like 4') and ALK ('anaplastic lymphoma kinase'), which results in constitutive kinase activity that contributes to carcinogenesis and seems to drive the malignant phenotype. The kinase activity of the fusion protein is inhibited by crizotinib. Patients with this gene fusion are typically younger non-smokers who do not have mutations in either the epidermal growth factor receptor gene (EGFR) or in the K-Ras gene. The number of new cases of ALK-fusion NSLC is about 9,000 per year in the U.S. and about 45,000 worldwide. ALK mutations are thought to be important in driving the malignant phenotype in about 15% of cases of neuroblastoma, a rare form of peripheral nervous system cancer that occurs almost exclusively in very young children. Crizotinib inhibits the c-Met/Hepatocyte growth factor receptor (HGFR) tyrosine kinase, which is involved in the oncogenesis of a number of other histological forms of malignant neoplasms. Crizotinib is currently thought to exert its effects through modulation of the growth, migration, and invasion of malignant cells. Other studies suggest that crizotinib might also act via inhibition of angiogenesis in malignant tumors. Crizotinib caused tumors to shrink or stabilize in 90% of 82 patients carrying the ALK fusion gene. Tumors shrank at least 30% in 57% of people treated. Most had adenocarcinoma, and had never smoked or were former smokers. They had undergone treatment with an average of three other drugs prior to receiving crizotinib, and only 10% were expected to respond to standard therapy. They were given 250 mg crizotinib twice daily for a median duration of six months. Approximately 50% of these patients suffered at least one side effect, such as nausea, vomiting, or diarrhea. Some responses to crizotinib have lasted up to 15 months. A phase 3 trial, PROFILE 1007, compares crizotinib to standard second line chemotherapy (pemetrexed or taxotere) in the treatment of ALK-positive NSCLC. Additionally, a phase 2 trial, PROFILE 1005, studies patients meeting similar criteria who have received more than one line of prior chemotherapy. Crizotinib (Xalkori) is approved to treat certain late-stage (locally advanced or metastatic) non-small cell lung cancers that express the abnormal anaplastic lymphoma kinase (ALK) gene. Approval required a companion molecular test for the EML4-ALK fusion.

Another anti-cancer agent is Crizotinib. Crizotinib is also being tested in clinical trials of advanced disseminated anaplastic large-cell lymphoma, and neuroblastoma.

An anti-cancer target includes Bcl-2 (B-cell lymphoma 2). Encoded by the BCL2 gene, is the founding member of the Bcl-2 family of regulator proteins that regulate cell death (apoptosis). Bcl-2 derives its name from B-cell lymphoma 2, as it is the second member of a range of proteins initially described in chromosomal translocations involving chromosomes 14 and 18 in follicular lymphomas. Bcl-2 orthologs have been identified in numerous mammals for which complete genome data are available. The two isoforms of Bcl-2, Isoform 1, also known as 1G5M, and Isoform 2, also known as 1G5O/1GJH, exhibit similar fold. However, results in the ability of these isoforms to bind to the BAD and BAK proteins, as well as in the structural topology and electrostatic potential of the binding groove, suggest differences in antiapoptotic activity for the two isoforms. Damage to the Bcl-2 gene has been identified as a cause of a number of cancers, including melanoma, breast, prostate, chronic lymphocytic leukemia, and lung cancer, and a possible cause of schizophrenia and autoimmunity. It is also a cause of resistance to cancer treatments. Cancer occurs as the result of a disturbance in the homeostatic balance between cell growth and cell death. Over-expression of anti-apoptotic genes, and under-expression of pro-apoptotic genes, can result in the lack of cell death that is characteristic of cancer. An example can be seen in lymphomas. The over-expression of the anti-apoptotic Bcl-2 protein in lymphocytes alone does not cause cancer. But simultaneous over-expression of Bcl-2 and the proto-oncogene myc may produce aggressive B-cell malignancies including lymphoma. In follicular lymphoma, a chromosomal translocation commonly occurs between the fourteenth and the eighteenth chromosomes—t(14;18)—which places the Bcl-2 gene next to the immunoglobulin heavy chain locus. This fusion gene is deregulated, leading to the transcription of excessively high levels of Bcl-2. This decreases the propensity of these cells for undergoing apoptosis. Apoptosis also plays a very active role in regulating the immune system. When it is functional, it can cause immune unresponsiveness to self-antigens via both central and peripheral tolerance. In the case of defective apoptosis, it may contribute to etiological aspects of autoimmune diseases. The autoimmune disease, type 1 diabetes can be caused by defective apoptosis, which leads to aberrant T cell AICD and defective peripheral tolerance. Due to the fact that dendritic cells are the most important antigen presenting cells of the immune system, their activity must be tightly regulated by such mechanisms as apoptosis. Researchers have found that mice containing dendritic cells that are Bim −/−, thus unable to induce effective apoptosis, obtain autoimmune diseases more so than those that have normal dendritic cells. Other studies have shown that the lifespan of dendritic cells may be partly controlled by a timer dependent on anti-apoptotic Bcl-2. Apoptosis plays a very important role in regulating a variety of diseases that have enormous social impacts. For example, schizophrenia is a neurodegenerative disease that may result from an abnormal ratio of pro- and anti-apoptotic factors. There is some evidence that this defective apoptosis may result from abnormal expression of Bcl-2 and increased expression of caspase-3. Further research into the family of Bcl-2 proteins will provide a more complete picture on how these proteins interact with each other to promote and inhibit apoptosis. An understanding of the mechanisms involved may help develop new therapies for treating cancer, autoimmune conditions, and neurological diseases. Bcl-2 inhibitors include: An antisense oligonucleotide drug Genasense (G3139) that targets Bcl-2. An antisense DNA or RNA strand is non-coding and complementary to the coding strand (which is the template for producing respectively RNA or protein). An antisense drug is a short sequence of RNA that hybridises with and inactivates mRNA, preventing the protein from being formed. It was shown that the proliferation of human lymphoma cells (with t(14;18) translocation) could be inhibited by antisense RNA targeted at the start codon region of Bcl-2 mRNA. In vitro studies led to the identification of Genasense, which is complementary to the first 6 codons of Bcl-2 mRNA. Another BCL-2 inhibitor is ABT-73. ABT-73 is a novel inhibitor of Bcl-2, Bcl-xL and Bcl-w, known as ABT-737. ABT-737 is one among many so-called BH3 mimetic small molecule inhibitors (SMI) targeting Bcl-2 and Bcl-2-related proteins such as Bcl-xL and Bcl-w but not A1 and Mcl-1, which may prove valuable in the therapy of lymphoma and other blood cancers. Another inhibitor is ABT-199. ABT-199 is a so-called BH3-mimetic drug designed to block the function of the Bcl-2 protein in patients with chronic lymphocytic leukemia. Another Bcl-2 inhibitors is obatoclax (GX15-070) for small-cell lung cancer. By inhibiting Bcl-2, Obatoclax induces apoptosis in cancer cells, preventing tumor growth.

Another family of anti-cancer agents are PARP inhibitors. PARP inhibitors are a group of pharmacological inhibitors of the enzyme poly ADP ribose polymerase (PARP). They are developed for multiple indications; the most important is the treatment of cancer. Several forms of cancer are more dependent on PARP than regular cells, making PARP an attractive target for cancer therapy. In addition to their use in cancer therapy, PARP inhibitors are considered a potential treatment for acute life-threatening diseases, such as stroke and myocardial infarction, as well as for long-term neurodegenerative diseases. DNA is damaged thousands of times during each cell cycle, and that damage must be repaired. BRCA1, BRCA2 and PALB2 are proteins that are important for the repair of double-strand DNA breaks by the error-free homologous recombination repair, or HRR, pathway. When the gene for either protein is mutated, the change can lead to errors in DNA repair that can eventually cause breast cancer. When subjected to enough damage at one time, the altered gene can cause the death of the cells. PARP1 is a protein that is important for repairing single-strand breaks ('nicks' in the DNA). If such nicks persist unrepaired until DNA is replicated (which must precede cell division), then the replication itself can cause double strand breaks to form. Drugs that inhibit PARP1 cause multiple double strand breaks to form in this way, and in tumors with BRCA1, BRCA2 or PALB2 mutations these double strand breaks cannot be efficiently repaired, leading to the death of the cells. Normal cells that don't replicate their DNA as often as cancer cells, and that lacks any mutated BRCA1 or BRCA2 still have homologous repair operating, which allows them to survive the inhibition of PARP. Some cancer cells that lack the tumor suppressor PTEN may be sensitive to PARP inhibitors because of down-regulation of Rad51, a critical homologous recombination component, although other data suggest PTEN may not regulate Rad51. Hence PARP inhibitors may be effective against many PTEN-defective tumors (e.g. some aggressive prostate cancers). Cancer cells that are low in oxygen (e.g. in fast growing tumors) are sensitive to PARP inhibitors. PARP inhibitors were originally thought to work primarily by blocking PARP enzyme activity, thus preventing the repair of DNA damage and ultimately causing cell death. PARP inhibitors have an additional mode of action: localizing PARP proteins at sites of DNA damage, which has relevance to their anti-tumor activity. The trapped PARP protein-DNA complexes are highly toxic to cells because they block DNA replication. When the researchers tested three PARP inhibitors for their differential ability to trap PARP proteins on damaged DNA, they found that the trapping potency of the inhibitors varied widely. The PARP family of proteins in humans includes PARP1 and PARP2, which are DNA binding and repair proteins. When activated by DNA damage, these proteins recruit other proteins that do the actual work of repairing DNA. Under normal conditions, PARP1 and PARP2 are released from DNA once the repair process is underway. However, as this study shows, when they are bound to PARP inhibitors, PARP1 and PARP2 become trapped on DNA. The researchers showed that trapped PARP-DNA complexes are more toxic to cells than the unrepaired single-strand DNA breaks that accumulate in the absence of PARP activity, indicating that PARP inhibitors act as PARP poisons. These findings suggest that there may be two classes of PARP inhibitors, catalytic inhibitors that act mainly to inhibit PARP enzyme activity and do not trap PARP proteins on DNA, and dual inhibitors that both block PARP enzyme activity and act as PARP poison. The main function of radiotherapy is to produce DNA strand breaks, causing severe DNA damage and leading to cell death. Radiotherapy has the potential to kill 100% of any targeted cells, but the dose required to do so would cause unacceptable side effects to healthy tissue. Radiotherapy therefore can only be given up to a certain level of radiation exposure. Combining radiation therapy with PARP inhibitors offers promise, since the inhibitors would lead to formation of double strand breaks from the single-strand breaks generated by the radiotherapy in tumor tissue with BRCA1/BRCA2 mutations. This combination could therefore lead to either more powerful therapy with the same radiation dose or similarly powerful therapy with a lower radiation dose. Examples of PARP inhibitors include: Iniparib (BSI 201) for breast cancer and squamous cell lung cancer; Olaparib (AZD-2281) for breast, ovarian and colorectal cancer; Rucaparib (AG014699, PF-01367338) for metastatic breast and ovarian cancer; Veliparib (ABT-888) for metastatic melanoma and breast cancer; CEP 9722 for non-small-cell lung cancer (NSCLC); MK 4827 which inhibits both PARP1 and PARP2; BMN-673 for advanced hematological malignancies and for advanced or recurrent solid tumors; and 3-aminobenzamide.

Another family of anti-cancer target is the PI3K/AKT/mTOR pathway. This pathway is an important signaling pathway for many cellular functions such as growth control, metabolism and translation initiation. Within this pathway there are many valuable anti-cancer drug treatment targets and for this reason it has been subject to a lot of research in recent years. A Phosphoinositide 3-kinase inhibitor (PI3K inhibitor) is a potential medical drug that functions by inhibiting a Phosphoinositide 3-kinase enzyme which is part of this pathway and therefore, through inhibition, often results in tumor suppression. There are a number of different classes and isoforms of PI3Ks. Class 1 PI3Ks have a catalytic subunit known as p110, with four types (isoforms)—p110 alpha, p110 beta, p110 gamma and p110 delta. The inhibitors being studied inhibit one or more isoforms of the class I PI3Ks. They are being actively investigated for treatment of various cancers. Examples include: Wortmannin an irreversible inhibitor of PI3K; demethoxyviridin a derivative of wortmannin; and LY294002 a reversible inhibitor of PI3K. Other PI3K inhibitors include: Perifosine, for colorectal cancer and multiple myeloma; CAL101 an oral PI3K delta for certain late-stage types of leukemia's; PX-866; IPI-145, a novel inhibitor of PI3K delta and gamma, especially for hematologic malignancies; BAY 80-6946, predominantly inhibiting PI3K$\alpha$,$\delta$ isoforms; BEZ235 a PI3K/mTOR dual inhibitor; RP6503, a dual PI3K delta/gamma inhibitor for the treatment of Asthma and COPD; TGR 1202, oral PI3K delta inhibitor (also known as RP5264); SF1126, the first PI3KI for B-cell chronic lymphocytic leukemia (CLL); INK1117, a PI3K-alpha inhibitor; GDC-0941 IC50 of 3 nM; BKM120; XL147 (also known as SAR245408); XL765 (also known as SAR245409); Palomid 529; GSK1059615, where clinical trials were terminated due to lack of sufficient exposure following single- and repeat-dosing; ZSTK474, a potent inhibitor against p110a; PWT33597, a dual PI3K-alpha/mTOR inhibitor—for advanced solid tumors; IC87114 a selective inhibitor of p110$\delta$. It has an IC50 of 100 nM for inhibition of p110-$\delta$; TG100-115, inhibits all four isoforms but has a 5-10 fold better potency against p110-$\gamma$ and p110-$\delta$; CAL263; RP6530, a dual PI3K delta/gamma inhibitor for T-cell Lymphomas; PI-103 a dual PI3K-mTOR inhibitor; GNE-477, a PI3K-alpha and mTOR inhibitor with IC50 values of 4 nM and 21 nM; CUDC-907, also an HDAC inhibitor; and AEZS-136, which also inhibits Erk1/2.

Another anti-cancer agent is Apatinib. Also known as YN968D1, Apatinib is a tyrosine kinase inhibitor that selectively inhibits the vascular endothelial growth factor receptor-2 (VEGFR2, also known as KDR). It is an orally bioavailable, small molecule agent which is thought to inhibit angiogenesis in cancer cells; specifically apatinib inhibits VEGF-mediated endothelial cell migration and proliferation thus blocking new blood vessel formation in tumor tissue. This agent also mildly inhibits c-Kit and c-SRC tyrosine kinases. Apatinib is an investigational cancer drug currently undergoing clinical trials as a potential targeted treatment for metastatic gastric carcinoma, metastatic breast cancer and advanced hepatocellular carcinoma. Cancer patients were administered varied doses of Apatinib daily for 28 days. Apatinib was well tolerated at doses below 750 mg/day, 3 of 3 dose limiting toxicities were reported at 1000 mg/day and the maximum tolerated dose is determined to be 850 mg/day. The investigator also reported of 65 cancer patients treated in Phase I/II, 1.54% had a complete response, 12.31% had a partial response, 66.15% had stable disease and 20% had progressive disease. A separate published report on the safety and pharmacokinetics of apatinib in Human clinical studies concludes that it has encouraging antitumor activity across a broad range of cancer types. Some cancer cells have the ability to develop resistance to the cytotoxic effects of certain cancer drugs (called multidrug resistance). A study concluded that apatinib may be useful in circumventing cancer cells' multidrug resistance to certain conventional antineoplastic drugs. The study showed that apatinib reverses the ABCB1- and ABCG2-mediated multidrug resistance by inhibiting those functions and increasing the intracellular concentrations of the antineoplastic drugs. This study suggests that apatinib will be potentially effective in combination therapies with conventional anticancer drugs especially in cases where resistance to chemotherapy exists.

Another family of anti-cancer target is BRAF. BRAF is a human gene that encodes B-Raf. The gene is also referred to as proto-oncogene B-Raf and v-Raf murine sarcoma viral oncogene homolog B1, while the protein is more formally known as serine/threonine-protein kinase B-Raf. The B-Raf protein is involved in sending signals inside cells, which are involved in directing cell growth. In 2002, it was shown to be faulty (mutated) in human cancers. Certain other inherited BRAF mutations cause birth defects. Drugs that treat cancers driven by BRAF have been developed. Vemurafenib and dabrafenib are approved for late-stage melanoma. B-Raf is a member of the Raf kinase family of growth signal transduction protein kinases. This protein plays a role in regulating the MAP kinase/ERKs signaling pathway, which affects cell division, differentiation, and secretion. B-Raf is a 766-amino acid, regulated signal transduction serine/threonine-specific protein kinase. Broadly speaking, it is composed of three conserved domains characteristic of the Raf kinase family: conserved region 1 (CR1), a Ras-GTP-binding self-regulatory domain, conserved region 2 (CR2), a serine-rich hinge region, and conserved region 3 (CR3), a catalytic protein kinase domain that phosphorylates a consensus sequence on protein substrates. In its active conformation, B-Raf forms dimers via hydrogen-bonding and electrostatic interactions of its kinase domains. B-Raf is a serine/threonine-specific protein kinase. As such, it catalyzes the phosphorylation of serine and threonine residues in a consensus sequence on target proteins by ATP, yielding ADP and a phosphorylated protein as products. Since it is a highly regulated signal transduction kinase, B-Raf must first bind Ras-GTP before becoming active as an enzyme. Once B-Raf is activated, a conserved protein kinase catalytic core phosphorylates protein substrates by promoting the nucleophilic attack of the activated substrate serine or threonine hydroxyl oxygen atom on the $\gamma$-phosphate group of ATP through bimolecular nucleophilic substitution. To effectively catalyze protein phosphorylation via the bimolecular substitution of serine and threonine residues with ADP as a leaving group, B-Raf must first bind ATP and then stabilize the transition state as the $\gamma$-phosphate of ATP is transferred. Since constitutively active B-Raf mutants commonly cause cancer (see Clinical Significance) by excessively signaling cells to grow, inhibitors of B-Raf have been developed for both the inactive and active conformations of the kinase domain as cancer therapeutic candidates. BAY43-9006 (Sorafenib, Nexavar) is a V600E mutant B-Raf and C-Raf inhibitor approved by the FDA for the treatment of primary liver and kidney cancer. Bay43-9006 disables the B-Raf kinase domain by locking the enzyme in its inactive form. The inhibitor accomplishes this by blocking the ATP binding pocket through high-affinity for the kinase domain. It then binds key activation loop and DFG motif residues to stop the movement of the activation loop and DFG motif to the active conformation. Finally, a trifluoromethyl phenyl moiety sterically blocks the DFG motif and activation loop active conformation site, making it impossible for the kinase domain to shift conformation to become active. The distal pyridyl ring of BAY43-9006 anchors in the hydrophobic nucleotide-binding pocket of the kinase N-lobe, interacting with W531, F583, and F595. The hydrophobic interactions with catalytic loop F583 and DFG motif F595 stabilize the inactive conformation of these structures, decreasing the likelihood of enzyme activation. Further hydrophobic interaction of K483, L514, and T529 with the center phenyl ring increase the affinity of the kinase domain for the inhibitor. Hydrophobic interaction of F595 with the center ring as well decreases the energetic favorability of a DFG conformation switch further. Finally, polar interactions of BAY43-9006 with the kinase domain continue this trend of increasing enzyme affinity for the inhibitor and stabilizing DFG residues in the inactive conformation. E501 and C532 hydrogen bond the urea and pyridyl groups of the inhibitor respectively while the urea carbonyl accepts a hydrogen bond from D594's backbone amide nitrogen to lock the DFG motif in place. The trifluoromethyl phenyl moiety cements the thermodynamic favorability of the inactive conformation when the kinase domain is bound to BAY43-9006 by sterically blocking the hydrophobic pocket between the $\alpha C$ and $\alpha E$ helices that the DFG motif and activation loop would inhabit upon shifting to their locations in the active conformation of the protein. PLX4032 (Vemurafenib) is a V600 mutant B-Raf inhibitor approved by the FDA for the treatment of late-stage melanoma. Unlike BAY43-9006, which inhibits the inactive form of the kinase domain, Vemurafenib inhibits the active "DFG-in" form of the kinase, firmly anchoring itself in the ATP-binding site. By inhibiting only the active form of the kinase, Vemurafenib selectively inhibits the proliferation of cells with unregulated B-Raf, normally those that cause cancer. Since Vemurafenib only differs from its precursor, PLX4720, in a phenyl ring added for pharmacokinetic reasons, PLX4720's mode of action is equivalent to Vemurafenib's. PLX4720 has good affinity for the ATP binding site partially because its anchor region, a 7-azaindole bicyclic, only differs from the natural adenine that occupies the site in two places where nitrogen atoms have been replaced by carbon. This enables strong intermolecular interactions like N7 hydrogen bonding to C532 and N1 hydrogen bonding to Q530 to be preserved. Excellent fit within the ATP-binding hydrophobic pocket (C532, W531, T529, L514, A481) increases binding affinity as well. Ketone linker hydrogen bonding to water and difluorophenyl fit in a second hydrophobic pocket (A481, V482, K483, V471, 1527, T529, L514, and F583) contribute to the exceptionally high binding affinity overall. Selective binding to active Raf is accomplished by the terminal propyl group that binds to a Raf-selective pocket created by a shift of the $\alpha C$ helix. Selectivity for the active conformation of the kinase is further increased by a pH-sensitive deprotonated sulfonamide group that is stabilized by hydrogen bonding with the backbone peptide NH of D594 in the active state. In the inactive state, the inhibitor's sulfonamide group interacts with the backbone carbonyl of that residue instead, creating repulsion. Thus, Vemurafenib binds preferentially to the active state of B-Rafs kinase domain. Mutations in the BRAF gene can cause disease in two ways. First, mutations can be inherited and cause birth defects. Second, mutations can appear later in life and cause cancer, as an oncogene. Inherited mutations in this gene cause cardiofaciocutaneous syndrome, a disease characterized by heart defects, mental retardation and a distinctive facial appearance. Acquired mutations in this gene have been found in cancers, including non-Hodgkin lymphoma, colorectal cancer, malignant melanoma, papillary thyroid carcinoma, non-small-cell lung carcinoma, and adenocarcinoma of the lung. The V600E mutation of the BRAF gene has been associated with hairy cell leukemia in numerous studies and has been suggested for use in screening for Lynch syndrome to reduce the number of patients undergoing unnecessary MLH1 sequencing. As mentioned above, some pharmaceutical firms are developing specific inhibitors of mutated B-raf protein for anticancer use because B-Raf is a well-understood, high yield target. Vemurafenib (RG7204 or PLX4032), licensed as Zelboraf for the treatment of metastatic melanoma, is the current state-of-the-art example for why active B-Raf inhibitors are being pursued as drug candidates. Vemurafenib is biochemically interesting as a mechanism to target cancer due to its high efficacy and selectivity. B-Raf not only increased metastatic melanoma patient chance of survival but raised the response rate to treatment from 7-12% to 53% in the same amount of time compared to the former best chemotherapeutic treatment: dacarbazine. In spite of the drug's high efficacy, 20% of tumors still develop resistance to the treatment. In mice, 20% of tumors become resistant after 56 days. While the mechanisms of this resistance are still disputed, some hypotheses include the overexpression of B-Raf to compensate for high concentrations of Vemurafenib and upstream upregulation of growth signaling. More general B-raf inhibitors include GDC-0879, PLX-4720, Sorafenib Tosylate, Dabrafenib and LGX818.

Another family of anti-cancer agent is the MEK inhibitor. These are a chemical or drug that inhibits the mitogen-activated protein kinase kinase enzymes MEK1 and/or MEK2. They can be used to affect the MAPK/ERK pathway which is often overactive in some cancers. Hence MEK inhibitors have potential for treatment of some cancers, especially BRAF-mutated melanoma, and KRAS/BRAF mutated colorectal cancer. Examples of MEK inhibitors include: Trametinib (GSK1120212), for treatment of BRAF-mutated melanoma and possible combination with BRAF inhibitor dabrafenib to treat BRAF-mutated melanoma; Selumetinib, for non-small cell lung cancer (NSCLC); MEK162, had phase 1 trial for biliary tract cancer and melanoma; PD-325901, for breast cancer, colon cancer, and melanoma; XL518; CI-1040 and PD035901.

Another family of anti-cancer agent is the CDK (Cyclin-dependent kinase) inhibitor. CDK inhibitors are chemicals that inhibits the function of CDKs. It is used to treat cancers by preventing overproliferation of cancer cells. In many human cancers, CDKs are overactive or CDK-inhibiting proteins are not functional. Therefore, it is rational to target CDK function to prevent unregulated proliferation of cancer cells. However, the validity of CDK as a cancer target should be carefully assessed because genetic studies have revealed that knockout of one specific type of CDK often does not affect proliferation of cells or has an effect only in specific tissue types. For example, most adult cells in mice proliferate normally even without both CDK4 and CDK2. Furthermore, specific CDKs are only active in certain periods of the cell cycle. Therefore, the pharmacokinetics and dosing schedule of the candidate compound must be carefully evaluated to maintain active concentration of the drug throughout the entire cell cycle. Types of CDK inhibitors include: Broad CDK inhibitors that target a broad spectrum of CDKs; specific CDK inhibitors that target a specific type of CDK; and multiple target inhibitors that target CDKs as well as additional kinases such as VEGFR or PDGFR. Specific examples include: P1446A-05 targeting CDK4 and PD-0332991 that targets CDK4 and CDK6 for leukemia, melanoma and solid tumors.

Another anti-cancer agent is Salinomycin. Salinomycin is an antibacterial and coccidiostat ionophore therapeutic drug. Salinomycin has been shown to kill breast cancer stem cells in mice at least 100 times more effectively than the anticancer drug paclitaxel. The study screened 16,000 different chemical compounds and found that only a small subset, including salinomycin and etoposide, targeted cancer stem cells responsible for metastasis and relapse. The mechanism of action by which salinomycin kills cancer stem cells specifically remains unknown, but is thought to be due to its action as a potassium ionophore due to the detection of nigericin in the same compound screen. Studies performed in 2011 showed that salinomycin could induce apoptosis of human cancer cells. Promising results from a few clinical pilote studies reveal that salinomycin is able to effectively eliminate CSCs and to induce partial clinical regression of heavily pretreated and therapy-resistant cancers. The ability of salinomycin to kill both CSCs and therapy-resistant cancer cells may define the compound as a novel and an effective anticancer drug. It has been also shown that Salinomycin and its derivatives exhibit potent antiproliferative activity against the drug-resistant cancer cell lines. Salinomycin is the key compound in the pharmaceutical company Verastem's efforts to produce an anti-cancer-stem-cell drug.

Drugs for non-small cell lung cancer may include: Abitrexate (methotrexate), Abraxane (Paclitaxel Albumin-stabilized Nanoparticle Formulation), Afatinib Dimaleate, Alimta (pemetrexed disodium), Avastin (Bevacizumab), Carboplatin, Cisplatin, Crizotinib, Erlotinib Hydrochloride, Folex (methotrexate), Folex PFS (methotrexate), Gefitinib Gilotrif (afatinib dimaleate), Gemcitabine Hydrochloride, Gemzar (gemcitabine hydrochloride), Iressa (Gefitinib), Methotrexate, Methotrexate LPF (methotrexate), Mexate (methotrexate), Mexate-AQ (methotrexate), Paclitaxel, Paclitaxel Albumin-stabilized Nanoparticle Formulation, Paraplat (carboplatin), Paraplatin (carboplatin), Pemetrexed Disodium, Platinol (cisplatin), Platinol-AQ (Cisplatin), Tarceva (Erlotinib Hydrochloride), Taxol (Paclitaxel), Taxotere or Docecad (docetaxel), and Xalkori (Crizotinib).

Combinations approved for non-small cell lung cancer may include: Carboplatin-Taxol and Gemcitabline-Cisplatin.

Drugs approved for small cell lung cancer may include: Abitrexate (methotrexate), Etopophos (etoposide phosphate), Etoposide, Etoposide Phosphate, Folex (methotrexate), Folex PFS (methotrexate), Hycamtin (topotecan hydrochloride), Methotrexate, Methotrexate LPF (methotrexate), Mexate (methotrexate), Mexate-AQ (methotrexate), Toposar (etoposide), Topotecan Hydrochloride, and VePesid (etoposide).

Aerosol administration directly to one or more desired regions of the respiratory tract, which includes the upper respiratory tract (e.g., nasal, sinus, and pharyngeal compartments), the respiratory airways (e.g., laryngeal, tracheal, and bronchial compartments) and the lungs or pulmonary compartments (e.g., respiratory bronchioles, alveolar ducts, alveoli), may be effected (e.g., "pulmonary delivery") in certain preferred embodiments through intra-nasal or oral inhalation to obtain high and titrated concentration of drug, pro-drug active or sustained-release delivery to a site of respiratory pathology. Aerosol administration such as by intra-nasal or oral inhalation may also be used to provide drug, pro-drug active or sustained-release delivery through the pulmonary vasculature (e.g., further to pulmonary delivery) to reach other tissues or organs, by non-limiting example, the heart, brain, liver central nervous system and/or kidney, with decreased risk of extra-respiratory toxicity associated with non-respiratory routes of drug delivery. Accordingly, because the efficacy of a particular pyridone compound (e.g., pirfenidone) therapeutic composition may vary depending on the formulation and delivery parameters, certain embodiments described herein reflect re-formulations of compositions and novel delivery methods for recognized active drug compounds. Other embodiments contemplate topical pathologies and/or infections that may also benefit from the discoveries described herein, for example, through direct exposure of a pirfenidone or pyridone analog compound formulation as provided herein to diseased skin, rectum, vagina, urethra, urinary bladder, eye, and/or ear, including aerosol delivery to a burn wound to prevent scarring.

In addition to the clinical and pharmacological criteria according to which any composition intended for therapeutic administration (such as the herein described pirfenidone or pyridone analog compound formulations) may be characterized, those familiar with the art will be aware of a number of physicochemical factors unique to a given drug composition. These include, but are not limited to aqueous solubility, viscosity, partitioning coefficient (Log P), predicted stability in various formulations, osmolality, surface tension, pH, pKa, pKb, dissolution rate, sputum permeability, sputum binding/inactivation, taste, throat irritability and acute tolerability.

Other factors to consider when selecting the particular product form include physical chemistry of the formulation (e.g., a pirfenidone or pyridone analog compound formulation), the intended disease indication(s) for which the formulation is to be used, clinical acceptance, and patient compliance. As non-limiting examples, a desired pirfenidone or pyridone analog compound formulation for aerosol delivery (e.g., by oral and/or intra-nasal inhalation of a mist such as a nebulized suspension of liquid particles, a dispersion of a dry powder formulation or aerosol generated by meter-dose propellant), may be provided in the form of a simple liquid such as an aqueous liquid (e.g., soluble pirfenidone or pyridone analog compound with non-encapsulating soluble excipients/salts), a complex liquid such as an aqueous liquid (e.g., pirfenidone or pyridone analog compound encapsulated or complexed with soluble excipients such as lipids, liposomes, cyclodextrins, microencapsulations, and emulsions), a complex suspension (e.g., pirfenidone or pyridone analog compound as a low-solubility, stable nanosuspension alone, as co-crystal/co-precipitate complexes, and/or as mixtures with low solubility lipids such as solid-lipid nanoparticles), a dry powder (e.g., dry powder pirfenidone or pyridone analog compound alone or in co-crystal/co-precipitate/spray-dried complex or mixture with low solubility excipients/salts or readily soluble blends such as lactose), or an organic soluble or organic suspension solution, for packaging and administration using an inhalation device such as a metered-dose inhalation device.

Selection of a particular pirfenidone or pyridone analog compound formulation or pirfenidone or pyridone analog compound formulation composition as provided herein according to certain preferred embodiments may be influenced by the desired product packaging. Factors to be considered in selecting packaging may include, for example, intrinsic product stability, whether the formulation may be subject to lyophilization, device selection (e.g., liquid nebulizer, dry-powder inhaler, meter-dose inhaler), and/or packaging form (e.g., simple liquid or complex liquid formulation, whether provided in a vial as a liquid or as a lyophilisate to be dissolved prior to or upon insertion into the device; complex suspension formulation whether provided in a vial as a liquid or as a lyophilisate, and with or without a soluble salt/excipient component to be dissolved prior to or upon insertion into the device, or separate packaging of liquid and solid components; dry powder formulations in a vial, capsule or blister pack; and other formulations packaged as readily soluble or low-solubility solid agents in separate containers alone or together with readily soluble or low-solubility solid agents.

Packaged agents may be manufactured in such a way as to be provide a pirfenidone or pyridone analog compound formulation composition for pulmonary delivery that comprises a solution which is provided as a pirfenidone or pyridone analog compound aqueous solution having a pH from about 3.0 to about 11.0, more preferably from about pH 4 to about pH 8, at a concentration of at least 0.1 mg/mL to about 50 mg/mL, and having a total osmolality at least 50 mOsmol/kg to about 1000 mOsmol/kg, more preferably 200 to about 500 mOsmol/kg.

In some embodiments, the present invention relates to the aerosol and/or topical delivery of a pyridone analog compound (e.g., pirfenidone). Pirfenidone has favorable solubility characteristics enabling dosing of clinically-desirable levels by aerosol (e.g., through liquid nebulization, dry powder dispersion or meter-dose administration) or topically (e.g., aqueous suspension, oily preparation or the like or as a drip, spray, suppository, salve, or an ointment or the like), and can be used in methods for acute or prophylactic treatment of a subject having pulmonary fibrosis, or of a subject at risk for having pulmonary fibrosis. Clinical criteria for determining when pulmonary fibrosis is present, or when a subject is at risk for having pulmonary fibrosis, are known to the art. Pulmonary delivery via inhalation permits direct and titrated dosing directly to the clinically-desired site with reduced systemic exposure.

In a preferred embodiment, the method treats or serves as prophylaxis against interstitial lung disease (ILD) by administering a pirfenidone or pyridone analog compound formulation as an aerosol (e.g., a suspension of liquid particles in air or another gas) to a subject having or suspected to have interstitial lung disease. Interstitial lung disease includes those conditions of idiopathic interstitial pneumonias as defined by American Thoracic Society/European Respiratory Society international multidisciplinary consensus classification of the idiopathic interstitial pneumonias, AM. J. Respir. Crit. Care Med. 165, 277-304 (2002). These include ILD of known cause or association with connective tissue diseases, occupational causes or drug side effect, idiopathic interstitial pneumonias (e.g. idiopathic pulmonary fibrosis, non-specific interstitial pneumonia, desquamative interstitial pneumonia, respiratory bronchiolitis-ILD, cryptogenic organizing pneumonia, acute interstitial pneumonia and lyphocytic interstitial pneumonia), granulomatous lung disease (e.g., sarcodosis, hypersensitivity pneumonitis and infection), and other forms of ILD (e.g., lymphangioleiomyomatosis, pulmonary Langerhans' cell histocytosis, eosinophilic pneumonia and pulmonary alveolar proteinosis).

The therapeutic method may also include a diagnostic step, such as identifying a subject with or suspected of having ILD. In some embodiments, the method further sub-classifies into idiopathic pulmonary fibrosis. In some embodiments, the delivered amount of aerosol pirfenidone or pyridone analog compound (or salt thereof) formulation is sufficient to provide acute, sub-acute, or chronic symptomatic relief, slowing of fibrosis progression, halting fibrosis progression, reversing fibrotic damage, and/or subsequent increase in survival and/or improved quality of life.

The therapeutic method may also include a diagnostic step, such as identifying a subject with or suspected of having fibrosis in other tissues, by non-limiting example in the heart, liver, kidney or skin. In some embodiments, the delivered amount of liquid nebulized, dry powder or metered-dose aerosol pirfenidone or pyridone analog compound (or salt thereof) formulation is sufficient to provide acute, sub-acute, or chronic symptomatic relief, slowing of fibrosis progression, halting fibrosis progression, reversing fibrotic damage, and/or subsequent increase in survival and/or improved quality of life.

The therapeutic method may also include a diagnostic step, such as identifying a subject with or suspected of having multiple sclerosis. In some embodiments, the delivered amount of liquid nebulized, dry powder or metered-dose aerosol pirfenidone or pyridone analog compound (or salt thereof) formulation is sufficient to provide acute, sub-acute, or chronic symptomatic relief, slowing of demylination progression, halting demylination progression, reversing demylinated damage, and/or subsequent increase in survival and/or improved quality of life.

In another embodiment, liquid nebulized, dry powder or metered-dose aerosol pirfenidone or pyridone analog compound (or salt thereof) may be co-administered, administered sequentially or prepared in a fixed-combination with antimicrobial agents to also provide therapy for a co-existing bacterial infection. By non-limiting example the bacteria may be a gram-negative bacteria such as *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus*. In some embodiments of the methods described above, the bacteria are gram-negative anaerobic bacteria, by non-limiting example these include *Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii,* and *Bacteroides splanchnicus*. In some embodiments of the methods described above, the bacteria are gram-positive bacteria, by non-limiting example these include: *Corynebacterium diphtheriae, Corynebacterium ulcerans, Streptococcus pneumoniae, Streptococcus agalactiae, Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus, Staphylococcus inter-*

*medius, Staphylococcus hyicus* subsp. *hyicus, Staphylococcus haemolyticus, Staphylococcus hominis,* and *Staphylococcus saccharolyticus.* In some embodiments of the methods described above, the bacteria are gram-positive anaerobic bacteria, by non-limiting example these include *Clostridium difficile, Clostridium perfringens, Clostridium tetini,* and *Clostridium botulinum.* In some embodiments of the methods described above, the bacteria are acid-fast bacteria, by non-limiting example these include *Mycobacterium tuberculosis, Mycobacterium avium, Mycobacterium intracellulare,* and *Mycobacterium leprae.* In some embodiments of the methods described above, the bacteria are atypical bacteria, by non-limiting example these include *Chlamydia pneumoniae* and *Mycoplasma pneumoniae.*

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts to produce and maintain threshold drug concentrations in the lung and/or targeted downstream tissue, which may be measured as drug levels in epithelial lining fluid (ELF), sputum, lung tissue, bronchial lavage fluid (BAL), or by deconvolution of blood concentrations through pharmacokinetic analysis. One embodiment includes the use of aerosol administration, delivering high or titrated concentration drug exposure directly to the affected tissue for treatment of pulmonary fibrosis and inflammation associated with ILD (including idiopathic pulmonary fibrosis), COPD and asthma in animals and humans. In one such embodiment, the peak lung ELF levels achieved following aerosol administration to the lung will be between 0.1 mg/mL and about 50 mg/mL pirfenidone or pyridone analog. In another embodiment, the peak lung wet tissue levels achieved following aerosol administration to the lung will be between 0.004 mcg/gram lung tissue and about 500 mcg/gram lung tissue pirfenidone or pyridone analog.

As a non-limiting example, in a preferred embodiment, a pyridone analog compound as provided herein (e.g., pirfenidone) formulated to permit mist, gas-liquid suspension or liquid nebulized, dry powder and/or metered-dose inhaled aerosol administration to supply effective concentrations or amounts to produce and maintain threshold drug concentrations in the blood and/or lung, which may be measured as drug levels in epithelial lining fluid (ELF), sputum, lung tissue, bronchial lavage fluid (BAL), or by deconvolution of blood concentrations through pharmacokinetic analysis that absorb to the pulmonary vasculature producing drug levels sufficient for extra-pulmonary therapeutics, maintenance or prophylaxis. One embodiment includes the use of aerosol administration, delivering high concentration drug exposure in the pulmonary vasculature and subsequent tissues and associated vasculature for treatment, maintenance and/or prophylaxis of, but not limited to cardiac fibrosis, kidney fibrosis, hepatic fibrosis, heart or kidney toxicity, or multiple sclerosis. In one such embodiment, the peak tissue-specific plasma levels (e.g., heart, kidney and liver) or cerebral spinal fluid levels (e.g. central nervous system) achieved following aerosol administration to the lung following oral inhalation or to the lung or nasal cavity following intra-nasal administration will be between 0.1 mcg/mL and about 50 mcg/mL pirfenidone or pyridone analog. In another embodiment, the peak lung wet tissue levels achieved following aerosol administration to the lung will be between 0.004 mcg/gram lung tissue and about 500 mcg/gram lung tissue pirfenidone or pyridone analog.

In another embodiment, a method is provided for acute or prophylactic treatment of a patient through non-oral or non-nasal topical administration of pirfenidone or pyridone analog (or a salt thereof) compound formulation to produce and maintain threshold drug concentrations at a burn site. One embodiment includes the use of aerosol administration, delivering high concentration drug exposure directly to the affected tissue for treatment or prevention of scarring in skin. For example according to these and related embodiments, the term aerosol may include a spray, mist, or other nucleated liquid or dry powder form.

In another embodiment, a method is provided for acute or prophylactic treatment of a patient through non-oral or non-nasal topical administration of pirfenidone or pyridone analog (or a salt thereof) compound formulation to produce and maintain threshold drug concentrations in the eye. One embodiment includes the use of aerosol administration or formulation drops to deliver high concentration drug exposure directly to the affected tissue for treatment or prevention of scarring following surgical glaucoma surgery (e.g., bleb fibrosis). For example according to these and related embodiments, the term aerosol may include a spray, mist, or other nucleated liquid or dry powder form. A drop may be simple liquid or suspension formulation.

In another embodiment, a pyridone analog compound as provided herein (e.g., pirfenidone) formulation by inhalation, wherein the inhaled liquid aerosol (e.g., following liquid nebulization or metered-dose administration) or dry powder aerosol has a mean particle size from about 1 micron to 10 microns mass median aerodynamic diameter and a particle size geometric standard deviation of less than or equal to about 3 microns. In another embodiment, the particle size is 2 microns to about 5 microns mass median aerodynamic diameter and a particle size geometric standard deviation of less than or equal to about 3 microns. In one embodiment, the particle size geometric standard deviation is less than or equal to about 2 microns.

As a non-limiting example, in a preferred embodiment, a pyridone analog compound as provided herein (e.g., pirfenidone) remains at the therapeutically effective concentration at the site of pulmonary pathology, suspected pulmonary pathology, and/or site of pulmonary absorption into the pulmonary vasculature for at least about 1 minute, at least about a 5 minute period, at least about a 10 min period, at least about a 20 min period, at least about a 30 min period, at least about a 1 hour period, at least a 2 hour period, at least about a 4 hour period, at least an 8 hour period, at least a 12 hour period, at least a 24 hour period, at least a 48 hour period, at least a 72 hour period, or at least one week. The effective pirfenidone or pyridone analog concentration is sufficient to cause a therapeutic effect and the effect may be localized or broad-acting to or from the site of pulmonary pathology.

As a non-limiting example, in a preferred embodiment, a pyridone analog compound as provided herein (e.g., pirfenidone or salt thereof) following inhalation administration remains at the therapeutically effective concentration at the site of cardiac fibrosis, kidney fibrosis, hepatic fibrosis, heart or kidney toxicity, or multiple sclerosis demylination for at least about 1 minute, at least about a 5 minute period, at least about a 10 min period, at least about a 20 min period, at least about a 30 min period, at least about a 1 hour period, at least a 2 hour period, at least about a 4 hour period, at least an 8 hour period, at least a 12 hour period, at least a 24 hour period, at least a 48 hour period, at least a 72 hour period, or at least one week. The effective pirfenidone or pyridone analog concentration is sufficient to cause a therapeutic effect and the effect may be localized or broad-acting to or from the site of extrapulmonary pathology.

In some embodiments, delivery sites such as a pulmonary site, the pirfenidone or pyridone analog compound formulation as provided herein is administered in one or more administrations so as to achieve a respirable delivered dose daily of pirfenidone or pyridone analog of at least about 0.1 mg to about 50 mg, including all integral values therein such as 0.1, 0.2, 0.4, 0.8, 1, 2, 4, 6, 10, 15, 20, 25, 30, 35, 40, 45, 50 milligrams. In some embodiments, a pirfenidone or pyridone analog compound formulation as provided herein is administered in one or more administrations so as to achieve a respirable delivered dose daily of pirfenidone or pyridone analog of at least about 0.1 mg to about 300 mg, including all integral values therein such as 0.1, 0.2, 0.4, 0.8, 1, 2, 4, 6, 10, 15, 20, 25, 30, 35, 40, 45, 50, 55, 60, 65, 70, 75, 80, 85, 90, 95, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 milligrams. The pirfenidone or pyridone analog formulation is administered in the described respirable delivered dose in less than 60 minutes, less than 50 minutes, less than 40 minutes, less than 30 minutes, less than 20 minutes, less than 15 minutes, less than 10 minutes, less than 7 minutes, less than 5 minutes, in less than 3 minutes, in less than 2 minutes, in less than 1 minute, 10 inhalation breaths, 8 inhalation breaths, 6 inhalation breaths, 4 inhalation breaths, 3 inhalation breaths, 2 inhalation breaths or 1 inhalation breath. In some embodiments, pirfenidone or pyridone analog formulation is administered in the described respirable delivered dose using a breathing pattern of 1 second inhalation and 2 seconds exhalation, 2 seconds inhalation and 2 seconds exhalation, 3 seconds inhalation and 2 seconds exhalation, 4 seconds inhalation and 2 seconds exhalation, 5 seconds inhalation and 2 seconds exhalation, 6 seconds inhalation and 2 seconds exhalation, 7 seconds inhalation and 2 seconds exhalation, and 8 seconds inhalation and 2 seconds exhalation.

In some embodiments, delivery sites such as the nasal cavity or sinus, pirfenidone or pyridone analog (or salt thereof) compound formulation is administered in one or more administrations so as to achieve a nasal cavity or sinus deposited dose daily of pirfenidone or pyridone analog of at least about 0.1 mg to about 50 mg, including all integral values therein such as 0.1, 0.2, 0.4, 0.8, 1, 2, 4, 6, 10, 15, 20, 25, 30, 35, 40, 45, 50 milligrams. In some embodiments, delivery sites such as the nasal cavity or sinus, pirfenidone or pyridone analog (or salt thereof) compound formulation is administered in one or more administrations so as to achieve a nasal cavity or sinus deposited dose daily of pirfenidone or pyridone analog of at least about 0.1 mg to about 300 mg, including all integral values therein such as 0.1, 0.2, 0.4, 0.8, 1, 2, 4, 6, 10, 15, 20, 25, 30, 35, 40, 45, 50, 55, 60, 65, 70, 75, 80, 85, 90, 95, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 milligrams. The pirfenidone or pyridone analog formulation is administered in the described nasal or sinus deposited dose in less than 20 minutes, less than 15 minutes, less than 10 minutes, less than 7 minutes, less than 5 minutes, in less than 3 minutes, in less than 2 minutes, in less than 1 minute, 10 intranasal inhalation breaths, 8 intranasal inhalation breaths, 6 intranasal inhalation breaths, 4 intranasal inhalation breaths, 3 intranasal inhalation breaths, 2 intranasal inhalation breaths or 1 intranasal inhalation breath. In some embodiments, pirfenidone or pyridone analog formulation is administered in the described respirable delivered dose using a breathing pattern of 1 second inhalation and 2 seconds exhalation, 2 seconds inhalation and 2 seconds exhalation, 3 seconds inhalation and 2 seconds exhalation, 4 seconds inhalation and 2 seconds exhalation, 5 seconds inhalation and 2 seconds exhalation, 6 seconds inhalation and 2 seconds exhalation, 7 seconds inhalation and 2 seconds exhalation, and 8 seconds inhalation and 2 seconds exhalation.

In some embodiments of the methods described above, the subject is a human. In some embodiments of the methods described above, the subject is a human with ILD. In some embodiments, the method further sub-classifies into idiopathic pulmonary fibrosis. In some embodiments of the methods describe above, the human subject may be mechanically ventilated.

In embodiments where a human is mechanically ventilated, aerosol administration would be performed using an in-line device (by non-limiting example, the Nektar Aeroneb Pro) or similar adaptor with device for liquid nebulization. Aerosol administration could also be performed using an in-line adaptor for dry powder or metered-dose aerosol generation and delivery.

In some embodiments of the methods described above, the subject is a human. In some embodiments of the methods described above, the subject is a human requiring cardiac fibrosis therapy. In some embodiments of the methods describe above, the human subject may be mechanically ventilated.

In some embodiments of the methods described above, the subject is a human. In some embodiments of the methods described above, the subject is a human requiring kidney fibrosis therapy. In some embodiments of the methods describe above, the human subject may be mechanically ventilated.

In some embodiments of the methods described above, the subject is a human. In some embodiments of the methods described above, the subject is a human requiring hepatic fibrosis therapy. In some embodiments of the methods describe above, the human subject may be mechanically ventilated.

In some embodiments of the methods described above, the subject is a human. In some embodiments of the methods described above, the subject is a human requiring cardiac or kidney toxicity therapy. In some embodiments of the methods describe above, the human subject may be mechanically ventilated.

In some embodiments of the methods described above, the subject is a human. In some embodiments of the methods described above, the subject is a human requiring COPD therapy. In some embodiments of the methods describe above, the human subject may be mechanically ventilated.

In some embodiments of the methods described above, the subject is a human. In some embodiments of the methods described above, the subject is a human requiring asthma therapy. In some embodiments of the methods describe above, the human subject may be mechanically ventilated.

In some embodiments of the methods described above, the subject is a human. In some embodiments of the methods described above, the subject is a human requiring multiple sclerosis therapy. In some embodiments of the methods describe above, the human subject may be mechanically ventilated.

In another embodiment, a pharmaceutical composition is provided that includes a simple liquid pirfenidone or pyridone analog (or salt thereof) compound formulation with non-encapsulating water soluble excipients as described above having an osmolality from about 50 mOsmol/kg to about 6000 mOsmol/kg. In one embodiment, the osmolality is from about 50 mOsmol/kg to about 1000 mOsmol/kg. In one embodiment, the osmolality is from about 400 mOsmol/kg to about 5000 mOsmol/kg. In other embodiments the osmolality is from about 50, 100, 150, 200, 250, 300, 350, 400, 450, 500 mOsmol/kg to about 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800 m 5000, 5200, 5400, 5600, 5800 and 6000 mOsmol/kg. With respect to osmolality, and also elsewhere in the present application, "about" when used to refer to a quantitative value means that a specified quantity may be greater than or less than the indicated amount by 1, 2, 3, 4, 5, 6, 7, 8, 9, 10, 11, 12, 13, 14, 15, 16, 17, 18, 19 or 20 percent of the stated numerical value.

In another embodiment, a pharmaceutical composition is provided that includes a simple liquid pirfenidone or pyridone analog (or salt thereof) compound formulation having a permeant ion concentration between from about 30 mM to about 300 mM and preferably between from about 50 mM to 200 mM. In one such embodiment, one or more permeant ions in the composition are selected from the group consisting of chloride and bromide.

In another embodiment, a pharmaceutical composition is provided that includes a complex liquid pirfenidone or pyridone analog (or salt thereof) compound formulation encapsulated or complexed with water soluble excipients such as lipids, liposomes, cyclodextrins, microencapsulations, and emulsions) as described above having a solution osmolality from about 50 mOsmol/kg to about 6000 mOsmol/kg. In one embodiment, the osmolality is from about 50 mOsmol/kg to about 1000 mOsmol/kg. In one embodiment, the osmolality is from about 100 mOsmol/kg to about 500 mOsmol/kg. In one embodiment, the osmolality is from about 400 mOsmol/kg to about 5000 mOsmol/kg.

In another embodiment, a pharmaceutical composition is provided that includes a complex liquid pirfenidone or pyridone analog (or salt thereof) compound formulation having a permeant ion concentration from about 30 mM to about 300 mM. In one such embodiment, one or more permeant ions in the composition are selected from the group consisting of chloride and bromide.

In another embodiment, a pharmaceutical composition is provided that includes a complex liquid pirfenidone or pyridone analog (or salt thereof) compound formulation having a permeant ion concentration from about 50 mM to about 200 mM. In one such embodiment, one or more permeant ions in the composition are selected from the group consisting of chloride and bromide.

In another embodiment, a pharmaceutical composition is provided that includes a simple liquid formulation of pirfenidone or pyridone analog (or salt thereof) compound formulation having a prifenidone or pyridone analog to multivalent cation positive charge molar ratio between about two pirfenidone or pyridone analog compounds to about 0.1 to about 4 multivalent cation positive charges. By non-limiting example, two pirfenidone or pyridone analog compounds to one magnesium ion (two cation positive charges), three prifenidone or pyridone analog compounds to one magnesium ions, four pirfenidone or pyridone analog compounds to one magnesium ions, and two pirfenidone or pyridone analog compounds to two magnesium ions.

An unexpected finding was that divalent cations, by non-limiting example magnesium, reduced pirfenidone dissolution time and increased pirfenidone aqueous solubility in a molar ratio-dependent manner. This increased saturation solubility is enabling to deliver predicted-sufficient quantities of inhaled liquid-nebulized pirfenidone to the lung. By example, one pirfenidone molecules to three magnesium molecules exhibited a slower dissolution time and reduced saturation solubility than one pirfenidone molecule to one magnesium molecule. Moreover, one pirfenidone molecules to one magnesium molecule exhibited a faster dissolution time and greater aqueous solubility than an equal-molar ratio of pirfenidone to sodium.

In another embodiment, a pharmaceutical composition is provided that includes a complex liquid formulation of pirfenidone or pyridone analog (or salt thereof) compound formulation having a prifenidone or pyridone analog to about 0.1 to about 4 multivalent cation positive charges. By non-limiting example, two pirfenidone or pyridone analog compounds to one magnesium ion (two cation positive charges), three prifenidone or pyridone analog compounds to one magnesium ions, four pirfenidone or pyridone analog compounds to one magnesium ions, and two pirfenidone or pyridone analog compounds to two magnesium ions.

In another embodiment, a pharmaceutical composition is provided that includes a complex liquid pirfenidone or pyridone analog (or salt thereof) compound formulation as a low water-soluble stable nanosuspension alone or in co-crystal/co-precipitate complexes, or mixtures with low solubility lipids, such as lipid nanosuspensions) as described above having a solution osmolality from about 50 mOsmol/kg to about 6000 mOsmol/kg. In one embodiment, the osmolality is from about 100 mOsmol/kg to about 500 mOsmol/kg. In one embodiment, the osmolality is from about 400 mOsmol/kg to about 5000 mOsmol/kg.

In another embodiment, a pharmaceutical composition is provided that includes a complex suspension of a pirfenidone or pyridone analog (or salt thereof) compound formulation having a permeant ion concentration from about 30 mM to about 300 mM. In one such embodiment, one or more permeant ions in the composition are selected from the group consisting of chloride and bromide.

In another embodiment, a pharmaceutical composition is provided that includes a complex suspension of a pirfenidone or pyridone analog (or salt thereof) compound formulation having a permeant ion concentration from about 50 mM to about 200 mM. In one such embodiment, one or more permeant ions in the composition are selected from the group consisting of chloride and bromide.

In another embodiment, a pharmaceutical composition is provided that includes a complex suspension of pirfenidone or pyridone analog (or salt thereof) compound formulation having a pirfenidone or pyridone analog to multivalent cation positive charge molar ratio between about one pirfenidone or pyridone analog compounds to about 0.1 to about 4 multivalent cation positive charges. By non-limiting example, two pirfenidone or pyridone analog compounds to one magnesium ion (two cation positive charges), three prifenidone or pyridone analog compounds to one magnesium ions, four pirfenidone or pyridone analog compounds to one magnesium ions, and two pirfenidone or pyridone analog compounds to two magnesium ions.

In other embodiments, a pirfenidone or pyridone analog (or salt thereof) compound formulation as provided herein, or a pharmaceutical composition, is provided that includes a taste-masking agent. As non-limiting examples, a taste-masking agent may include a sugar, saccharin (e.g., sodium saccharin), sweetener or other compound or agent that beneficially affects taste, after-taste, perceived unpleasant saltiness, sourness or bitterness, or that reduces the tendency of an oral or inhaled formulation to irritate a recipient (e.g., by causing coughing or sore throat or other undesired side effect, such as may reduce the delivered dose or adversely influence patient compliance with a prescribed therapeutic regimen). Certain taste-masking agents may form complexes with a pirfenidone or pyridone analog (or salt thereof) compound.

In certain preferred embodiments that relate to the pirfenidone or pyridone analog (or salt thereof) compound formulations disclosed herein, the formulation comprises a pirfenidone or pyridone analog (or salt thereof) compound and a taste-masking agent and may be optimized with respect to a desired osmolality, and/or an optimized permeant ion concentration. In certain such embodiments, the taste-masking agent comprises saccharin (e.g., sodium saccharin), which according to non-limiting theory affords certain advantages associated with the ability of this taste-masking agent to provide desirable taste effects even when present in extremely low concentrations, such as may have little or no effect on the detectable osmolality of a solution, thereby permitting the herein described formulations to deliver aqueous solutions, organic or dry powder formulations in a well-tolerated manner. In certain such embodiments, the taste-masking agent comprises a chelating agent (e.g., EDTA or divalent cation such as magnesium), which according to non-limiting theory affords certain advantages associated with the ability of this taste-masking agent to provide desirable taste effects by masking taste-stimulating chemical moieties on pirfenidone of pyridone analog. With divalent cations, inclusion as a taste-masking agent may also substitute as an osmolality adjusting agent, and pending the salt form may also provide the permeant ion (e.g. magnesium chloride), thereby permitting the herein described formulations to deliver aqueous solutions, organic or dry powder formulations in a well-tolerated manner. Non-limiting examples of these and related embodiments include a pirfenidone or pyridone analog (or salt thereof) compound formulation for pulmonary delivery as described herein that comprises an aqueous solution having a pH of from about 4 to about 8 and an osmolality of from about 50 to about 1000 mOsmol/kg (e.g., adjusted with sodium chloride), the solution comprising pirfenidone or pyridone analog (or salt thereof) compound and sodium saccharin where the aqueous solution contains from about 0.1 mM to about 2.0 mM saccharin. A related non-limiting example further comprises citrate (e.g., citric acid) in an aqueous solution containing from about 1 mM to about 100 mM citrate. A related non-limiting example further comprises or replace citrate with phosphate (e.g., sodium phosphate) in an aqueous solution containing from about 0.0 mM to about 100 mM phosphate. Another related non-limiting example further comprises or replace citrate with phosphate (e.g., sodium phosphate) in an aqueous solution containing from about 0.5 mM to about 100 mM phosphate. By another non-limiting examples, these and related embodiments include a pirfenidone or pyridone analog (or salt thereof) compound formulation for pulmonary delivery as described herein that comprises an aqueous solution having a pH of from about 4 to about 8 and an osmolality of from about 50 to about 5000 mOsmol/kg (e.g., adjusted with magnesium chloride), the solution comprising pirfenidone or pyridone analog (or salt thereof) compound, wherein a divalent cation (e.g., berilium, magnesium, or calcium) serves both to adjust osmolality and as a taste-masking agent. Where included as a taste-masking agent, divalent cation (e.g., magnesium) is added stoichiometrically with pirfenidone or pyridone analog. By example, 1 mol divalent ion to 2 mols pirfenidone or pyridone analog, 1.5 mols divalent ion to 2 mols pirfenidone or pyridone analog, 2 mols divalent ion to 2 mols pirfenidone or pyridone analog, 3 mols divalent ion to 2 mols pirfenidone or pyridone analog, or 4 mols divalent ion to 2 mols pirfenidone or pyridone analog. Where osmolality required further increase sodium chloride or additional divalent salt may be used. A related non-limiting example further comprises citrate (e.g., citric acid) in an aqueous solution containing from about 1 mM to about 100 mM citrate. A related non-limiting example citrate is replaced with phosphate (e.g., sodium phosphate) in an aqueous solution containing from about 0.0 mM to about 100 mM phosphate. In another related non-limiting example citrate is replaced with phosphate (e.g., sodium phosphate) in an aqueous solution containing from about 0.0 mM to about 100 mM phosphate.

In another embodiment, while the inclusion of the correct molar ratio of magnesium to pirfenidone reduces dissolution time and increases saturation solubility to a level required for sufficient liquid nebulization delivery to the lung, an unexpected finding was that this formulation additionally requires a taste masking agent for acute tolerability upon inhalation of a nebulized solution. To this end, between 0.1 and 1.0 micromolar saccharin enables the use of this solubility-enabling formulation.

In another embodiment, a pharmaceutical composition may be protected from light to avoid photodegradation. By non-limiting example, this may occur by light-protected vials, ampoules, blisters, capsules, or other colored or light-protected primary packaging. By another non-limiting example, this may occur by use of secondary packaging such as an aluminum or other light-protected over-pouch, box or other secondary packaging.

In another embodiment, a pharmaceutical composition may be protected from oxygen to protect from oxidation. By non-limiting example, in solution this may occur by removing oxygen from solution prior to or during compounding (e.g., sparging), and or controlled the primary packaging head-space gas (e.g. using of inert gas such as argon or nitrogen in the head space). Similarly, by another non-limiting example, controlling the included secondary packaging gas (e.g. with inert gas) may also be required. For powder formulations this may be controlled by use of insert gas in primary and/or secondary packaging. Meter-dose inhaled products may benefit by the same means as described above for solution products.

In another embodiment, pirfenidone or pyridone analog present in a pharmaceutical composition may be protected from hydrolysis by inclusion of a cationic metal ion. By non-limiting example, acid hydrolysis of amide bonds decreases with an increased salt concentration. Specifically, hydration number is important for this rate decrease, as electrolyte hydration decreases the availability of free water for the reaction. Thus, the rate decreases with increased salt and increased hydration number. The order of increasing hydration number: potassium<sodium<lithium<magnesium. The rate decrease also nearly parallels ionic strength. By non-limiting example, the addition of magnesium will stabilize the 2-pyridone structure of pirfenidone. It is known that pirfenidone chelates Fe(III) at a ratio of 3 pirfenidone molecules to 1 Fe(III). From this it follows that pirfenidone will chelate magnesium at 2 pirfenidone molecules to 1 magnesium+2 charge. Therefore, for this purpose the addition of magnesium or other cationic metal ion may be stoichiometric to the amount of pirfenidone or pyridone analog. By non-limiting example, 2 pirfenidone molecules to 0.1 magnesium molecules, 2 pirfenidone molecules to 0.25 magnesium molecules, 2 pirfenidone molecules to 0.5 magnesium molecules, 2 pirfenidone molecules to 0.75 magnesium molecules, 2 pirfenidone molecules to 1 magnesium molecules, 2 pirfenidone molecules to 1.5 magnesium molecules, 2 pirfenidone molecules to 2 magnesium molecules, 2 pirfenidone molecules to 3 magnesium molecules, 2 pirfenidone molecules to 4 magnesium molecules, 2 pirfenidone molecules to 5 magnesium molecules, 2 pirfenidone molecules to 6 magnesium molecules, 2 pirfenidone molecules to 7 magnesium molecules, 2 pirfenidone molecules to 8 magnesium molecules, 2 pirfenidone molecules to 9 magnesium molecules, 2 pirfenidone molecules to 10 magnesium molecules, 2 pirfenidone molecules to 12 magnesium molecules, 2 pirfenidone molecules to 14 magnesium molecules, 2 pirfenidone molecules to 16 magnesium molecules, 2 pirfenidone molecules to 18 magnesium molecules, or 2 pirfenidone molecules to 20 magnesium molecules. Potassium, sodium, lithium or iron may substitute for magnesium in these ratios and pharmaceutical composition. Included in the above pharmaceutical composition is the maintenance of the buffers described herein, at a pH from about 4.0 to about 8.0, and include MgCl2 or cationic salt thereof at a level that provides an osmolality of 300 mOsmo/kg and 600 mOsmo/kg. While 300 mOsmo/kg is discussed in the literature as important for acute tolerability upon inhalation of this in a nebulized solution, 600 mOsmo/kg has been shown in unpublished studies to be well tolerated with other drug solutions. However, a final solution osmolality up to 6000 mOsmo/kg is contemplated. Unexpectantly, formulations described herein demonstrate good tolerability at high osmolalities.

In another embodiment, a pharmaceutical composition of liquid pirfenidone or pyridone analog may contain a solubility enhancing agent or co-solvent. By non-limiting example, these may include ethanol, cetylpridinium chloride, glycerin, lecithin, propylene glycol, polysorbate (including polysorbate 20, 40, 60, 80 and 85), sorbitan triolate, and the like. By further example, cetylpridinium chloride may be used from about 0.01 mg/mL to about 4 mg/mL pharmaceutical composition. Similarly, by another non-limiting example, ethanol may be used from about 0.01% to about 30% pharmaceutical composition. Similarly, by another non-limiting example, glycerin may be used from about 0.01% to about 25% pharmaceutical composition. Similarly, by another non-limiting example, lecithin may be used from about 0.01% to about 4% pharmaceutical composition. Similarly, by another non-limiting example, propylene glycol may be used from about 0.01% to about 30% pharmaceutical composition. Similarly, by another non-limiting example, polysorbates may also be used from about 0.01% to about 10% pharmaceutical composition. Similarly, by another non-limiting example, sorbitan triolate may be used from about 0.01% to about 20% pharmaceutical composition.

In another embodiment, a pharmaceutical composition of liquid or dry powder pirfenidone or pyridone analog may contain a chelated metal ion to assist in solubility and/or dissolution of pirfenidone or pyridone analog. By non-limiting example, these may include iron, magnesium, or calcium.

In another embodiment, a pharmaceutical composition of liquid or dry powder pirfenidone or pyridone analog may contain a chelated metal ion to assist in scavenging reactive oxygen species. By non-limiting example, these may include iron, magnesium, or calcium. By non-limiting example, for this purpose the addition of magnesium or other cationic metal ion may be stoichiometric to the amount of pirfenidone or pyridone analog. By non-limiting example, 2 pirfenidone molecules to 0.1 magnesium molecules, 2 pirfenidone molecules to 0.25 magnesium molecules, 2 pirfenidone molecules to 0.5 magnesium molecules, 2 pirfenidone molecules to 0.75 magnesium molecules, 2 pirfenidone molecules to 1 magnesium molecules, 2 pirfenidone molecules to 1.5 magnesium molecules, 2 pirfenidone molecules to 2 magnesium molecules, 2 pirfenidone molecules to 3 magnesium molecules, 2 pirfenidone molecules to 4 magnesium molecules, 2 pirfenidone molecules to 5 magnesium molecules, 2 pirfenidone molecules to 6 magnesium molecules, 2 pirfenidone molecules to 7 magnesium molecules, 2 pirfenidone molecules to 8 magnesium molecules, 2 pirfenidone molecules to 9 magnesium molecules, 2 pirfenidone molecules to 10 magnesium molecules, 2 pirfenidone molecules to 12 magnesium molecules, 2 pirfenidone molecules to 14 magnesium molecules, 2 pirfenidone molecules to 16 magnesium molecules, 2 pirfenidone molecules to 18 magnesium molecules, or 2 pirfenidone molecules to 20 magnesium molecules. Potassium, sodium, lithium or iron may substitute for magnesium in these ratios and pharmaceutical composition. Included in the above pharmaceutical composition is the maintenance of the buffers described herein, at a pH from about 4.0 to about 8.0, and include $MgCl_2$ or cationic salt thereof at a level that provides an osmolality of 300 mOsmo/kg and 600 mOsmo/kg. While 300 mOsmo/kg is discussed in the literature as important for acute tolerability upon inhalation of this in a nebulized solution, 600 mOsmo/kg has been shown in unpublished studies to be well tolerated with other drug solutions. However, a final solution osmolality up to 5000 mOsmo/kg is contemplated.

In some embodiments, described herein is a pharmaceutical composition that includes: pirfenidone; water; phosphate buffer or citrate buffer; and optionally sodium chloride or magnesium chloride. In other embodiments, described herein is a pharmaceutical composition that includes: pirfenidone; water; a buffer; and at least one additional ingredient selected from sodium chloride, magnesium chloride, ethanol, propylene glycol, glycerol, polysorbate 80, and cetylpyridinium bromide (or chloride). In some embodiments, the buffer is phosphate buffer. In other embodiments, the buffer is citrate buffer. In some embodiments, the pharmaceutical composition includes 1 mg to 500 mg of pirfenidone, for example, 5 mg, 10 mg, 15 mg, 25 mg, 37.5 mg, 75 mg, 100 mg, 115 mg, 150 mg, 190 mg, 220 mg, or 500 mg. In some embodiments, the osmolality of the pharmaceutical composition described herein is between about 50 mOsmo/kg to 6000 mOsmo/kg. In some embodiments, the pharmaceutical composition optionally includes saccharin (e.g. sodium salt). Non-limiting examples of pharmaceutical compositions described herein include any one of the pharmaceutical compositions described in Tables 1-1 to Table 1-11 of Example 1.

Solutions of pirfenidone should remain protected from light as the API in solution is subject to degradation In another embodiment, a pharmaceutical composition is provided that includes a simple dry powder pirfenidone or pyridone analog (or salt thereof) compound alone in dry powder form with or without a blending agent such as lactose.

In another embodiment, the pharmaceutical composition used in a liquid, dry powder or meter-dose inhalation device is provided such that pirfenidone or pyridone analog is not in a salt form.

In another embodiment, a pharmaceutical composition is provided that includes a complex dry powder pirfenidone or pyridone analog (or salt thereof) compound formulation in co-crystal/co-precipitate/spray dried complex or mixture with low water soluble excipients/salts in dry powder form with or without a blending agent such as lactose.

In another embodiment, a system is provided for administering a pirfenidone or pyridone analog (or salt thereof) compound that includes a container comprising a solution of a pirfenidone or pyridone analog (or salt thereof) compound formulation and a nebulizer physically coupled or co-packaged with the container and adapted to produce an aerosol of the solution having a particle size from about 1 microns to about 5 microns mean mass aerodynamic diameter, volumetric mean diameter (VMD) or mass median diameter (MMD) and a particle size geometric standard deviation of less than or equal to about 2.5 microns mean mass aerodynamic diameter. In one embodiment, the particle size geometric standard deviation is less than or equal to about 3.0 microns. In one embodiment, the particle size geometric standard deviation is less than or equal to about 2.0 microns.

In another embodiment, a system is provided for administering a pirfenidone or pyridone analog (or salt thereof) compound that includes a container comprising a dry powder of a pirfenidone or pyridone analog (or salt thereof) compound and a dry powder inhaler coupled to the container and adapted to produce a dispersed dry powder aerosol having a particle size from about 1 microns to about 5 microns mean mass aerodynamic and a particle size standard deviation of less than or equal to about 3.0 microns. In one embodiment, the particle size standard deviation is less than or equal to about 2.5 microns. In one embodiment, the particle size standard deviation is less than or equal to about 2.0 microns.

In another embodiment, a kit is provided that includes a container comprising a pharmaceutical formulation comprising a pirfenidone or pyridone analog (or salt thereof) compound and an aerosolizer adapted to aerosolize the pharmaceutical formulation (e.g., in certain preferred embodiments, a liquid nebulizer) and deliver it to the lower respiratory tract, for instance, to a pulmonary compartment such as alveoli, alveolar ducts and/or bronchioles, following intraoral administration. The formulation may also be delivered as a dry powder or through a metered-dose inhaler.

In another embodiment, a kit is provided that includes a container comprising a pharmaceutical formulation comprising a pirfenidone or pyridone analog (or salt thereof) compound and an aerosolizer adapted to aerosolize the pharmaceutical formulation (e.g., in certain preferred embodiments, a liquid nebulizer) and deliver it to a nasal cavity following intranasal administration. The formulation may also be delivered as a dry powder or through a metered-dose inhaler.

It should be understood that many carriers and excipients may serve several functions, even within the same formulation.

Contemplated pharmaceutical compositions provide a therapeutically effective amount of pirfenidone or pyridone analog compound enabling, for example, once-a-day, twice-a-day, three times a day, etc. administration. In some embodiments, pharmaceutical compositions for inhaled delivery provide an effective amount of pirfenidone or pyridone analog compound enabling once-a-day dosing. In some embodiments, pharmaceutical compositions for inhaled delivery provide an effective amount of pirfenidone or pyridone analog compound enabling twice-a-day dosing. In some embodiments, pharmaceutical compositions for inhaled delivery provide an effective amount of pirfenidone or pyridone analog compound enabling three times-a-day dosing.

It is to be understood that both the foregoing general description and the following detailed description are exemplary and explanatory only and are not restrictive of the invention, as claimed.

Certain Terminology

The term "mg" refers to milligram.
The term "mcg" refers to microgram.
The term "microM" refers to micromolar.
The term "QD" refers to once a day dosing.
The term "BID" refers to twice a day dosing.
The term "TID" refers to three times a day dosing.
The term "QID" refers to four times a day dosing.

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, which are also effective and safe.

As used herein, the terms "comprising," "including," "such as," and "for example" are used in their open, non-limiting sense.

The terms "administration" or "administering" and "delivery" or "delivery" refer to a method of giving to a mammal a dosage of a therapeutic or prophylactic formulation, such as a pirfenidone or pyridone analog (or salt thereof) compound formulation described herein, for example as an anti-inflammatory, anti-fibrotic and/or anti-demylination pharmaceutical composition, or for other purposes. The preferred delivery method or method of administration can vary depending on various factors, e.g., the components of the pharmaceutical composition, the desired site at which the formulation is to be introduced, delivered or administered, the site where therapeutic benefit is sought, or the proximity of the initial delivery site to the downstream diseased organ (e.g., aerosol delivery to the lung for absorption and secondary delivery to the heart, kidney, liver, central nervous system or other diseased destination). In some embodiments, pharmaceutical compositions described herein are administered by pulmonary administration.

The terms "pulmonary administration" or "inhalation" or "pulmonary delivery" or "oral inhalation" or "intranasal inhalation" and other related terms refer to a method of giving to a mammal a dosage of a therapeutic or prophylactic formulation, such as a pirfenidone or pyridone analog (or salt thereof) compound formulation described herein, by a route such that the desired therapeutic or prophylactic agent is delivered to the lungs of a mammal. Such delivery to the lung may occur by intranasal administration, oral inhalation administration. Each of these routes of administration may occur as inhalation of an aerosol of formulations described herein. In some embodiments, pulmonary administration occurs by passively delivering an aerosol described herein by mechanical ventilation.

The terms "intranasal inhalation administration" and "intranasal inhalation delivery" refer to a method of giving to a mammal a dosage of a pirfenidone or pyridone analog (or salt thereof) compound formulation described herein, by a route such that the formulation is targeting delivery and absorption of the therapeutic formulation directly in the lungs of the mammal through the nasal cavity. In some embodiments, intranasal inhalation administration is performed with a nebulizer.

The terms "intranasal administration" and "intranasal delivery" refer to a method of giving to a mammal a dosage of a therapeutic or prophylactic formulation, such as a pirfenidone or pyridone analog (or salt thereof) compound formulation described herein, by a route such that the desired therapeutic or prophylactic agent is delivered to the nasal cavity or diseased organs downstream (e.g., aerosol delivery to the nasal cavity for absorption and secondary delivery to the central nervous system or other diseased destination). Such delivery to the nasal cavity may occur by intranasal administration, wherein this route of administration may occur as inhalation of an aerosol of formulations described herein, injection of an aerosol of formulations described herein, gavage of a formulation described herein, or passively delivered by mechanical ventilation.

The terms "intraoccular administration" and "intraoccular delivery" refer to a method of giving to a mammal a dosage of a therapeutic or prophylactic formulation, such as a pirfenidone or pyridone analog (or salt thereof) compound formulation described herein, by a route such that the desired therapeutic or prophylactic agent is delivered to the eye. Such delivery to the eye may occur by direct administration to the eye. This route of administration may occur as spray of an aerosol of formulations described herein, injection of an aerosol of formulations described herein, or drops of a formulation described herein.

"Oral administration" or "orally" or "oral" is a route of administration where a substance (e.g. a pharmaceutical composition) is taken through the mouth. In some embodiments, when it is used without any further descriptors, it refers to administration of a substance through the mouth and directly into the gastrointestinal tract. Oral administration generally includes a number of forms, such as tablets, pills, capsules, and solutions.

The terms "oral inhalation administration" or "oral inhalation delivery" or "oral inhalation" refer to a method of giving to a mammal a dosage of a pirfenidone or pyridone analog (or salt thereof) compound formulation described herein, through the mouth for delivery and absorption of the formulation directly to the lungs of the mammal. In some embodiments, oral inhalation administration is carried out by the use of a nebulizer.

The term "abnormal liver function" may manifest as abnormalities in levels of biomarkers of liver function, including alanine transaminase, aspartate transaminase, bilirubin, and/or alkaline phosphatase, and may be an indicator of drug-induced liver injury. See FDA Draft Guidance for Industry. Drug-Induced Liver Injury: Premarketing Clinical Evaluation, October 2007.

"Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN.

"Gastrointestinal adverse events" include but are not limited to any one or more of the following: dyspepsia, nausea, diarrhea, gastroesophageal reflux disease (GERD) and vomiting.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

A "diagnostic" as used herein is a compound, method, system, or device that assists in the identification and characterization of a health or disease state. The diagnostic can be used in standard assays as is known in the art.

"Patient" or "subject" are used interchangeably and refer to a mammal.

The term "mammal" is used in its usual biological sense. In some embodiments, a mammal is a human.

The term "ex vivo" refers to experimentation or manipulation done in or on living tissue in an artificial environment outside the organism.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention and, which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, naphtoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsufuric acid, naphthalene-1,5-disulfonic acid, naphthalene-2-sulfonic acid, and saccharin.

The term "pH-reducing acid" refers to acids that retain the biological effectiveness and properties of the compounds of this invention and, which are not biologically or otherwise undesirable. Pharmaceutically acceptable pH-reducing acids include, for example, inorganic acids such as, e.g., hydrochloric acid, hydrobromic acid, sulfuric acid, nitric acid, phosphoric acid, and the like. Also by nonlimiting example, pH-reducing acids may also include organic acids such as citric acid, acetic acid, propionic acid, naphtoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like.

According to certain herein disclosed embodiments a pirfenidone or a pyridone analog compound formulation may comprise an "acidic excipient" that is typically present as an acidic excipient aqueous solution. Examples of may include acid salts such as phosphate, sulphate, nitrate, acetate, formate, citrate, tartrate, propionate and sorbate, organic acids such as carboxylic acids, sulfonic acids, phosphonic acids, phosphinic acids, phosphoric monoesters, and phosphoric diesters, and/or other organic acids that contain from 1 to 12 carbon atoms, citric acid, acetic acid, formic acid, propionic acid, butyric acid, benzoic acid, mono-, di-, and trichloroacetic acid, salicylic acid, trifluoroacetic acid, benzenesulfonic acid, toluenesulfonic acid, methylphosphonic acid, methylphosphinic acid, dimethylphosphinic acid, and phosphonic acid monobutyl ester.

A "buffer" refers to a compound that functions to regulate pH. In certain related embodiments the pH buffer is present under conditions and in sufficient quantity to maintain a pH that is "about" a recited pH value. "About" such a pH refers to the functional presence of that buffer, which, as is known in the art, may be a consequence of a variety of factors including pKa value(s) of the buffer, buffer concentration, working temperature, effects of other components of the composition on pKa (i.e., the pH at which the buffer is at equilibrium between protonated and deprotonated forms, typically the center of the effective buffering range of pH values), and other factors.

Hence, "about" in the context of pH may be understood to represent a quantitative variation in pH that may be more or less than the recited value by no more than 0.5 pH units, more preferably no more than 0.4 pH units, more preferably no more than 0.3 pH units, still more preferably no more than 0.2 pH units, and most preferably no more than 0.1-0.15 pH units. As also noted above, in certain embodiments a substantially constant pH (e.g., a pH that is maintained within the recited range for an extended time period) may be from about pH 4.0 to about pH 8.0, from about pH 4.0 to about pH 7.0, or from about pH 4.0 to about pH 6.8, or any other pH or pH range as described herein, which in preferred embodiments may be from about pH 4.0 to about pH 8.0 for a pirfenidone or pyridone analog compound formulation, and greater than about pH 8.0 for a pirfenidone or pyridone analog compound aqueous solution.

Therefore the pH buffer typically may comprise a composition that, when present under appropriate conditions and in sufficient quantity, is capable of maintaining a desired pH level as may be selected by those familiar with the art, for example, buffers comprising citrate, formate, malate, formate, pyridine, piperazine, succinate, histidine, maleate, bis-Tris, pyrophosphate, PIPES, ACES, histidine, MES, cacodylic acid, H2CO3/NaHCO$_3$ and N-(2-Acetamido)-2-iminodiacetic acid (ADA) or other buffers for maintaining, preserving, enhancing, protecting or otherwise promoting desired biological or pharmacological activity of a pirfenidone or pyridone analog compound, based on the disclosure herein. Suitable buffers may include those in Table 1 or known to the art (see, e.g., Calbiochem® Biochemicals & Immunochemicals Catalog 2004/2005, pp. 68-69 and catalog pages cited therein, EMD Biosciences, La Jolla, Calif.).

Non-limiting examples of buffers that may be used according to certain embodiments disclosed herein, include but are not limited to formate (pKa 3.77), Citric acid (pKa2 4.76), Malate (pKa2 5.13), Pyridine (pKa 5.23), Piperazine ((pKa1) 5.33), Succinate ((pKa2) 5.64), Histidine (pKa 6.04), Maleate ((pKa2) 6.24), Citric acid ((pKa3) 6.40), Bis-Tris (pKa 6.46), Pyrophosphate ((pKa3) 6.70), PIPES (pKa 6.76), ACES (pKa 6.78), Histidine (pKa 6.80), MES (pKa 6.15), Cacodylic acid (pKa 6.27), H2CO3/NaHCO3 (pKa1) (6.37), ADA (N-(2-Acetamido)-2-iminodiacetic acid) (pKa 6.60). In some embodiments, pharmaceutical compositions disclosed herein include a citrate buffer or a phosphate buffer. In some embodiments, pharmaceutical compositions disclosed herein include a citrate buffer. In some embodiments, pharmaceutical compositions disclosed herein include a phosphate buffer.

"Solvate" refers to the compound formed by the interaction of a solvent and pirfenidone or a pyridone analog compound, a metabolite, or salt thereof. Suitable solvates are pharmaceutically acceptable solvates including hydrates.

By "therapeutically effective amount" or "pharmaceutically effective amount" is meant pirfenidone or a pyridone analog compound, as disclosed for this invention, which has a therapeutic effect. The doses of pirfenidone or a pyridone analog compound which are useful in treatment are therapeutically effective amounts. Thus, as used herein, a therapeutically effective amount means those amounts of pirfenidone or a pyridone analog compound which produce the desired therapeutic effect as judged by clinical trial results and/or model animal pulmonary fibrosis, cardiac fibrosis, kidney fibrosis, hepatic fibrosis, heart or kidney toxicity, multiple sclerosis, COPD or asthma. In particular embodiments, the pirfenidone or pyridone analog compounds are administered in a pre-determined dose, and thus a therapeutically effective amount would be an amount of the dose administered. This amount and the amount of the pirfenidone or pyridone analog compound can be routinely determined by one of skill in the art, and will vary, depending on several factors, such as the therapeutic or prophylactic effect for fibrotic, inflammatory or demylination injury occurs, and how distant that disease site is from the initial respiratory location receiving the initial inhaled aerosol dose. This amount can further depend upon the patient's height, weight, sex, age and medical history. For prophylactic treatments, a therapeutically effective amount is that amount which would be effective to prevent a fibrotic, inflammatory or demylination injury.

A "therapeutic effect" relieves, to some extent, one or more of the symptoms associated with inflammation, fibrosis and/or demylination. This includes slowing the progression of, or preventing or reducing additional inflammation, fibrosis and/or demylination. For IPF, a "therapeutic effect" is defined as a patient-reported improvement in quality of life and/or a statistically significant increase in or stabilization of exercise tolerance and associated blood-oxygen saturation, reduced decline in baseline forced vital capacity, decreased incidence in acute exacerbations, increase in progression-free survival, increased time-to-death or disease progression, and/or reduced lung fibrosis. For cardiac fibrosis, a "therapeutic effect" is defined as a patient-reported improvement in quality of life and/or a statistically significant improvement in cardiac function, reduced fibrosis, reduced cardiac stiffness, reduced or reversed valvular stenosis, reduced incidence of arrhythmias and/or reduced atrial or ventricular remodeling. For kidney fibrosis, a "therapeutic effect" is defined as a patient-reported improvement in quality of life and/or a statistically significant improvement in glomular filtration rate and associated markers. For hepatic fibrosis, a "therapeutic effect" is defined as a patient-reported improvement in quality of life and/or a statistically significant lowering of elevated aminotransferases (e.g., AST and ALT), alkaline phosphatases, gamma-glutamyl transferase, bilirubin, prothrombin time, globulins, as well as reversal of thromobocytopenia, leukopenai and neutropenia and coagulation defects. Further a potential reversal of imaging, endoscopic or other pathological findings. For COPD, a "therapeutic effect" is defined as a patient-reported improvement in quality of life and/or a statistically significant improved exercise capacity and associated blood-oxygen saturation, FEV1 and/or FVC, a slowed or halted progression in the same, progression-free survival, increased time-to-death or disease progression, and/or reduced incidence or acute exacerbation. For asthma, a "therapeutic effect" is defined as a patient-reported improvement in quality of life and/or a statistically significantly improved exercise capacity, improved FEV1 and/or FVC, and/or reduced incidence or acute exacerbation. For multiple sclerosis, a "therapeutic effect" is defined as a patient-reported improvement in quality of life and/or a statistically significantly improved Scripps Neurological Rating Scale score, improvement in bladder dysfunction, improved Disability Status Socres, MRI lesion count, and/or an slowed or halted progression of disease.

"Treat," "treatment," or "treating," as used herein refers to administering a pharmaceutical composition for therapeutic purposes. In some embodiments, treating refers to alleviating, abating or ameliorating at least one symptom of a disease or condition, preventing any additional symptoms from arising, arresting the progression of at least one current symptom of the disease or condition, relieving at least one of the symptoms of a disease or condition, causing regression of the disease or condition, relieving a condition caused by the disease or condition, or stopping the symptoms of the disease or condition. In some embodiments, the compositions described herein are used for prophylactic treatment. The term "prophylactic treatment" refers to treating a patient who is not yet diseased but who is susceptible to, or otherwise at risk of, a particular disease, or who is diseased but whose condition does not worsen while being treated with the pharmaceutical compositions described herein. The term "therapeutic treatment" refers to administering treatment to a patient already suffering from a disease. Thus, in preferred embodiments, treating is the administration to a mammal (either for therapeutic or prophylactic purposes) of therapeutically effective amounts of pirfenidone or a pyridone analog compound.

"Treat," "treatment," or "treating," as used herein refers to administering a pharmaceutical composition for prophylactic and/or therapeutic purposes. The term "prophylactic treatment" refers to treating a patient who is not yet diseased, but who is susceptible to, or otherwise at risk of, a particular disease. The term "therapeutic treatment" refers to administering treatment to a patient already suffering from a disease. Thus, in preferred embodiments, treating is the administration to a mammal (either for therapeutic or prophylactic purposes) of therapeutically effective amounts of pirfenidone or a pyridone analog compound.

The term "dosing interval" refers to the time between administrations of the two sequential doses of a pharmaceutical's during multiple dosing regimens.

The "respirable delivered dose" is the amount of aerosolized pirfenidone or a pyridone analog compound particles inhaled during the inspiratory phase of the breath simulator that is equal to or less than 5 microns.

"Lung Deposition" as used herein, refers to the fraction of the nominal dose of an active pharmaceutical ingredient (API) that is deposited on the inner surface of the lungs.

"Nominal dose," or "loaded dose" refers to the amount of drug that is placed in the nebulizer prior to administration to a mammal. The volume of solution containing the nominal dose is referred to as the "fill volume."

"Enhanced pharmacokinetic profile" means an improvement in some pharmacokinetic parameter. Pharmacokinetic parameters that may be improved include, AUClast, AUC (0-∞) Tmax, and optionally a Cmax. In some embodiments, the enhanced pharmacokinetic profile may be measured quantitatively by comparing a pharmacokinetic parameter obtained for a nominal dose of an active pharmaceutical ingredient (API) administered with one type of inhalation device with the same pharmacokinetic parameter obtained with oral administration of a composition of the same active pharmaceutical ingredient (API).

"Blood plasma concentration" refers to the concentration of an active pharmaceutical ingredient (API) in the plasma component of blood of a subject or patient population.

"Respiratory condition," as used herein, refers to a disease or condition that is physically manifested in the respiratory tract, including, but not limited to, pulmonary fibrosis, chronic obstructive pulmonary disease (COPD), bronchitis, chronic bronchitis, emphysema, or asthma.

"Nebulizer," as used herein, refers to a device that turns medications, compositions, formulations, suspensions, and mixtures, etc. into a fine mist or aerosol for delivery to the lungs. Nebulizers may also be referred to as atomizers.

"Drug absorption" or simply "absorption" typically refers to the process of movement of drug from site of delivery of a drug across a barrier into a blood vessel or the site of action, e.g., a drug being absorbed in the pulmonary capillary beds of the alveoli.

Pirfenidone and Pyridone Analog Compounds

As also noted elsewhere herein, in preferred embodiments the pyridone compound for use in a pyridone compound formulation as described herein comprises pirfenidone (5-methyl-1-phenyl-2-(1H)-pyridone) or a salt thereof. Although various embodiments are described with the use of pirfenidone, it is noted that other pyridone analog compounds, or salts thereof, may be used in place of pirfenidone.

Pirfenidone is also known as 5-methyl-1-phenyl-2-(1H)-pyridone and has the structure:

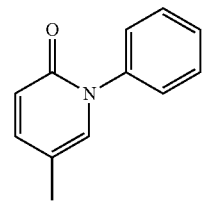

"Pyridone analog" or "pyridone compound" refers to compounds that have the same type of biological activity and effectiveness as pirfenidone. Such pyridone analog compounds are those that upon administration to a mammal produce anti-inflammatory, anti-fibrotic and/or anti-demylination activity for therapeutic or prophylactic purposes. In some embodiments, a pyridone analog is a compound that has a substituted 2-(1H)pyridone or 3-(1H)pyridone core structure. In some embodiments, a pyridone analog is a compound that has a substituted 2-(1H)pyridone core structure.

1-Phenyl-2-(1H)pyridone, 5-methyl-1-(4-methylphenyl)-2-(1H)-pyridone, 5-methyl-1-(4-hydroxyphenyl)-2-(1H)-pyridone, 5-methyl-1-(4-methoxyphenyl)-2-(1H)-pyridone, 5-Methyl-1-(2'-pyridyl)-2-(1H)pyridone, 6-Methyl-1-phenyl-3-(1H)pyridone, 6-Methyl-1-phenyl-2-(1H)pyridone, 5-Methyl-1-p-tolyl-3-(1H)pyridone, 5-Methyl-3-phenyl-1-(2'-thienyl)-2-(1H)pyridone, 5-Methyl-1-(2'-naphthyl)-3-(1H)pyridone, 5-Methyl-1-(2'-naphthyl)-2-(1H)pyridone, 5-Methyl-1-phenyl-3-(1H)pyridone, 5-Methyl-1-p-tolyl-2-(1H)pyridone, 5-Methyl-1-(1'naphthyl)-2-(1H)pyridone, 5-Methyl-1-(5'-quinolyl)-3-(1H)pyridone, 5-Ethyl-1-phenyl-2-(1H)pyridone, 5-Ethyl-1-phenyl-3-(1H)pyridone, 5-Methyl-1-(5'-quinolyl)-2-(1H)pyridone, 5-Methyl-1-(4'-methoxyphenyl)-3-(1H)pyridone, 5-Methyl-1-(4'-quinolyl)-2-(1H)pyridone, 4-Methyl-1-phenyl-3-(1H)pyridone, 5-Methyl-1-(4'-pyridyl)-2-(1H)pyridone, 5-Methyl-1-(3'-pyridyl)-3-(1H)pyridone, 3-Methyl-1-phenyl-2-(1H)pyridone, 5-Methyl-1-(4'-methoxyphenyl)-2-(1H)pyridone, 5-Methyl-1-(2'-Thienyl)-3-(1H)pyridone, 5-Methyl-1-(2'-pyridyl)-3-(1H)pyridone, 1,3-Diphenyl-2-(1H)pyridone, 1,3-Diphenyl-5-methyl-2-(1H)pyridone, 5-Methyl-1-(2'-quinolyl)-3-(1H)pyridone, 5-Methyl-1-(3'-trifluoromethylphenyl)-2-(1H)pyridone, 1-Phenyl-3-(1H)pyridone, 1-(2'-Furyl)-5-methyl-3-(1H)-pyridone, 3-Ethyl-1-phenyl-2-(1H)pyridone, 1-(4'-Chlorophenyl)-5-methyl-(1H)pyridone, 5-Methyl-1-(3'-pyridyl)-2-3-(1H)pyridone, 5-Methyl-1-(3-nitrophenyl)-2-(1H)pyridone, 3-(4'-Chlorophenyl)-5-Methyl-1-phenyl-2-(1H)pyridone, 5-Methyl-1-(2'-Thienyl)-2-(1H)pyridone, 5-Methyl-1-(2'-thiazolyl)-2-(1H)pyridone, 3,6-Dimethyl-1-phenyl-2-(1H)pyridone, 1-(4'Chlorophenyl)-5-Methyl-2-(1H)pyridone, 1-(2'-Imidazolyl)-5-Methyl-2-(1H)pyridone, 1-(4'-Nitrophenyl)-2-(1H)pyridone, 1-(2'-Furyl)-5-Methyl-2-(1H)pyridone, 1-Phenyl-3-(4'-chlorophenyl)-2-(1H)pyridone.

In some embodiments, a pyridone analog compound is a compound described in US patent publication no. US20090005424; US patent publication no. 20070092488; U.S. Pat. Nos. 8,022,087; 6,090,822; 5,716,632; 5,518,729; 5,310,562; 4,052,509; 4,042,699; 3,839,346; or U.S. Pat. No. 3,974,281; each of which is herein incorporated by reference for such compounds.

In some embodiments, a pyridone analog compound is a compound described in US patent publication no. US20140107110; US patent publication no. 20140094456; or WO/2014/055548; each of which is herein incorporated by reference for such compounds.

In some embodiments, a pyridone analog compound is ITMN-30162, or a pharmaceutically acceptable salt thereof.

In some embodiments, a pyridone analog is a deuterated pirfenidone compound, where 1 or more hydrogen atoms of pirfenidone are replaced with deuterium.

According to certain other distinct embodiments of the compositions and methods described herein, the pyridone compound is selected from the group consisting of bis(2-hydroxyethyl)azanium; 2-(3,5-diiodo-4-oxopyridin-1-yl)acetate, propyl 2-(3,5-diiodo-4-oxopyridin-1-yl)acetate, 2-[3-[4-(3-chlorophenyl)piperazin-1-yl]propyl][1,2,4]triazolo[4,3-a]pyridin-3-one hydrochloride, 2-[3-[4-(3-chlorophenyl)piperazin-1-yl]propyl]-[1,2,4]triazolo[4,3-a]pyridin-3-one, 3-anilino-1-phenylpropan-1-one, 2-[3-[4-(3-chlorophenyl)piperazin-1-yl]propyl]-[1,2,4]triazolo[4,3-a]pyridin-3-one hydrochloride, 2-[3-[4-(3-chlorophenyl)piperazin-1-yl]propyl]-[1,2,4]triazolo[4,3a]pyridin-3-one, 2S)-2-amino-3-(3-hydroxy-4-oxopyridin-1-yl)propanoic acid, 2-[3-[4 (3-chlorophenyl)piperazin-1-yl]propyl]-[1,2,4]triazolo[4,3-a]pyridin-3-one, 2-[3-[4-(3-chlorophenyl)piperazin-1-yl]propyl]-[1,2,4]triazolo[4,3-a]pyridin-3-one hydrochloride, 2-[3-[4-(3-chlorophenyl)piperazin-1-yl]propyl]-[1,2,4]triazolo[4,3-a]pyridin-3-one hydrochloride, (2S)-2-[(3-hydroxy-4-oxopyridin-1-yl)amino] propanoic acid, 2-[3-[4-(3 chlorophenyl)piperazin-1-yl]propyl]-[1,2,4]triazolo[4,3-a]pyridin-3-one hydrochloride, 2-amino-3-(3-hydroxy-4-oxopyridin-1-yl)propanoic acid, 2-[3-[4-(3chlorophenyl)piperazin-1-yl]propyl]-[1,2,4]triazolo[4,3-a]pyridin-3-one hydrochloride, propyl 2-(3,5-diiodo-4-oxopyridin-1-yl)acetate, 2-(3,5-diiodo-4-oxopyridin-1-yl)acetic acid; 2-(2 hydroxyethylamino)ethanol, (2S)-2-amino-3-(3-hydroxy-4-oxopyridin-1-yl)propanoic acid, (2R)-2-amino-3-(3-hydroxy-4-oxopyridin-1-yl)propanoic acid, 2-amino-3-(3-hydroxy-4-oxopyridin-1-yl)propanoic acid, 5-cyano-6-methyl-N-[4 (methylsulfonyl)benzyl]-2-oxo-1-[3-(trifluoromethyl)phenyl]-1,2-dihydropyridine-3-carboxamide, 6-methyl-N-[4-(methylsulfonyl)benzyl]-5-nitro-2-oxo-1-[3-(trifluoromethyl)phenyl]-1,2-dihydropyridine-3-carboxamide, 5-(1-butoxyvinyl)-6-methyl-N-[4-(methylsulfonyl)benzyl]-2-oxo-1-[3-(trifluoromethyl)phenyl]-1,2-dihydropyridine-3-carboxamide, 5-acetyl-6-methyl-N-[4-(methyl sulfonyl)benzyl]-2-oxo-1-[3-(t rifluoromethyl)phenyl]-1,2-dihydropyridine-3-carboxamide, 5-[(1E)-N-methoxyethanimidoyl]-6-methyl-N-[4-(methylsulfonyl)benzyl]-2-oxo-1-[3-(trifluoromethyl)phenyl]-1,2-dihydropyridine-3-carboxamide, 5-[(1E)-N-hydroxyethanimidoyl]-6-methyl-N-[4-(methylsulfonyl)benzyl]-2-oxo-1-[3-(trifluoromethyl)phenyl]-1,2-dihydropyridine-3-carboxamide, 6-methyl-N-[4-(methylsulfonyl)benzyl]-2-oxo-5-(pyridin-3-ylethynyl)-1-[3-(trifluoromethyl)phenyl]-1,2-dihydropyridine-3-carboxamide, 6-methyl-N-[4-(methylsulfonyl)benzyl]-2-oxo-5-(2-pyridin-3-ylethyl)-1-[3-(trifluoromethyl)phenyl]-1,2-dihydropyridine-3-carboxamide, 6-methyl-N-[4-(methylsulfonyl)benzyl]-2-oxo-1-[3-(trifluoromethyl)phenyl]-5-vinyl-1,2-dihydropyridine-3-carboxamide, ethyl 2-methyl-5-({[4 (methylsulfonyl)benzyl]amino} carbonyl)-6-oxo-1-[3-(trifluoromethyl)phenyl]-1,6-dihydropyridine-3-carboxy late, 5-(4-methanesulfonyl-benzylcarbamoyl)-2-methyl-6-oxo-1-(3-trifluoromethyl-phenyl)-1,6-dihydro-pyridine-3-carboxylic acid, 6-methyl-2-oxo-1-(3-trifluoromethyl-phenyl)-1,2-dihydro-pyridine-3,5-dicarboxylic acid 5-dimethylamide 3-(4-methanesulfonyl-benzylamide), 6-methyl-2-oxo-1-(3-trifluoromethyl-phenyl)-1,2-dihydropyridine-3,5-dicarboxylic acid 5-amide 3-(4-methanesulfonyl-benzylamide), 6-methyl-2-oxo-1-(3-trifluoromethyl-phenyl)-1,2-dihydro-pyridine-3,5-dicarboxylic acid 3-(4-methanesulfonyl-benzylamide)5-methylamide, 6-methyl-2-oxo-1-(3-trifluoromethyl-phenyl)-1,2-dihydro-pyridine-3,5-dicarboxylic acid 5-[(2-hydroxy-ethyl)-methyl-amide]3-(4-methanesulfonyl-benzylamide), 6-methyl-2-oxo-1-(3-trifluoromethyl-phenyl)-1,2-dihydro-pyridine-3,5-dicarboxylic acid 3-(4-methanesulfonyl-benzylamide)5-(methyl-propyl-amide), 6-methyl-2-oxo-5-(pyrrolidine-1-carbonyl)-1-(3-trifluoromethyl-phenyl)-1,2-dihydro-pyridine-3,5-dicarboxylic acid 3-(4-methanesulfonyl-benzylamide), 6-methyl-2-oxo-1-(3-trifluoromethyl-phenyl)-1,2-dihydro-pyridine-3,5-dicarboxylic acid 5-[(2-dimethylamino-ethyl)-methyl-amide]3-(4-methanesulfonyl-benzylamide), 5-((2R)-2-hydroxymethyl-pyrrolidine-1-carbonyl)-6-methyl-2-oxo-1-(3-trifluoromethyl-phenyl)-1, 2-dihydro-pyridine-3-carboxylic acid 3-(4-methanesulfonyl-benzylamide), 5-(3-hydroxy-pyrrolidine-1-carbonyl)-6-methyl-2-oxo-1-(3-trifluoromethyl-phenyl)-

1,2-dihydro-pyridine-3,5-dicarboxylic acid 3-(4-methanesulfonyl-benzylamide), N 3-[(1,1-dioxido-2,3-dihydro-1-benzothien-5-yl)methyl]-N 5,N 5,6-trimethyl-2-oxo-1-[3-(trifluoromethyl)phenyl]-1,2-dihydropyridine-3,5-dicarboxamide, 5-(N 1-acetyl-hydrazinocarbonyl)-6-methyl-2-oxo-1-(3-trifluoromethyl-phenyl)-1,2-dihydro-pyridine-3-carboxylic acid 4-methanesulfonyl-benzylamide, 5-[N 1-(2-cyano-acetyl)-hydrazinocarbonyl]-6-methyl-2-oxo-1-(3-trifluoromethyl-phenyl)-1,2-dihydro-pyridine-3-carboxylic acid 4-methanesulfonyl-benzylamide, 5-{[2-(aminocarbonothioyl)hydrazino]carbonyl}-6-methyl-N-[4-(methylsulfonyl)benzyl]-2-oxo-1-[3-(trifluoromethyl)phenyl]-1,2-dihydropyridine-3-carboxamide, 5-hydrazinocarbonyl-6-methyl-2-oxo-1-(3-trifluoromethyl-phen yl)-1,2-dihydro-pyridine-3-carboxylic acid 4-methanesulfonyl-benzylamide, 5-({2-[(ethylamino)carbonyl]hydrazino}carbonyl)-6-methyl-N-[4-(methylsulfonyl)benzyl]-2-oxo-1-[3-(trifluoromethyl)phenyl]-1,2-dihydropyridine-3-carboxamide, 5-({2-[(N,N-dimethylamino)carbonyl]hydrazino}carbonyl)-6-methyl-N-[4-(methylsulfonyl)benzyl]-2-oxo-1-[3-(trifluoromethyl)phenyl]-1,2-dihydropyridine-3-carboxamide, 5-(3,3-dimethyl-ureido)-6-methyl-2-oxo-1-(3-trifluoromethyl-phenyl)-1,2-dihydro-pyridine-3-carboxylic acid 4-methanesulfonyl-benzylamide, 6-methyl-5-(3-methyl-ureido)-2-oxo-1-(3-trifluoromethyl-phen yl)-1,2-dihydro-pyridine-3-carboxylic acid 4-methanesulfonyl-benzylamide, 6-methyl-2-oxo-1-(3-trifluoromethyl-phenyl)-5-ureido-1,2-dihydro-pyridine-3-carboxylic acid 4-methanesulfonyl-benzylamide, 5-amino-6-methyl-2-oxo-1-(3-trifluoromethyl-phenyl)-1,2-dihydro-pyridine-3-carboxylic acid 4-methanesulfonyl-benzylamide, 6-methyl-N-[4-(methylsulfonyl)benzyl]-2-oxo-5-propionyl-1-[3-(trifluoromethyl)phenyl]-1,2-dihydropyridine-3-carboxamide, 5-formyl-6-methyl-N-[4-(methyl sulfonyl)benzyl]-2-oxo-1-[3-(t rifluoromethyl)phenyl]-1,2-dihydropyridine-3-carboxamide, 6-methyl-N-[4-(methylsulfonyl)benzyl]-2-oxo-5-(3-oxobutyl)-1-[3-(trifluoromethyl)phenyl]-1,2-dihydropyridine-3-carboxamide, 5-acetyl-N-[4-(isopropylsulfonyl)benzyl]-6-methyl-2-oxo-1-[3-(trifluoromethyl)phenyl]-1,2-dihydropyridine-3-carboxamide, 5-acetyl-1-(3-cyano-phenyl)-6-methyl-2-oxo-1,2-dihydro-pyridine-3-carboxylic acid 4-methanesulfonyl-benzylamide, 5-acetyl-1-(3-chloro-phenyl)-6-methyl-2-oxo-1,2-dihydro-pyridine-3-carboxylic acid 4-methanesulfonyl-benzylamide, 5-acetyl-6-methyl-2-oxo-1-m-tolyl-1,2-dihydro-pyridine-3-carboxylic acid 4-methanesulfonyl-benzylamide, 5-(1-hydroxyethyl)-6-methyl-N-[4-(methylsulfonyl)benzyl]-2-oxo-1-[3-(trifluoromethyl)phenyl]-1,2-dihydropyridine-3-carboxamide, 5-(1-azidoethyl)-6-methyl-N-[4-(methylsulfonyl) benzyl]-2-oxo-1-[3-(trifluoromethyl)phenyl]-1,2-dihydropyridine-3-carboxamide, 6-methyl-N-[4-(methylsulfonyl)benzyl]-5-(1-morpholin-4-ylethyl)-2-oxo-1-[3-(trifluoromethyl)phenyl]-1,2-dihydropyridine-3-carboxamide, 5-(1-hydroxypropyl)-6-methyl-N-[4-(methylsulfonyl)benzyl]-2-oxo-1-[3-(trifluoromethyl)phenyl]-1,2-dihydropyridine-3-carb oxamide, 5-(1-hydroxyethyl)-N-[4-(isopropylsulfonyl)benzyl]-6-methyl-2-oxo-1-[3-(trifluoromethyl)phenyl]-1,2-dihydropyridine-3-carboxamide, N-[4-(cyclopropylsulfonyl)benzyl]-5-formyl-6-methyl-2-oxo 1-[3-(trifluoromethyl)phenyl]-1,2-dihydropyridine-3-carboxamide, 5-[(E)-(methoxyimino) methyl]-6-methyl-N-[4-(methylsulfonyl)benzyl]-2-oxo-1-[3-(trifluoromethyl)phenyl]-1,2-dihydropyridine-3-carboxamide, 5-(hydroxymethyl)-6-methyl-N-[4-(methyl sulfonyl)benzyl]-2-oxo-1-[3-(trifluoromethyl)phenyl]-1,2-dihydropyridine-3-carboxamide, 5-[(dimethylamino)methyl]-6-methyl-N-[4-(methylsulfonyl)benzyl]-2-oxo-1-[3-(trifluoromethyl)phenyl]-1,2-dihydropyridine-3-carboxamide, 6-methyl-5-[(methylamino)methyl]-N-[4-(methylsulfonyl)benzyl]-2-oxo 1-[3-(trifluoromethyl) phenyl]-1,2-dihydropyridine-3-carboxamide, 6-methyl-N-[4-(methylsulfonyl)benzyl]-5-(morpholin-4-ylmethyl)-2-oxo-1-[3-(trifluoromethyl)phenyl]-1,2-dihydropyridine-3-carboxamide, 5-{[(2-furylmethyl)amino]methyl}-6-methyl-N-[4-(methylsulfonyl)benzyl]-2-oxo-1-[3-(trifluoromethyl)phenyl]-1,2-dihydropyridine-3-carboxamide, 5-[(cyclopropylamino)methyl]-6-methyl-N-[4-(methylsulfonyl)benzyl]-2-oxo-1-[3-(trifluoromethyl)phenyl]-1,2-dihydropyridine-3-carboxamide, 5-{[(2-hydroxypropyl)amino]methyl}-6-methyl-N-[4-(methylsulfonyl)benzyl]-2-oxo-1-[3-(trifluoromethyl) phenyl]-1,2-dihydropyridine-3-carboxamide, 5-[(cyclopentylamino) methyl]-6-methyl-N-[4-(methylsulfonyl)benzyl]-2-oxo-1-[3-(trifluoromethyl)phenyl]-1,2-dihydropyridine-3-carboxamide, 5-{[(2-hydroxyethyl)(methyl)amino]methyl}-6-methyl-N-[4-(methylsulfonyl)benzyl]-2-oxo-1-[3-(trifluoromethyl)phenyl]-1,2-dihydropyridine-3-carboxamide, 6-methyl-N-[4-(methylsulfonyl)benzyl]-2-oxo-5-(pyrrolidin-1-ylmethyl)-1-[3-(trifluoromethyl)phenyl]-1,2-dihydropyridine-3-carboxamide, 5-{[methoxy(methyl) amino]methyl}-6-methyl-N-[4-(methylsulfonyl) benzyl]-2-oxo-1-[3-(trifluoromethyl)phenyl]-1,2-dihydropyridine-3-carboxamide, 5-{[(cyanomethyl)amino]methyl}-6-methyl-N-[4-(methylsulfonyl)benzyl]-2-oxo-1-[3-(trifluoromethyl)phenyl]-1,2-dihydropyridine-3-carboxamide, 5-{[(cyclopropylmethyl)amino]methyl}-6-methyl-N-[4-(methylsulfonyl)benzyl]-2-oxo-1-[3-(trifluoromethyl) phenyl]-1,2-dihydropyridine-3-carboxamide, 5-[(3-hydroxypyrrolidin-1-yl)methyl]-6-methyl-N-[4-(methylsulfonyl)benzyl]-2-oxo-1-[3-(trifluoromethyl)phenyl]-1,2-dihydropyridine-3-carboxamide, 5-(2-hydroxyethoxy)-N-[4-(isopropylsulfonyl)benzyl]-6-methyl-2-oxo-1-[3-(trifluoromethyl)phenyl]-1,2-dihydropyridine-3-carboxamide, 2-methyl-5-({[4-(methylsulfonyl)benzyl]amino} carbonyl)-6-oxo-1-[3-(trifluoromethyl) phenyl]-1,6-dihydropyridin-3-yl acetate, 5-methoxy-6-methyl-N-[4-(methylsulfonyl) benzyl]-2-oxo-1-[3-(trifluoromethyl) phenyl]-1,2-dihydropyridine-3-carboxamide, 5-(3-methoxypropoxy)-6-methyl-N-[4-(methylsulfonyl)benzyl]-2-oxo-1-[3-(trifluoromethyl)phenyl]-1,2-dihydropyridine-3-carboxamide, 2-methyl-5-({[4-(methylsulfonyl)benzyl]amino}carbonyl)-6-oxo-1-[3-(trifluoromethyl)phenyl]-1,6-dihydropyridin-3-yl methanesulfonate, 5-ethoxy-6-methyl-N-[4-(methylsulfonyl) benzyl]-2-oxo-1-[3-(trifluoromethyl)phenyl]-1,2-dihydropyridine-3-carboxamide, 5-(2-hydroxyethoxy)-6-methyl-N-[4-(methylsulfonyl)benzyl]-2-oxo-1-[3-(trifluoro methyl)phenyl]-1,2-dihydropyridine-3-carboxamide, 5-(cyanomethoxy)-6-methyl-N-[4-(methylsulfonyl)benzyl]-2-oxo-1-[3-(trifluoromethyl) phenyl]-1,2-dihydropyridine-3-carboxamide, 2-({2-methyl-5-({[4-(methylsulfonyl) benzyl]amino}carbonyl)-6-oxo-1-[3-(trifluoromethyl)phenyl]-1,6-dihydropyridin-3-yl}oxy) ethyl acetate, 5-[2-(dimethylamino)-2-oxoethoxy]-6-methyl-N-[4-(methylsulfonyl)benzyl]-2-oxo-1-[3-(trifluoromethyl)phenyl]-1,2-dihydropyridine-3-carboxamide, 5-(2-aminoethoxy)-N-[4-(isopropylsulfonyl)benzyl]-6-methyl-2-oxo-1-[3-(trifluoromethyl)phenyl]-1,2-dihydropyridine-3-carboxamide, 5-(acetylamino)-6-methyl-N-[4-(methylsulfonyl) benzyl]-2-oxo-1-[3-(trifluoromethyl) phenyl]-1,2-dihydropyridine-3-carboxamide, N-[4-(isopropylsulfonyl)benzyl]-6-methyl-5-[3-(methylamino)propoxy]-2-oxo-1-[3-(trifluoromethyl)phenyl]-1,2-dihydropyridine-3-carboxamide, 5-(1-methoxyethyl)-6- methyl-N-[4-(methylsulfonyl)benzyl]-2-oxo-1-[3-(trifluoromethyl)phenyl]-1,2-dihydropyridine-3-carboxamide, 5-(2-bromo-1-methoxyethyl)-6-methyl-N-[4-(methylsulfonyl)benzyl]-2-oxo-1-[3-(trifluoromethyl) phenyl]-1,2-dihydropyridine-3-carboxamide, 5-(1-isopropoxyethyl)-6-methyl-N-[4-(methylsulfonyl)benzyl]-2-oxo-1-[3-(trifluoromethyl)phenyl]-1,2-dihydropyridine-3-carboxamide, 5-(N 1-isobutyryl-hydrazinocarbonyl)-6-methyl-2-oxo-1-(3-trifluoromethyl-phenyl)-1,2-dihydro-pyridine-3-carboxylic acid 4-methanesulfonyl-benzylamide, N 5-methoxy-6-methyl-N 3-[4-(methylsulfonyl)benzyl]-2-oxo-1-[3-(trifluoromethyl)phenyl]-1,2-dihydro pyridine-3,5-dicarboxamide, N 5-methoxy-N 5,6-dimethyl-N 3-[4-(methylsulfonyl) benzyl]-2-oxo-1-[3-(trifluoromethyl) phenyl]-1,2-dihydropyridine-3,5-dicarboxamide, 5-[(2,5-dimethyl-2,5-dihydro-1H-pyrrol-1-yl)carbonyl]-6-methyl-N-[4-(methyl sulfonyl)benzyl]-2-oxo-1-[3-(trifluoromethyl)phenyl]-1,2-dihydropyridine-3-carboxamide, 6-methyl-N 3-[4-(methylsulfonyl)benzyl]-2-oxo-N 5-pyrrolidin-1-yl-1-[3-(trifluoromethyl)phenyl]-1,2-dihydropyridine-3,5-dicarboxamide, 6-methyl-N-[4-(methylsulfonyl)benzyl]-2-oxo-5-(piperidin-1-ylcarbonyl)-1-[3-(trifluoromethyl) phenyl]-1,2-dihydropyridine-3-carboxamide, 6-methyl-N 3-[4-(methylsulfonyl) benzyl]-N 5-morpholin-4-yl-2-oxo-1-[3-(trifluoromethyl) phenyl]-1,2-dihydro pyridine-3,5-dicarboxamide, 6-methyl-5-[(4-methylpiperidin-1-yl)carbonyl]-N-[4-(methylsulfonyl)benzyl]-2-oxo-1-[3-(trifluoromethyl)phenyl]-1,2-dihydropyridine-3-carboxamide, 6-methyl-N 3-[4-(methylsulfonyl)benzyl]-2-oxo-N 5-piperidin-1-yl-1-[3-(trifluoromethyl)phenyl]-1,2-dihydropyridine-3,5-dicarboxamide, N 5-(tert-butyl)-N 5,6-dimethyl-N 3-[4-(methylsulfonyl)benzyl]-2-oxo-1-[3-(trifluoromethyl)phenyl]-1,2-dihydropyridine-3,5-dicarboxamide, N 5-butyl-N 5,6-dimethyl-N 3-[4-(methylsulfonyl)benzyl]-2-oxo-1-[3-(trifluoromethyl) phenyl]-1,2-dihydropyridine-3,5-dicarboxamide, N 5-ethyl-N 5-isopropyl-6-methyl-N 3-[4-(methylsulfonyl) benzyl]-2-oxo-1-[3-(trifluoromethyl)phenyl]-1,2-dihydropyridine-3,5-dicarboxamide, 5-[N 1-(formyl-hydrazinocarbonyl]-6-methyl-2-oxo-1-(3-trifluoromethyl-phenyl)-1,2-dihydro-pyridine-3-carboxylic acid 4-methanesulfonyl-benzylamide, N 1-[5-(4-methanesulfonyl-benzylcarbamoyl)-2-methyl-6-oxo-1-(3-trifluoromethyl-phenyl)-1,6-dihydro-pyridine-3-carbonyl]-hydrazinecarboxylic acid ethyl ester, 5-({2-[(ethylamino)carbonothioyl] hydrazino}carbonyl)-6-methy 1-N-[4-(methylsulfonyl) benzyl]-2-oxo-1-[3-(trifluoromethyl) phenyl]-1,2-dihydropyridine-3-carboxamide, 5-(isoxazolidin-2-ylcarbonyl)-6-methyl-N-[4-(methylsulfonyl) benzyl]-2-oxo-1-[3-(trifluoromethyl)phenyl]-1,2-dihydropyridine-3-carboxamide, 6-methyl-2-oxo-1-(3-trifluoromethyl-phenyl)-1,2-dihydro-pyridine-3,5-dicarboxylic acid 5-(methoxy-methyl-amide)3-[4-(propane-2-sulfonyl)-benzylamide], 6-methyl-2-oxo-1-(3-trifluoromethyl-phenyl)-1,2-dihydro-pyridine-3,5-dicarboxylic acid 3-(4-ethanesulfonyl-benzylamide)5-(methoxy-methyl-amide), 6-methyl-2-oxo-1-(3-trifluoromethyl-phenyl)-1,2-dihydro-pyridine-3,5-dicarboxylic acid 3-(4-cyclopropanesulfonyl-benzylamide)5-(methoxy-methyl-amide), 6-methyl-2-oxo-1-(3-trifluoromethyl-phenyl)-1,2-dihydro-pyridine-3,5-dicarboxylic acid 5-[(2-hydroxy-ethyl)-amide]3-(4-methanesulfonyl-benzylamide, 5-(isoxazolidine-2-carbonyl)-6-methyl-2-oxo-1-(3-trifluoromethyl-phenyl)1,2-dihydro-pyridine-3-carboxylic acid 4-ethanesulfonyl-benzylamide, 5-(isoxazolidine-2-carbonyl)-6-methyl-2-oxo-1-(3-trifluoromethylphenyl) 1,2dihydropyridine-3-carboxylic acid 4-cyclopropane sulfonylbenzylamide, 5-(N-hydroxycarbamimidoyl)-6-methyl-2-oxo-1-(3-trifluoro methyl-phenyl)-1,2-dihydro-pyridine-3-carboxylic acid 4-methanesulfonyl-benzylamide, N 3-(cyclohexylmethyl)-N 5,N 5,6-trimethyl-2-oxo-1-[3-(trifluoro methyl) phenyl]-1,2-dihydropyridine-3,5-dicarboxamide, N 5,N 5,6-trimethyl-2-oxo-N 3-(pyridin-3-ylmethyl)-1-[3-(trifluoromethyl)-phenyl]-1,2-dihydropyridine-3,5-dicarboxamide, N 5,N 5,6-trimethyl-N 3-(2-morpholin-4-ylethyl)-2-oxo-1-[3-(trifluoromethyl)-phenyl]-1,2-dihydropyridine-3,5-dicarboxamide, N 5,N 5,6-trimethyl-N 3-(3-morpholin-4-ylpropyl)-2-oxo-1-[3-(trifluoromethyl)-phenyl]-1,2-dihydropyridine-3,5-dicarboxamide, N 3-benzyl-N 5,N 5,6-trimethyl-2-oxo-1-[3-(trifluoromethyl)phenyl]-1,2-dihydro-pyridine-3,5-dicarboxamide, N 3-[2-(1H-indol-3-yl)ethyl]-N 5,N 5,6-trimethyl-2-oxo-1-[3-(trifluoromethyl)-phenyl]-1,2-dihydro pyridine-3,5-dicarboxamide, N 5,N 5,6-trimethyl-2-oxo-N 3-(1-phenylethyl)-1-[3-(trifluoromethyl)phenyl]-1,2-dihydropyridine-3,5-dicarboxamide, N 5,N 5,6-trimethyl-2-oxo-N 3-(2-phenylethyl)-1-[3-(trifluoromethyl)phenyl]-1,2-dihydropyridine-3,5-dicarboxamide, N 5,N 5,6-trimethyl-2-oxo-N 3-[(2R)-2-phenylcyclopropyl]-1-[3-(trifluoromethyl)-phenyl]-1,2-dihydropyridine-3,5-dicarboxamide, N 3-(2,3-dihydro-1H-inden-2-yl)-N 5,N 5,6-trimethyl-2-oxo-1-[3-(trifluoromethyl)-phenyl]-1,2-dihydropyridine-3,5-dicarboxamide, N 3-[2-(1,3-benzodioxol-5-yl)ethyl]-N 5,N 5,6-trimethyl-2-oxo-1-[3-(trifluoromethyl)phenyl]-1,2-dihydropyridine-3,5-dicarboxamide, 5-{[4-(2-hydroxyethyl)piperazin-1-yl]carbonyl}-N,N,2-trimethyl-6-oxo-1-[3-(trifluoromethyl)phenyl]-1,6-dihydropyridine-3-carboxamide, N 3-[(1-ethylpyrrolidin-2-yl)methyl]-N 5,N 5,6-trimethyl-2-oxo-1-[3-(trifluoromethyl)phenyl]-1,2-dihydropyridine-3,5-dicarboxamide, N 5,N 5,6-trimethyl-N 3-[3-(2-methylpiperidin-1-yl)propyl]-2-oxo-1-[3-(trifluoromethyl)phenyl]-1,2-dihydropyridine-3,5-dicarboxamide, N 5,N 5,6-trimethyl-N 3-(1-naphthylmethyl)-2-oxo-1-[3-(trifluoromethyl)phenyl]-1,2-dihydropyridine-3,5-dicarboxamide, N 3-(1,3-benzodioxol-5-ylmethyl)-N 5,N 5,6-trimethyl-2-oxo-1-[3-(trifluoromethyl) phenyl]-1,2-dihydropyridine-3,5-dicarboxamide, N 3-(3,4-difluorobenzyl)-N 5,N 5,6-trimethyl-2-oxo-1-[3-(trifluoromethyl)phenyl]-1,2-dihydropyridine-3,5-dicarboxamide, N 3-(2-chloro-4-fluorobenzyl)-N 5,N 5,6-trimethyl-2-oxo-1-[3-(trifluoromethyl)-phenyl]-1,2-dihydropyridine-3,5-dicarboxamide, N 5,N 5,6-trimethyl-2-oxo-N 3-(2-thienylmethyl)-1-[3-(trifluoromethyl)phenyl]-1,2-dihydro pyridine-3,5-dicarboxamide, N 3-(3,4-dichlorobenzyl)-N 5,N 5,6-trimethyl-2-oxo-1-[3-(trifluoromethyl)phenyl]-1,2-dihydropyridine-3,5-dicarboxamide, N 3-[2-(2,4-dichlorophenyl)ethyl]-N 5,N 5,6-trimethyl-2-oxo-1-[3-(trifluoromethyl)-phenyl]-1,2-dihydropyridine-3,5-dicarboxamide, N 3-(2-cyclohex-1-en-1-ylethyl)-N 5,N 5,6-trimethyl-2-oxo-1-[3-(trifluoromethyl)-phenyl]-1,2-dihydropyridine-3,5-dicarboxamide, N 3-[1-(4-chlorophenyl)ethyl]-N 5,N 5,6-trimethyl-2-oxo-1-[3-(trifluoromethyl)-phenyl]-1,2-dihydropyridine-3,5-dicarboxamide, N 5,N 5,6-trimethyl-2-oxo-N 3-[3-(2-oxopyrrolidin-1-yl)propyl]-1-[3-(trifluoromethyl)phenyl]-1,2-dihydropyridine-3,5-dicarboxamide, N 5,N 5,6-trimethyl-2-oxo-N 3-(pyridin-4-ylmethyl)-1-[3-(trifluoromethyl)phenyl]-1,2-dihydropyridine-3,5-dicarboxamide, N,N,2-trimethyl-6-oxo-5-[(4-phenylpiperazin-1-yl)carbonyl]-1-[3-(trifluoromethyl) phenyl]-1,6-dihydropyridine-3-carboxamide, N,N,2-trimethyl-6-oxo-5-[(4-pyridin-4-ylpiperazin-1-yl)carbonyl]-1-[3-(trifluoromethyl)phenyl]-1,6-dihydropyridine-3-carboxamide, N 3-(2,3-dihydro-1- benzofuran-5-ylmethyl)-N 5,N 5,6-trimethyl-2-oxo-1-[3-(trifluoromethyl)phenyl]-1,2-dihydropyridine-3,5-dicarboxamide, methyl 4-{[({5-[(dimethylamino)carbonyl]-6-methyl-2-oxo-1-[3-(trifluoromethyl)phenyl]-1,2-dihydropyridin-3-yl}carbonyl)amino]methyl}benzoate, 5-{[3-(dimethylamino) pyrrolidin-1-yl]carbonyl}-N,N,2-trimethyl-6-oxo-1-[3-(trifluoromethyl)phenyl]-1,6-dihydropyridine-3-carboxamide, N 5,N 5,6-trimethyl-2-oxo-N 3-[2-(2-thienyl)ethyl]-1-[3-(trifluoromethyl)phenyl]-1,2-dihydropyridine-3,5-dicarboxamide, N 5,N 5,6-trimethyl-2-oxo-N 3-(4-phenoxybenzyl)-1-[3-(trifluoromethyl)phenyl]-1,2-dihydropyridine-3,5-dicarboxamide, N 5,N 5,6-trimethyl-2-oxo-N 3-(3-thienylmethyl)-1-[3-(trifluoromethyl)phenyl]-1,2-dihydropyridine-3,5-dicarboxamide, N 3-[2-(4-tert-butylphenyl)ethyl]-N 5,N 5,6-trimethyl-2-oxo-1-[3-(trifluoromethyl)-phenyl]-1,2-dihydropyridine-3,5-dicarboxamide, N 3-{2-[4-(amino sulfonyl)phenyl]ethyl}-N 5,N 5,6-trimethyl-2-oxo-1-[3-(trifluoromethyl)phenyl]-1,2-dihydropyridine-3,5-dicarboxamide, N 5,N 5,6-trimethyl-2-oxo-N 3-[4-(1H-pyrazol-1-yl)benzyl]-1-[3-(trifluoromethyl)-phenyl]-1,2-dihydropyridine-3,5-dicarboxamide, N 5,N 5,6-trimethyl-2-oxo-N 3-phenoxy-1-[3-(trifluoromethyl)phenyl]-1,2-dihydro-pyridine-3,5-dicarboxamide, N 3-(2,3-dihydro-1,4-benzodioxin-2-ylmethyl)-N 5,N 5,6-trimethyl-2-oxo-1-[3-(trifluoromethyl)phenyl]-1,2-dihydro-pyridine-3,5-dicarboxamide, N 3-[(6-fluoro-4H-1,3-benzodioxin-8-yl)methyl]-N 5,N 5,6-trimethyl-2-oxo-1-[3-(trifluoromethyl)phenyl]-1,2-dihydropyridine-3,5-dicarboxamide, N 3-(1-benzothien-3-ylmethyl)-N 5,N 5,6-trimethyl-2-oxo-1-[3-(trifluoromethyl)-phenyl]-1,2-dihydropyridine-3,5-dicarboxamide, N 5,N 5,6-trimethyl-2-oxo-N 3-[2-(tetrahydro-2H-pyran-4-yl)ethyl]-1-[3-(trifluoromethyl)phenyl]-1,2-dihydropyridine-3,5-dicarboxamide, N 5,N 5,6-trimethyl-N 3-[(1-methyl-1H-pyrazol-4-yl)methyl]-2-oxo-1-[3-(trifluoromethyl)phenyl]-1,2-dihydropyridine-3,5-dicarboxamide, N 5,N 5,6-trimethyl-2-oxo-N 3-[(1-phenyl-1H-pyrazol-4-yl)methyl]-1-[3-(trifluoromethyl)phenyl]-1,2-dihydropyridine-3,5-dicarboxamide, N 3-[(5-methoxy-4-oxo-4H-pyran-2-yl) methyl]-N 5,N 5,6-trimethyl-2-oxo-1-[3-(trifluoromethyl) phenyl]-1,2-dihydropyridine-3,5-dicarboxamide, N 3-(3-azepan-1-ylpropyl)-N 5,N 5,6-trimethyl-2-oxo-1-[3-(trifluoromethyl)phenyl]-1,2-dihydropyridine-3,5-dicarboxamide, N 3-(4-cyanobenzyl)-N 5,N 5,6-trimethyl-2-oxo-1-[3-(trifluoromethyl)phenyl]-1,2-dihydropyridine-3,5-dicarboxamide, N 5,N 5,6-trimethyl-2-oxo-N 3-[3-(5-oxo-4,5-dihydro-1H-pyrazol-4-yl)propyl]-1-[3-(t rifluoromethyl)phenyl]-1,2-dihydropyridine-3,5-dicarboxamide, N 3-{[(2R)-1-ethylpyrrolidin-2-yl]methyl}-N 5,N 5,6-trimethyl-2-oxo-1-[3-(trifluoromethyl)phenyl]-1,2-dihydropyridine-3,5-dicarboxamide, 5-cyclopropyl-6-methyl-N-[4-(methylsulfonyl)benzyl]-2-oxo-1-[3-(trifluoromethyl) phenyl]-1,2-dihydropyridine-3-carboxamide, 6-methyl-5-(2-methyl-1,3-dioxolan-2-yl)-N-[4-(methylsulfonyl)benzyl]-2-oxo-1-[3-(trifluoromethyl)phenyl]-1,2-dihydro pyridine-3-carboxamide, 5-(4,5-dihydro-oxazol-2-yl)-6-methyl-2-oxo-1-(3-trifluoromethyl-phenyl)-1,2-dihydro-pyridine-3-carboxylic acid 4-methanesulfonyl-benzylamide, 5-cyclopropyl-6-methyl-N-{[5-(methylsulfonyl)pyridin-2-yl]methyl}-2-oxo-1-[3-(trifluoromethyl)phenyl]-1,2-dihydropyridine-3-carboxamide, 2-amino-3-(3-hydroxy-4-oxopyridin-1-yl)propanoic acid, (2S)-2-amino-3-(3-hydroxy-4-oxopyridin-1-yl)propanoic acid, 2-amino-3-(3-hydroxy-4-oxopyridin-1-yl)propanoic acid, (2S)-2-amino-3-(3-hydroxy-4-oxopyridin-1-yl)propanoic acid, 2-amino-3-(3-hydroxy-4-oxopyridin-1-yl)propanoic acid, 2-amino-3-(3-hydroxy-4-oxopyridin-1-yl)propanoic acid, propyl 2-(3,5-diiodo-4-oxopyridin-1-yl)acetate, (2S)-2-azaniumyl-3-(3-hydroxy-4-oxopyridin-1-yl)propanoate, propyl 2-(3,5-di-iodo-4-oxopyridin-1-yl)acetate, 2-(4-aminophenyl)ethanol, 4-hydroxy-5-(3-methylanilino)-1H-pyrimidin-6-one, 6-cyclohexyl-1-hydroxy-4-methylpyridin-2-one, 1,6-dimethyl-2-oxo-5-pyridin-4-ylpyridine-3-carbonitrile, (2-oxo-1H-pyridin-3-yl) acetate, 3-methyl-1-(2,4,6-trimethylphenyl) butan-1-one, 5-methyl-1-phenylpyridin-2-one, 6-cyclohexyl-1-hydroxy-4-methylpyridin-2-one, 2-aminoethanol; 6-cyclohexyl-1-hydroxy-4-methylpyridin-2-one, 4-[(3,5-diiodo-4-oxopyridin-1-yl)methyl]benzoic acid, 2-aminoethanol; 3-[(6-hydroxy-5-methyl-2-oxo-1H-pyridin-3-yl)imino]-5-methylpyridine-2,6-dione, 5-ethyl-3-[(5-ethyl-2-methoxy-6-methylpyridin-3-yl)methylamino]-6-methyl-1H-pyridin-2-one, 6-cyclohexyl-1-hydroxy-4-methyl pyridin-2-one, 5-(2,5-dihydroxyphenyl)-1H-pyridin-2-one, 6-(4,4-dimethyl-5-oxofuran-2-yl)-1H-pyridin-2-one, N'-(6-oxo-1H-pyridin-2-yl)-N,N-dipropyl methanimid-amide, [6-oxo-1-[(2R,3R,4S,5S,6R)-3,4,5-trihydroxy-6-(hydroxyl methyl)oxan-2-yl]pyridin-2-yl]acetic acid, 5-(2,5-dihydroxyphenyl)-H-pyridin-2-one, 3-[(6-hydroxy-5-methyl-2-oxo-H-pyridin-3-yl)imino]-5-methylpyridine-2,6-dione, 5-(4-cyanophenyl)-6-methyl-2-oxo-1H-pyridine-3-carbonitrile, 3,3-diethyl-1-[(piperazin-1-ylamino)methyl] pyridine-2,4-dione, 5-ethyl-3-[(5-ethyl-2-methoxy-6-methylpyridin-3-yl)methylamino]-6-methyl-1H-pyridin-2-one and pharmaceutically acceptable salts thereof.

In some embodiments, the pirfendione or pyridone analog compound is used in compositions and methods described herein in free-base or free-acid form. In other embodiments, the pirfendione or pyridone analog compound is used as pharmaceutically acceptable salts. In some embodiments, pharmaceutically acceptable salts are obtained by reacting the compound with an acid or with a base. The type of pharmaceutical acceptable salts, include, but are not limited to: (1) acid addition salts, formed by reacting the free base form of the compound with a pharmaceutically acceptable: (1) acid such as, for example, hydrochloric acid, hydrobromic acid, sulfuric acid, phosphoric acid, metaphosphoric acid, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; or (2) base, where an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, the pirfendione or pyridone analog compound is reacted with an organic base, such as, but not limited to, ethanolamine, diethanolamine, triethanolamine, tromethamine, N-methylglucamine, dicyclohexylamine, tris(hydroxymethyl)methylamine or with an amino acid such as, but not limited to, arginine, lysine, and the like.

Advantages of Inhaled Aerosol and Topical (Non-Oral) Drug Delivery

Inhalation therapy of aerosolized pirfenidone or a pyridone analog compound enables direct deposition of the sustained-release or active substance in the respiratory tract (be that intra-nasal or pulmonary) for therapeutic action at that site of deposition or systemic absorption to regions immediately down stream of the vascular absorption site. In the case of central nervous system (CNS) deposition, intranasal inhalation aerosol delivery deposits pirfenidone or a pyridone analog compound directly upstream of the CNS compartment.

Similar to the intra-nasal and pulmonary applications described above, treatment or prevention of organs outside the respiratory tract requires absorption to the systemic vascular department for transport to these extra-respiratory sites. In the case of treating or preventing fibrotic or inflammatory diseases associated with the heart, liver and kidney, deposition of drug in the respiratory tract, more specifically the deep lung will enable direct access to these organs through the left atrium to either the carotid arteries or coronary arteries. Similarly, in the case of treating CNS disorder (e.g., multiple sclerosis), deposition of drug in the respiratory tract (as defined above) or nasal cavity, more specifically the absorption from the nasal cavity to the nasal capillary beds for immediate access to the brain and CNS. This direct delivery will permit direct dosing of high concentration pirfenidone or a pyridone analog compound in the absence of unnecessary systemic exposure. Similarly, this route permits titration of the dose to a level that may be critical for these indications.

Pharmaceutical Compositions

For purposes of the method described herein, a pyridone analog compound, most preferably pirfenidone may be administered using a liquid nebulization, dry powder or metered-dose inhaler. In some embodiments, pirfenidone or a pyridone analog compound disclosed herein is produced as a pharmaceutical composition suitable for aerosol formation, dose for indication, deposition location, pulmonary or intra-nasal delivery for pulmonary, intranasal/sinus, or extra-respiratory therapeutic action, good taste, manufacturing and storage stability, and patient safety and tolerability.

In some embodiments, the isoform content of the manufactured pyridone analog compound, most preferably pirfenidone may be optimized for drug substance and drug product stability, dissolution (in the case of dry powder or suspension formulations) in the nose and/or lung, tolerability, and site of action (be that lung, nasal/sinus, or regional tissue).

Manufacture

In some embodiments, pirfenidone drug product (DP) includes pirfenidone at a concentration of about 1 mg/mL to about 100 mg/mL in aqueous buffer (citrate or phosphate pH=4 to 8), plus optional added salts (NaCl and/or $MgCl_2$ and/or $MgSO_4$). In some embodiments, the pirfenidone drug product also includes co-solvent(s) (by non-limiting example ethanol, propylene glycol, and glycerin) and/or surfactant(s) (by non-limiting example Tween 80, Tween 60, lecithin, Cetylpyridinium, and Tween 20). In some embodiments, the formulation also includes a taste-masking agent (by non-limiting example sodium saccharin).

To achieve pirfenidone concentrations above 3 mg/mL, manufacturing process are described. In one embodiment, the manufacturing process includes high temperature pirfenidone aqueous dissolution, followed by co-solvent and/or surfactant and/or salt addition, and subsequent cooling to ambient temperature. In this process, added co-solvent and/or surfactant and/or salt stabilize the high-temperature-dissolved pirfenidone during the cooling process and provide a stable, high-concentration, ambient-temperature formulation of pirfenidone. In some embodiments, the processing temperature is 30° C., 35° C., 40° C., 45° C., 50° C., 55° C., 60° C., 65° C., 70° C., 75° C., 80° C., 85° C., 90° C., 95° C., 100° C. or other pressure-enabled increased temperature. In some embodiments, the process includes addition of surfactant and/or co-solvent and/or salt at the highest temperature or incrementally-lower temperature as the solution is cooled. In some embodiments, addition of surfactant and/or co-solvent and/or salt occurs all at once or incrementally during a maintained temperature or as the solution is cooled. The time by which the solution is maintained at the highest temperature is from 0 minutes to 24 hours. The time by which the solution is cooled from the highest temperature is from 0 minutes to 24 hours. In some embodiments, the solution is protected from light. In some embodiments, the solution is sparged to remove or lower the oxygen concentration. In some embodiments, the head space of the reaction container includes an inert gas or mixture of inert gases. Inert gases include, but are not limited to, nitrogen and argon. In some embodiments, the pirfenidone drug product includes co-solvent(s) in the concentration range of 0% to 100% in otherwise buffered aqueous solution. In some embodiments, the pirfenidone drug product includes co-solvent(s) at a concentration of about 1% to about 25%. Co-solvents include, but are not limited to, ethanol, glycerin or propylene glycol. In some embodiments, the pirfenidone drug product includes surfactant(s) in the concentration range of 0% to 100% in otherwise buffered aqueous solution. In some embodiments, the pirfenidone drug product includes surfactant(s) at a concentration of about 0.1% to about 10%. Surfactants include, but are not limited to Tween 20, Tween 60, Tween 80, Cetylpyridinium Bromide, or Lecithin. In some embodiments, the pirfenidone drug product includes a buffer. In some embodiments, the buffer includes salt and/or acid forms of agents such as citrate, phosphate or formate at a concentration between 0 mM to 1000 mM. In some embodiments, the buffer includes salt and/or acid forms of agents such as citrate, phosphate or formate at a concentration between about 1 mM and about 50 mM. In some embodiments, the pirfenidone drug product includes a salt. In some embodiments, the salt is present at a concentration between 0% to 100%. In some embodiments, the salt is present at a concentration between about 0.1% and about 5%. In some embodiments, the salt is sodium chloride, magnesium chloride, magnesium sulfate or barium chloride. In some embodiments, a sweetening agent is added to the pirfenidone drug product. In some embodiments, the sweetening agent is saccharin or a salt thereof. In some embodiments, the sweetening agent is present at a concentration between about 0.01 mM and about 10 mM. In some embodiments, the pH of the buffered solution will be between about 2.0 and about 10.0.

In another embodiment, the manufacturing process includes excess co-solvent and/or surfactant and/or cation addition to a super-saturated pirfenidone aqueous solution. Upon dissolution in the excess co-solvent and/or surfactant and/or cation aqueous solution, the formulation is diluted to reduce co-solvent and/or surfactant and/or cation concentrations to within the concentration range generally-recognized as safe and/or non-toxic and/or non-irritable.

In some embodiments, the manufacturing process is as described in Example 5.

Administration

The pyridone analog compound, most preferably pirfenidone as disclosed herein can be administered at a therapeutically effective dosage, e.g., a dosage sufficient to provide treatment for the disease states previously described. Generally, for example, a daily aerosol dose of pirfenidone in a pirfenidone compound formulation may be from about 0.001 mg to about 6.6 mg pirfenidone/kg of body weigh per dose. Thus, for administration to a 70 kg person, the dosage range would be about 0.07 mg to about 463 mg pirfenidone per dose or up to about 0.280 mg to about 1852 mg pirfenidone day. The amount of active compound administered will, of course, be dependent on the subject and disease state being treated, the severity of the affliction, the manner and schedule of administration, the location of the disease (e.g., whether it is desired to effect intra-nasal or upper airway delivery, pharyngeal or laryngeal delivery, bronchial delivery, pulmonary delivery and/or pulmonary delivery with subsequent systemic or central nervous system absorption), and the judgment of the prescribing physician; for example, a likely dose range for aerosol administration of pirfenidone in preferred embodiments, or in other embodiments of pyridone analog compound, would be about 0.28 to 1852 mg per day.

Another unexpected observation is that inhalation delivery of aerosol pirfenidone to the lung exhibits less metabolism of pirfenidone observed with oral administration. Thus, oral or intranasal inhalation of pirfenidone or pyridone analog will permit maximum levels of active substance to the pulmonary tissue in the absence of substantial metabolism to inactive agents.

Inhibitors of CYP enzymes reduce pirfenidone metabolism resulting in elevated blood levels and associated toxicity. As many products effecting CYP enzymes are useful to fibrosis patients, permitting their use would be beneficial. While the oral route is already at the maximum permissible dose (which provides only moderate efficacy), any inhibition of the enzymes described above elevates pirfenidone blood levels and increases the rate and severity of the toxic events described herein. Because oral and intranasal inhalation delivery of pirfenidone or pyridone analogs can achieve effective tissue levels with much less drug than that required by the oral product, resulting blood levels are significantly lower and consequences associated with CYP enzyme inhibitory properties described herein are removed. Thus, permitting use of these CYP inhibitory enzyme products currently contraindicated with the oral medicine.

The primary metabolite of pirfenidone is 5-carboxy-pirfenidone. Following oral or intravenous administration, this metabolite appears quickly at high concentrations in blood. 5-carboxy-pirfenidone does not appear to have anti-fibrotic or anti-inflammatory activity, its high blood levels occur at the loss of pirfenidone blood concentrations. Thus, while the oral product is dosed at the highest possible level, once pirfenidone enters the blood it is rapidly metabolized to a non-active species further reducing the drugs potential to achieve sufficient lung levels required for substantial efficacy. Because oral and intranasal inhalation delivery of pirfenidone or pyridone analogs can achieve effective lung tissue levels directly extra-lung metabolism is not a factor.

Administration of the pyridone analog compound, most preferably pirfenidone as disclosed herein, such as a pharmaceutically acceptable salt thereof, can be via any of the accepted modes of administration for agents that serve similar utilities including, but not limited to, aerosol inhalation such as nasal and/or oral inhalation of a mist or spray containing liquid particles, for example, as delivered by a nebulizer.

Pharmaceutically acceptable compositions thus may include solid, semi-solid, liquid and aerosol dosage forms, such as, e.g., powders, liquids, suspensions, complexations, liposomes, particulates, or the like. Preferably, the compositions are provided in unit dosage forms suitable for single administration of a precise dose. The unit dosage form can also be assembled and packaged together to provide a patient with a weekly or monthly supply and can also incorporate other compounds such as saline, taste masking agents, pharmaceutical excipients, and other active ingredients or carriers.

The pyridone analog compound, most preferably pirfenidone as disclosed herein, such as a pharmaceutically acceptable salt thereof, can be administered either alone or more typically in combination with a conventional pharmaceutical carrier, excipient or the like (e.g., mannitol, lactose, starch, magnesium stearate, sodium saccharin, talcum, cellulose, sodium crosscarmellose, glucose, gelatin, sucrose, magnesium carbonate, magnesium chloride, magnesium sulfate, calcium chloride, lactose, sucrose, glucose and the like). If desired, the pharmaceutical composition can also contain minor amounts of nontoxic auxiliary substances such as wetting agents, emulsifying agents, solubilizing agents, pH buffering agents and the like (e.g., citric acid, ascorbic acid, sodium phosphate, potassium phosphate, sodium acetate, sodium citrate, cyclodextrin derivatives, sorbitan monolaurate, triethanolamine acetate, triethanolamine oleate, and the like). Generally, depending on the intended mode of administration, the pharmaceutical formulation will contain about 0.005% to 95%, preferably about 0.1% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In one preferred embodiment, the compositions will take the form of a unit dosage form such as vial containing a liquid, solid to be suspended, dry powder, lyophilisate, or other composition and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. However, percentages of active ingredient of 0.01% to 90% in solution are employable, and will be higher if the composition is a solid, which will be subsequently diluted to the above percentages. In some embodiments, the composition will comprise 0.25%-50.0% of the active agent in solution.

Pirfenidone or pyridone analog compound formulations can be separated into two groups; those of simple formulation and complex formulations providing taste-masking for improved tolerability, pH-optimized for stability and tolerability, immediate or sustained-release, and/or area-under-the-curve (AUC) shape-enhancing properties. Simple formulations can be further separated into three groups. 1. Simple formulations may include water-based liquid formulations for nebulization. By non-limiting example water-based liquid formulations may consist of pirfenidone or pyridone analog compound alone or with non-encapsulating water soluble excipients. 2. Simple formulations may also include organic-based liquid formulations for nebulization or meter-dose inhaler. By non-limiting example organic-based liquid formulations may consist of pirfenidone or pyridone analog compound or with non-encapsulating organic soluble excipients. 3. Simple formulations may also include dry powder formulations for administration with a dry powder inhaler. By non-limiting example dry powder formulations may consist of pirfenidone or pyridone analog compound alone or with either water soluble or organic soluble non-encapsulating excipients with or without a blending agent such as lactose. Complex formulations can be further separated into five groups. 1. Complex formulations may include water-based liquid formulations for nebulization. By non-limiting example water-based liquid complex formulations may consist of pirfenidone or pyridone analog compound encapsulated or complexed with water-soluble excipients such as lipids, liposomes, cyclodextrins, microencapsulations, and emulsions. 2. Complex formulations may also include organic-based liquid formulations for nebulization or meter-dose inhaler. By non-limiting example organic-based liquid complex formulations may consist of pirfenidone or pyridone analog compound encapsulated or complexed with organic-soluble excipients such as lipids, microencapsulations, and reverse-phase water-based emulsions. 3. Complex formulations may also include low-solubility, water-based liquid formulations for nebulization. By non-limiting example low-solubility, water-based liquid complex formulations may consist of pirfenidone or pyridone analog compound as a low-water soluble, stable nano-suspension alone or in co-crystal/co-precipitate excipient complexes, or mixtures with low solubility lipids, such as lipid nanosuspensions. 4. Complex formulations may also include low-solubility, organic-based liquid formulations for nebulization or meter-dose inhaler. By non-limiting example low-solubility, organic-based liquid complex formulations may consist of pirfenidone or pyridone analog compound as a low-organic soluble, stable nanosuspension alone or in co-crystal/co-precipitate excipient complexes, or mixtures with low solubility lipids, such as lipid nanosuspensions. 5. Complex formulations may also include dry powder formulations for administration using a dry powder inhaler. By non-limiting example, complex dry powder formulations may consist of pirfenidone or pyridone analog compound in co-crystal/co-precipitate/spray dried complex or mixture with low-water soluble excipients/salts in dry powder form with or without a blending agent such as lactose. Specific methods for simple and complex formulation preparation are described herein.

Aerosol Delivery

Pirfenidone or pyridone analog compounds as described herein are preferably directly administered as an aerosol to a site of pulmonary pathology including pulmonary fibrosis, COPD or asthma. The aerosol may also be delivered to the pulmonary compartment for absorption into the pulmonary vasculature for therapy or prophylaxis of extra-pulmonary pathologies such as fibrosis and inflammatory diseases of the heart, kidney and liver, or pulmonary or intra-nasal delivery for extra-pulmonary or extra-nasal cavity demylination diseases associated with the central nervous system.

Several device technologies exist to deliver either dry powder or liquid aerosolized products. Dry powder formulations generally require less time for drug administration, yet longer and more expensive development efforts. Conversely, liquid formulations have historically suffered from longer administration times, yet have the advantage of shorter and less expensive development efforts. Pirfenidone or pyridone analog compounds disclosed herein range in solubility, are generally stable and have a range of tastes. In one such embodiment, pirfenidone or pyridone analog compounds are water soluble at pH 4 to pH 8, are stable in aqueous solution and have limited to no taste. Such a pyridone includes pirfenidone.

Accordingly, in one embodiment, a particular formulation of the pirfenidone or pyridone analog compound disclosed herein is combined with a particular aerosolizing device to provide an aerosol for inhalation that is optimized for maximum drug deposition at a site of infection, pulmonary arterial hypertension, pulmonary or intra-nasal site for systemic absorption for extra-nasal and/or extra-pulmonary indications, and maximal tolerability. Factors that can be optimized include solution or solid particle formulation, rate of delivery, and particle size and distribution produced by the aerosolizing device.

Particle Size and Distribution

The distribution of aerosol particle/droplet size can be expressed in terms of either: the mass median aerodynamic diameter (MMAD)—the droplet size at which half of the mass of the aerosol is contained in smaller droplets and half in larger droplets;

volumetric mean diameter (VMD);

mass median diameter (MMD);

the fine particle fraction (FPF)—the percentage of particles that are <5 μm in diameter.

These measures have been used for comparisons of the in vitro performance of different inhaler device and drug combinations. In general, the higher the fine particle fraction, the higher the proportion of the emitted dose that is likely to deposit the lung.

Generally, inhaled particles are subject to deposition by one of two mechanisms: impaction, which usually predominates for larger particles, and sedimentation, which is prevalent for smaller particles. Impaction occurs when the momentum of an inhaled particle is large enough that the particle does not follow the air stream and encounters a physiological surface. In contrast, sedimentation occurs primarily in the deep lung when very small particles which have traveled with the inhaled air stream encounter physiological surfaces as a result of random diffusion within the air stream.

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 1 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled. Measures of particle size can be referred to as volumetric mean diameter (VMD), mass median diameter (MMD), or MMAD. These measurements may be made by impaction (MMD and MMAD) or by laser (VMD). For liquid particles, VMD, MMD and MMAD may be the same if environmental conditions are maintained, e.g., standard humidity. However, if humidity is not maintained, MMD and MMAD determinations will be smaller than VMD due to dehydration during impactor measurements. For the purposes of this description, VMD, MMD and MMAD measurements are considered to be under standard conditions such that descriptions of VMD, MMD and MMAD will be comparable. Similarly, dry powder particle size determinations in MMD and MMAD are also considered comparable.

In some embodiments, the particle size of the aerosol is optimized to maximize the pirfenidone or pyridone analog compound deposition at the site of pulmonary pathology and/or extra-pulmonary, systemic or central nervous system distribution, and to maximize tolerability (or in the later case, systemic absorption). Aerosol particle size may be expressed in terms of the mass median aerodynamic diameter (MMAD). Large particles (e.g., MMAD>5 μm) may deposit in the upper airway because they are too large to navigate the curvature of the upper airway. Small particles (e.g., MMAD<2 μm) may be poorly deposited in the lower airways and thus become exhaled, providing additional opportunity for upper airway deposition. Hence, intolerability (e.g., cough and bronchospasm) may occur from upper airway deposition from both inhalation impaction of large particles and settling of small particles during repeated inhalation and expiration. Thus, in one embodiment, an optimum particle size is used (e.g., MMAD=2-5 μm) in order to maximize deposition at a mid-lung and to minimize intolerability associated with upper airway deposition. Moreover, generation of a defined particle size with limited geometric standard deviation (GSD) may optimize deposition and tolerability. Narrow GSD limits the number of particles outside the desired MMAD size range. In one embodiment, an aerosol containing one or more compounds disclosed herein is provided having a MMAD from about 2 microns to about 5 microns with a GSD of less than or equal to about 2.5 microns. In another embodiment, an aerosol having an MMAD from about 2.8 microns to about 4.3 microns with a GSD less than or equal to 2 microns is provided. In another embodiment, an aerosol having an MMAD from about 2.5 microns to about 4.5 microns with a GSD less than or equal to 1.8 microns is provided.

In some embodiments, the pirfenidone or pyridone analog compound that is intended for respiratory delivery (for either systemic or local distribution) can be administered as aqueous formulations, as suspensions or solutions in halogenated hydrocarbon propellants, or as dry powders. Aqueous formulations may be aerosolized by liquid nebulizers employing either hydraulic or ultrasonic atomization. Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

Lung Deposition as used herein, refers to the fraction of the nominal dose of an active pharmaceutical ingredient (API) that is bioavailable at a specific site of pharmacologic activity upon administration of the agent to a patient via a specific delivery route. For example, a lung deposition of 30% means 30% of the active ingredient in the inhalation device just prior to administration is deposited in the lung. Likewise, a lung deposition of 60% means 60% of the active ingredient in the inhalation device just prior to administration is deposited in the lung, and so forth. Lung deposition can be determined using methods of scintigraphy or deconvolution. In some embodiments, the present invention provides for methods and inhalation systems for the treatment or prophylaxis of a respiratory condition in a patient, comprising administering to the patient a nominal dose of pirfenidone or a pyridone analog compound with a liquid nebulizer. In some embodiments, the liquid nebulizer is a high efficiency liquid nebulizer. In some embodiments a lung deposition of pirfenidone or a pyridone analog compound of at least about 7%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85%, based on the nominal dose of pirfenidone or a pyridone analog compound is achieved.

There are two main methods used to measure aerosol deposition in the lungs. First, γ-scintigraphy is performed by radiolabeling the drug with a substance like 99m-technetium, and scanning the subject after inhalation of the drug. This technique has the advantage of being able to quantify the proportion of aerosol inhaled by the patient, as well as regional distribution in the upper airway and lungs. Second, since most of the drug deposited in the lower airways will be absorbed into the bloodstream, pharmacokinetic techniques are used to measure lung deposition. This technique can assess the total amount of ICSs that interacts with the airway epithelium and is absorbed systemically, but will miss the small portion that may be expectorated or swallowed after mucociliary clearance, and cannot tell us about regional distribution. Therefore, γ-scintigraphy and pharmacokinetic studies are in many cases considered complementary.

In some embodiments, administration of the pirfenidone or pyridone analog compound with a liquid nebulizer provides a GSD of emitted droplet size distribution of about 1.0 μm to about 2.5 m, about 1.2 km to about 2.0 m, or about 1.0 km to about 2.0 km. In some embodiments, the MMAD is about 0.5 μm to about 5 m, or about 1 to about 4 m or less than about 5 km. In some embodiments, the VMD is about 0.5 μm to about 5 μm, or about 1 to about 4 μm or less than about 5 km.

Fine Particle Fraction (FPF) describes the efficiency of a nebulizer inhalation device. FPF represents the percentage of the delivered aerosol dose, or inhaled mass, with droplets of diameter less than 5.0 μm. Droplets of less than 5.0 μm in diameter are considered to penetrate to the lung. In some embodiments, administration of an aqueous inhalation pirfenidone or pyridone analog solution with a liquid nebulizer provides a RDD of at least about 30%, at least about 35%, at least about 40%, at least about 45%, at least about 50%, at least about 55%, at least about 60%, at least about 65%, at least about 70%, at least about 75%, or at least about 80%.

The Delivered Dose (DD) of drug to a patient is the certain portion of volume of liquid filled into the nebulizer, i.e. the fill volume, which is emitted from the mouthpiece of the device. The difference between the nominal dose and the DD is the amount of volume lost primarily to residues, i.e. the amount of fill volume remaining in the nebulizer after administration, or is lost in aerosol form during expiration of air from the patient and therefore not deposited in the patient's body. In some embodiments, the DD of the nebulized formulations described herein is at least about 30%, at least about 35%, at least about 40%, at least about 45%, at least about 50%, at least about 55%, at least about 60%, at least about 65%, at least about 70%, or at least about 80%.

The Respirable Delivered Dose (RDD) is an expression of the delivered mass of drug contained within emitted droplets from a nebulizer that are small enough to reach and deposit on the surface epithelium of the patients lung. The RDD is determined by multiplying the DD by the FPF.

In one embodiment, described herein an aqueous droplet containing pirfenidone or pyridone analog compound, wherein the aqueous droplet has a diameter less than about 5.0 μm. In some embodiments, the aqueous droplet has a diameter less than about 5.0 μm, less than about 4.5 m, less than about 4.0 m, less than about 3.5 am, less than about 3.0 am, less than about 2.5 μm, less than about 2.0 μm, less than about 1.5 μm, or less than about 1.0 μm. In some embodiments, the aqueous droplet further comprises one or more colsolvents. In some embodiments, the one or more cosolvents are selected from ethanol and propylene glycol. In some embodiments, the aqueous droplet further comprises a buffer. In some embodiments, the buffer is a citrate buffer or a phosphate buffer. In some embodiments, the dioplet was produced from a liquid nebulizer and an aqueous solution of pirfenidone or pyridone analog compound as described herein. In some embodiments, the aqueous droplet was produced from an aqueous solution that has concentration of pirfenidone or pyridone analog compound between about 0.1 mg/mL and about 60 mg/mL and an osmolality from about 50 mOsmol/kg to about 6000 mOsmol/kg. In some embodiments, the osmolality is greater than about 100 mOsmol/kg. In some embodiments, the osmolality is greater than about 400 mOsmol/kg. In some embodiments, the osmolality is greater than about 1000 mOsmol/kg. In some embodiments, the osmolality is greater than about 2000 mOsmol/kg. In some embodiments, the osmolality is greater than about 3000 mOsmol/kg. In some embodiments, the osmolality is greater than about 4000 mOsmol/kg. In some embodiments, the osmolality is greater than about 5000 mOsmol/kg.

Also described are aqueous aerosols comprising a plurality of aqueous droplets of pirfenidone or pyridone analog compound as described herein. In some embodiments, the at least about 30% of the aqueous droplets in the aerosol have a diameter less than about 5 m. In some embodiments, at least about 35%, at least about 40%, at least about 45%, at least about 50%, at least about 55%, at least about 60%, at least about 65%, at least about 70%, at least about 75%, at least about 80%, at least about 85%, or at least about 90% of the aqueous droplets in the aerosol have a diameter less than about 5 am. In some embodiments, the aqueous aerosols are produced with a liquid nebulizer. In some embodiments, the aqueous aerosols are produced with a high efficiency liquid nebulizer.

Liquid Nebulizer

In one embodiment, a nebulizer is selected on the basis of allowing the formation of an aerosol of a pirfenidone or pyridone analog compound disclosed herein having an MMAD predominantly between about 1 to about 5 microns. In one embodiment, the delivered amount of pirfenidone or pyridone analog compound provides a therapeutic effect for pulmonary pathology and/or extra-pulmonary, systemic, tissue or central nervous system distribution.

Previously, two types of nebulizers, jet and ultrasonic, have been shown to be able to produce and deliver aerosol particles having sizes between 2 and 4 micron. These particle sizes have been shown as being optimal for middle airway deposition. However, unless a specially formulated solution is used, these nebulizers typically need larger volumes to administer sufficient amount of drug to obtain a therapeutic effect. A jet nebulizer utilizes air pressure breakage of an aqueous solution into aerosol droplets. An ultrasonic nebulizer utilizes shearing of the aqueous solution by a piezoelectric crystal. Typically, however, the jet nebulizers are only about 10% efficient under clinical conditions, while the ultrasonic nebulizer is only about 5% efficient. The amount of pharmaceutical deposited and absorbed in the lungs is thus a fraction of the 10% in spite of the large amounts of the drug placed in the nebulizer. The amount of drug that is placed in the nebulizer prior to administration to the mammal is generally referred to the "nominal dose," or "loaded dose." The volume of solution containing the nominal dose is referred to as the "fill volume." Smaller particle sizes or slow inhalation rates permit deep lung deposition. In addition to slow inhalation, devices such as the Philips Ineb Adaptive Aerosol Delivery (AAD) System and the Activaero Flow And Volume Regulated Inhalation Technology (FAVORITE) use controlled device features to assist inspiratory flow to maximize delivery efficiency, peripheral deposition and improve dose reproducibility while reducing side effects. Both middle-lung and alveolar deposition may be desired for this invention depending on the indication, e.g., middle and/or alveolar deposition for pulmonary fibrosis and systemic delivery. Exemplary disclosure of compositions and methods for formulation delivery using nebulizers can be found in, e.g., US 2006/0276483, including descriptions of techniques, protocols and characterization of aerosolized mist delivery using a vibrating mesh nebulizer.

Accordingly, in one embodiment, a vibrating mesh nebulizer is used to deliver in preferred embodiments an aerosol of the pirfenidone compound as disclosed herein, or in other embodiments, a pyridone analog compound as disclosed herein. A vibrating mesh nebulizer comprises a liquid storage container in fluid contact with a diaphragm and inhalation and exhalation valves. In one embodiment, about 1 to about 6 ml of the pirfenidone compound formulation (or in another related embodiment, of a pyridone analog compound formulation) is placed in the storage container and the aerosol generator is engaged producing atomized aerosol of particle sizes selectively between about 1 and about 5 micron. In one embodiment, about 1 to about 10 mL of the pirfenidone compound formulation (or in another related embodiment, of a pyridone analog compound formulation) is placed in the storage container and the aerosol generator is engaged producing atomized aerosol of particle sizes selectively between about 1 and about 5 micron. In one embodiment, about the volume of the pirfenidone compound formulation (or in another related embodiment, of a pyridone analog compound formulation) that is originally placed in the storage container and the aerosol generator is replaced to increase the administered dose size.

In some embodiments a pirfenidone or pyridone analog compound formulation as disclosed herein, is placed in a liquid nebulization inhaler and prepared in dosages to deliver from about 34 mcg to about 463 mg from a dosing solution of about 0.5 to about 6 ml with MMAD particles sizes between about 1 to about 5 micron being produced.

In some embodiments a pirfenidone or pyridone analog compound formulation as disclosed herein, is placed in a liquid nebulization inhaler and prepared in dosages to deliver from about 34 mcg to about 463 mg from a dosing solution of about 0.5 to about 7 ml with MMAD particles sizes between about 1 to about 5 micron being produced.

By non-limiting example, a nebulized pirfenidone or pyridone analog compound may be administered in the described respirable delivered dose in less than about 20 min, less than about 15 min, less than about 10 min, less than about 7 min, less than about 5 min, less than about 3 min, or less than about 2 min.

By non-limiting example, a nebulized pirfenidone or pyridone analog compound may be administered in the described respirable delivered dose using a breath-actuated nebulizer in less than about 20 min, less than about 10 min, less than about 7 min, less than about 5 min, less than about 3 min, or less than about 2 min.

By non-limiting example, in other circumstances, a nebulized pirfenidone or pyridone analog compound may achieve improved tolerability and/or exhibit an area-under-the-curve (AUC) shape-enhancing characteristic when administered over longer periods of time. Under these conditions, the described respirable delivered dose in more than about 2 min, preferably more than about 3 min, more preferably more than about 5 min, more preferably more than about 7 min, more preferably more than about 10 min, and in some cases most preferable from about 10 to about 20 min.

As disclosed herein, there is provided a pyridone analog compound formulation composition comprising a pirfenidone compound aqueous solution having a pH from about 4.0 to about pH 8.0 where the pirfenidone compound is present at a concentration from about 34 mcg/mL to about 463 mg/mL pirfenidone. In certain other embodiments the pirfenidone compound formulation is provided as an aqueous solution having a pH of from about 4.0 to about 8.0, the solution comprising a pirfenidone compound at a concentration of from about 34 mcg/mL to about 463 mg/mL pirfenidone; and citrate buffer or phosphate buffer at a concentration of from about 0 mM to about 50 mM. In certain other embodiments the pirfenidone compound formulation is provided as an aqueous solution having a pH of from about 4.0 to about 8.0, the solution comprising a pirfenidone compound at a concentration of from about 34 mcg/mL to about 463 mg/mL pirfenidone; and a buffer that has a pKa between 4.7 and 6.8 and that is present at a concentration sufficient to maintain or maintain after titration with acid or base a pH from about 4.0 to about 8.0 for a time period sufficient to enable marketable product shelf-life storage.

In some embodiments, described herein is a pharmaceutical composition that includes: pirfenidone; water; phosphate buffer or citrate buffer; and optionally sodium chloride or magnesium chloride. In other embodiments, described herein is a pharmaceutical composition that includes: pirfenidone; water; a buffer; and at least one additional ingredient selected from sodium chloride, magnesium chloride, ethanol, propylene glycol, glycerol, polysorbate 80, and cetylpyridinium bromide (or chloride). In some embodiments, the buffer is phosphate buffer. In other embodiments, the buffer is citrate buffer. In some embodiments, the pharmaceutical composition includes 1 mg to 500 mg of pirfenidone, for example, 5 mg, 10 mg, 15 mg, 25 mg, 37.5 mg, 75 mg, 100 mg, 115 mg, 150 mg, 190 mg, 220 mg, or 500 mg. In some embodiments, the osmolality of the pharmaceutical composition described herein is between about 50 mOsmo/kg to 6000 mOsmo/kg. In some embodiments, the osmolality of the pharmaceutical composition described herein is between about 50 mOsmo/kg to 5000 mOsmo/kg. In some embodiments, the pharmaceutical composition optionally includes saccharin (e.g. sodium salt). In some embodiments, such a pharmaceutical composition is placed in a liquid nebulization inhaler to deliver from about 1 mg to about 500 mg from a dosing solution of about 0.5 to about 6 mL with MMAD particles sizes between about 1 to about 5 micron being produced. In some embodiments, such a pharmaceutical composition is placed in a liquid nebulization inhaler to deliver from about 1 mg to about 500 mg from a dosing solution of about 0.5 to about 7 mL with MMAD particles sizes between about 1 to about 5 micron being produced. In some embodiments such a nebulized pharmaceutical composition may deliver between about 0.0001 mg and about 25 mg pirfenidone or pyridone analog in aerosol particles with a MMAD between 1 and 5 microns in each inhaled breath. In some embodiments, 1 mg pirfenidone or pyridone analog delivered in 10 breaths over 1 minute, whereby 50% of the inhaled particles are between 1 and 5 microns, 0.05 mg pirfenidone or pyridine analog will be delivered in each breath. In some embodiments, 1 mg pirfenidone or pyridone analog delivered in 15 breaths per minute over 10 minutes, whereby 50% of the inhaled particles are between 1 and 5 microns, 0.0033 mg pirfenidone or pyridone analog will be delivered in each breath. In some embodiments, 1 mg pirfenidone or pyridone analog delivered in 20 breaths per minute over 20 minutes, whereby 50% of the inhaled particles are between 1 and 5 microns, 0.00125 mg pirfenidone or pyridone analog will be delivered in each breath. In some embodiments, 200 mg pirfenidone or pyridone analog delivered in 10 breaths over 1 minute, whereby 50% of the inhaled particles are between 1 and 5 microns, 10 mg pirfenidone or pyridone analog will be delivered in each breath. In some embodiments, 200 mg pirfenidone or pyridone analog delivered in 15 breaths per minute over 10 minutes, whereby 50% of the inhaled particles are between 1 and 5 microns, 0.67 mg pirfenidone or pyridone analog will be delivered in each breath. By another non-limiting example, In some embodiments, 200 mg pirfenidone or pyridone analog delivered in 20 breaths per minute over 20 minutes, whereby 50% of the inhaled particles are between 1 and 5 microns, 0.25 mg pirfenidone or pyridone analog will be delivered in each breath. In some embodiments, 500 mg pirfenidone or pyridine analog delivered in 10 breaths over 1 minute, whereby 50% of the inhaled particles are between 1 and 5 microns, 25 mg pirfenidone or pyridone analog will be delivered in each breath. In some embodiments, 500 mg pirfenidone or pyridone analog delivered in 15 breaths per minute over 10 minutes, whereby 50% of the inhaled particles are between 1 and 5 microns, 1.67 mg pirfenidone or pyridone analog will be delivered in each breath. In some embodiments, 500 mg pirfenidone or pyridone analog delivered in 20 breaths per minute over 20 minutes, whereby 50% of the inhaled particles are between 1 and 5 microns, 0.625 mg pirfenidone or pyridone analog will be delivered in each breath.

In some embodiments, a nebulized pirfenidone or pyridone analog compound may be administered in the described respirable delivered dose in less than about 20 min, less than about 10 min, less than about 7 min, less than about 5 min, less than about 3 min, or less than about 2 min.

For aqueous and other non-pressurized liquid systems, a variety of nebulizers (including small volume nebulizers) are available to aerosolize the formulations. Compressor-driven nebulizers incorporate jet technology and use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers rely on mechanical energy in the form of vibration of a piezoelectric crystal to generate respirable liquid droplets and are commercially available from, for example, Omron Heathcare, Inc., Boehringer Ingelheim, and DeVilbiss Health Care, Inc. Vibrating mesh nebulizers rely upon either piezoelectric or mechanical pulses to respirable liquid droplets generate. Other examples of nebulizers for use with pirfenidone or pyridone analogs described herein are described in U.S. Pat. Nos. 4,268,460; 4,253,468; 4,046,146; 3,826,255; 4,649,911; 4,510,929; 4,624,251; 5,164,740; 5,586,550; 5,758,637; 6,644,304; 6,338,443; 5,906,202; 5,934,272; 5,960,792; 5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303 all of which are hereby incorporated by reference in their entirety.

Any known inhalation nebulizer suitable to provide delivery of a medicament as described herein may be used in the various embodiments and methods described herein. Such nebulizers include, e.g., jet nebulizers, ultrasonic nebulizers, pulsating membrane nebulizers, nebulizers with a vibrating mesh or plate with multiple apertures, and nebulizers comprising a vibration generator and an aqueous chamber (e.g., Pari eFlow®). Commercially available nebulizers suitable for use in the present invention can include the Aeroneb®, MicroAir®, Aeroneb® Pro, and Aeroneb® Go, Aeroneb® Solo, Aeroneb® Solo/Idehaler combination, Aeroneb® Solo or Go Idehaler-Pocket® combination, PARI LC-Plus®, PARI LC-Star®, PARI Sprint®, eFlow and eFlow Rapid®, Pari Boy® N and Pari Duraneb® (PARI, GmbH), MicroAir® (Omron Healthcare, Inc.), Halolite® (Profile Therapeutics Inc.), Respimat® (Boehringer Ingelheim), Aerodose® (Aerogen, Inc, Mountain View, Calif.), Omron Elite® (Omron Healthcare, Inc.), Omron Microair® (Omron Healthcare, Inc.), Mabismist II® (Mabis Healthcare, Inc.), Lumiscope® 6610, (The Lumiscope Company, Inc.), Airsep Mystique®, (AirSep Corporation), Acorn-1 and Acorn-II (Vital Signs, Inc.), Aquatower® (Medical Industries America), Ava-Neb® (Hudson Respiratory Care Incorporated), Cirrus® (Intersurgical Incorporated), Dart® (Professional Medical Products), Devilbiss® Pulmo Aide (DeVilbiss Corp.), Downdraft® (Marquest), Fan Jet® (Marquest), MB-5 (Mefar), Misty Neb® (Baxter), Salter 8900 (Salter Labs), Sidestream® (Medic-Aid), Updraft-II® (Hudson Respiratory Care), Whisper Jet® (Marquest Medical Products), Aiolos® (Aiolos Medicnnsk Teknik), Inspiron® (Intertech Resources, Inc.), Optimist® (Unomedical Inc.), Prodomo®, Spira® (Respiratory Care Center), AERx® and AERx Essence™ (Aradigm), Respirgard II®, Sonik® LDI Nebulizer (Evit Labs), Swirler W Radioaerosol System (AMICI, Inc.), Maquet SUN 145 ultrasonic, Schill untrasonic, compare and compare Elite from Omron, Monoghan AeroEclipse BAN, Transneb, DeVilbiss 800, AerovectRx, Porta-Neb®, Freeway Freedom™, Sidestream, Ventstream and I-neb produced by Philips, Inc. By further non-limiting example, U.S. Pat. No. 6,196,219, is hereby incorporated by reference in its entirety.

Any of these and other known nebulizers suitable to provide delivery of a aqueous inhalation medicament as described herein may be used in the various embodiments and methods described herein. In some embodiments, the nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Omron, Bremed, AirSep, Luminscope, Medisana, Siemens, Aerogen, Mountain Medical, Aerosol Medical Ltd. (Colchester, Essex, UK), AFP Medical (Rugby, Warwickshire, UK), Bard Ltd. (Sunderland, UK), Carri-Med Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Other nebulizers suitable for use in the methods and systems describe herein can include, but are not limited to, jet nebulizers (optionally sold with compressors), ultrasonic nebulizers, and others. Exemplary jet nebulizers for use herein can include Pari LC plus/ProNeb, Pari LC plus/ProNeb Turbo, Pari LCPlus/Dura Neb 1000 & 2000 Pari LC plus/Walkhaler, Pari LC plus/Pari Master, Pari LC star, Omron CompAir XL Portable Nebulizer System (NE-C18 and JetAir Disposable nebulizer), Omron compare Elite Compressor Nebulizer System (NE-C21 and Elite Air Reusable Nebulizer, Pari LC Plus or Pari LC Star nebulizer with Proneb Ultra compressor, Pulomo-aide, Pulmo-aide LT, Pulmo-aide traveler, Invacare Passport, Inspiration Healthdyne 626, Pulmo-Neb Traveler, DeVilbiss 646, Whisper Jet, AcornII, Misty-Neb, Allied aerosol, Schuco Home Care, Lexan Plasic Pocet Neb, SideStream Hand Held Neb, Mobil Mist, Up-Draft, Up-DraftII, T Up-Draft, ISO-NEB, Ava-Neb, Micro Mist, and PulmoMate.

Exemplary ultrasonic nebulizers suitable to provide delivery of a medicament as described herein can include MicroAir, UltraAir, Siemens Ultra Nebulizer 145, CompAir, Pulmosonic, Scout, 5003 Ultrasonic Neb, 5110 Ultrasonic Neb, 5004 Desk Ultrasonic Nebulizer, Mystique Ultrasonic, Lumiscope's Ultrasonic Nebulizer, Medisana Ultrasonic Nebulizer, Microstat Ultrasonic Nebulizer, and Mabismist Hand Held Ultrasonic Nebulizer. Other nebulizers for use herein include 5000 Electromagnetic Neb, 5001 Electromagnetic Neb 5002 Rotary Piston Neb, Lumineb I Piston Nebulizer 5500, Aeroneb Portable Nebulizer System, Aerodose Inhaler, and AeroEclipse Breath Actuated Nebulizer. Exemplary nebulizers comprising a vibrating mesh or plate with multiple apertures are described by R. Dhand in New Nebuliser Technology-Aerosol Generation by Using a Vibrating Mesh or Plate with Multiple Apertures, Long-Term Healthcare Strategies 2003, (July 2003), p. 1-4 and Respiratory Care, 47: 1406-1416 (2002), the entire disclosure of each of which is hereby incorporated by reference.

Additional nebulizers suitable for use in the presently described invention include nebulizers comprising a vibration generator and an aqueous chamber. Such nebulizers are sold commercially as, e.g., Pari eFlow, and are described in U.S. Pat. Nos. 6,962,151, 5,518,179, 5,261,601, and 5,152,456, each of which is specifically incorporated by reference herein.

The parameters used in nebulization, such as flow rate, mesh membrane size, aerosol inhalation chamber size, mask size and materials, valves, and power source may be varied as applicable to provide delivery of a medicament as described herein to maximize their use with different types and aqueous inhalation mixtures.

In some embodiments, the drug solution is formed prior to use of the nebulizer by a patient. In other embodiments, the drug is stored in the nebulizer in liquid form, which may include a suspension, solution, or the like. In other embodiments, the drug is store in the nebulizer in solid form. In this case, the solution is mixed upon activation of the nebulizer, such as described in U.S. Pat. No. 6,427,682 and PCT Publication No. WO 03/035030, both of which are hereby incorporated by reference in their entirety. In these nebulizers, the solid drug, optionally combined with excipients to form a solid composition, is stored in a separate compartment from a liquid solvent.

The liquid solvent is capable of dissolving the solid composition to form a liquid composition, which can be aerosolized and inhaled. Such capability is, among other factors, a function of the selected amount and, potentially, the composition of the liquid. To allow easy handling and reproducible dosing, the sterile aqueous liquid may be able to dissolve the solid composition within a short period of time, possibly under gentle shaking. In some embodiments, the final liquid is ready to use after no longer than about 30 seconds. In some cases, the solid composition is dissolved within about 20 seconds, and advantageously, within about 10 seconds. As used herein, the terms "dissolve(d)", "dissolving", and "dissolution" refer to the disintegration of the solid composition and the release, i.e., the dissolution, of the active compound. As a result of dissolving the solid composition with the liquid solvent a liquid composition is formed in which the active compound is contained in the dissolved state. As used herein, the active compound is in the dissolved state when at least about 90 wt.-% are dissolved, and more preferably when at least about 95 wt.-% are dissolved.

With regard to basic separated-compartment nebulizer design, it primarily depends on the specific application whether it is more useful to accommodate the aqueous liquid and the solid composition within separate chambers of the same container or primary package, or whether they should be provided in separate containers. If separate containers are used, these are provided as a set within the same secondary package. The use of separate containers is especially preferred for nebulizers containing two or more doses of the active compound. There is no limit to the total number of containers provided in a multi-dose kit. In one embodiment, the solid composition is provided as unit doses within multiple containers or within multiple chambers of a container, whereas the liquid solvent is provided within one chamber or container. In this case, a favorable design provides the liquid in a metered-dose dispenser, which may consist of a glass or plastic bottle closed with a dispensing device, such as a mechanical pump for metering the liquid. For instance, one actuation of the pumping mechanism may dispense the exact amount of liquid for dissolving one dose unit of the solid composition.

In another embodiment for multiple-dose separated-compartment nebulizers, both the solid composition and the liquid solvent are provided as matched unit doses within multiple containers or within multiple chambers of a container. For instance, two-chambered containers can be used to hold one unit of the solid composition in one of the chambers and one unit of liquid in the other. As used herein, one unit is defined by the amount of drug present in the solid composition, which is one unit dose. Such two-chambered containers may, however, also be used advantageously for nebulizers containing only one single drug dose.

In one embodiment of a separated-compartment nebulizer, a blister pack having two blisters is used, the blisters representing the chambers for containing the solid composition and the liquid solvent in matched quantities for preparing a dose unit of the final liquid composition. As used herein, a blister pack represents a thermoformed or pressure-formed primary packaging unit, most likely comprising a polymeric packaging material that optionally includes a metal foil, such as aluminum. The blister pack may be shaped to allow easy dispensing of the contents. For instance, one side of the pack may be tapered or have a tapered portion or region through which the content is dispensable into another vessel upon opening the blister pack at the tapered end. The tapered end may represent a tip.

In some embodiments, the two chambers of the blister pack are connected by a channel, the channel being adapted to direct fluid from the blister containing the liquid solvent to the blister containing the solid composition. During storage, the channel is closed with a seal. In this sense, a seal is any structure that prevents the liquid solvent from contacting the solid composition. The seal is preferably breakable or removable; breaking or removing the seal when the nebulizer is to be used will allow the liquid solvent to enter the other chamber and dissolve the solid composition. The dissolution process may be improved by shaking the blister pack. Thus, the final liquid composition for inhalation is obtained, the liquid being present in one or both of the chambers of the pack connected by the channel, depending on how the pack is held.

According to another embodiment, one of the chambers, preferably the one that is closer to the tapered portion of the blister pack communicates with a second channel, the channel extending from the chamber to a distal position of the tapered portion. During storage, this second channel does not communicate with the outside of the pack but is closed in an air-tight fashion. Optionally, the distal end of the second channel is closed by a breakable or removable cap or closure, which may e.g., be a twist-off cap, a break-off cap, or a cut-off cap.

In one embodiment, a vial or container having two compartments is used, the compartment representing the chambers for containing the solid composition and the liquid solvent in matched quantities for preparing a dose unit of the final liquid composition. The liquid composition and a second liquid solvent may be contained in matched quantities for preparing a dose unit of the final liquid composition (by non-limiting example in cases where two soluble excipients or the pirfenidone or pyridone analog compound and excipient are unstable for storage, yet desired in the same mixture for administration.

In some embodiments, the two compartments are physically separated but in fluid communication such as when so the vial or container are connected by a channel or breakable barrier, the channel or breakable barrier being adapted to direct fluid between the two compartments to enable mixing prior to administration. During storage, the channel is closed with a seal or the breakable barrier intact. In this sense, a seal is any structure that prevents mixing of contents in the two compartments. The seal is preferably breakable or removable; breaking or removing the seal when the nebulizer is to be used will allow the liquid solvent to enter the other chamber and dissolve the solid composition or in the case of two liquids permit mixing. The dissolution or mixing process may be improved by shaking the container. Thus, the final liquid composition for inhalation is obtained, the liquid being present in one or both of the chambers of the pack connected by the channel or breakable barrier, depending on how the pack is held.

The solid composition itself can be provided in various different types of dosage forms, depending on the physicochemical properties of the drug, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In a preferred embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form as defined above. Examples of multiple units are powders, granules, microparticles, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution.

Another type of multiparticulate system which is also capable of achieving rapid drug dissolution is that of powders, granules, or pellets from water-soluble excipients which are coated with the drug, so that the drug is located at the outer surface of the individual particles. In this type of system, the water-soluble low molecular weight excipient is useful for preparing the cores of such coated particles, which can be subsequently coated with a coating composition comprising the drug and, preferably, one or more additional excipients, such as a binder, a pore former, a saccharide, a sugar alcohol, a film-forming polymer, a plasticizer, or other excipients used in pharmaceutical coating compositions.

In another embodiment, the solid composition resembles a coating layer that is coated on multiple units made of insoluble material. Examples of insoluble units include beads made of glass, polymers, metals, and mineral salts. Again, the desired effect is primarily rapid disintegration of the coating layer and quick drug dissolution, which is achieved by providing the solid composition in a physical form that has a particularly high surface-to-volume ratio. Typically, the coating composition will, in addition to the drug and the water-soluble low molecular weight excipient, comprise one or more excipients, such as those mentioned above for coating soluble particles, or any other excipient known to be useful in pharmaceutical coating compositions.

To achieve the desired effects, it may be useful to incorporate more than one water-soluble low molecular weight excipient into the solid composition. For instance, one excipient may be selected for its drug carrier and diluent capability, while another excipient may be selected to adjust the pH. If the final liquid composition needs to be buffered, two excipients that together form a buffer system may be selected.

In one embodiment, the liquid to be used in a separated-compartment nebulizer is an aqueous liquid, which is herein defined as a liquid whose major component is water. The liquid does not necessarily consist of water only; however, in one embodiment it is purified water. In another embodiment, the liquid contains other components or substances, preferably other liquid components, but possibly also dissolved solids. Liquid components other than water which may be useful include propylene glycol, glycerol, and polyethylene glycol. One of the reasons to incorporate a solid compound as a solute is that such a compound is desirable in the final liquid composition, but is incompatible with the solid composition or with a component thereof, such as the active ingredient.

Another desirable characteristic for the liquid solvent is that it is sterile. An aqueous liquid would be subject to the risk of considerable microbiological contamination and growth if no measures were taken to ensure sterility. In order to provide a substantially sterile liquid, an effective amount of an acceptable antimicrobial agent or preservative can be incorporated or the liquid can be sterilized prior to providing it and to seal it with an air-tight seal. In one embodiment, the liquid is a sterilized liquid free of preservatives and provided in an appropriate air-tight container. However, according to another embodiment in which the nebulizer contains multiple doses of the active compound, the liquid may be supplied in a multiple-dose container, such as a metered-dose dispenser, and may require a preservative to prevent microbial contamination after the first use.

High Efficiency Liquid Nebulizers

High efficiency liquid nebulizers are inhalation devices that are adapted to deliver a large fraction of a loaded dose to a patient. Some high efficiency liquid nebulizers utilize microperforated membranes. In some embodiments, the high efficiency liquid nebulizer also utilizes one or more actively or passively vibrating microperforated membranes. In some embodiments, the high efficiency liquid nebulizer contains one or more oscillating membranes. In some embodiments, the high efficiency liquid nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the patient inhales the aerosol from the mixing chamber. In yet some other embodiments, the high efficiency liquid nebulizer contains a pulsating membrane. In some embodiments, the high efficiency liquid nebulizer is continuously operating.

In some embodiments, the high efficiency liquid nebulizer contains a vibrating microperforated membrane of tapered nozzles against a bulk liquid will generate a plume of droplets without the need for compressed gas. In these embodiments, a solution in the microperforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments the high efficiency liquid nebulizers use passive nozzle membranes and a separate piezoelectric transducer that are in contact with the solution. In contrast, some high efficiency liquid nebulizers employ an active nozzle membrane, which use the acoustic pressure in the nebulizer to generate very fine droplets of solution via the high frequency vibration of the nozzle membrane.

Some high efficiency liquid nebulizers contain a resonant system. In some such high efficiency liquid nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the high efficiency liquid nebulizer may be made of a nickel-palladium alloy by electroforming.

In some embodiments, the high efficiency liquid nebulizer (i) achieves lung deposition of at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85%, based on the nominal dose of the pirfenidone or pyridone analog compound administered to the mammal.

In some embodiments, the high efficiency liquid nebulizer (ii) provides a Geometric Standard Deviation (GSD) of emitted droplet size distribution of the solution administered with the high efficiency liquid nebulizer of about 1.0 µm to about 2.5 µm, about 1.2 µm to about 2.5 m, about 1.3 m to about 2.0 m, at least about 1.4 m to about 1.9 µm, at least about 1.5 µm to about 1.9 µm, about 1.5 µm, about 1.7 µm, or about 1.9 µm.

In some embodiments, the high efficiency liquid nebulizer (iii) provides a mass median aerodynamic diameter (MMAD) of droplet size of the solution emitted with the high efficiency liquid nebulizer of about 1 μm to about 5 μm, about 2 to about 4 μm, or about 2.5 to about 4.0 μm. In some embodiments, the high efficiency liquid nebulizer (iii) provides a volumetric mean diameter (VMD) 1 m to about 5 μm, about 2 to about 4 μm, or about 2.5 to about 4.0 μm. In some embodiments, the high efficiency liquid nebulizer (iii) provides a mass median diameter (MMD) 1 μm to about 5 μm, about 2 to about 4 μm, or about 2.5 to about 4.0 am.

In some embodiments, the high efficiency liquid nebulizer (iv) provides a fine particle fraction (FPF=%≤5 microns) of droplets emitted from the high efficiency nebulizer of at least about 60%, at least about 65%, at least about 70%, at least about 75%, at least about 80%, at least about 85%, or at least about 90%.

In some embodiments, the high efficiency liquid nebulizer (v) provides an output rate of at least 0.1 mL/min, at least 0.2 mL/min, at least 0.3 mL/min, at least 0.4 mL/min, at least 0.5 mL/min, at least 0.6 mL/min, at least 0.8 mL/min, or at least 1.0 mL/min.

In some embodiments, the high efficiency liquid nebulizer (vi) delivers at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% of the fill volume to the mammal.

In some embodiments, the high efficiency liquid nebulizer provides an RDD of at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or at least about 85%.

In some embodiments, the high efficiency liquid nebulizer is characterized as providing one or more of (i), (ii), (iii) (iv), (v), or (vi). In some embodiments, the high efficiency liquid nebulizer is characterized as providing at least one, at least two, at least three, at least four, at least five, or all six of (i), (ii), (iii) (iv), (v), or (vi).

Additional features of a high efficiency liquid nebulizer with perforated membranes are disclosed in U.S. Pat. Nos. 6,962,151, 5,152,456, 5,261,601, and 5,518,179, 6,983,747, each of which is hereby incorporated by reference in its entirety. Other embodiments of the high efficiency liquid nebulizers contain oscillatable membranes. Features of these high efficiency liquid nebulizers are disclosed in U.S. Pat. Nos. 7,252,085; 7,059, 320; 6,983,747, each of which is hereby incorporated by reference in its entirety.

Commercial high efficiency liquid nebulizers are available from: PARI (Germany) under the trade name eFlow®; Nektar Therapeutics (San Carlos, Calif.) under the trade names AeroNeb® Go and AeroNeb® Pro, and AeroNeb® Solo, Respironics (Murrysville, Calif.) under the trade names I-Neb®, Omron (Bannockburn, Ill.) under the trade name Micro-Air®, and Activaero (Germany) under the trade name Akita®. Commercial High Efficiency Nebulizers are also available from Aerogen (Galaway, Ireland) utilizing the OnQ® nebulizer technology.

Meter Dose Inhaler (MDI)

A propellant driven inhaler (pMDI) releases a metered dose of medicine upon each actuation. The medicine is formulated as a suspension or solution of a drug substance in a suitable propellant such as a halogenated hydrocarbon. pMDIs are described in, for example, Newman, S. P., Aerosols and the Lung, Clarke et al., eds., pp. 197-224 (Butterworths, London, England, 1984).

In some embodiments, the particle size of the drug substance in an MDI may be optimally chosen. In some embodiments, the particles of active ingredient have diameters of less than about 50 microns. In some embodiments, the particles have diameters of less than about 10 microns. In some embodiments, the particles have diameters of from about 1 micron to about 5 microns. In some embodiments, the particles have diameters of less than about 1 micron. In one advantageous embodiment, the particles have diameters of from about 2 microns to about 5 microns.

By non-limiting example, metered-dose inhalers (MDI), the pirfenidone or pyridone analog compound disclosed herein are prepared in dosages to deliver from about 34 mcg to about 463 mg from a formulation meeting the requirements of the MDI. The pirfenidone or pyridone analog compound disclosed herein may be soluble in the propellant, soluble in the propellant plus a co-solvent (by non-limiting example ethanol), soluble in the propellant plus an additional moiety promoting increased solubility (by non-limiting example glycerol or phospholipid), or as a stable suspension or micronized, spray-dried or nanosuspension.

By non-limiting example, a metered-dose pirfenidone or pyridone analog compound may be administered in the described respirable delivered dose in 10 or fewer inhalation breaths, more preferably in 8 or fewer inhalation breaths, more preferably in 6 or fewer inhalation breaths, more preferably in 8 or fewer inhalation breaths, more preferably in 4 or fewer inhalation breaths, more preferably in 2 or fewer inhalation breaths.

The propellants for use with the MDIs may be any propellants known in the art. Examples of propellants include chlorofluorocarbons (CFCs) such as dichlorodifluoromethane, trichlorofluorometbane, and dichlorotetrafluoroethane; hydrofluoroalkanes (HFAs); and carbon dioxide. It may be advantageous to use HFAs instead of CFCs due to the environmental concerns associated with the use of CFCs. Examples of medicinal aerosol preparations containing HFAs are presented in U.S. Pat. Nos. 6,585,958; 2,868,691 and 3,014,844, all of which are hereby incorporated by reference in their entirety. In some embodiments, a co-solvent is mixed with the propellant to facilitate dissolution or suspension of the drug substance.

In some embodiments, the propellant and active ingredient are contained in separate containers, such as described in U.S. Pat. No. 4,534,345, which is hereby incorporated by reference in its entirety.

In some embodiments, the MDI used herein is activated by a patient pushing a lever, button, or other actuator. In other embodiments, the release of the aerosol is breath activated such that, after initially arming the unit, the active compound aerosol is released once the patient begins to inhale, such as described in U.S. Pat. Nos. 6,672,304; 5,404,871; 5,347,998; 5,284,133; 5,217,004; 5,119,806; 5,060,643; 4,664,107; 4,648,393; 3,789,843; 3,732,864; 3,636,949; 3,598,294; 3,565,070; 3,456,646; 3,456,645; and 3,456,644, each of which is hereby incorporated by reference in its entirety. Such a system enables more of the active compound to get into the lungs of the patient. Another mechanism to help a patient get adequate dosage with the active ingredient may include a valve mechanism that allows a patient to use more than one breath to inhale the drug, such as described in U.S. Pat. Nos. 4,470,412 and 5,385,140, both of which are hereby incorporated by reference in their entirety.

Additional examples of MDIs known in the art and suitable for use herein include U.S. Pat. Nos. 6,435,177; 6,585,958; 5,642,730; 6,223,746; 4,955,371; 5,404,871; 5,364,838; and 6,523,536, all of which are hereby incorporated by reference in their entirety.

Dry Powder Inhaler (DPI)

There are two major designs of dry powder inhalers. One design is the metering device in which a reservoir for the drug is placed within the device and the patient adds a dose of the drug into the inhalation chamber. The second is a factory-metered device in which each individual dose has been manufactured in a separate container. Both systems depend upon the formulation of drug into small particles of mass median diameters from about 1 to about 5 micron, and usually involve co-formulation with larger excipient particles (typically 100 micron diameter lactose particles). Drug powder is placed into the inhalation chamber (either by device metering or by breakage of a factory-metered dosage) and the inspiratory flow of the patient accelerates the powder out of the device and into the oral cavity. Non-laminar flow characteristics of the powder path cause the excipient-drug aggregates to decompose, and the mass of the large excipient particles causes their impaction at the back of the throat, while the smaller drug particles are deposited deep in the lungs.

As with liquid nebulization and MDIs, particle size of the pirfenidone or pyridone analog compound aerosol formulation may be optimized. If the particle size is larger than about 5 micron MMAD then the particles are deposited in upper airways. If the particle size of the aerosol is smaller than about 1 micron then it is delivered into the alveoli and may get transferred into the systemic blood circulation.

By non-limiting example, in dry powder inhalers, the pirfenidone or pyridone analog compound disclosed herein are prepared in dosages to disperse and deliver from about 34 mcg to about 463 mg from a dry powder formulation.

By non-limiting example, a dry powder pirfenidone or pyridone analog compound may be administered in the described respirable delivered dose in 10 or fewer inhalation breaths, more preferably in 8 or fewer inhalation breaths, more preferably in 6 or fewer inhalation breaths, more preferably in 8 or fewer inhalation breaths, more preferably in 4 or fewer inhalation breaths, more preferably in 2 or fewer inhalation breaths.

In some embodiments, a dry powder inhaler (DPI) is used to dispense the pirfenidone or pyridone analog compound described herein. DPIs contain the drug substance in fine dry particle form. Typically, inhalation by a patient causes the dry particles to form an aerosol cloud that is drawn into the patient's lungs. The fine dry drug particles may be produced by any technique known in the art. Some well-known techniques include use of a jet mill or other comminution equipment, precipitation from saturated or super saturated solutions, spray drying, in situ micronization (Hovione), or supercritical fluid methods. Typical powder formulations include production of spherical pellets or adhesive mixtures. In adhesive mixtures, the drug particles are attached to larger carrier particles, such as lactose monohydrate of size about 50 to about 100 microns in diameter. The larger carrier particles increase the aerodynamic forces on the carrier/drug agglomerates to improve aerosol formation. Turbulence and/or mechanical devices break the agglomerates into their constituent parts. The smaller drug particles are then drawn into the lungs while the larger carrier particles deposit in the mouth or throat. Some examples of adhesive mixtures are described in U.S. Pat. No. 5,478,578 and PCT Publication Nos. WO 95/11666, WO 87/05213, WO 96/23485, and WO 97/03649, all of which are incorporated by reference in their entirety. Additional excipients may also be included with the drug substance.

There are three common types of DPIs, all of which may be used with the pirfenidone or pyridone analog compounds described herein. In a single-dose DPI, a capsule containing one dose of dry drug substance/excipients is loaded into the inhaler. Upon activation, the capsule is breached, allowing the dry powder to be dispersed and inhaled using a dry powder inhaler. To dispense additional doses, the old capsule must be removed and an additional capsule loaded. Examples of single-dose DPIs are described in U.S. Pat. Nos. 3,807,400; 3,906,950; 3,991,761; and 4,013,075, all of which are hereby incorporated by reference in their entirety. In a multiple unit dose DPI, a package containing multiple single dose compartments is provided. For example, the package may comprise a blister pack, where each blister compartment contains one dose. Each dose can be dispensed upon breach of a blister compartment. Any of several arrangements of compartments in the package can be used. For example, rotary or strip arrangements are common. Examples of multiple unit does DPIs are described in EPO Patent Application Publication Nos. 0211595A2, 0455463A1, and 0467172A1, all of which are hereby incorporated by reference in their entirety. In a multi-dose DPI, a single reservoir of dry powder is used. Mechanisms are provided that measure out single dose amounts from the reservoir to be aerosolized and inhaled, such as described in U.S. Pat. Nos. 5,829,434; 5,437,270; 2,587,215; 5,113,855; 5,840,279; 4,688,218; 4,667,668; 5,033,463; and 4,805,811 and PCT Publication No. WO 92/09322, all of which are hereby incorporated by reference in their entirety.

In some embodiments, auxiliary energy in addition to or other than a patient's inhalation may be provided to facilitate operation of a DPI. For example, pressurized air may be provided to aid in powder de-agglomeration, such as described in U.S. Pat. Nos. 3,906,950; 5,113,855; 5,388,572; 6,029,662 and PCT Publication Nos. WO 93/12831, WO 90/07351, and WO 99/62495, all of which are hereby incorporated by reference in their entirety. Electrically driven impellers may also be provided, such as described in U.S. Pat. Nos. 3,948,264; 3,971,377; 4,147,166; 6,006,747 and PCT Publication No. WO 98/03217, all of which are hereby incorporated by reference in their entirety. Another mechanism is an electrically powered tapping piston, such as described in PCT Publication No. WO 90/13327, which is hereby incorporated by reference in its entirety. Other DPIs use a vibrator, such as described in U.S. Pat. Nos. 5,694,920 and 6,026,809, both of which are hereby incorporated by reference in their entirety. Finally, a scraper system may be employed, such as described in PCT Publication No. WO 93/24165, which is hereby incorporated by reference in its entirety.

Additional examples of DPIs for use herein are described in U.S. Pat. Nos. 4,811,731; 5,113,855; 5,840,279; 3,507,277; 3,669,113; 3,635,219; 3,991,761; 4,353,365; 4,889,144, 4,907,538; 5,829,434; 6,681,768; 6,561,186; 5,918,594; 6,003,512; 5,775,320; 5,740,794; and 6,626,173, all of which are hereby incorporated by reference in their entirety.

In some embodiments, a spacer or chamber may be used with any of the inhalers described herein to increase the amount of drug substance that gets absorbed by the patient, such as is described in U.S. Pat. Nos. 4,470,412; 4,790,305; 4,926,852; 5,012,803; 5,040,527; 5,024,467; 5,816,240; 5,027,806; and 6,026,807, all of which are hereby incorporated by reference in their entirety. For example, a spacer may delay the time from aerosol production to the time when the aerosol enters a patient's mouth. Such a delay may improve synchronization between the patient's inhalation and the aerosol production. A mask may also be incorporated for infants or other patients that have difficulty using the traditional mouthpiece, such as is described in U.S. Pat. Nos. 4,809,692; 4,832,015; 5,012,804; 5,427,089; 5,645,049; and 5,988,160, all of which are hereby incorporated by reference in their entirety.

Dry powder inhalers (DPIs), which involve deaggregation and aerosolization of dry powder particles, normally rely upon a burst of inspired air that is drawn through the unit to deliver a drug dosage. Such devices are described in, for example, U.S. Pat. No. 4,807,814, which is directed to a pneumatic powder ejector having a suction stage and an injection stage; SU 628930 (Abstract), describing a hand-held powder disperser having an axial air flow tube; Fox et al., Powder and Bulk Engineering, pages 33-36 (March 1988), describing a venturi eductor having an axial air inlet tube upstream of a venturi restriction; EP 347 779, describing a hand-held powder disperser having a collapsible expansion chamber, and U.S. Pat. No. 5,785,049, directed to dry powder delivery devices for drugs.

Commercial examples of dry powder inhalers that can be used with the pirfenidone or pyridone analog compound formulations described herein include the Aerolizer, Turohaler, Handihaler and Discus.

Solution/Dispersion Formulations

In one embodiment, aqueous formulations containing soluble or nanoparticulate drug particles are provided. For aqueous aerosol formulations, the drug may be present at a concentration from about 34 mcg/mL to about 463 mg/mL. In some embodiments the drug is present at a concentration from about 1 mg/mL to about 463 mg/mL, or about 1 mg/mL to about 400 mg/mL, or about 0.1 mg/mL to about 360 mg/mL, or about 1 mg/mL to about 300 mg/mL, or about 1 mg/mL to about 200 mg/mL, about 1 mg/mL to about 100 mg/mL, or about 1 mg/mL to about 50 mg/mL, or about 5 mg/mL to about 50 mg/mL, or about 10 mg/mL to about 50 mg/mL, or about 15 mg/mL to about 50 mg/mL, or about 20 mg/mL to about 50 mg/mL. Such formulations provide effective delivery to appropriate areas of the lung, with the more concentrated aerosol formulations having the additional advantage of enabling large quantities of drug substance to be delivered to the lung in a very short period of time. In one embodiment, a formulation is optimized to provide a well tolerated formulation. Accordingly, in one embodiment, pirfenidone or pyridone analog compound disclosed herein are formulated to have good taste, pH from about 4.0 to about 8.0, osmolarity from about 100 to about 5000 mOsmol/kg. In some embodiments, the osmolarity is from about 100 to about 1000 mOsmol/kg. In some embodiments, the osmolarity is from about 200 to about 500 mOsmol/kg. In some embodiments, the permeant ion concentration is from about 30 to about 300 mM.

In some embodiments, described herein is an aqueous pharmaceutical composition comprising pirfenidone or pyridone analog compound, water and one or more additional ingredients selected from co-solvents, tonicity agents, sweeteners, surfactants, wetting agents, chelating agents, anti-oxidants, salts, and buffers. It should be understood that many excipients may serve several functions, even within the same formulation.

In some embodiments, pharmaceutical compositions described herein do not include any thickening agents.

In some embodiments, the concentration of pirfenidone or pyridone analog compound in the aqueous pharmaceutical composition is between about 0.1 mg/mL and about 100 mg/mL. In some embodiments, the concentration of pirfenidone or pyridone analog compound in the pharmaceutical composition is between about 1 mg/mL and about 100 mg/mL, between about 10 mg/mL and about 100 mg/mL between about 20 mg/mL and about 100 mg/mL, between about 25 mg/mL and about 100 mg/mL, between about 30 mg/mL and about 100 mg/mL, between about 15 mg/mL and about 50 mg/mL, between about 20 mg/mL and about 50 mg/mL, between about 25 mg/mL and about 50 mg/mL, or between about 30 mg/mL and about 50 mg/mL.

In some embodiments, the pH is between about pH 4.0 and about pH 8.0. In some embodiments, the pH is between about pH 5.0 and about pH 8.0. In some embodiments, the pH is between about pH 6.0 and about pH 8.0. In some embodiments, the pH is between about pH 6.5 and about pH 8.0.

In some embodiments, the aqueous pharmaceutical composition includes one or more co-solvents. In some embodiments, the aqueous pharmaceutical composition includes one or more co-solvents, where the total amount of co-solvents is from about 1% to about 50% v/v of the total volume of the composition. In some embodiments, the aqueous pharmaceutical composition includes one or more co-solvents, where the total amount of co-solvents is from about 1% to about 50% v/v, from about 1% to about 40% v/v, from about 1% to about 30% v/v, or from about 1% to about 25% v/v, of the total volume of the composition. Co-solvents include, but are not limited to, ethanol, propylene glycol and glycerol. In some embodiments, the aqueous pharmaceutical composition includes ethanol at about 1% v/v to about 25%. In some embodiments, the aqueous pharmaceutical composition includes ethanol at about 1% v/v to about 15%. In some embodiments, the aqueous pharmaceutical composition includes ethanol at about 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, 16% v/v, 17% v/v, 18% v/v, 19% v/v, 20% v/v, 21% v/v, 22% v/v, 23% v/v, 24% v/v, or 25% v/v. In some embodiments, the aqueous pharmaceutical composition includes glycerol at about 1% v/v to about 25%. In some embodiments, the aqueous pharmaceutical composition includes glycerol at about 1% v/v to about 15%. In some embodiments, the aqueous pharmaceutical composition includes glycerol at about 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, 16% v/v, 17% v/v, 18% v/v, 19% v/v, 20% v/v, 21% v/v, 22% v/v, 23% v/v, 24% v/v, or 25% v/v. In some embodiments, the aqueous pharmaceutical composition includes propylene glycol at about 1% v/v to about 50%. In some embodiments, the aqueous pharmaceutical composition includes propylene glycol at about 1% v/v to about 25%. In some embodiments, the aqueous pharmaceutical composition includes propylene glycol at about 1% v/v, 2% v/v, 3% v/v, 4% v/v, 5% v/v, 6% v/v, 7% v/v, 8% v/v, 9% v/v, 10% v/v, 11% v/v, 12% v/v, 13% v/v, 14% v/v, 15% v/v, 16% v/v, 17% v/v, 18% v/v, 19% v/v, 20% v/v, 21% v/v, 22% v/v, 23% v/v, 24% v/v, or 25% v/v.

In some embodiments, the aqueous pharmaceutical composition includes ethanol at about 1% v/v to about 25% and propylene glycol at about 1% v/v to about 50%. In some embodiments, the aqueous pharmaceutical composition includes ethanol at about 1% v/v to about 15% and propylene glycol at about 1% v/v to about 30%. In some embodiments, the aqueous pharmaceutical composition includes ethanol at about 1% v/v to about 8% and propylene glycol at about 1% v/v to about 16%. In some embodiments, the aqueous pharmaceutical composition includes ethanol and twice as much propylene glycol, based on volume.

In some embodiments, the aqueous pharmaceutical composition includes a buffer. In some embodiments, the buffer is a citrate buffer or a phosphate buffer. In some embodiments, the buffer is a citrate buffer. In some embodiments, the buffer is a phosphate buffer.

In some embodiments, the aqueous pharmaceutical composition consists essentially of pirfenidone or pyridone analog compound, water, ethanol and/or propylene glycol, a buffer to maintain the pH at about 4 to 8 and optionally one or more ingredients selected from salts, surfactants, and sweeteners (taste-masking agents). In some embodiments, the one or more salts are selected from tonicity agents. In some embodiments, the one or more salts are selected from sodium chloride and magnesium chloride.

In some embodiments, the aqueous pharmaceutical composition consists essentially of pirfenidone or pyridone analog compound at a concentration of about 10 mg/mL to about 50 mg/mL, water, one or two cosolvents (ethanol at a concentration of about 1% v/v to about 25% v/v and/or propylene glycol at a concentration of about 1% v/v to about 50% v/v), a buffer to maintain the pH at about 4 to 8 and optionally one or more ingredients selected from salts, surfactants, and sweeteners (taste-masking agents).

In one embodiment, the solution or diluent used for preparation of aerosol formulations has a pH range from about 4.0 to about 8.0. This pH range improves tolerability. When the aerosol is either acidic or basic, it can cause bronchospasm and cough. Although the safe range of pH is relative and some patients may tolerate a mildly acidic aerosol, while others will experience bronchospasm. Any aerosol with a pH of less than about 4.0 typically induces bronchospasm. Aerosols having pH greater than about 8.0 may have low tolerability because body tissues are generally unable to buffer alkaline aerosols. Aerosols with controlled pH below about 4.0 and over about 8.0 typically result in lung irritation accompanied by severe bronchospasm cough and inflammatory reactions. For these reasons as well as for the avoidance of bronchospasm, cough or inflammation in patients, the optimum pH for the aerosol formulation was determined to be between about pH 4.0 to about pH 8.0.

By non-limiting example, compositions may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine, hydrochloride, or phosphate buffers.

Many patients have increased sensitivity to various chemical tastes, including bitter, salt, sweet, metallic sensations. To create well-tolerated drug products, by non-limiting example taste masking may be accomplished through the addition of taste-masking excipients, adjusted osmolality, and sweeteners.

Many patients have increased sensitivity to various chemical agents and have high incidence of bronchospastic, asthmatic or other coughing incidents. Their airways are particularly sensitive to hypotonic or hypertonic and acidic or alkaline conditions and to the presence of any permanent ion, such as chloride. Any imbalance in these conditions or a presence of chloride above certain value leads to bronchospastic or inflammatory events and/or cough which greatly impair treatment with inhalable formulations. Both these conditions prevent efficient delivery of aerosolized drugs into the endobronchial space.

In some embodiments, the osmolality of aqueous solutions of the pirfenidone or pyridone analog compound disclosed herein are adjusted by providing excipients. In some cases, a certain amount of chloride or another anion is needed for successful and efficacious delivery of aerosolized pirfenidone or pyridone analog compound.

In some embodiments, the osmolality of aqueous solutions of the pirfenidone or pyridone analog compound disclosed herein is greater than 100 mOsmol/kg. In some embodiments, the osmolality of aqueous solutions of the pirfenidone or pyridone analog compound disclosed herein is greater than 300 mOsmol/kg. In some embodiments, the osmolality of aqueous solutions of the pirfenidone or pyridone analog compound disclosed herein is greater than 1000 mOsmol/kg. In some embodiments, aerosol delivery of aqueous solutions with high osmolality (i.e. greater than about 300 mOsmol/kg) have high incidence of bronchospastic, asthmatic or other coughing incidents. In some embodiments, aerosol delivery of the aqueous solutions having high osmolality (i.e. greater than about 300 mOsmol/kg) as described do not increase the incidence of bronchospastic, asthmatic or other coughing incidents.

In some embodiments, the osmolality of aqueous solutions of the pirfenidone or pyridone analog compound disclosed herein are greater than 100 mOsmol/kg above by providing excipients. In some cases, a certain amount of chloride or another anion is needed for successful and efficacious delivery of aerosolized pirfenidone or pyridone analog compound In some embodiments, the formulation for an aerosol pirfenidone or pyridone analog compound may comprise from about 34 mcg to about 463 mg pirfenidone or pyridone analog compound per about 1 to about 5 ml of dilute saline (between 1/10 to 2/1 normal saline). Accordingly, the concentration of a pirfenidone or pyridone analog compound solution may be greater than about 34 mcg/ml, greater than about 463 mcg/ml, greater than about 1 mg/ml, greater than about 2 mg/mL, greater than about 3.0 mg/mL, greater than about 3.7 mg/mL, greater than about 10 mg/mL, greater than about 37 mg/mL, greater than about 50 mg/ml, greater than about 100 mg/mL, or greater than 463 mg/mL.

In some embodiments, solution osmolality is from about 100 mOsmol/kg to about 6000 mOsmol/kg. In some embodiments, solution osmolality is from about 100 mOsmol/kg to about 5000 mOsmol/kg. In some other embodiments, the solution osmolality is from about 400 mOsmol/kg to about 5000 mOsmol/kg.

In one embodiments, permeant ion concentration is from about 25 mM to about 400 mM. In various other embodiments, permeant ion concentration is from about 30 mM to about 300 mM; from about 40 mM to about 200 mM; and from about 50 mM to about 150 mM.

Solid Particle Formulations

In some embodiments, solid drug nanoparticles are provided for use in generating dry aerosols or for generating nanoparticles in liquid suspension. Powders comprising nanoparticulate drug can be made by spray-drying aqueous dispersions of a nanoparticulate drug and a surface modifier to form a dry powder which consists of aggregated drug nanoparticles. In one embodiment, the aggregates can have a size of about 1 to about 2 microns which is suitable for deep lung delivery. The aggregate particle size can be increased to target alternative delivery sites, such as the upper bronchial region or nasal mucosa by increasing the concentration of drug in the spray-dried dispersion or by increasing the droplet size generated by the spray dryer.

Alternatively, an aqueous dispersion of drug and surface modifier can contain a dissolved diluent such as lactose or mannitol which, when spray dried, forms respirable diluent particles, each of which contains at least one embedded drug nanoparticle and surface modifier. The diluent particles with embedded drug can have a particle size of about 1 to about 2 microns, suitable for deep lung delivery. In addition, the diluent particle size can be increased to target alternate delivery sites, such as the upper bronchial region or nasal mucosa by increasing the concentration of dissolved diluent in the aqueous dispersion prior to spray drying, or by increasing the droplet size generated by the spray dryer.

Spray-dried powders can be used in DPIs or pMDIs, either alone or combined with freeze-dried nanoparticulate powder. In addition, spray-dried powders containing drug nanoparticles can be reconstituted and used in either jet or ultrasonic nebulizers to generate aqueous dispersions having respirable droplet sizes, where each droplet contains at least one drug nanoparticle. Concentrated nanoparticulate dispersions may also be used in these embodiments of the invention.

Nanoparticulate drug dispersions can also be freeze-dried to obtain powders suitable for nasal or pulmonary delivery. Such powders may contain aggregated nanoparticulate drug particles having a surface modifier. Such aggregates may have sizes within a respirable range, e.g., about 1 to about 5 microns MMAD.

Freeze dried powders of the appropriate particle size can also be obtained by freeze drying aqueous dispersions of drug and surface modifier, which additionally contain a dissolved diluent such as lactose or mannitol. In these instances the freeze dried powders consist of respirable particles of diluent, each of which contains at least one embedded drug nanoparticle.

Freeze-dried powders can be used in DPIs or pMDIs, either alone or combined with spray-dried nanoparticulate powder. In addition, freeze-dried powders containing drug nanoparticles can be reconstituted and used in either jet or ultrasonic nebulizers to generate aqueous dispersions that have respirable droplet sizes, where each droplet contains at least one drug nanoparticle.

One embodiment of the invention is directed to a process and composition for propellant-based systems comprising nanoparticulate drug particles and a surface modifier. Such formulations may be prepared by wet milling the coarse drug substance and surface modifier in liquid propellant, either at ambient pressure or under high pressure conditions. Alternatively, dry powders containing drug nanoparticles may be prepared by spray-drying or freeze-drying aqueous dispersions of drug nanoparticles and the resultant powders dispersed into suitable propellants for use in conventional pMDIs. Such nanoparticulate pMDI formulations can be used for either nasal or pulmonary delivery. For pulmonary administration, such formulations afford increased delivery to the deep lung regions because of the small (e.g., about 1 to about 2 microns MMAD) particle sizes available from these methods. Concentrated aerosol formulations can also be employed in pMDIs.

Another embodiment is directed to dry powders which contain nanoparticulate compositions for pulmonary or nasal delivery. The powders may consist of respirable aggregates of nanoparticulate drug particles, or of respirable particles of a diluent which contains at least one embedded drug nanoparticle. Powders containing nanoparticulate drug particles can be prepared from aqueous dispersions of nanoparticles by removing the water via spray-drying or lyophilization (freeze drying). Spray-drying is less time consuming and less expensive than freeze-drying, and therefore more cost-effective. However, certain drugs, such as biologicals benefit from lyophilization rather than spray-drying in making dry powder formulations.

Conventional micronized drug particles used in dry powder aerosol delivery having particle diameters of from about 1 to about 5 microns MMAD are often difficult to meter and disperse in small quantities because of the electrostatic cohesive forces inherent in such powders. These difficulties can lead to loss of drug substance to the delivery device as well as incomplete powder dispersion and sub-optimal delivery to the lung. Many drug compounds, particularly proteins and peptides, are intended for deep lung delivery and systemic absorption. Since the average particle sizes of conventionally prepared dry powders are usually in the range of from about 1 to about 5 microns MMAD, the fraction of material which actually reaches the alveolar region may be quite small. Thus, delivery of micronized dry powders to the lung, especially the alveolar region, is generally very inefficient because of the properties of the powders themselves.

The dry powder aerosols which contain nanoparticulate drugs can be made smaller than comparable micronized drug substance and, therefore, are appropriate for efficient delivery to the deep lung. Moreover, aggregates of nanoparticulate drugs are spherical in geometry and have good flow properties, thereby aiding in dose metering and deposition of the administered composition in the lung or nasal cavities.

Dry nanoparticulate compositions can be used in both DPIs and pMDIs. As used herein, "dry" refers to a composition having less than about 5% water.

In one embodiment, compositions are provided containing nanoparticles which have an effective average particle size of less than about 1000 nm, more preferably less than about 400 nm, less than about 300 nm, less than about 250 nm, or less than about 200 nm, as measured by light-scattering methods. By "an effective average particle size of less than about 1000 nm" it is meant that at least 50% of the drug particles have a weight average particle size of less than about 1000 nm when measured by light scattering techniques. Preferably, at least 70% of the drug particles have an average particle size of less than about 1000 nm, more preferably at least 90% of the drug particles have an average particle size of less than about 1000 nm, and even more preferably at least about 95% of the particles have a weight average particle size of less than about 1000 nm.

For aqueous aerosol formulations, the nanoparticulate pirfenidone or pyridone analog compound agent may be present at a concentration of about 34 mcg/mL up to about 463 mg/mL. For dry powder aerosol formulations, the nanoparticulate agent may be present at a concentration of about 34 mg/g up to about 463 mg/g, depending on the desired drug dosage. Concentrated nanoparticulate aerosols, defined as containing a nanoparticulate drug at a concentration of about 34 mcg/mL up to about 463 mg/mL for aqueous aerosol formulations, and about 34 mg/g up to about 463 mg/g for dry powder aerosol formulations, are specifically provided. Such formulations provide effective delivery to appropriate areas of the lung or nasal cavities in short administration times, i.e., less than about 3-15 seconds per dose as compared to administration times of up to 4 to 20 minutes as found in conventional pulmonary nebulizer therapies.

Nanoparticulate drug compositions for aerosol administration can be made by, for example, (1) nebulizing a dispersion of a nanoparticulate drug, obtained by either grinding or precipitation; (2) aerosolizing a dry powder of aggregates of nanoparticulate drug and surface modifier (the aerosolized composition may additionally contain a diluent); or (3) aerosolizing a suspension of nanoparticulate drug or drug aggregates in a non-aqueous propellant. The aggregates of nanoparticulate drug and surface modifier, which may additionally contain a diluent, can be made in a non-pressurized or a pressurized non-aqueous system. Concentrated aerosol formulations may also be made via such methods.

Milling of aqueous drug to obtain nanoparticulate drug may be performed by dispersing drug particles in a liquid dispersion medium and applying mechanical means in the presence of grinding media to reduce the particle size of the drug to the desired effective average particle size. The particles can be reduced in size in the presence of one or more surface modifiers. Alternatively, the particles can be contacted with one or more surface modifiers after attrition. Other compounds, such as a diluent, can be added to the drug/surface modifier composition during the size reduction process. Dispersions can be manufactured continuously or in a batch mode.

Another method of forming nanoparticle dispersion is by microprecipitation. This is a method of preparing stable dispersions of drugs in the presence of one or more surface modifiers and one or more colloid stability enhancing surface active agents free of any trace toxic solvents or solubilized heavy metal impurities. Such a method comprises, for example, (1) dissolving the drug in a suitable solvent with mixing; (2) adding the formulation from step (1) with mixing to a solution comprising at least one surface modifier to form a clear solution; and (3) precipitating the formulation from step (2) with mixing using an appropriate nonsolvent. The method can be followed by removal of any formed salt, if present, by dialysis or diafiltration and concentration of the dispersion by conventional means. The resultant nanoparticulate drug dispersion can be utilized in liquid nebulizers or processed to form a dry powder for use in a DPI or pMDI.

In a non-aqueous, non-pressurized milling system, a non-aqueous liquid having a vapor pressure of about 1 atm or less at room temperature and in which the drug substance is essentially insoluble may be used as a wet milling medium to make a nanoparticulate drug composition. In such a process, a slurry of drug and surface modifier may be milled in the non-aqueous medium to generate nanoparticulate drug particles. Examples of suitable non-aqueous media include ethanol, trichloromonofluoromethane, (CFC-11), and dichlorotetafluoroethane (CFC-114). An advantage of using CFC-11 is that it can be handled at only marginally cool room temperatures, whereas CFC-114 requires more controlled conditions to avoid evaporation. Upon completion of milling the liquid medium may be removed and recovered under vacuum or heating, resulting in a dry nanoparticulate composition. The dry composition may then be filled into a suitable container and charged with a final propellant. Exemplary final product propellants, which ideally do not contain chlorinated hydrocarbons, include HFA-134a (tetrafluoroethane) and HFA-227 (heptafluoropropane). While non-chlorinated propellants may be preferred for environmental reasons, chlorinated propellants may also be used in this embodiment of the invention.

In a non-aqueous, pressurized milling system, a non-aqueous liquid medium having a vapor pressure significantly greater than 1 atm at room temperature may be used in the milling process to make nanoparticulate drug compositions. If the milling medium is a suitable halogenated hydrocarbon propellant, the resultant dispersion may be filled directly into a suitable pMDI container. Alternately, the milling medium can be removed and recovered under vacuum or heating to yield a dry nanoparticulate composition. This composition can then be filled into an appropriate container and charged with a suitable propellant for use in a pMDI.

Spray drying is a process used to obtain a powder containing nanoparticulate drug particles following particle size reduction of the drug in a liquid medium. In general, spray-drying may be used when the liquid medium has a vapor pressure of less than about 1 atm at room temperature. A spray-dryer is a device which allows for liquid evaporation and drug powder collection. A liquid sample, either a solution or suspension, is fed into a spray nozzle. The nozzle generates droplets of the sample within a range of about 20 to about 100 micron in diameter which are then transported by a carrier gas into a drying chamber. The carrier gas temperature is typically from about 80 to about 200° C. The droplets are subjected to rapid liquid evaporation, leaving behind dry particles which are collected in a special reservoir beneath a cyclone apparatus. Smaller particles in the range down about 1 micron to about 5 microns are also possible.

If the liquid sample consists of an aqueous dispersion of nanoparticles and surface modifier, the collected product will consist of spherical aggregates of the nanoparticulate drug particles. If the liquid sample consists of an aqueous dispersion of nanoparticles in which an inert diluent material was dissolved (such as lactose or mannitol), the collected product will consist of diluent (e.g., lactose or mannitol) particles which contain embedded nanoparticulate drug particles. The final size of the collected product can be controlled and depends on the concentration of nanoparticulate drug and/or diluent in the liquid sample, as well as the droplet size produced by the spray-dryer nozzle. Collected products may be used in conventional DPIs for pulmonary or nasal delivery, dispersed in propellants for use in pMDIs, or the particles may be reconstituted in water for use in nebulizers.

In some instances it may be desirable to add an inert carrier to the spray-dried material to improve the metering properties of the final product. This may especially be the case when the spray dried powder is very small (less than about 5 micron) or when the intended dose is extremely small, whereby dose metering becomes difficult. In general, such carrier particles (also known as bulking agents) are too large to be delivered to the lung and simply impact the mouth and throat and are swallowed. Such carriers typically consist of sugars such as lactose, mannitol, or trehalose. Other inert materials, including polysaccharides and cellulosics, may also be useful as carriers.

Spray-dried powders containing nanoparticulate drug particles may used in conventional DPIs, dispersed in propellants for use in pMDIs, or reconstituted in a liquid medium for use with nebulizers.

For compounds that are denatured or destabilized by heat, such as compounds having a low melting point (i.e., about 70 to about 150° C.), or for example, biologics, sublimation is preferred over evaporation to obtain a dry powder nanoparticulate drug composition. This is because sublimation avoids the high process temperatures associated with spray-drying. In addition, sublimation, also known as freeze-drying or lyophilization, can increase the shelf stability of drug compounds, particularly for biological products. Freeze-dried particles can also be reconstituted and used in nebulizers. Aggregates of freeze-dried nanoparticulate drug particles can be blended with either dry powder intermediates or used alone in DPIs and pMDIs for either nasal or pulmonary delivery.

Sublimation involves freezing the product and subjecting the sample to strong vacuum conditions. This allows for the formed ice to be transformed directly from a solid state to a vapor state. Such a process is highly efficient and, therefore, provides greater yields than spray-drying. The resultant freeze-dried product contains drug and modifier(s). The drug is typically present in an aggregated state and can be used for inhalation alone (either pulmonary or nasal), in conjunction with diluent materials (lactose, mannitol, etc.), in DPIs or pMDIs, or reconstituted for use in a nebulizer.

Liposomal Compositions

In some embodiments, pirfenidone or pyridone analog compounds disclosed herein may be formulated into liposome particles, which can then be aerosolized for inhaled delivery. Lipids which are useful in the present invention can be any of a variety of lipids including both neutral lipids and charged lipids. Carrier systems having desirable properties can be prepared using appropriate combinations of lipids, targeting groups and circulation enhancers. Additionally, the compositions provided herein can be in the form of liposomes or lipid particles, preferably lipid particles. As used herein, the term "lipid particle" refers to a lipid bilayer carrier which "coats" a nucleic acid and has little or no aqueous interior. More particularly, the term is used to describe a self-assembling lipid bilayer carrier in which a portion of the interior layer comprises cationic lipids which form ionic bonds or ion-pairs with negative charges on the nucleic acid (e.g., a plasmid phosphodiester backbone). The interior layer can also comprise neutral or fusogenic lipids and, in some embodiments, negatively charged lipids. The outer layer of the particle will typically comprise mixtures of lipids oriented in a tail-to-tail fashion (as in liposomes) with the hydrophobic tails of the interior layer. The polar head groups present on the lipids of the outer layer will form the external surface of the particle.

Liposomal bioactive agents can be designed to have a sustained therapeutic effect or lower toxicity allowing less frequent administration and an enhanced therapeutic index. Liposomes are composed of bilayers that entrap the desired pharmaceutical. These can be configured as multilamellar vesicles of concentric bilayers with the pharmaceutical trapped within either the lipid of the different layers or the aqueous space between the layers.

By non-limiting example, lipids used in the compositions may be synthetic, semi-synthetic or naturally-occurring lipids, including phospholipids, tocopherols, steroids, fatty acids, glycoproteins such as albumin, negatively-charged lipids and cationic lipids. Phosholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC) and dioleoylphosphatidylglycerol (DOPG). Other examples include dimyristoylphosphatidycholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPG), and single acylated phospholipids like mono-oleoyl-phosphatidylethanolamine (MOPE).

In a preferred embodiment, PEG-modified lipids are incorporated into the compositions of the present invention as the aggregation-preventing agent. The use of a PEG-modified lipid positions bulky PEG groups on the surface of the liposome or lipid carrier and prevents binding of DNA to the outside of the carrier (thereby inhibiting cross-linking and aggregation of the lipid carrier). The use of a PEG-ceramide is often preferred and has the additional advantages of stabilizing membrane bilayers and lengthening circulation lifetimes. Additionally, PEG-ceramides can be prepared with different lipid tail lengths to control the lifetime of the PEG-ceramide in the lipid bilayer. In this manner, "programmable" release can be accomplished which results in the control of lipid carrier fusion. For example, PEG-ceramides having C20-acyl groups attached to the ceramide moiety will diffuse out of a lipid bilayer carrier with a half-life of 22 hours. PEG-ceramides having C14- and C8-acyl groups will diffuse out of the same carrier with half-lives of 10 minutes and less than 1 minute, respectively. As a result, selection of lipid tail length provides a composition in which the bilayer becomes destabilized (and thus fusogenic) at a known rate. Though less preferred, other PEG-lipids or lipid-polyoxyethylene conjugates are useful in the present compositions. Examples of suitable PEG-modified lipids include PEG-modified phosphatidylethanolamine and phosphatidic acid, PEG-modified diacylglycerols and dialkylglycerols, PEG-modified dialkylamines and PEG-modified 1,2-diacyloxypropan-3-amines. Particularly preferred are PEG-ceramide conjugates (e.g., PEG-Cer-C8, PEG-Cer-C14 or PEG-Cer-C20) which are described in U.S. Pat. No. 5,820,873, incorporated herein by reference.

The compositions of the present invention can be prepared to provide liposome compositions which are about 50 nm to about 400 nm in diameter. One with skill in the art will understand that the size of the compositions can be larger or smaller depending upon the volume which is encapsulated. Thus, for larger volumes, the size distribution will typically be from about 80 nm to about 300 nm.

Surface Modifiers

Pirfenidone or pyridone analog compounds disclosed herein may be prepared in a pharmaceutical composition with suitable surface modifiers which may be selected from known organic and inorganic pharmaceutical excipients. Such excipients include low molecular weight oligomers, polymers, surfactants and natural products. Preferred surface modifiers include nonionic and ionic surfactants. Two or more surface modifiers can be used in combination.

Representative examples of surface modifiers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens™, such as e.g., Tween 20™ and Tween 80™, (ICI Specialty Chemicals)); polyethylene glycols (e.g., Carbowaxs 3350™, and 1450™, and Carbopol 934™, (Union Carbide)), dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers (e.g., Pluronics F68™, and F108™, which are block copolymers of ethylene oxide and propylene oxide); poloxamnines (e.g., Tetronic 908™, also known as Poloxamine 908™, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508™; (T-1508) (BASF Wyandotte Corporation), dialkylesters of sodium sulfosuccinic acid (e.g., Aerosol OT™, which is a dioctyl ester of sodium sulfosuccinic acid (American Cyanamid)); Duponol P™, which is a sodium lauryl sulfate (DuPont); Tritons X-200™, which is an alkyl aryl polyether sulfonate (Rohm and Haas); Crodestas F-110™, which is a mixture of sucrose stearate and sucrose distearate (Croda Inc.); p-isononylphenoxypoly-(glycidol), also known as Olin-Log™, or Surfactant 10-G™, (Olin Chemicals, Stamford, Conn.); Crodestas SL-40™, (Croda, Inc.); and SA9OHCO, which is $C_1 8H_{37}CH_2$ $(CON(CH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucarmide; n-octyl-β-D-glucopyranoside; octyl β-D-thioglucopyranoside; and the like. Tyloxapol is a particularly preferred surface modifier for the pulmonary or intranasal delivery of steroids, even more so for nebulization therapies.

Examples of surfactants for use in the solutions disclosed herein include, but are not limited to, ammonium laureth sulfate, cetamine oxide, cetrimonium chloride, cetyl alcohol, cetyl myristate, cetyl palmitate, cocamide DEA, cocamidopropyl betaine, cocamidopropylamine oxide, cocamide MEA, DEA lauryl sulfate, di-stearyl phthalic acid amide, dicetyl dimethyl ammonium chloride, dipalmitoylethyl hydroxethylmonium, disodium laureth sulfosuccinate, di(hydrogenated) tallow phthalic acid, glyceryl dilaurate, glyceryl distearate, glyceryl oleate, glyceryl stearate, isopropyl myristate nf, isopropyl palmitate nf, lauramide DEA, lauramide MEA, lauramide oxide, myristamine oxide, octyl isononanoate, octyl palmitate, octyldodecyl neopentanoate, olealkonium chloride, PEG-2 stearate, PEG-32 glyceryl caprylate/caprate, PEG-32 glyceryl stearate, PEG-4 and PEG-150 stearate & distearate, PEG-4 to PEG-150 laurate & dilaurate, PEG-4 to PEG-150 oleate & dioleate, PEG-7 glyceryl cocoate, PEG-8 beeswax, propylene glycol stearate, sodium C14-16 olefin sulfonate, sodium lauryl sulfoacetate, sodium lauryl sulphate, sodium trideceth sulfate, stearalkonium chloride, stearamide oxide, TEA-dodecylbenzene sulfonate, TEA lauryl sulfate Most of these surface modifiers are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference. The surface modifiers are commercially available and/or can be prepared by techniques known in the art. The relative amount of drug and surface modifier can vary widely and the optimal amount of the surface modifier can depend upon, for example, the particular drug and surface modifier selected, the critical micelle concentration of the surface modifier if it forms micelles, the hydrophilic-lipophilic-balance (HLB) of the surface modifier, the melting point of the surface modifier, the water solubility of the surface modifier and/or drug, the surface tension of water solutions of the surface modifier, etc.

In the present invention, the optimal ratio of drug to surface modifier is ~0.1% to ~99.9% pirfenidone or pyridone analog compound, more preferably about 10% to about 90%.

Microspheres

Microspheres can be used for pulmonary delivery of pirfenidone or pyridone analog compounds by first adding an appropriate amount of drug compound to be solubilzed in water. For example, an aqueous pirfenidone or pyridone analog compound solution may be dispersed in methylene chloride containing a predetermined amount (0.1-1% w/v) of poly(DL-lactide-co-glycolide) (PLGA) by probe sonication for 1-3 min on an ice bath. Separately, a pirfenidone or pyridone analog compound may be solubilized in methylene chloride containing PLGA (0.1-1% w/v). The resulting water-in-oil primary emulsion or the polymer/drug solution will be dispersed in an aqueous continuous phase consisting of 1-2% polyvinyl alcohol (previously cooled to 4° C.) by probe sonication for 3-5 min on an ice bath. The resulting emulsion will be stirred continuously for 2-4 hours at room temperature to evaporate methylene chloride. Microparticles thus formed will be separated from the continuous phase by centrifuging at 8000-10000 rpm for 5-10 min. Sedimented particles will be washed thrice with distilled water and freeze dried. Freeze-dried pirfenidone or pyridone analog compound microparticles will be stored at −20° C.

By non-limiting example, a spray drying approach will be employed to prepare pirfenidone or pyridone analog compound microspheres. An appropriate amount of pirfenidone or pyridone analog compound will be solubilized in methylene chloride containing PLGA (0.1-1%). This solution will be spray dried to obtain the microspheres.

By non-limiting example, pirfenidone or pyridone analog compound microparticles will be characterized for size distribution (requirement: 90%<5 μm, 95%<10 μm), shape, drug loading efficiency and drug release using appropriate techniques and methods.

By non-limiting example, this approach may also be used to sequester and improve the water solubility of solid, AUC shape-enhancing formulations, such as low-solubility pirfenidone or pyridone analog compounds or salt forms for nanoparticle-based formulations.

A certain amount of pirfenidone or pyridone analog compound can be first dissolved in the minimal quantity of ethanol 96% necessary to maintain the fluoroquinolone in solution when diluted with water from 96 to 75%. This solution can then be diluted with water to obtain a 75% ethanol solution and then a certain amount of paracetamol can be added to obtain the following w/w drug/polymer ratios: 1:2, 1:1, 2:1, 3:1, 4:1, 6:1, 9:1, and 19:1. These final solutions are spray-dried under the following conditions: feed rate, 15 mL/min; inlet temperature, 110° C.; outlet temperature, 85° C.; pressure 4 bar and throughput of drying air, 35 m3/hr. Powder is then collected and stored under vacuum in a dessiccator.

Solid Lipid Particles

Preparation of pirfenidone or pyridone analog compound solid lipid particles may involve dissolving the drug in a lipid melt (phospholipids such as phophatidyl choline and phosphatidyl serine) maintained at least at the melting temperature of the lipid, followed by dispersion of the drug-containing melt in a hot aqueous surfactant solution (typically 1-5% w/v) maintained at least at the melting temperature of the lipid. The coarse dispersion will be homogenized for 1-10 min using a Microfluidizer® to obtain a nanoemulsion. Cooling the nanoemulsion to a temperature between 4-25° C. will re-solidify the lipid, leading to formation of solid lipid nanoparticles. Optimization of formulation parameters (type of lipid matrix, surfactant concentration and production parameters) will be performed so as to achieve a prolonged drug delivery. By non-limiting example, this approach may also be used to sequester and improve the water solubility of solid, AUC shape-enhancing formulations, such as low-solubility pirfenidone or pyridone analog compounds or salt forms for nanoparticle-based formulations.

Melt-Extrusion AUC Shape-Enhancing Formulation

Melt-Extrusion AUC shape-enhancing pirfenidone or pyridone analog compound formulations may be preparation by dissolving the drugs in micelles by adding surfactants or preparing micro-emulsion, forming inclusion complexes with other molecules such as cyclodextrins, forming nanoparticles of the drugs, or embedding the amorphous drugs in a polymer matrix. Embedding the drug homogeneously in a polymer matrix produces a solid dispersion. Solid dispersions can be prepared in two ways: the solvent method and the hot melt method. The solvent method uses an organic solvent wherein the drug and appropriate polymer are dissolved and then (spray) dried. The major drawbacks of this method are the use of organic solvents and the batch mode production process. The hot melt method uses heat in order to disperse or dissolve the drug in an appropriate polymer. The melt-extrusion process is an optimized version of the hot melt method. The advantage of the melt-extrusion approach is lack of organic solvent and continuous production process. As the melt-extrusion is a novel pharmaceutical technique, the literature dealing with it is limited. The technical set-up involves a mixture and extrusion of pirfenidone or pyridone analog compound, hydroxypropyl-b-cyclodextrin (HP-b-CD), and hydroxypropylmethylcellulose (HPMC), in order to, by non-limiting example create a AUC shape-enhancing formulation of pirfenidone or pyridone analog compound. Cyclodextrin is a toroidal-shaped molecule with hydroxyl groups on the outer surface and a cavity in the center. Cyclodextrin sequesters the drug by forming an inclusion complex. The complex formation between cyclodextrins and drugs has been investigated extensively. It is known that water-soluble polymer interacts with cyclodextrin and drug in the course of complex formation to form a stabilized complex of drug and cyclodextrin co-complexed with the polymer. This complex is more stable than the classic cyclodextrin-drug complex. As one example, HPMC is water soluble; hence using this polymer with HP-b-CD in the melt is expected to create an aqueous soluble AUC shape-enhancing formulation. By non-limiting example, this approach may also be used to sequester and improve the water solubility of solid, AUC shape-enhancing formulations, such as low-solubility pirfenidone or pyridone analog compounds or salt forms for nanoparticle-based formulations.

Co-Precipitates

Co-precipitate pirfenidone or pyridone analog compound formulations may be prepared by formation of co-precipitates with pharmacologically inert, polymeric materials. It has been demonstrated that the formation of molecular solid dispersions or co-precipitates to create an AUC shape-enhancing formulations with various water-soluble polymers can significantly slow their in vitro dissolution rates and/or in vivo absorption. In preparing powdered products, grinding is generally used for reducing particle size, since the dissolution rate is strongly affected by particle size. Moreover, a strong force (such as grinding) may increase the surface energy and cause distortion of the crystal lattice as well as reducing particle size. Co-grinding drug with hydroxypropylmethylcellulose, b-cyclodextrin, chitin and chitosan, crystalline cellulose, and gelatin, may enhance the dissolution properties such that AUC shape-enhancement is obtained for otherwise readily bioavailable pirfenidone or pyridone analog compounds. By non-limiting example, this approach may also be used to sequester and improve the water solubility of solid, AUC shape-enhancing formulations, such as low-solubility pirfenidone or pyridone analog compounds or salt forms for nanoparticle-based formulations.

Dispersion-Enhancing Peptides

Compositions may include one or more di- or tripeptides containing two or more leucine residues. By further non-limiting example, U.S. Pat. No. 6,835,372 disclosing dispersion-enhancing peptides, is hereby incorporated by reference in its entirety. This patent describes the discovery that di-leucyl-containing dipeptides (e.g., dileucine) and tripeptides are superior in their ability to increase the dispersibility of powdered composition.

In another embodiment, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F)— O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO(aliphatic group, substituted aliphatic, benzyl, substituted benzyl, aryl or substituted aryl group), —CONH$_2$, —CONH(aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(.dbd.NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or benzyl group can have one or more substituents. Modifying an amino acid substituent can increase, for example, the lyophilicity or hydrophobicity of natural amino acids which are hydrophilic.

A number of the suitable amino acids, amino acids analogs and salts thereof can be obtained commercially. Others can be synthesized by methods known in the art.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm3.

Methods of forming and delivering particles which include an amino acid are described in U.S. Pat. No. 6,586,008, entitled Use of Simple Amino Acids to Form Porous Particles During Spray Drying, the teachings of which are incorporated herein by reference in their entirety.

Proteins/Amino Acids

Protein excipients may include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrates

By non-limiting example, carbohydrate excipients may include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol, isomalt, trehalose and the like.

Polymers

By non-limiting example, compositions may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), polyethylene glycols, and pectin may also be used.

Highly dispersible particles administered comprise a bioactive agent and a biocompatible, and preferably biodegradable polymer, copolymer, or blend. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(DL-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., Macromolecules, 28: 4736-4739 (1995); and Hrkach et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphael M, Ottenbrite et al., Eds., American Chemical Society, Chapter 8, pp. 93-101, 1996.

In a preferred embodiment of the invention, highly dispersible particles including a bioactive agent and a phospholipid are administered. Examples of suitable phospholipids include, among others, pho sphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidyicholine (DSPC), dipalmitoyl phosphatidyl glycerol (DPPG) or any combination thereof. Other phospholipids are known to those skilled in the art. In a preferred embodiment, the phospholipids are endogenous to the lung.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, about or above the physiological body temperature of a patient. Preferred phase transition temperatures range from 30 degrees C. to 50 degrees C. (e.g., within +/−10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures.

Taste Masking, Flavor, Other

As also described above, pirfenidone or pyridone analog compound formulations disclosed herein and related compositions, may further include one or more taste-masking agents such as flavoring agents, inorganic salts (e.g., sodium chloride), sweeteners, antioxidants, antistatic agents, surfactants (e.g., polysorbates such as "TWEEN 20" and "TWEEN 80"), sorbitan esters, saccharin (e.g., sodium saccharin or other saccharin forms, which as noted elsewhere herein may be present in certain embodiments at specific concentrations or at specific molar ratios relative to a pyridone analog compound such as pirfenidone), bicarbonate, cyclodextrins, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998).

By way of non-limiting example, taste-masking agents in pirfenidone or pyridone analog compound formulations, may include the use of flavorings, sweeteners, and other various coating strategies, for instance, sugars such as sucrose, dextrose, and lactose, carboxylic acids, menthol, amino acids or amino acid derivatives such as arginine, lysine, and monosodium glutamate, and/or synthetic flavor oils and flavoring aromatics and/or natural oils, extracts from plants, leaves, flowers, fruits, etc. and combinations thereof. These may include cinnamon oils, oil of wintergreen, peppermint oils, clover oil, bay oil, anise oil, *eucalyptus*, vanilla, citrus oil such as lemon oil, orange oil, grape and grapefruit oil, fruit essences including apple, peach, pear, strawberry, raspberry, cherry, plum, pineapple, apricot, etc. Additional sweeteners include sucrose, dextrose, aspartame (Nutrasweet®), acesulfame-K, sucralose and saccharin (e.g., sodium saccharin or other saccharin forms, which as noted elsewhere herein may be present in certain embodiments at specific concentrations or at specific molar ratios relative to a pyridone analog compound such as pirfenidone), organic acids (by non-limiting example citric acid and aspartic acid). Such flavors may be present at from about 0.05 to about 4 percent by weight, and may be present at lower or higher amounts as a factor of one or more of potency of the effect on flavor, solubility of the flavorant, effects of the flavorant on solubility or other physicochemical or pharmacokinetic properties of other formulation components, or other factors.

Another approach to improve or mask the unpleasant taste of an inhaled drug may be to decrease the drug's solubility, e.g., drugs must dissolve to interact with taste receptors. Hence, to deliver solid forms of the drug may avoid the taste response and result in the desired improved taste affect. Non-limiting methods to decrease solubility of a pirfenidone or pyridone analog compound solubility are described herein, for example, through the use in formulation of particular salt forms of pyridone analog compound, such as complexation with xinafoic acid, oleic acid, stearic acid and/or pamoic acid. Additional co-precipitating agents include dihydropyridines and a polymer such as polyvinyl pyrrolidone.

Moreover, taste-masking may be accomplished by creation of lipopilic vesicles. Additional coating or capping agents include dextrates (by non-limiting example cyclodextrins may include, 2-hydroxypropyl-beta-cyclodextrin, 2-hydroxypropyl-gamma-cyclodextrin, randomly methylated beta-cyclodextrin, dimethyl-alpha-cyclodextrin, dimethyl-beta-cyclodextrin, maltosyl-alpha-cyclodextrin, glucosyl-1-alpha-cyclodextrin, glucosyl-2-alpha-cyclodextrin, alpha-cyclodextrin, beta-cyclodextrin, gamma-cyclodextrin, and sulfobutylether-beta-cyclodextrin), modified celluloses such as ethyl cellulose, methyl cellulose, hydroxypropyl cellulose, hydroxyl propyl methyl cellulose, polyalkylene glycols, polyalkylene oxides, sugars and sugar alcohols, waxes, shellacs, acrylics and mixtures thereof. By non-limiting example, other methods to deliver non-dissolved forms of a pirfenidone or pyridone analog compound according to certain embodiments or, in other embodiments, non-dissolved forms of a pirfenidone or pyridone analog compound, are to administer the drug alone or in a simple, non-solubility affecting formulation, such as a crystalline micronized, dry powder, spray-dried, and/or nanosuspension formulation.

An alternative according to certain other preferred embodiments is to include taste-modifying agents in the pirfenidone or pyridone analog compound formulation. These embodiments contemplate including in the formulation a taste-masking substance that is mixed with, coated onto or otherwise combined with the active medicament pirfenidone or pyridone analog compound or salt thereof. Inclusion of one or more such agents in these formulations may also serve to improve the taste of additional pharmacologically active compounds that are included in the formulations in addition to the pirfenidone or pyridone analog compound, e.g., a mucolytic agent. Non-limiting examples of such taste-modifying substances include acid phospholipids, lysophospholipid, tocopherol polyethyleneglycol succinate, and embonic acid (pamoate). Many of these agents can be used alone or in combination with pirfenidone or pyridone analog compound (or a salt thereof) or, in separate embodiments, pirfenidone or pyridone analog compound for aerosol administration.

Mucolytic Agents

Methods to produce formulations that combine agents to reduce sputum viscosity during aerosol treatment with a pirfenidone or pyridone analog compound include the following. These agents can be prepared in fixed combination or be administered in succession with aerosol pirfenidone or pyridone analog compound therapy.

The most commonly prescribed agent is N-acetylcysteine (NAC), which depolymerizes mucus in vitro by breaking disulphide bridges between macromolecules. It is assumed that such reduction of sputum tenacity facilitates its removal from the respiratory tract. In addition, NAC may act as an oxygen radical scavenger. NAC can be taken either orally or by inhalation. Differences between these two methods of administration have not been formally studied. After oral administration, NAC is reduced to cysteine, a precursor of the antioxidant glutathione, in the liver and intestine. The antioxidant properties could be useful in preventing decline of lung function in cystic fibrosis (CF), chronic obstructive pulmonary disease (COPD) or pulmonary fibrotic diseases (e.g., idiopathic pulmonary fibrosis). Nebulized NAC is commonly prescribed to patients with CF, in particular in continental Europe, in order to improve expectoration of sputum by reducing its tenacity. The ultimate goal of this is to slow down the decline of lung function in CF.

L-lysine-N-acetylcysteinate (ACC) or Nacystelyn (NAL) is a novel mucoactive agent possessing mucolytic, antioxidant, and anti-inflammatory properties. Chemically, it is a salt of ACC. This drug appears to present an activity superior to its parent molecule ACC because of a synergistic mucolytic activity of L-lysine and ACC. Furthermore, its almost neutral pH (6.2) allows its administration in the lungs with a very low incidence of bronchospasm, which is not the case for the acidic ACC (pH 2.2). NAL is difficult to formulate in an inhaled form because the required lung dose is very high (approximately 2 mg) and the micronized drug is sticky and cohesive and it is thus problematic to produce a redispersible formulation. NAL was first developed as a chlorofluorocarbon (CFC) containing metered-dose inhaler (MDI) because this form was the easiest and the fastest to develop to begin the preclinical and the first clinical studies. NAL MDI delivered 2 mg per puff, from which approximately 10% was able to reach the lungs in healthy volunteers. One major inconvenience of this formulation was patient compliance because as many as 12 puffs were necessary to obtain the required dose. Furthermore, the progressive removal of CFC gases from medicinal products combined with the problems of coordination met in a large proportion of the patient population (12) have led to the development of a new galenical form of NAL. A dry powder inhaler (DPI) formulation was chosen to resolve the problems of compliance with MDIs and to combine it with an optimal, reproducible, and comfortable way to administer the drug to the widest possible patient population, including young children.

The DPI formulation of NAL involved the use of a nonconventional lactose (usually reserved for direct compression of tablets), namely, a roller-dried (RD) anhydrous p3-lactose. When tested in vitro with a monodose DPI device, this powder formulation produces a fine particle fraction (FPF) of at least 30% of the nominal dose, namely three times higher than that with MDIs. This approach may be used in combination with a pirfenidone or pyridone analog compound for either co-administration or fixed combination therapy.

In addition to mucolytic activity, excessive neutrophil elastase activity within airways of cystic fibrosis (CF) patients results in progressive lung damage. Disruption of disulfide bonds on elastase by reducing agents may modify its enzymatic activity. Three naturally occurring dithiol reducing systems were examined for their effects on elastase activity: 1) *Escherichia coli* thioredoxin (Trx) system, 2) recombinant human thioredoxin (rhTrx) system, and 3) dihydrolipoic acid (DHLA). The Trx systems consisted of Trx, Trx reductase, and NADPH. As shown by spectrophotometric assay of elastase activity, the two Trx systems and DHLA inhibited purified human neutrophil elastase as well as the elastolytic activity present in the soluble phase (sol) of CF sputum. Removal of any of the three Trx system constituents prevented inhibition. Compared with the monothiols N-acetylcysteine and reduced glutathione, the dithiols displayed greater elastase inhibition. To streamline Trx as an investigational tool, a stable reduced form of rhTrx was synthesized and used as a single component. Reduced rhTrx inhibited purified elastase and CF sputum sol elastase without NADPH or Trx reductase. Because Trx and DHLA have mucolytic effects, we investigated changes in elastase activity after mucolytic treatment. Unprocessed CF sputum was directly treated with reduced rhTrx, the Trx system, DHLA, or DNase. The Trx system and DHLA did not increase elastase activity, whereas reduced rhTrx treatment increased sol elastase activity by 60%. By contrast, the elastase activity after DNase treatment increased by 190%. The ability of Trx and DHLA to limit elastase activity combined with their mucolytic effects makes these compounds potential therapies for CF.

In addition, bundles of F-actin and DNA present in the sputum of cystic fibrosis (CF) patients but absent from normal airway fluid contribute to the altered viscoelastic properties of sputum that inhibit clearance of infected airway fluid and exacerbate the pathology of CF. One approach to alter these adverse properties is to remove these filamentous aggregates using DNase to enzymatically depolymerize DNA to constituent monomers and gelsolin to sever F-actin to small fragments. The high densities of negative surface charge on DNA and F-actin suggest that the bundles of these filaments, which alone exhibit a strong electrostatic repulsion, may be stabilized by multivalent cations such as histones, antimicrobial peptides, and other positively charged molecules prevalent in airway fluid. Furthermore, as a matter-a-fact, it has been observed that bundles of DNA or F-actin formed after addition of histone H1 or lysozyme are efficiently dissolved by soluble multivalent anions such as polymeric aspartate or glutamate. Addition of poly-aspartate or poly-glutamate also disperses DNA and actin-containing bundles in CF sputum and lowers the elastic moduli of these samples to levels comparable to those obtained after treatment with DNase I or gelsolin. Addition of poly-aspartic acid also increased DNase activity when added to samples containing DNA bundles formed with histone H1. When added to CF sputum, poly-aspartic acid significantly reduced the growth of bacteria, suggesting activation of endogenous antibacterial factors. These findings suggest that soluble multivalent anions have potential alone or in combination with other mucolytic agents to selectively dissociate the large bundles of charged biopolymers that form in CF sputum.

Hence, NAC, unfractionated heparin, reduced glutathione, dithiols, Trx, DHLA, other monothiols, DNAse, dornase alfa, hypertonic formulations (e.g., osmolalities greater than about 350 mOsmol/kg), multivalent anions such as polymeric aspartate or glutamate, glycosidases and other examples listed above can be combined with pirfenidone or pyridone analog compounds and other mucolytic agents for aerosol administration to improve antifibrotic and/or antiinflammatory activity through better distribution from reduced sputum viscosity, and improved clinical outcome through improved pulmonary function (from improved sputum mobility and mucociliary clearance) and decreased lung tissue damage from the immune inflammatory response.

Characterization of Inhalation Devices

The efficiency of a particular inhalation device can be measured by many different ways, including an analysis of pharmacokinetic properties, measurement of lung deposition percentage, measurement of respirable delivery dose (RDD), a determination of output rates, geometric standard deviation values (GSD), and mass median aerodynamic diameter values (MMAD) among others.

Methods and systems for examining a particular inhalation device are known. One such system consists of a computer means and a hollow cylinder in a pump means with a connecting piece to which an inhalation device is to be connected. In the pump means there is a piston rod, which extends out of the hollow cylinder. A linear drive unit can be activated in such a manner that one or more breathing pattern will be simulated on the connecting piece of the pump means. In order to be able to carry out the evaluation of the inhalation device, the computer is connected in an advantageous configuration with a data transmission means. With the aid of the data transmission means, the computer can be connected with another computer with specific data banks, in order to exchange the data of breathing patterns. In this manner, a breathing pattern library which is as representative as possible can be very rapidly formed. U.S. Pat. No. 6,106,479 discloses this method for examining an inhalation device in more detail, and is hereby incorporated by reference in its entirety.

Pharmacokinetic Profile

Pharmacokinetics is concerned with the uptake, distribution, metabolism and excretion of a drug substance. A pharmacokinetic profile comprises one or more biological measurements designed to measure the absorption, distribution, metabolism and excretion of a drug substance. One way of visualizing a pharmacokinetic profile is by means of a blood plasma concentration curve, which is a graph depicting mean active ingredient blood plasma concentration on the Y-axis and time (usually in hours) on the X-axis. Some pharmacokinetic parameters that may be visualized by means of a blood plasma concentration curve include:

Cmax: The maximum plasma concentration in a patient.
AUC: area under the curve
TOE: time of exposure
T½: period of time it takes for the amount in a patient of drug to decrease by half
$T_{max}$: The time to reach maximum plasma concentration in a patient Pharmacokinetics (PK) is concerned with the time course of a therapeutic agent, such as pirfenidone, or a pyridone analog compound concentration in the body. Pharmacodynamics (PD) is concerned with the relationship between pharmacokinetics and efficacy in vivo. PK/PD parameters correlate the therapeutic agent, such as exposure with efficacious activity. Accordingly, to predict the therapeutic efficacy of a therapeutic agent, such as with diverse mechanisms of action different PK/PD parameters may be used.

Any standard pharmacokinetic protocol can be used to determine blood plasma concentration profile in humans following administration of a formulation comprising pirfenidone or a pyridone analog compound described herein, and thereby establish whether that formulation meets the pharmacokinetic criteria set out herein. For example, but in no way limiting, a type of a randomized single-dose crossover study can be utilized using a group of healthy adult human subjects. The number of subjects can be sufficient to provide adequate control of variation in a statistical analysis, and is typically about 8 or greater, although in certain embodiments a smaller group can be used. In one embodiment, a subject receives administration, at time zero, a single dose of a test inhalation mixture comprising pirfenidone or a pyridone analog compound. Blood samples are collected from each subject prior to administration and at several intervals after administration. Plasma can be separated from the blood samples by centrifugation and the separated plasma is analyzed, for example, by a validated high performance liquid chromatography/tandem weight spectrometry (LC/APCI-MS/MS) procedure such as, for example, those described in Ramu et al., Journal of Chromatography B, 751:49-59 (2001). In other embodiments, data from a single subject may be collected and may be used to construct a pK profile and may be indicative of an enhanced pharmacokinetic profile. In still other embodiments, appropriate in vitro models may be used to construct a pK profile and may be demonstrate or indicate an enhanced pharmacokinetic profile.

In some embodiments, a human pK profile can be may be obtained by the use of allometric scaling. In one embodiment, rat aerosol lung data and plasma delivery is scaled to provide an indication of possible humans data. In one embodiment, allometric scaling uses parameters established in the US FDA Guidance for Industry—Estimating the Maximum Safe Starting Dose in Initial Clinical Trials for Therapeutics in Adult Healthy Volunteers.

Any aqueous inhalable mixture giving the desired pharmacokinetic profile may be suitable for administration according to the present methods.

As used herein, the "peak period" of a pharmaceutical's in vivo concentration is defined as that time of the pharmaceutical dosing interval when the pharmaceutical concentration is not less than 50% of its maximum plasma or site-of-disease concentration. In some embodiments, "peak period" is used to describe an interval of pirfenidone or a pyridone analog compound dosing.

In some embodiments, when considering treatment of lung diseases, a method or system described herein provides at least a two-fold enhancement in pharmacokinetic profile for treatment of the lung disease. In some embodiments, the methods and systems described herein provide at least a two-fold enhancement in the lung tissue pharmacokinetic profile of pirfenidone or pyridone analog compound as compared to oral administration.

In some embodiments, a delayed appearance of 5-carboxy-pirfenidone (the primary pirfenidone liver metabolite) has been observed from the methods and systems described herein. In some embodiments, rapid elimination of pirfenidone from the lung tissue has been observed. Comparing the initial rapid elimination of pirfenidone from the lung tissue and parallel appearance of pirfenidone in the plasma suggest that direct pulmonary administration may be a good route for systemic administration of pirfenidone. The delayed appearance of 5-carboxy-pirfenidone metabolite supports this hypothesis in that this metabolite serves as a marker for re-circulation of pirfenidone to the lung and other tissues following direct aerosol administration to the lung. In some embodiments, re-circulated pirfenidone is likely important to support long-term, elevated pirfenidone levels in the lung and other tissues of potential efficacy.

In some embodiments, the amount of pirfenidone or pyridone analog compound that is administered to a human by inhalation may be calculated by measuring the amount of pirfenidone or pyridone analog compound and associated metabolites that are found in the urine. In some embodiments, about 80% of administered pirfenidone is excreted in the urine (with 95% being the primary metabolite, 5-carboxy-pirfenidone). In some embodiments, the calculation based on compound and metabolites in urine may be done through a 48 urine collection (following a single administration), whereby the total amount of pirfenidone or pyridone analog compound delivered to the human is the sum of measured pirfenidone and its metabolites. By non-limiting example, knowing that 80% of pirfenidone is excreted, a 50 mg sum urinary measurement of pirfenidone and its metabolites would translate to a delivered dose of about 63 mg (50 mg divided by 80%). If by non-limiting example the inhaled aerosol fine-particle fraction (FPF) is 75%, one may assume that about 75% of the drug deposited in the lung (and about 25% was swallowed, and subsequently absorbed from the gut with 80% excreted in the urine). Integrating these two calculations, of a 63 mg delivered dose (as measured by urinary excretion), about 47 mg would be the amount of inhaled aerosol pirfenidone delivered to the lung (the actual RDD; calculated as the product of 63 mg and a 75% FPF). This RDD can then be used in a variety of calculations, including lung tissue concentration.

In some embodiments, method or systems described herein provide pharmacokinetic profiles of pirfenidone or pyridone analog compounds as described herein. In some embodiments, method or systems described herein provide pharmacokinetic profiles of pirfenidone or pyridone analog compounds as in Examples 6 and 7.

In some embodiments, efficacy of pirfenidone or pyridone analog compounds in the treatment of pulmonary fibrosis is achieved through repeated administration to a human by inhalation. As shown in Examples 6 and 7, administration of pirfenidone or pyridone analog compounds to a human by inhalation provides higher Cmax levels as compared to oral delivery. In some embodiments, solutions of pirfenidone or pyridone analog compounds that are administered by inhalation provide higher Cmax levels as compared to oral delivery. In some embodiments, the peak period is used to define the optimal dosing schedule of the pirfenidone or pyridone analog compound. In some embodiments, solutions of pirfenidone or pyridone analog compounds are administered more than once a week.

Small intratracheal aerosol doses deliver a rapidly-eliminated high lung Cmax and low AUC. Human, animal and in vitro studies all indicate that pirfenidone efficacy is dose responsive (i.e. larger doses correlate with improved efficacy) and suggest Cmax is a key driver in pirfenidone efficacy. While lung Cmax appears important for efficacy, more regular pirfenidone exposure also appears important to enhance this effect. In some embodiments, in the context of treating lung diseases in a human, more frequent direct-lung administration of pirfenidone or pyridone analog compound may provide benefit through both repeat high Cmax dosing and providing more regular exposure of the active therapeutic agent.

In some embodiments, described herein is a method for the treatment of lung disease in a mammal comprising administering directly to the lungs of the mammal in need thereof pirfenidone or a pyridone analog compound on a continuous dosing schedule, wherein the observed lung tissue Cmax of a dose of pirfenidone or a pyridone analog compound is greater than 0.1 mcg/gram lung tissue. In some embodiments, the observed lung tissue Cmax from a dose of pirfenidone or a pyridone analog compound is greater than 0.5 mcg/gram lung tissue. In some embodiments, the observed lung tissue Cmax from a dose of pirfenidone or a pyridone analog compound is greater than 1.0 mcg/gram lung tissue. In some embodiments, the observed lung tissue Cmax from a dose of pirfenidone or a pyridone analog compound is greater than 5 mcg/gram lung tissue. In some embodiments, the observed lung tissue Cmax from a dose of pirfenidone or a pyridone analog compound is greater than 10 mcg/gram lung tissue. In some embodiments, the observed lung tissue Cmax from a dose of pirfenidone or a pyridone analog compound is greater than 15 mcg/gram lung tissue. In some embodiments, the observed lung tissue Cmax from a dose of pirfenidone or a pyridone analog compound is greater than 20 mcg/gram lung tissue. In some embodiments, the observed lung tissue Cmax from a dose of pirfenidone or a pyridone analog compound is greater than 25 mcg/gram lung tissue. In some embodiments, the observed lung tissue Cmax from a dose of pirfenidone or a pyridone analog compound is greater than 30 mcg/gram lung tissue. In some embodiments, the observed lung tissue Cmax from a dose of pirfenidone or a pyridone analog compound is greater than 35 mcg/gram lung tissue. In some embodiments, the observed lung tissue Cmax from a dose of pirfenidone or a pyridone analog compound is greater than 40 mcg/gram lung tissue. In some embodiments, the observed lung tissue Cmax from a dose of pirfenidone or a pyridone analog compound is greater than 45 mcg/gram lung tissue. In some embodiments, the observed lung tissue Cmax from a dose of pirfenidone or a pyridone analog compound is greater than 50 mcg/gram lung tissue. In some embodiments, the dose comprises an aqueous solution of pirfenidone or a pyridone analog compound. In some embodiments, the dose is administered with a liquid nebulizer. In some embodiments, the pirfenidone or a pyridone analog compound is administered more than once a week. In some embodiments, the pirfenidone or a pyridone analog compound is administered on a continuous daily dosing schedule. In some embodiments, the single doses of pirfenidone or a pyridone analog compound is administered more than once a week, more than twice a week, more than three times a week, more than four times a week, more than five times a week more than six times a week or daily. In some embodiments, the pirfenidone or a pyridone analog compound is administered on a continuous daily dosing schedule. In some embodiments, the pirfenidone or a pyridone analog compound is administered once a day, twice a day, or three times a day.

In some embodiments, described herein is a method for the treatment of lung disease in a mammal comprising administering directly to the lungs of the mammal in need thereof pirfenidone or a pyridone analog compound on a continuous dosing schedule. In some embodiments, a) the lung tissue Cmax of pirfenidone or pyridone analog compound from a dose that is directly administered to the lungs of the mammal is at least equivalent to or greater than a lung tissue Cmax of up to 801 mg of an orally administered dosage of pirfenidone or pyridone analog compound; and/or b) the blood $AUC_{0-24}$ of pirfenidone or pyridone analog compound from a dose that is directly administered to the lungs of the mammal is less than or equivalent to the blood $AUC_{0-24}$ of up to 801 mg of an orally administered dosage of pirfenidone or pyridone analog compound. In some embodiments, a) the lung tissue Cmax of pirfenidone or pyridone analog compound from a dose that is directly administered to the lungs of the mammal is at least equivalent to or greater than a lung tissue Cmax of up to 801 mg of an orally administered dosage of pirfenidone or pyridone analog compound; and b) the blood $AUC_{0-24}$ of pirfenidone or pyridone analog compound from a dose that is directly administered to the lungs of the mammal is less than or equivalent to the blood $AUC_{0-24}$ of up to 801 mg of an orally administered dosage of pirfenidone or pyridone analog compound. In some embodiments, a) the lung tissue Cmax of pirfenidone or pyridone analog compound from a dose that is directly administered to the lungs of the mammal is at least equivalent to or greater than a lung tissue Cmax of up to 801 mg of an orally administered dosage of pirfenidone or pyridone analog compound; or b) the blood $AUC_{0-24}$ of pirfenidone or pyridone analog compound from a dose that is directly administered to the lungs of the mammal is less than or equivalent to the blood $AUC_{0-24}$ of up to 801 mg of an orally administered dosage of pirfenidone or pyridone analog compound. In some embodiments, the dose comprises an aqueous solution of pirfenidone or a pyridone analog compound. In some embodiments, the dose is administered with a liquid nebulizer. In some embodiments, the pirfenidone or a pyridone analog compound is administered more than once a week. In some embodiments, the single doses of pirfenidone or a pyridone analog compound is administered more than once a week, more than twice a week, more than three times a week, more than four times a week, more than five times a week more than six times a week or daily. In some embodiments, the pirfenidone or a pyridone analog compound is administered on a continuous daily dosing schedule. In some embodiments, the pirfenidone or a pyridone analog compound is administered once a day, twice a day, or three times a day.

Methods of Dosing and Treatment Regimens

In one aspect, pirfenidone or a pyridone analog compound is administered daily to humans in need of therapy with pirfenidone or a pyridone analog compound. In some embodiments, pirfenidone or a pyridone analog compound is administered by inhalation to the human. In some embodiments, pirfenidone or a pyridone analog compound is administered once-a-day. In some embodiments, pirfenidone or a pyridone analog compound is administered twice-a-day. In some embodiments, pirfenidone or a pyridone analog compound is administered three times-a-day. In some embodiments, pirfenidone or a pyridone analog compound is administered every other day. In some embodiments, pirfenidone or a pyridone analog compound is administered twice a week.

In general, doses of pirfenidone or a pyridone analog compound employed for treatment of the diseases or conditions described herein in humans are typically in the range of from about 0.001 mg to about 10 mg pirfenidone/kg of body weigh per dose. In one embodiment, the desired dose is conveniently presented in a single dose or in divided doses administered simultaneously (or over a short period of time) or at appropriate intervals, for example as two, three, four or more sub-doses per day. In some embodiments, pirfenidone or a pyridone analog compound is conveniently presented in divided doses that are administered simultaneously (or over a short period of time) once a day. In some embodiments, pirfenidone or a pyridone analog compound is conveniently presented in divided doses that are administered in equal portions twice-a-day.

In some embodiments, pirfenidone or a pyridone analog compound is administered by inhalation daily to the human. In some embodiments, pirfenidone or a pyridone analog compound is administered orally to the human at a dose from about 0.001 mg to about 10 mg pirfenidone/kg of body weigh per dose. In some embodiments, pirfenidone or a pyridone analog compound is administered by inhalation to the human on a continuous daily dosing schedule.

The term "continuous dosing schedule" refers to the administration of a particular therapeutic agent at regular intervals. In some embodiments, continuous dosing schedule refers to the administration of a particular therapeutic agent at regular intervals without any drug holidays from the particular therapeutic agent. In some other embodiments, continuous dosing schedule refers to the administration of a particular therapeutic agent in cycles. In some other embodiments, continuous dosing schedule refers to the administration of a particular therapeutic agent in cycles of drug administration followed by a drug holiday (for example, a wash out period or other such period of time when the drug is not administered) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. In some embodiments, daily administration is once a day. In some embodiments, daily administration is twice a day. In some embodiments, daily administration is three times a day. In some embodiments, daily administration is more than three times a day.

The term "continuous daily dosing schedule" refers to the administration of a particular therapeutic agent everyday at roughly the same time each day. In some embodiments, daily administration is once a day. In some embodiments, daily administration is twice a day. In some embodiments, daily administration is three times a day. In some embodiments, daily administration is more than three times a day.

In some embodiments, the amount of pirfenidone or a pyridone analog compound is administered once-a-day. In some other embodiments, the amount of pirfenidone or a pyridone analog compound is administered twice-a-day. In some other embodiments, the amount of pirfenidone or a pyridone analog compound is administered three times a day.

In certain embodiments wherein improvement in the status of the disease or condition in the human is not observed, the daily dose of pirfenidone or a pyridone analog compound is increased. In some embodiments, a once-a-day dosing schedule is changed to a twice-a-day dosing schedule. In some embodiments, a three times a day dosing schedule is employed to increase the amount of pirfenidone or a pyridone analog compound that is administered. In some embodiments, the frequency of administration by inhalation is increased in order to provide repeat high Cmax levels on a more regular basis. In some embodiments, the frequency of administration by inhalation is increased in order to provide maintained or more regular exposure to pirfenidone. In some embodiments, the frequency of administration by inhalation is increased in order to provide repeat high Cmax levels on a more regular basis and provide maintained or more regular exposure to pirfenidone.

In some embodiments, the amount of repeat high Cmax dosing providing more regular exposure of the active therapeutic agent that is given to the human varies depends upon factors such as, but not limited to, condition and severity of the disease or condition, and the identity (e.g., weight) of the human, and the particular additional therapeutic agents that are administered (if applicable).

EXAMPLES

Example 1: Pirfenidone Formulations

Non-limiting examples of compositions of pirfenidone include those described in Table 1-1 through Table 1-11.

TABLE 1-1

| | | Ingredient and Amount | | | | | |
|---|---|---|---|---|---|---|---|
| Composition no. | Pirfenidone | Phosphate Buffer (sodium salt), pH 6.2 (mM) | Phosphate Buffer (sodium salt), pH 7.3 (mM) | Citrate Buffer (acid/sodium salt), pH 5.8 (mM) | Sodium Chloride (µmols) | Magnesium Chloride (µmols) | Water |
| 1 | 1 mg to 500 mg (5 µmols to 3 mmols) | — | — | 0.01 mM to 500 mM | — | — | q.s. to 5 mL |
| 2 | 1 mg to 500 mg (5 µmols to 3 mmols) | 0.01 mM to 500 mM | — | — | — | — | q.s. to 5 mL |
| 3 | 1 mg to 500 mg (5 µmols to 3 mmols) | — | 0.01 mM to 500 mM | — | — | — | q.s. to 5 mL |
| 4 | 54 µmols | 0.01 to 500 | — | — | 150 | — | q.s. to 5 mL |
| 5 | 54 µmols | — | 0.01 to 500 | — | 150 | — | q.s. to 5 mL |
| 6 | 54 µmols | — | — | 0.01 to 500 | 150 | — | q.s. to 5 mL |
| 7 | 54 µmols | 0.01 to 500 | — | — | — | 150 | q.s. to 5 mL |
| 8 | 54 µmols | — | 0.01 to 500 | — | — | 150 | q.s. to 5 mL |
| 9 | 54 µmols | — | — | 0.01 to 500 | — | 150 | q.s. to 5 mL |
| 10 | 54 µmols | 0.01 to 500 | — | — | 13.5 | — | q.s. to 5 mL |
| 11 | 54 µmols | — | 0.01 to 500 | — | 13.5 | — | q.s. to 5 mL |
| 12 | 54 µmols | — | — | 0.01 to 500 | 13.5 | — | q.s. to 5 mL |
| 13 | 54 µmols | 0.01 to 500 | — | — | — | 13.5 | q.s. to 5 mL |
| 14 | 54 µmols | — | 0.01 to 500 | — | — | 13.5 | q.s. to 5 mL |
| 15 | 54 µmols | — | — | 0.01 to 500 | — | 13.5 | q.s. to 5 mL |

TABLE 1-1-continued

| Composition no. | Pirfenidone | Phosphate Buffer (sodium salt), pH 6.2 (mM) | Phosphate Buffer (sodium salt), pH 7.3 (mM) | Citrate Buffer (acid/sodium salt), pH 5.8 (mM) | Sodium Chloride (μmols) | Magnesium Chloride (μmols) | Water |
|---|---|---|---|---|---|---|---|
| 16 | 54 μmols | 0.01 to 500 | — | — | 54 | — | q.s. to 5 mL |
| 17 | 54 μmols | — | 0.01 to 500 | — | 54 | — | q.s. to 5 mL |
| 18 | 54 μmols | — | — | 0.01 to 500 | 54 | — | q.s. to 5 mL |
| 19 | 54 μmols | 0.01 to 500 | — | — | — | 54 μmols | q.s. to 5 mL |
| 20 | 54 μmols | — | 0.01 to 500 | — | — | 54 μmols | q.s. to 5 mL |
| 21 | 54 μmols | — | — | 0.01 to 500 | — | 54 μmols | q.s. to 5 mL |
| 22 | 54 μmols | 0.01 to 500 | — | — | 27 | — | q.s. to 5 mL |
| 23 | 54 μmols | — | 0.01 to 500 | — | 27 | — | q.s. to 5 mL |
| 24 | 54 μmols | — | — | 0.01 to 500 | 27 | — | q.s. to 5 mL |
| 25 | 54 μmols | 0.01 to 500 | — | — | — | 27 | q.s. to 5 mL |
| 26 | 54 μmols | — | 0.01 to 500 | — | — | 27 | q.s. to 5 mL |
| 27 | 54 μmols | — | — | 0.01 to 500 | — | 27 | q.s. to 5 mL |

TABLE 1-2

| Composition no. | Pirfenidone | Citrate Buffer (acid/sodium salt), pH 2.0 to 9.0 (mM) | Phosphate Buffer (monobasic/dibasic sodium salts), pH 2.0 to 9.0 (mM) | Sodium Chloride (μmols) | Magnesium Chloride | Saccharin (sodium salt) (mM) | Water |
|---|---|---|---|---|---|---|---|
| 28 | 5 μmols to 3 mmols | 0.01 to 500 | — | — | 1 μmol to 15 mmols | 0.01 to 10.0 | q.s. to 5 mL |
| 29 | 5 μmols to 3 mmols | — | 0.01 to 500 | — | 1 μmol to 15 mmols | 0.01 to 10.0 | q.s. to 5 mL |
| 30 | 5 μmols to 3 mmols | 0.01 to 500 | — | 1 μmol to 15 mmols | — | 0.01 to 10.0 | q.s. to 5 mL |
| 31 | 5 μmols to 3 mmols | — | 0.01 to 500 | 1 μmol to 15 mmols | — | 0.01 to 10.0 | q.s. to 5 mL |

TABLE 1-3

| Composition no. | Pirfenidone | Citrate Buffer (acid/sodium salt), pH 5.8 (mM) | Phosphate Buffer (monobasic/dibasic sodium salts), pH 6.2 (mM) | Phosphate Buffer (monobasic/dibasic sodium salts), pH 7.3 (mM) | Saccharin (sodium salt) (mM) | Water |
|---|---|---|---|---|---|---|
| 32 | 1 mg to 500 mg (5 μmols to 3 mmols) | 0.01 to 500 | — | — | 0.01 to 10.0 | q.s. to 5 mL |
| 33 | 1 mg to 500 mg (5 μmols to 3 mmols) | — | 0.01 to 500 | — | 0.01 to 10.0 | q.s. to 5 mL |
| 34 | 1 mg to 500 mg (5 μmols to 3 mmols) | — | — | 0.01 to 500 | 0.01 to 10.0 | q.s. to 5 mL |

In some embodiments, pirfenidone exhibited aqueous solubility to ~17 mg/mL across a pH range of about 4.0 to about 8.0. However, at this (and lower) concentration it was determined that salt addition was required to improve acute tolerability upon inhalation of a nebulized solution (otherwise a hypotonic solution). To address tonicity, NaCl or $MgCl_2$ were added. In some embodiments, addition of NaCl improved acute tolerability, but destabilized the formulation and resulted in precipitation upon ambient storage. In some embodiments, it was determined that addition of $MgCl_2$ maintained a stable, soluble solution at this concentration with an osmolality in a tolerable range. By non-limiting example, 81 mM $MgCl_2$ provides a 1:1 mole ratio of magnesium to pirfenidone where pirfenidone is at 15 mg/mL (or 81 mM). This effect was also observed at various pirfenidone concentrations with 1:1 and 1:2 mole ratios of magnesium to pirfenidone, but not at ratios less than or equal to 0.25:1 or greater than or equal to 1:0.33 magnesium to pirfenidone, respectively. This effect was observed in 5 mM to 50 mM citrate buffer at pH 4.0 and pH 5.8, and 5 mM to 50 mM phosphate buffer at pH 6.2, pH 7.3 and pH 7.8. Other observations included: 1) Formulations of both buffer systems exhibited a metallic, bitter flavor and throat irritation; 2) From 0.1 to 0.7 mM sodium saccharin was required to taste mask these formulations; 3) 0.6 mM sodium saccharin was the best concentration and improved the flavor of 2:1 mol ratio pirfenidone to magnesium in phosphate buffer more so than the 1:1 mol ratio; 4) The taste of 2:1 mol ratio pirfenidone to magnesium in citrate buffer without sodium saccharin was equivalent to the 1:1 mol ratio pirfenidone to magnesium in phosphate buffer with 0.6 mM sodium saccharin; 5) The taste of 2:1 mol ratio pirfenidone to magnesium in citrate buffer with 0.2 mM sodium saccharin was equivalent to the 2:1 mol ratio pirfenidone to magnesium in phosphate buffer with 0.6 mM sodium saccharin; 6) The taste of 1:1 mol ratio pirfenidone to magnesium in citrate buffer with 0.6 mM sodium saccharin was equivalent to 2:1 mol ratio pirfenidone to magnesium in phosphate buffer 0.6 mM sodium saccharin; and 7) 1:1 mol ratio pirfenidone to magnesium dissolved in up to 40% the time required to dissolve 2:1 mol ratio pirfenidone to magnesium in either buffer system at ~pH 6. This effect was not observed at ~pH 8.

TABLE 1-4

| Composition no. | Pirfenidone (mg) | Phosphate Buffer (monobasic/dibasic sodium salts), pH 5.5 to 8.5 (mM) | Ethanol (% v/v) | Propylene Glycol (% v/v) | Glycerol (% v/v) | Polysorbate 80 (% v/v) | Cetylpyridinium Bromide (or chloride) (%) | Osmolality (mOsmo/kg) | Water |
|---|---|---|---|---|---|---|---|---|---|
| 35 | 1 to 500 | 0.01 to 500 | 0.001 to 25 | — | — | — | — | 50 to 5000 | q.s. to 5 mL |
| 36* | 1 to 500 | 0.01 to 500 | — | 0.001 to 25 | — | — | — | 50 to 5000 | q.s. to 5 mL |
| 37 | 1 to 500 | 0.01 to 500 | — | — | 0.001 to 25 | — | — | 50 to 5000 | q.s. to 5 mL |
| 38 | 1 to 500 | 0.01 to 500 | — | — | — | 0.0001 to 1.0 | — | 50 to 5000 | q.s. to 5 mL |
| 39* | 1 to 500 | 0.01 to 500 | — | — | — | — | 0.0001 to 5.0 | 50 to 5000 | q.s. to 5 mL |
| 40 | 1 to 500 | 0.01 to 500 | 0.001 to 25 | 0.001 to 25 | — | — | — | 50 to 5000 | q.s. to 5 mL |
| 41 | 1 to 500 | 0.01 to 500 | 0.001 to 25 | — | 0.001 to 25 | — | — | 50 to 5000 | q.s. to 5 mL |
| 42 | 1 to 500 | 0.01 to 500 | 0.001 to 25 | — | — | 0.0001 to 1.0 | — | 50 to 5000 | q.s. to 5 mL |
| 43 | 1 to 500 | 0.01 to 500 | 0.001 to 25 | — | — | — | 0.0001 to 5.0 | 50 to 5000 | q.s. to 5 mL |
| 44 | 1 to 500 | 0.01 to 500 | 0.001 to 25 | 0.001 to 25 | 0.001 to 25 | — | — | 50 to 5000 | q.s. to 5 mL |
| 45 | 1 to 500 | 0.01 to 500 | 0.001 to 25 | 0.001 to 25 | — | 0.0001 to 1.0 | — | 50 to 5000 | q.s. to 5 mL |
| 46 | 1 to 500 | 0.01 to 500 | 0.001 to 25 | 0.001 to 25 | — | — | 0.0001 to 5.0 | 50 to 5000 | q.s. to 5 mL |
| 47 | 1 to 500 | 0.01 to 500 | 0.001 to 25 | 0.001 to 25 | 0.001 to 25 | 0.0001 to 1.0 | — | 50 to 5000 | q.s. to 5 mL |
| 48 | 1 to 500 | 0.01 to 500 | 0.001 to 25 | 0.001 to 25 | — | 0.0001 to 1.0 | — | 50 to 5000 | q.s. to 5 mL |
| 49 | 1 to 500 | 0.01 to 500 | 0.001 to 25 | 0.001 to 25 | 0.001 to 25 | — | 0.0001 to 5.0 | 50 to 5000 | q.s. to 5 mL |
| 50 | 1 to 500 | 0.01 to 500 | 0.001 to 25 | 0.001 to 25 | — | — | 0.0001 to 5.0 | 50 to 5000 | q.s. to 5 mL |

*Phosphate Buffer (monobasic/dibasic sodium salts), pH 6.2

TABLE 1-5

| Composition no. | Pirfenidone (mg) | Citrate Buffer (citric acid/sodium citrate), pH 3.5 to pH 6.5 | Ethanol (% v/v) | Propylene Glycol (% v/v) | Glycerol (% v/v) | Polysorbate 80 (% v/v) | Cetylpyridinium Bromide (or chloride) (%) | Osmolality (mOsmo/kg) | Water |
|---|---|---|---|---|---|---|---|---|---|
| 51 | 1 to 500 | 0.01 to 500 | 0.001 to 25 | — | — | — | — | 50 to 5000 | q.s. to 5 mL |
| 52 | 1 to 500 | 0.01 to 500 | — | 0.001 to 25 | — | — | — | 50 to 5000 | q.s. to 5 mL |
| 53 | 1 to 500 | 0.01 to 500 | — | — | 0.001 to 25 | — | — | 50 to 5000 | q.s. to 5 mL |
| 54 | 1 to 500 | 0.01 to 500 | — | — | — | 0.0001 to 1.0 | — | 50 to 5000 | q.s. to 5 mL |
| 55 | 1 to 500 | 0.01 to 500 | — | — | — | — | 0.0001 to 5.0 | 50 to 5000 | q.s. to 5 mL |
| 56 | 1 to 500 | 0.01 to 500 | 0.001 to 25 | 0.001 to 25 | — | — | — | 50 to 5000 | q.s. to 5 mL |
| 57 | 1 to 500 | 0.01 to 500 | 0.001 to 25 | — | 0.001 to 25 | — | — | 50 to 5000 | q.s. to 5 mL |
| 58 | 1 to 500 | 0.01 to 500 | 0.001 to 25 | — | — | 0.0001 to 1.0 | — | 50 to 5000 | q.s. to 5 mL |
| 59 | 1 to 500 | 0.01 to 500 | 0.001 to 25 | — | — | — | 0.0001 to 5.0 | 50 to 5000 | q.s. to 5 mL |
| 60 | 1 to 500 | 0.01 to 500 | 0.001 to 25 | 0.001 to 25 | 0.001 to 25 | — | — | 50 to 5000 | q.s. to 5 mL |
| 61 | 1 to 500 | 0.01 to 500 | 0.001 to 25 | 0.001 to 25 | — | 0.0001 to 1.0 | — | 50 to 5000 | q.s. to 5 mL |
| 62 | 1 to 500 | 0.01 to 500 | 0.001 to 25 | 0.001 to 25 | — | — | 0.0001 to 5.0 | 50 to 5000 | q.s. to 5 mL |
| 63 | 1 to 500 | 0.01 to 500 | 0.001 to 25 | 0.001 to 25 | 0.001 to 25 | 0.0001 to 1.0 | — | 50 to 5000 | q.s. to 5 mL |
| 64 | 1 to 500 | 0.01 to 500 | 0.001 to 25 | 0.001 to 25 | — | 0.0001 to 1.0 | — | 50 to 5000 | q.s. to 5 mL |
| 65 | 1 to 500 | 0.01 to 500 | 0.001 to 25 | 0.001 to 25 | 0.001 to 25 | — | 0.0001 to 5.0 | 50 to 5000 | q.s. to 5 mL |
| 66 | 1 to 500 | 0.01 to 500 | 0.001 to 25 | 0.001 to 25 | — | — | 0.0001 to 5.0 | 50 to 5000 | q.s. to 5 mL |

TABLE 1-6

| Composition no. | Pirfenidone (mg) | Phosphate Buffer (monobasic/dibasic sodium salts), pH 5.5 to 8.5 (mM) | Ethanol (% v/v) | Propylene Glycol (% v/v) | Glycerol (% v/v) | Polysorbate 80 (%) | Cetylpyridinium Bromide (or chloride) (%) | Chloride ion (sodium, magnesium or calcium salts) (%) | Osmolality (mOsmo/kg) | Water |
|---|---|---|---|---|---|---|---|---|---|---|
| 67 | 1 to 500 | 0.01 to 500 | 0.001 to 25 | — | — | — | — | 0.01 to 5 | 50 to 5000 | q.s. to 5 mL |
| 68* | 1 to 500 | 0.01 to 500 | — | 0.001 to 25 | — | — | — | 0.01 to 5 | 50 to 5000 | q.s. to 5 mL |
| 69 | 1 to 500 | 0.01 to 500 | — | — | 0.001 to 25 | — | — | 0.01 to 5 | 50 to 5000 | q.s. to 5 mL |
| 70 | 1 to 500 | 0.01 to 500 | — | — | — | 0.0001 to 1.0 | — | 0.01 to 5 | 50 to 5000 | q.s. to 5 mL |
| 71* | 1 to 500 | 0.01 to 500 | — | — | — | — | 0.0001 to 5.0 | 0.01 to 5 | 50 to 5000 | q.s. to 5 mL |
| 72 | 1 to 500 | 0.01 to 500 | 0.001 to 25 | 0.001 to 25 | — | — | — | 0.01 to 5 | 50 to 5000 | q.s. to 5 mL |
| 73 | 1 to 500 | 0.01 to 500 | 0.001 to 25 | — | 0.001 to 25 | — | — | 0.01 to 5 | 50 to 5000 | q.s. to 5 mL |
| 74 | 1 to 500 | 0.01 to 500 | 0.001 to 25 | — | — | 0.0001 to 1.0 | — | 0.01 to 5 | 50 to 5000 | q.s. to 5 mL |
| 75 | 1 to 500 | 0.01 to 500 | 0.001 to 25 | — | — | — | 0.0001 to 5.0 | 0.01 to 5 | 50 to 5000 | q.s. to 5 mL |
| 76 | 1 to 500 | 0.01 to 500 | 0.001 to 25 | 0.001 to 25 | 0.001 to 25 | — | — | 0.01 to 5 | 50 to 5000 | q.s. to 5 mL |
| 77 | 1 to 500 | 0.01 to 500 | 0.001 to 25 | 0.001 to 25 | — | 0.0001 to 1.0 | — | 0.01 to 5 | 50 to 5000 | q.s. to 5 mL |
| 78 | 1 to 500 | 0.01 to 500 | 0.001 to 25 | 0.001 to 25 | — | — | 0.0001 to 5.0 | 0.01 to 5 | 50 to 5000 | q.s. to 5 mL |
| 79 | 1 to 500 | 0.01 to 500 | 0.001 to 25 | 0.001 to 25 | 0.001 to 25 | 0.0001 to 1.0 | — | 0.01 to 5 | 50 to 5000 | q.s. to 5 mL |

TABLE 1-6-continued

| Composition no. | Pirfenidone (mg) | Phosphate Buffer (monobasic/ dibasic sodium salts), pH 5.5 to 8.5 (mM) | Ethanol (% v/v) | Propylene Glycol (% v/v) | Glycerol (% v/v) | Polysorbate 80 (%) | Cetylpyridinium Bromide (or chloride) (%) | Chloride ion (sodium, magnesium or calcium salts) (%) | Osmolality (mOsmo/kg) | Water |
|---|---|---|---|---|---|---|---|---|---|---|
| 80 | 1 to 500 | 0.01 to 500 | 0.001 to 25 | 0.001 to 25 | — | 0.0001 to 1.0 | — | 0.01 to 5 | 50 to 5000 | q.s. to 5 mL |
| 81 | 1 to 500 | 0.01 to 500 | 0.001 to 25 | 0.001 to 25 | 0.001 to 25 | — | 0.0001 to 5.0 | 0.01 to 5 | 50 to 5000 | q.s. to 5 mL |
| 82 | 1 to 500 | 0.01 to 500 | 0.001 to 25 | 0.001 to 25 | — | — | 0.0001 to 5.0 | 0.01 to 5 | 50 to 5000 | q.s. to 5 mL |

*Phosphate Buffer (monobasic/dibasic sodium salts), pH 6.2

TABLE 1-7

| Composition no. | Pirfenidone (mg) | Citrate Buffer (citric acid/ sodium citrate), pH 3.5 to pH 6.5 (mM) | Ethanol (% v/v) | Propylene Glycol (% v/v) | Glycerol (% v/v) | Polysorbate 80 (%) | Cetylpyridinium Bromide (or chloride) (%) | Chloride ion (sodium, magnesium or calcium salts) (%) | Osmolality (mOsmo/kg) | Water |
|---|---|---|---|---|---|---|---|---|---|---|
| 83 | 1 to 500 | 0.01 to 500 | 0.001 to 25 | — | — | — | — | 0.01 to 5 | 50 to 5000 | q.s. to 5 mL |
| 84 | 1 to 500 | 0.01 to 500 | — | 0.001 to 25 | — | — | — | 0.01 to 5 | 50 to 5000 | q.s. to 5 mL |
| 85 | 1 to 500 | 0.01 to 500 | — | — | 0.001 to 25 | — | — | 0.01 to 5 | 50 to 5000 | q.s. to 5 mL |
| 86 | 1 to 500 | 0.01 to 500 | — | — | — | 0.0001 to 1.0 | — | 0.01% to 5% | 50 to 5000 | q.s. to 5 mL |
| 87 | 1 to 500 | 0.01 to 500 | — | — | — | — | 0.0001 to 5.0 | 0.01 to 5 | 50 to 5000 | q.s. to 5 mL |
| 88 | 1 to 500 | 0.01 to 500 | 0.001 to 25 | 0.001 to 25 | — | — | — | 0.01 to 5 | 50 to 5000 | q.s. to 5 mL |
| 89 | 1 to 500 | 0.01 to 500 | 0.001 to 25 | — | 0.001 to 25 | — | — | 0.01 to 5 | 50 to 5000 | q.s. to 5 mL |
| 90 | 1 to 500 | 0.01 to 500 | 0.001 to 25 | — | — | 0.0001 to 1.0 | — | 0.01 to 5 | 50 to 5000 | q.s. to 5 mL |
| 91 | 1 to 500 | 0.01 to 500 | 0.001 to 25 | — | — | — | 0.0001 to 5.0 | 0.01 to 5 | 50 to 5000 | q.s. to 5 mL |
| 92 | 1 to 500 | 0.01 to 500 | 0.001 to 25 | 0.001 to 25 | 0.001 to 25 | — | — | 0.01 to 5 | 50 to 5000 | q.s. to 5 mL |
| 93 | 1 to 500 | 0.01 to 500 | 0.001 to 25 | 0.001 to 25 | — | 0.0001 to 1.0 | — | 0.01 to 5 | 50 to 5000 | q.s. to 5 mL |
| 94 | 1 to 500 | 0.01 to 500 | 0.001 to 25 | 0.001 to 25 | — | — | 0.0001 to 5.0 | 0.01 to 5 | 50 to 5000 | q.s. to 5 mL |
| 95 | 1 to 500 | 0.01 to 500 | 0.001 to 25 | 0.001 to 25 | 0.001 to 25 | 0.0001 to 1.0 | — | 0.01 to 5 | 50 to 5000 | q.s. to 5 mL |
| 96 | 1 to 500 | 0.01 to 500 | 0.001 to 25 | 0.001 to 25 | — | 0.0001 to 1.0 | — | 0.01 to 5 | 50 to 5000 | q.s. to 5 mL |
| 97 | 1 to 500 | 0.01 to 500 | 0.001 to 25 | 0.001 to 25 | 0.001 to 25 | — | 0.0001 to 5.0 | 0.01 to 5 | 50 to 5000 | q.s. to 5 mL |
| 98 | 1 to 500 | 0.01 to 500 | 0.001 to 25 | 0.001 to 25 | — | — | 0.0001 to 5.0 | 0.01 to 5 | 50 to 5000 | q.s. to 5 mL |

TABLE 1-8

| Composition no. | Pirfenidone (mg) | Citrate Buffer (citric acid/ sodium citrate), pH 4.0 to pH 5.0 (mM) | Ethanol (% v/v) | Propylene Glycol (% v/v) | Osmolality (mOsmo/kg) | Water |
|---|---|---|---|---|---|---|
| 99 | 5 mg (27 μmols) | 5 | 0.5% | 1.0% | 200 to 400 | q.s. to 5 mL |
| 100 | 5 mg (27 μmols) | 5 | 1.0% | 2.0% | 400 to 600 | q.s. to 5 mL |
| 101 | 10 mg (54 μmols) | 5 | 1.0% | 2.0% | 400 to 600 | q.s. to 5 mL |
| 102 | 15 (81 μmols) | 5 | 1.0% | 2.0% | 400 to 600 | q.s. to 5 mL |
| 103 | 25 mg (135 μmols) | 5 | 1.0% | 2.0% | 400 to 600 | q.s. to 5 mL |
| 104 | 37.5 mg (202 μmols) | 5 | 1.0% | 2.0% | 400 to 600 | q.s. to 5 mL |
| 105 | 75 mg (405 μmols) | 5 | 1.0% | 2.0% | 400 to 600 | q.s. to 5 mL |
| 106 | 100 mg (541 μmols) | 5 | 2.0% | 4.0% | 900 to 1100 | q.s. to 5 mL |
| 107 | 115 mg (621 μmols) | 5 | 4.0% | 8.0% | 1800 to 2100 | q.s. to 5 mL |
| 108 | 150 mg (810 μmols) | 5 | 6.0% | 12.0% | 1800 to 2100 | q.s. to 5 mL |
| 109 | 190 mg (1027 μmols) | 5 | 8.0% | 16.0% | 3500 to 3900 | q.s. to 5 mL |
| 110 | 220 mg (1189 μmols) | 5 | 8.0% | 16.0% | 3600 to 4000 | q.s. to 5 mL |

TABLE 1-9

| Composition no. | Pirfenidone (mg) | Phosphate Buffer (monobasic/dibasic sodium salts), pH 6.0 to pH 7.0 (mM) | Ethanol (% v/v) | Propylene Glycol (% v/v) | Osmolality (mOsmo/kg) | Water |
|---|---|---|---|---|---|---|
| 111 | 5 mg (27 μmols) | 5 | 0.5% | 1.0% | 200 to 400 | q.s. to 5 mL |
| 112 | 5 mg (27 μmols) | 5 | 1.0% | 2.0% | 200 to 600 | q.s. to 5 mL |
| 113 | 10 mg (54 μmols) | 5 | 1.0% | 2.0% | 400 to 600 | q.s. to 5 mL |
| 114 | 15 (81 μmols) | 5 | 1.0% | 2.0% | 400 to 600 | q.s. to 5 mL |
| 115 | 25 mg (135 μmols) | 5 | 1.0% | 2.0% | 400 to 600 | q.s. to 5 mL |
| 116 | 37.5 mg (202 μmols) | 5 | 1.0% | 2.0% | 400 to 600 | q.s. to 5 mL |
| 117 | 75 mg (405 μmols) | 5 | 1.0% | 2.0% | 400 to 600 | q.s. to 5 mL |
| 118 | 100 mg (541 μmols) | 5 | 2.0% | 4.0% | 900 to 1100 | q.s. to 5 mL |
| 119 | 115 mg (621 μmols) | 5 | 4.0% | 8.0% | 1800 to 2100 | q.s. to 5 mL |
| 120 | 150 mg (810 μmols) | 5 | 6.0% | 12.0% | 1800 to 2100 | q.s. to 5 mL |
| 121 | 190 mg (1027 μmols) | 5 | 8.0% | 16.0% | 3500 to 3900 | q.s. to 5 mL |
| 122 | 220 mg (1189 μmols) | 5 | 8.0% | 16.0% | 3600 to 4000 | q.s. to 5 mL |

TABLE 1-10

| Composition no. | Pirfenidone (mg) | Citrate Buffer (citric acid/ sodium citrate), pH 4.0 to pH 5.0 (mM) | Ethanol (% v/v) | Propylene Glycol (% v/v) | Chloride ion (sodium, magnesium or calcium salts) | Osmolality (mOsmo/kg) | Water |
|---|---|---|---|---|---|---|---|
| 123 | 5 mg (27 μmols) | 5 | 0.5% | 1.0% | 0.1% to 0.9% | 200 to 500 | q.s. to 5 mL |
| 124 | 5 mg (27 μmols) | 5 | 1.0% | 2.0% | 0.1% to 0.9% | 400 to 700 | q.s. to 5 mL |
| 125 | 10 mg (54 μmols) | 5 | 1.0% | 2.0% | 0.1% to 0.9% | 400 to 700 | q.s. to 5 mL |
| 126 | 15 (81 μmols) | 5 | 1.0% | 2.0% | 0.1% to 0.9% | 400 to 700 | q.s. to 5 mL |
| 127 | 25 mg (135 μmols) | 5 | 1.0% | 2.0% | 0.1% to 0.9% | 400 to 700 | q.s. to 5 mL |
| 128 | 37.5 mg (202 μmols) | 5 | 1.0% | 2.0% | 0.1% to 0.9% | 400 to 700 | q.s. to 5 mL |
| 129 | 75 mg (405 μmols) | 5 | 1.0% | 2.0% | 0.1% to 0.9% | 400 to 700 | q.s. to 5 mL |
| 130 | 100 mg (541 μmols) | 5 | 2.0% | 4.0% | 0.1% to 0.9% | 900 to 1200 | q.s. to 5 mL |
| 131 | 115 mg (621 μmols) | 5 | 4.0% | 8.0% | 0.1% to 0.9% | 1800 to 2200 | q.s. to 5 mL |
| 132 | 150 mg (810 μmols) | 5 | 6.0% | 12.0% | 0.1% to 0.9% | 1800 to 2200 | q.s. to 5 mL |
| 133 | 190 mg (1027 μmols) | 5 | 8.0% | 16.0% | 0.1% to 0.9% | 3500 to 4000 | q.s. to 5 mL |
| 134 | 220 mg (1189 μmols) | 5 | 8.0% | 16.0% | 0.1% to 0.9% | 3600 to 4100 | q.s. to 5 mL |

TABLE 1-11

| Composition no. | Pirfenidone (mg) | Phosphate Buffer (monobasic/dibasic sodium salts), pH 6.0 to pH 7.0 (mM) | Ethanol | Propylene Glycol | Chloride ion (sodium, magnesium or calcium salts) | Osmolality (mOsmo/kg) | Water |
|---|---|---|---|---|---|---|---|
| 135 | 5 mg (27 μmols) | 5 | 0.5% | 1.0% | 0.1% to 0.9% | 200 to 500 | q.s. to 5 mL |
| 136 | 5 mg (27 μmols) | 5 | 1.0% | 2.0% | 0.1% to 0.9% | 200 to 700 | q.s. to 5 mL |
| 137 | 10 mg (54 μmols) | 5 | 1.0% | 2.0% | 0.1% to 0.9% | 400 to 700 | q.s. to 5 mL |
| 138 | 15 (81 μmols) | 5 | 1.0% | 2.0% | 0.1% to 0.9% | 400 to 700 | q.s. to 5 mL |
| 139 | 25 mg (135 μmols) | 5 | 1.0% | 2.0% | 0.1% to 0.9% | 400 to 700 | q.s. to 5 mL |
| 140 | 37.5 mg (202 μmols) | 5 | 1.0% | 2.0% | 0.1% to 0.9% | 400 to 700 | q.s. to 5 mL |
| 141 | 75 mg (405 μmols) | 5 | 1.0% | 2.0% | — | 400 to 700 | q.s. to 5 mL |
| 142 | 100 mg (541 μmols) | 5 | 2.0% | 4.0% | 0.1% to 0.9% | 900 to 1200 | q.s. to 5 mL |
| 143 | 115 mg (621 μmols) | 5 | 4.0% | 8.0% | 0.1% to 0.9% | 1800 to 2200 | q.s. to 5 mL |
| 144 | 150 mg (810 μmols) | 5 | 6.0% | 12.0% | 0.1% to 0.9% | 1800 to 2200 | q.s. to 5 mL |
| 145 | 190 mg (1027 μmols) | 5 | 8.0% | 16.0% | 0.1% to 0.9% | 3500 to 4000 | q.s. to 5 mL |
| 146 | 220 mg (1189 μmols) | 5 | 8.0% | 16.0% | 0.1% to 0.9% | 3600 to 4100 | q.s. to 5 mL |

Example 2: Buffer and pH Effects Development Study

Pirfenidone solubility in citrate and phosphate buffers were investigated (Table 2). Pirfenidone (250 mg) was reconstituted with 5 mL of buffer in water or water alone and mixed thoroughly with sonication and vortexing. The sample was agitated at ambient temperature overnight. The sample was visually inspected, appearance recorded, centrifuged to sediment any un-dissolved material, and the supernatant withdrawn via syringe through a 0.22 μm PVDF filter. The filtered sample was tested with respect to: appearance, pH (USP <791>), osmolality (USP <785>), and Pirfenidone concentration and Pirfenidone % purity by RP-HPLC. The remaining filtered sample was split into three equal volumes in glass vials and placed at 25° C./60 RH, 40° C./75 RH and refrigeration. Samples were wrapped in aluminum foil to reduce light exposure. After the first night of incubation, samples were briefly visually inspected for any signs of discoloration or precipitate formation.

TABLE 2

Buffer/pH Effects Study Results

| Buffer | Buffer (mM) | pH | Pirfenidone Saturation Solubility (mg/mL) |
|---|---|---|---|
| Citrate | 5 | 4 | 18.4 |
| Citrate | 50 | 4 | 18.1 |
| Citrate | 5 | 6 | 18.4 |
| Citrate | 50 | 6 | 16.4 |
| Phosphate | 5 | 6 | 18.3 |
| Phosphate | 50 | 6 | 17.2 |
| Phosphate | 5 | 7.5 | 19.0 |
| Phosphate | 50 | 7.5 | 16.3 |
| Water | 0 | 7.9 | 18.4 |

Table 2 shows the observed solubility of pirfenidone under the conditions described.

Example 3: Co-Solvent and Surfactant Effects

Pirfenidone solubility in the presence of added co-solvent (ethanol, propylene glycol, or glycerin) and surfactant (polysorbate 80 or cetylpyridinium bromide) were investigated. The buffer type, strength, and pH of the aqueous vehicle are selected based on results from the Buffer/pH Effects study results (Example 2). Pirfenidone (375 mg) is reconstituted with 5 mL of each solvent system shown in Table 3.

TABLE 3

Co-Solvent/Surfactant Effects Study Results

| Added Co-Solvent and/or Surfactant, % | | | | | % Water | % Citrate Buffer (10 mM) | % Phosphate Buffer (5 mM) | pH | Pirfenidone Saturation Solubility (mg/mL) |
|---|---|---|---|---|---|---|---|---|---|
| EtOH | PG | Gly | PS80 | CPB | | | | | |
| 0 | 0 | 0 | 0.04 | 0 | 100.0 | 0 | 0 | 6.5 | 19.9 |
| 0 | 0 | 0 | 0 | 0.1 | 99.9 | 0 | 0 | 6.2 | 20.0 |
| 0 | 0 | 0 | 0.04 | 0 | 100.0 | 0 | 0 | 4.8 | 8.3 |
| 0 | 0 | 0 | 0 | 0.1 | 99.9 | 0 | 0 | 4.6 | 19.3 |
| 0 | 0 | 0 | 0.04 | 0 | 0 | 100.0 | 0 | 4.5 | 19.1 |
| 0 | 0 | 0 | 0 | 0.1 | 0 | 99.9 | 0 | 4.5 | 19.3 |
| 4 | 0 | 0 | 0 | 0 | 96.0 | 0 | 0 | 6.9 | 24.3 |
| 0 | 8 | 0 | 0 | 0 | 92.0 | 0 | 0 | 6.8 | 24.6 |
| 0 | 0 | 4 | 0 | 0 | 96.0 | 0 | 0 | 6.7 | 20.1 |
| 4 | 0 | 0 | 0 | 0 | 96.0 | 0 | 0 | 5.0 | 22.8 |
| 0 | 8 | 0 | 0 | 0 | 92.0 | 0 | 0 | 5.0 | 24.3 |
| 0 | 0 | 4 | 0 | 0 | 96.0 | 0 | 0 | 4.8 | 20.1 |
| 4 | 0 | 0 | 0 | 0 | 0 | 96.0 | 0 | 4.5 | 22.3 |
| 0 | 8 | 0 | 0 | 0 | 0 | 92.0 | 0 | 4.4 | 23.2 |
| 0 | 0 | 4 | 0 | 0 | 0 | 96.0 | 0 | 4.4 | 19.8 |
| 4 | 0 | 0 | 0.04 | 0 | 96.0 | 0 | 0 | 6.7 | 24.5 |
| 0 | 8 | 0 | 0.04 | 0 | 92.0 | 0 | 0 | 6.6 | 23.2 |
| 0 | 0 | 4 | 0.04 | 0 | 96.0 | 0 | 0 | 6.5 | 20.2 |
| 4 | 0 | 0 | 0.04 | 0 | 96.0 | 0 | 0 | 4.7 | 22.5 |
| 0 | 8 | 0 | 0.04 | 0 | 92.0 | 0 | 0 | 4.6 | 23.4 |
| 0 | 0 | 4 | 0.04 | 0 | 96.0 | 0 | 0 | 4.9 | 20.0 |
| 4 | 0 | 0 | 0.04 | 0 | 0 | 96.0 | 0 | 4.5 | 21.9 |
| 0 | 8 | 0 | 0.04 | 0 | 0 | 92.0 | 0 | 4.5 | 23.2 |
| 0 | 0 | 4 | 0.04 | 0 | 0 | 96.0 | 0 | 4.4 | 17.6 |
| 4 | 0 | 0 | 0 | 0.1 | 95.9 | 0 | 0 | 6.1 | 23.9 |
| 0 | 8 | 0 | 0 | 0.1 | 91.9 | 0 | 0 | 6.2 | 23.4 |
| 0 | 0 | 4 | 0 | 0.1 | 95.9 | 0 | 0 | ND | ND |
| 4 | 0 | 0 | 0 | 0.1 | 95.9 | 0 | 0 | 4.9 | 20.2 |
| 0 | 8 | 0 | 0 | 0.1 | 91.9 | 0 | 0 | 5.0 | 22.3 |
| 0 | 0 | 4 | 0 | 0.1 | 95.9 | 0 | 0 | ND | ND |
| 4 | 0 | 0 | 0 | 0.1 | 0 | 95.9 | 0 | 4.5 | 20.4 |
| 0 | 8 | 0 | 0 | 0.1 | 0 | 91.9 | 0 | 4.5 | 21.0 |
| 0 | 0 | 4 | 0 | 0.1 | 0 | 95.9 | 0 | ND | ND |
| 4 | 8 | 0 | 0 | 0 | 88.0 | 0 | 0 | 6.2 | 30.0 |
| 4 | 8 | 0 | 0.04 | 0 | 88.0 | 0 | 0 | 5.8 | 28.9 |
| 4 | 8 | 0 | 0 | 0 | 0 | 0 | 88.0 | 6.6 | 27.2 |
| 4 | 8 | 0 | 0.04 | 0 | 0 | 0 | 88.0 | 6.6 | 29.4 |
| 6 | 12 | 0 | 0 | 0 | 0 | 0 | 82.0 | 7.0 | 34.7 |
| 8 | 16 | 0 | 0 | 0 | 0 | 0 | 76.0 | 7.0 | 43.7 |
| 8 | 0 | 0 | 0 | 0 | 0 | 0 | 92 | 6.6 | 26.7 |
| 8 | 4 | 0 | 0 | 0 | 0 | 0 | 88 | 6.8 | 30.4 |
| 8 | 8 | 0 | 0 | 0 | 0 | 0 | 84 | 6.8 | 35.0 |
| 8 | 12 | 0 | 0 | 0 | 0 | 0 | 80 | 6.7 | 37.7 |
| 8 | 16 | 0 | 0 | 0 | 0 | 0 | 76 | 6.8 | 45.4 |
| 6 | 16 | 0 | 0 | 0 | 0 | 0 | 78 | 6.9 | 40.9 |

TABLE 3-continued

Co-Solvent/Surfactant Effects Study Results

| Added Co-Solvent and/or Surfactant, % | | | | | % Water | % Citrate Buffer (10 mM) | % Phosphate Buffer (5 mM) | pH | Pirfenidone Saturation Solubility (mg/mL) |
|---|---|---|---|---|---|---|---|---|---|
| EtOH | PG | Gly | PS80 | CPB | | | | | |
| 4 | 16 | 0 | 0 | 0 | 0 | 0 | 80 | 6.9 | 36.8 |
| 2 | 16 | 0 | 0 | 0 | 0 | 0 | 82 | 6.8 | 31.0 |
| 0 | 16 | 0 | 0 | 0 | 0 | 0 | 84 | 6.8 | 29.3 |

\* Buffer type, buffer strength, and pH chosen on the basis of Buffer/pH study results (Example 2).
EtOH: ethanol, PG: propylene glycol, Gly: glycerol, PS80: polysorbate 80 (Tween 80), CPB: Cetylpyridinium chloride.
% in Table 3 refers to volume/volume.

Each sample was agitated at ambient temperature overnight. The samples were visually inspected and appearance recorded. Samples were centrifuged to sediment any undissolved material and the supernatant withdrawn via syringe through a 0.22 μm PVDF filter. The filtered sample was tested with respect to: appearance, pH (USP <791>), osmolality (USP <785>), and Pirfenidone concentration and Pirfenidone % purity by RP-HPLC. The remaining filtered sample was split into three equal volumes in glass vials and placed at 25° C./60 RH, 40° C./75 RH and refrigeration. Samples are wrapped in aluminum foil to reduce light exposure. After the first night of incubation, samples are briefly visually inspected for any signs of discoloration or precipitate formation.

Both ethanol (EtOH) and propylene glycol (PG) increase the saturation solubility of pirfenidone. Ethanol and propylene glycol together have an additive effect in increasing the saturation solubility of pirfenidone.

Selected formulations were subjected to osmolality determination and nebulization for taste testing and throat irritation and or cough response. Table 4 shows these results.

TABLE 4

Compositions and Additional Analysis

| Added Co-Solvent and/or Surfactant (%)[a] | | Sodium Saccharin (mM) | % Phosphate Buffer (5 mM) | pH | Pirfenidone (mg/mL) | Osmolality (mOsmo/Kg) | Taste | Throat Irritation? | Cough Response? |
|---|---|---|---|---|---|---|---|---|---|
| EtOH | PG | | | | | | | | |
| 4 | 8 | 0 | 88 | 6.6 | 27.2 | ~1830* | 4.5 micron aerosol particle: Mild taste, unremarkable flavor | No | No |
| 6 | 12 | 0 | 82 | 7.0 | 34.7 | ~2750* | 4.5 micron aerosol particle: Mild taste, slight sweet flavor, slight bitter after-taste | No | No |
| 8 | 16 | 0 | 76 | 7.0 | 43.7 | 3672 | 4.5 micron aerosol particle: Mild taste, moderate sweet flavor, moderate bitter after-taste 3.5 micron aerosol particle: Mild taste, similar sweet flavor and bitter after-taste as 6% EtOH + 12% PG | No | No |
| 8 | 16 | 0.3 | 76 | 7.0 | 43.7 | 3672 | 3.5 micron aerosol particle: Mild taste, similar sweet flavor and slightly bitter after-taste similar to 6% EtOH + 12% PG | No | No |
| 8 | 16 | 0 | 76 | 4.5 | 0 | 3672 | 3.5 micron aerosol particle: Mild taste, slightly sweeter than 6% EtOH + 12% PG, with similar bitter after-taste | No | No |

*Calculated.
[a]% volume/volume

Results from Table 4 show that co-solvent-containing formulations contain a relatively high osmolality. Unexpectedly, these high osmolar solutions do not exhibit poor inhalation tolerability. Solutions containing up to 8% (v/v) ethanol plus 16% (v/v) propylene glycol are well-tolerated, have a slight sweet flavor with minimal bitter after-taste, minimal throat irritation and minimal stimulation of cough response. Formulations lacking co-solvents are limited to about 15 mg/mL. These same formulations exhibited a bitter, slightly metallic taste. Unexpectedly, co-solvent-enabling high concentration pirfenidone formulations (by non-limiting example up to 44 mg/mL) do not exhibit these poor taste characteristics.

Saturated pirfenidone formulations appeared stable out to 2-5 days under the tested conditions. However, in all cases pirfenidone eventually re-crystallized. This re-crystallization was not inhibited by pre-filtration of the sample. From this observation, pirfenidone concentrations less then saturation were explored. 85% saturation pirfenidone concentrations were exposed to several temperatures. These results are shown in Table 5.

TABLE 5

Compositions and Additional Analysis

| Added Co-Solvent (%) | | % Phosphate Buffer (5 mM) | pH | Pirfenidone (mg/mL) | Recrystallization upon storage$^a$ | | | |
|---|---|---|---|---|---|---|---|---|
| EtOH | PG | | | | 25° C. | 15° C. | 4° C. | −20° C. |
| 4 | 8 | 88 | 6.6 | 27.2$^b$ | Yes | ND$^d$ | ND | ND |
| 4 | 8 | 88 | 6.6 | 23.0$^e$ | No | No | No | Yes$^f$ |
| 6 | 12 | 82 | 7.0 | 34.7 | Yes | ND | ND | ND |
| 6 | 12 | 82 | 7.0 | 29.5 | No | No | No | Yes$^f$ |
| 8 | 16 | 76 | 7.0 | 43.7 | Yes | ND | ND | ND |
| 8 | 16 | 76 | 7.0 | 37.0 | No | No | No | Yes$^f$ |

$^a$Observation after overnight storage at designated temperature
$^b$Pirfenidone saturation solubility at given formulation
c. Calculated
$^d$Not determined
$^e$Pirfenidone concentration at 85% saturation solubility
$^f$Crystals re-dissolved at 25° C. without agitation
% refers to % v/v Results from Table 5 show that these 85% pirfenidone saturation formulations do not re-crystallize down to 4° C. (at least following overnight incubation). These results suggest that these formulations will survive periodic exposures down to 4° C., and even upon freezing will re-dissolve without agitation.

Additional studies examined pirfenidone stability in 5 mM sodium phosphate buffer, pH 6.5, as a function of optimized co-solvent strength for stability assessment. The target concentrations represent roughly 85% of the saturated concentration possible at each specified co-solvent concentration. Two additional formulations examined pirfenidone stability at 1 mg/mL in specific formulations. Pirfenidone (amounts are outlined in Table 6) was reconstituted with 100 mL vehicle as described and mixed thoroughly by agitation. The sample was agitated until completely dissolved. Once dissolved, samples were filtered via syringe through a 0.22 μm PVDF filter.

Samples were refrigerated to reduce evaporative loss of volatile co-solvents (ethanol) during filtration and dispensing. An approximate 5.0-mL aliquot of each formulation was transferred to class A glass 6 ml containers with suitable closures (20 mm stopper). At least 8 containers are being maintained in the upright orientation at 25° C./60 RH, and another 8 containers maintained at 40° C./75 RH. One container for each formulation was used for the initial evaluation, t=0, with testing for: appearance, pH, osmolality, HPLC=RP-HPLC for pirfenidone assay (reported as % label claim) and individual impurities (reported as % pirfenidone and RRT). Stability time point testing will evaluate for appearance, and HPLC=RP-HPLC for pirfenidone assay (reported as % label claim) and individual impurities (reported as % pirfenidone and RRT).

TABLE 6

Representative Pirfenidone Formulations for Stability Assessment

| Target 5 mM Phosphate Buffer, pH 6.5, plus | Target Pirfenidone (mg/mL) | Add Pirfenidone (mg) | Add Buffer (mL) | Add Ethanol (mL) | Add PG (mL) |
|---|---|---|---|---|---|
| 8% (v/v) EtOH, 16% (v/v) PG | 38 | 3800 | 20 | 8.0 | 16.0 |
| 8% (v/v) EtOH, 16% (v/v) PG | 1 | 100 | 20 | 8.0 | 16.0 |
| 6% (v/v) EtOH, 12% (v/v) PG | 30 | 300 | 20 | 6.0 | 12.0 |
| 4% (v/v) EtOH, 8% (v/v) PG | 23 | 230 | 20 | 4.0 | 8.0 |
| 1% (v/v) EtOH, 2% (v/v) PG | 15 | 150 | 20 | 1.0 | 2.0 |
| 1% (v/v) EtOH, 2% (v/v) PG | 1 | 100 | 20 | 1.0 | 2.0 |

For each variant Formulation, samples are tested according to the schedule shown in Table 7.

TABLE 7

Stability Schedule

| | Tests* Performed at Time Point (mo) = | | | | | | | | |
|---|---|---|---|---|---|---|---|---|---|
| Condition | 0 | 0.5** | 1 | 3 | 6 | 9 | 12 | contingency | total |
| 25° C./60% RH | 1 | 1 | 1 | 1 | 1 | 1 | 1 | 2 | 9 |
| 40° C./75% RH | | 1 | 1 | 1 | 1 | 1 | 1 | 2 | 8 |

*all samples will be tested for appearance by visual observation, pH, HPLC = RP-HPLC for pirfenidone assay (reported as % label claim), and individual impurities (reported as % pirfenidone and RRT). At t = 0, testing will also include osmolality.
**Appearance only TABLE 8a Time-Zero Stability Assessment

| Target 5 mM Phosphate Buffer, pH 6.5, plus | Target Pirfenidone (mg/mL) | Measured Pirfenidone (mg/mL) | pH | mOsmol/kg | App. |
|---|---|---|---|---|---|
| 8% (v/v) EtOH, 16% (v/v) PG | 38 | 38.9 | 7.04 | 3750 | * |
| 8% (v/v) EtOH, 16% (v/v) PG | 1 | 1.0 | 6.98 | 3590 | * |
| 6% (v/v) EtOH, 12% (v/v) PG | 30 | 30.3 | 6.90 | 2863 | * |
| 4% (v/v) EtOH, 8% (v/v) PG | 23 | 24.1 | 6.78 | 1928 | * |
| 1% (v/v) EtOH, 2% (v/v) PG | 15 | 16.1 | 6.65 | 512 | * |
| 1% (v/v) EtOH, 2% (v/v) PG | 1 | 1.0 | 6.69 | 452 | * |

* All solutions are clear and colorless without visible signs of crystallization.

TABLE 8b

Pirfenidone Measurements at 25° C./60% RH

| Target 5 mM Phosphate Buffer, pH 6.5, plus | Target Pirfenidone (mg/mL) | Pirfenidone (mg/mL) at Time = 0 | Pirfenidone (mg/mL) at Time = 1 month | Pirfenidone (mg/mL) at Time = 3 month | Pirfenidone (mg/mL) at Time = 6 month |
|---|---|---|---|---|---|
| 8% (v/v) EtOH, 16% (v/v) PG | 38 | 38.9 | 38.3 | 38.0 | 39.2 |
| 8% (v/v) EtOH, 16% (v/v) PG | 1 | 1.0 | 1.0 | 1.0 | 1.0 |
| 6% (v/v) EtOH, 12% (v/v) PG | 30 | 30.3 | 30.1 | 29.6 | 31.0 |
| 4% (v/v) EtOH, 8% (v/v) PG | 23 | 24.1 | 22.1 | 22.3 | 23.2 |
| 1% (v/v) EtOH, 2% (v/v) PG | 15 | 16.1 | 15.1 | 14.9 | 15.4 |
| 1% (v/v) EtOH, 2% (v/v) PG | 1 | 1.0 | 1.0 | 1.0 | 1.0 |

* All solutions are clear and colorless without visible signs of crystallization.

TABLE 8c

Pirfenidone Measurements at 40° C./75% RH

| Target 5 mM Phosphate Buffer, pH 6.5, plus | Target Pirfenidone (mg/mL) | Pirfenidone (mg/mL) at Time = 0 | Pirfenidone (mg/mL) at Time = 1 month | Pirfenidone (mg/mL) at Time = 3 month | Pirfenidone (mg/mL) at Time = 6 month |
|---|---|---|---|---|---|
| 8% (v/v) EtOH, 16% (v/v) PG | 38 | 38.9 | 38.4 | 38.0 | 37.9 |
| 8% (v/v) EtOH, 16% (v/v) PG | 1 | 1.0 | 1.0 | 1.0 | 1.0 |
| 6% (v/v) EtOH, 12% (v/v) PG | 30 | 30.3 | 30.3 | 30.0 | 31.1 |
| 4% (v/v) EtOH, 8% (v/v) PG | 23 | 24.1 | 22.4 | 22.1 | 23.3 |
| 1% (v/v) EtOH, 2% (v/v) PG | 15 | 16.1 | 15.1 | 14.8 | 15.5 |
| 1% (v/v) EtOH, 2% (v/v) PG | 1 | 1.0 | 1.0 | 1.0 | 1.0 |

* All solutions are clear and colorless without visible signs of crystallization.

Selected formulations were prepared for pharmacokinetic analysis following aerosol delivery to rat lung. In these studies, lung, heart, kidney and plasma tissue samples were analyzed for pirfenidone and metabolite content (Tables 16-19). Formulations prepared for this study are outlined in Table 9. Briefly, this study prepared pirfenidone in 5 mM sodium phosphate buffer, pH 6.5, as a function of optimized co-solvent strength. The target concentration in each formulation is 12.5 mg/mL. Pirfenidone (amounts as described in Table 9) were reconstituted with 30 mL vehicle as described and mixed thoroughly by agitation. The sample was agitated until completely dissolved. Once pirfenidone had dissolved completely, formulations were filtered via syringe through a 0.22 μm PVDF filter. Filtered samples were analyzed by HPLC.

The samples were then refrigerated to reduce evaporative loss of volatile co-solvents (ethanol) during filtration and dispensing. Formulations were transferred to class A glass containers (approximately 10 mL) with suitable closures (20 mm stopper).

TABLE 9

Formulations for Co-Solvent Effects Pharmacokinetic and Tissue Distribution Study

| Dosing Group | Target 5 mM Phosphate Buffer, pH 6.5, plus | Vol. (mL)* | Target Pirfenidone (mg/mL) | Add Pirfenidone (mg) | Add Buffer** (mL) | Add EtOH (mL) | Add PG (mL) | Add NaCl (g) |
|---|---|---|---|---|---|---|---|---|
| 1 | 8% (v/v) EtOH, 16% (v/v) PG | 30 | 12.5 | 375 | 6 | 2.4 | 4.8 | 0 |
| 2 | 6% (v/v) EtOH, 12% (v/v) PG | 30 | 12.5 | 375 | 6 | 1.8 | 3.6 | 0 |

TABLE 9-continued

Formulations for Co-Solvent Effects Pharmacokinetic and Tissue Distribution Study

| Dosing Group | Target 5 mM Phosphate Buffer, pH 6.5, plus | Vol. (mL)* | Target Pirfenidone (mg/mL) | Add Pirfenidone (mg) | Add Buffer** (mL) | Add EtOH (mL) | Add PG (mL) | Add NaCl (g) |
|---|---|---|---|---|---|---|---|---|
| 3 | 4% (v/v) EtOH, 8% (v/v) PG | 30 | 12.5 | 375 | 6 | 1.2 | 2.4 | 0 |
| 4 | 2% (v/v) EtOH, 4% (v/v) PG | 30 | 12.5 | 375 | 6 | 0.6 | 1.2 | 0 |
| 5 | 1% (v/v) EtOH, 2% (v/v) PG | 30 | 12.5 | 375 | 6 | 0.3 | 0.6 | 0 |
| 6 | 0.4% NaCl | 30 | 12.5 | 375 | 6 | 0 | 0 | 0.12 |

*Pirfenidone was reconstituted with 30 mL of the indicated Vehicle by QS'ing the remaining volume with water.
**25 mM NaPO4, pH 6.5 (5X solution)

Example 4: Nebulization Device Performance

Selected formulations were prepared for nebulization device aerosol characterization. Briefly, this study prepared pirfenidone in 5 mM sodium phosphate buffer, pH 6.5, as a function of optimized co-solvent strength. These formulations are outlined in Table 10. Pirfenidone (amounts as listed in Table 10) were reconstituted as described and mixed thoroughly by agitation. Each sample was agitated until completely dissolved. Once dissolved completely, formulations were filtered via syringe through a 0.45 μm PVDF filter. Filtered samples were analyzed by HPLC.

Each sample was refrigerated to reduce evaporative loss of volatile co-solvents (ethanol) during filtration and dispensing. As described in Table 10, each formulation was transferred to class A glass containers with suitable closures.

TABLE 10

Formulations for Nebulization Device Aerosol Performance Studies

| Test Article | Target 5 mM Phosphate Buffer, pH 6.5, plus | Vol. (mL) | Target Pirfenidone (mg/mL) | Add Pirfenidone (mg) | Add Buffer* (mL) | Add Ethanol (mL) | Add PG (mL) | Add NaCl (g) |
|---|---|---|---|---|---|---|---|---|
| 1 | 8% (v/v) EtOH, 16% (v/v) PG | 200 | 38** | 7600 | 40 | 16 | 32 | 0 |
| 2 | 8% (v/v) EtOH, 16% (v/v) PG | 200 | 0 | 0 | 40 | 16 | 32 | 0 |
| 3 | 1% (v/v) EtOH, 2% (v/v) PG | 200 | 0 | 0 | 40 | 2 | 4 | 0 |
| 4 | 0.2% (v/v) EtOH, 0.4% (v/v) PG | NA | 0.475 | Diluted Test Articles 1 and 3 | | | | |
| 5 | 0.4% NaCl | 200 | 0 | 0 | 40 | 0 | 0 | 0.8 |

*25 mM NaPO4, pH 6.5 (5X solution)
**Active formulations were diluted with water and vehicle by the device characterization facility as necessary to characterize lower pirfenidone concentrations.

Philips I-Neb® AAD System

For aerosol analysis, three units of each I-neb breath-actuated nebulizer were studied in triplicate for each device/formulation combination. Using Malvern Mastersizer aerosol particle sizer, the particle size and distribution was characterized. Parameters reported were mass median diameter (MMD), span, fine particle fraction (FPF=%≤5 microns), output rate (mg formulation per second), nebulized volume, delivered volume (volume of dose in range of FPF), respirable delivered dose (mg pirfenidone delivered volume). Aerosol output was measured using a 5 second inhalation, 2 second exhalation breathing pattern with a 1.25 L tidal volume. The results are shown in Table 11.

TABLE 11

Nebulization of Pirfenidone Formulations using the Philips I-neb Device

| Parameter | Test Article 1 | Test Article 2 | Test Article 3 | Test Article 4 | Test Article 5 |
|---|---|---|---|---|---|
| MMD (micron) | 3.31 | 3.64 | 4.95 | 5.52 | 4.95 |
| Span (micron) | 1.13 | 1.36 | 1.21 | 1.14 | 1.20 |
| FPF (% < 5 microns) | 84.41 | 74.70 | 51.40 | 42.01 | 51.11 |
| Output rate (mg/sec) | 0.96 | 1.31 | 3.52 | 6.92 | 4.60 |
| Nebulized vol (mg) | 776.63 | 810.42 | 846.42 | 853.30 | 814.51 |
| Delivered vol (mg) | 653.44 | 605.83 | 436.19 | 345.55 | 417.12 |
| RDD (mg)* | 24.83 | NA | NA | 0.16 | NA |

*Exemplary (RDD = FPF × Nebulized Volume × loaded dose)

PARI eFlow®—35 Head

For aerosol analysis, three units of each eFlow nebulizer containing a 35-head were studied in duplicate for each device/formulation combination. Using an Insitec Spraytec Laser Particle sizer, the particle size and distribution was characterized. Parameters reported were volumetric mean diameter (VMD), geometric standard deviation (GSD), time to nebulize dose (duration), remaining dose following nebulization (dead volume), and fine particle fraction (FPF=%≤5 microns). 4 mL of each formulation was tested. The results are shown in Table 12.

TABLE 12

Nebulization of Pirfenidone Formulations using the PARI eFlow Device

| Parameter | Test Article 1 | Test Article 2 | Test Article 3 | Test Article 4 | Test Article 5 |
|---|---|---|---|---|---|
| Loaded Dose (mg) | 152 | 0 | 0 | 1.9 | 0 |
| VMD (micron) | 2.60 | 2.84 | 3.60 | 3.88 | 3.81 |
| GSD (micron) | 1.86 | 1.85 | 1.74 | 1.68 | 1.68 |
| FPF (% < 5 microns) | 85.47 | 81.81 | 71.26 | 67.70 | 68.78 |
| Duration (min) | 9.87 | 8.85 | 6.26 | 5.99 | 5.86 |
| Dead volume (mL) | 0.15 | 0.16 | 0.19 | 0.18 | 0.16 |
| Output rate (mL/min) | 0.40 | 0.44 | 0.61 | 0.64 | 0.67 |
| Nebulized vol (mL) | 3.85 | 3.84 | 3.81 | 3.82 | 3.84 |
| RDD (mg)* | 87.04 | NA | NA | 0.86 | NA |
| RDD (mg)/minute | 8.82 | NA | NA | 0.14 | NA |

*Exemplary (RDD = FPF × Inhaled Mass × Loaded Dose). For the exemplary calculation, assume a 67% delivered dose (i.e. inhaled mass). (Representative of a 1:1 inhalation: exhalation breathing pattern using the eFlow device with 35 head.)

Aerogen Aeroneb® Solo

For aerosol analysis, between two and four units of each Aeroneb® Solo nebulizer with Aeroneb® Pro-X controller were studied with each formulation. Using a Malvern Spraytech aerosol particle sizer, the particle size and distribution were characterized. Parameters reported were volumetric mean diameter (VMD), geometric standard deviation (GSD), time to nebulize dose (duration), remaining dose following nebulization (dead volume), and fine particle fraction (FPF=%≤5 microns). 1 mL of each formulation was tested. The results are shown in Table 13.

TABLE 13

Nebulization of Pirfenidone Formulations using the Aeroneb Solo Device

| Parameter | Test Article 1 | Test Article 2 | Test Article 3 | Test Article 5 |
|---|---|---|---|---|
| Loaded Dose (mg) | 38 | 0 | 0 | 0 |
| VMD (micron) | 9.73 | 5.49 | 4.31 | 4.76 |
| GSD (micron) | 3.21 | 3.43 | 2.25 | 2.23 |
| FPF (% < 5 microns) | 38.97 | 48.13 | 59.09 | 53.77 |
| Duration (min) | 5.88 | 5.56 | 4.17 | 2.17 |
| Output rate (mL/min) | 0.17 | 0.18 | 0.24 | 0.46 |
| RDD (mg)* | 9.9 | NA | NA | NA |
| RDD (mg)*/minute | 1.68 | NA | NA | NA |

*Exemplary (RDD = FPF × Inhaled Mass × Loaded Dose). For the exemplary calculation, assume a 67% inhaled mass.

Example 5: Process Temperature Development Study

This study examined the above-ambient temperature stability of pirfenidone in aqueous solution to best understand stability at this temperature and saturation solubility. This information may be utilized with manufacturing process embodiments of the present invention wherein high temperature pirfenidone aqueous dissolution, in the presence of or followed by co-solvent and/or surfactant and/or cation addition, and subsequent cooling to ambient temperature provide higher pirfenidone saturation solubility then ambient temperature dissolution alone. In this process, added co-solvent and/or surfactant and/or cation may stabilize the high-temperature-dissolved pirfenidone during the cooling process and provide a stable, high-concentration, ambient-temperature formulation for long-term storage. Alternatively, the added co-solvent and/or surfactant and/or cation may provide access to greater soluble pirfenidone for which to maintain in solution then ambient temperature dissolution alone. Alternatively, high-temperature dissolution may be integrated into manufacturing process embodiments to reduce dissolution time and/or reduce the effects of lot-to-lot crystal structure, amorphic content and polymorph variability on dissolution time and degree of dissolution.

Formulations were prepared as described in Table 11. Briefly, this study prepared 250 mg pirfenidone in 5 mM sodium phosphate buffer, pH 6.5, in the presence of ethanol, propylene glycol and/or polysorbate 80. The final volume of each formulation was 5 mL. Pirfenidone (amounts as listed in Table 11) were reconstituted as described and mixed thoroughly by agitation. Each sample was mixed thoroughly and agitated overnight at 60° C. Rapid cooling and step-wise cooling from 60° C. to 25° C. was performed. HPLC analysis was performed on samples taken after overnight incubation and after cooling to 25° C. Prior to HPLC analysis, formulations were filtered via syringe through a 0.45 μm PVDF filter. Results for this evaluation are shown in Table 14.

TABLE 14

Formulations for Process Temperature Study

| Added Co-Solvent and/or Surfactant (% v/v) | | | % Phosphate | | Pirfenidone (mg/mL) | | Observations |
|---|---|---|---|---|---|---|---|
| EtOH | PG | PS80 | Buffer (5 mM) | pH | >60° C.[a] | >Re-crystal[b] | |
| 4 | 8 | 0 | 88 | 6.7 | 50.34 | 27.6 | Fully dissolved after overnight at 60° C. Stable at 25° C. for >4 hours before re-crystallization |
| 4 | 8 | 0.04 | 88 | 6.7 | 51.8 | 26.8 | Fully dissolved after overnight at 60° C. Stable at 25° C. for >4 hours before re-crystallization |
| 4 | 0 | 0.04 | 96 | 6.6 | 50.7 | 22.4 | Fully dissolved after overnight at 60° C. Stable at 25° C. for >4 hours before re-crystallization |
| 0 | 8 | 0.04 | 92 | 6.7 | 52.8 | 22.3 | Fully dissolved after overnight at 60° C. Stable at 25° C. for >4 hours before re-crystallization |
| 0 | 8 | 0 | 92 | 6.6 | 54.6 | 18.6 | Fully dissolved after overnight at 60° C. Stable at 25° C. for >4 hours before re-crystallization |

[a]Pirfenidone assay content after stepwise cooling to 25° C.
[b]Pirfenidone assay content after stepwise cooling to 25° C. and then later re-crystallization
c. Calculated
d. Not determined
e. Pirfenidone concentration at 85% saturation solubility
f. Crystals re-dissolved at 25° C. without agitation The results in Table 14 show that heating pirfenidone to 60° C. enables full dissolution up to or potentially greater than 50 mg/mL. Rapid cooling to 25° C. of this dissolved material led to rapid recrystallization (data not shown). Slow cooling to 25° C. (step-wise from 60° C. to 40° C. to 30° C. then 25° C., with temperature equilibration occurring at each step prior to further reducing the temperature) enabled pirfenidone to stay in solution at about 50 mg/mL for several hours before each solution ultimately re-crystallized. Filtering each formulation prior to re-crystallization (either at 30° C. or after equilibrium at 25° C.) did not noticeably extend or prevent re-crystallization. Pirfenidone dissolution time is reduced by heating and appears to be stable at this temperature during the dissolution process. Thus, heating pirfenidone formulations can be beneficial in a manufacturing process embodiments to overcome the slower dissolution observed at ambient temperature.

Example 6: Pharmacokinetics and Lung-Tissue Distribution

Sprague-Dawley rats (300-350 grams) were administered pirfenidone by either the oral (gavage) or aerosol (intratracheal Penn Century MicroSprayer® nebulizing catheter) routes. For oral administration, 50 mg pirfenidone was dissolved in 3.33 mL distilled water containing 0.5% CMC to a final concentration of 15 mg/mL. Solutions were vortexed until all crystals dissolved. Rats were administered 70 mg/kg pirfenidone (~1.4 mL). Plasma samples were taken at pre-dose, 0.08, 0.16, 0.25, 0.5, 0.75, 1.0, 1.5, 2, 4, and 6 hours post dosing. For lung tissue samples, eight additional rats were also dosed 70 mg/kg by the oral route. Lungs were taken at pre-dose 0.08, 0.5, 2, and 4 hours post dosing. Materials were extracted and pirfenidone quantitated as µg/mL plasma and µg/gram lung tissue. For aerosol administration, 60 mg pirfenidone was dissolved in 10 mM phosphate buffer, pH 6.2 containing 81 mM $MgCl_2$ (1:1 pirfenidone to magnesium). Rats were administered 5 mg/kg pirfenidone (~100 µL) by nebulizing catheter. Plasma samples were taken at pre-dose, 0.08, 0.16, 0.25, 0.5, 0.75, 1.0, 1.5, 2, 4, and 6 hours post dosing. For lung tissue samples, eight additional rats were also dosed 70 mg/kg by the oral route. Lungs were taken at pre-dose 0.08, 0.5, 2, and 4 hours post dosing. Materials were extracted and pirfenidone quantitated as µg/mL plasma and µg/gram lung tissue. Results from these studies are shown in Table 15.

TABLE 15

Pirfenidone pharmacokinetics and tissue distribution following oral and aerosol administration to rats.

| | | Aerosol Measured[a] | | Oral |
|---|---|---|---|---|
| Rat dose (mg/kg) | | 1 | 5 | 70 |
| Lung | Cmax[b] | 101 | 508 | 3.6 |
| | $T_{1/2}$[c] | <1, 45 | <1, 45 | 45 |
| | AUC[d] | 5.2 | 25.4 | 4.3 |
| | TOE[e] | 5 | 84 | 89 |
| Plasma | Cmax[f] | 1.1 | 7.0 | 8.1 |
| | $T_{1/2}$ | 30 | 30 | 30 |
| | $AUC_{0-6\ hrs}$[g] | 0.9 | 4.5 | 13.5 |

[a]Bolus aerosol intratracheal delivery
[b]$C_{max}$: Lung tissue (µg/g) immediate post-dose calculated from the direct-lung delivered dose. All other time points measured. Plasma measured (µg/mL)
[c]$T_{1/2}$: Minutes (aerosol = α, β; oral = α only observed)
[d]AUC: Lung tissue (mg · hr/kg for time >1 µg/g)
[e]TOE: Time of exposure as minutes over 1 µg/g lung tissue)
[f]Cmax: Plasma (µg/mL)
[g]$AUC_{0-6\ hrs}$: Plasma (mg · hr/L)

Example 7: Pharmacokinetics and Tissue Distribution of Co-Solvent Formulations To assess the pharmacokinetics and tissue distribution of co-solvent formulations (described in Table 9), Sprague-Dawley rats (350-400 grams) in triplicate were administered pirfenidone by bolus aerosol (intratracheal Penn Century MicroSprayer® nebulizing catheter). Rats were dosed about 4 mg/kg pirfenidone (~150 µL) by nebulizing catheter. Plasma samples, and entire lungs, hearts and kidneys were taken at pre-dose, 0.033, 0.067, 0.1, 0.167, 0.333, 0.667, 1.0, 1.5, 2, and 2.5 hours post dosing. Materials were extracted and pirfenidone quantitated as µg/mL plasma and µg/gram lung, heart or kidney tissue. Results from these studies are shown in Table 16 thru 19. No adverse events were noted in these studies.

TABLE 16

Pirfenidone Pharmacokinetics and Lung Tissue Distribution - Co-Solvent-Based Formulation Study (Dosing group formulations listed in Table 9)

| Analyte | Time (hr) | Group 1 Mean µg/gram | Group 2 Mean µg/gram | Group 3 Mean µg/gram | Group 4 Mean µg/gram | Group 5 Mean µg/gram | Group 6 Mean µg/gram |
|---|---|---|---|---|---|---|---|
| PIRFENIDONE | 0[A] | | | 393.72 | | | |
| | 0.0333 | 14.28 | 15.73 | 22.23 | 12.63 | 19.66 | 8.81 |
| | 0.0667 | 10.40 | 8.53 | 17.26 | 7.77 | 10.70 | 7.93 |
| | 0.1 | 7.53 | 5.98 | 7.34 | 7.50 | 5.83 | 6.83 |
| | 0.167 | 5.36 | 5.71 | 6.16 | 5.23 | 8.78 | 5.17 |
| | 0.333 | 4.15 | 3.79 | 3.79 | 3.66 | 4.70 | 3.83 |
| | 0.667 | 2.09 | 2.41 | 2.43 | 2.40 | 1.91 | 2.28 |
| | 1 | 1.53 | 1.24 | 1.03 | 1.20 | 1.44 | 1.22 |
| | 1.5 | 0.60 | 0.71 | 0.46 | 0.67 | 0.48 | 0.37 |
| | 2 | 0.26 | 0.35 | 0.32 | 0.21 | 0.26 | 0.31 |
| | 2.5 | 0.08 | 0.13 | 0.13 | 0.10 | 0.07 | 0.22 |
| 5-CARBOXY-N-phenyl-5-1H-pyridone | 0 MIN | | | 0.00 | | | |
| | 0.0333 H | 0.12 | NOT TESTED | 0.05 | NOT TESTED | 0.17 | 0.17 |
| | 0.0667 H | 0.13 | | 0.36 | | 0.42 | 0.43 |
| | 0.100 H | 0.48 | | 0.55 | | 0.35 | 0.37 |
| | 0.167 H | 0.49 | | 0.86 | | 0.53 | 0.64 |
| | 0.333 H | 0.96 | | 1.09 | | 1.32 | 0.94 |
| | 0.667 H | 0.96 | | 0.81 | | 0.96 | 0.92 |
| | 1 H | 0.73 | | 0.70 | | 0.75 | 0.78 |
| | 1.50 H | 0.48 | | 0.52 | | 0.45 | 0.43 |
| | 2 H | 0.21 | | 0.32 | | 0.18 | 0.24 |
| | 2.50 H | 0.10 | | 0.14 | | 0.10 | 0.14 |

[A]Average of 18 immediate post-dose measurements

TABLE 17

Pirfenidone Plasma Pharmacokinetics - Co-Solvent-Based Formulation Study (Dosing group formulations listed in Table 9)

| Analyte | Time (hr) | Group 1 Mean µg/mL | Group 2 Mean µg/mL | Group 3 Mean µg/mL | Group 4 Mean µg/mL | Group 5 Mean µg/mL | Group 6 Mean µg/mL |
|---|---|---|---|---|---|---|---|
| PIRFENIDONE | 0 | 0.03 | 0.01 | 0.06 | 0.01 | 0.02 | 0.06 |
| | 0.0333 | 6.80 | 6.20 | 7.47 | 7.23 | 7.72 | 6.84 |
| | 0.0667 | 6.09 | 6.04 | 6.52 | 7.43 | 7.05 | 7.31 |
| | 0.1 | 5.72 | 5.12 | 5.39 | 3.98 | 5.55 | 5.75 |
| | 0.167 | 5.56 | 5.60 | 5.51 | 4.75 | 4.59 | 5.31 |
| | 0.333 | 3.94 | 4.53 | 4.53 | 3.98 | 3.84 | 4.26 |
| | 0.667 | 2.74 | 3.02 | 2.54 | 2.41 | 2.24 | 2.87 |
| | 1 | 1.93 | 1.65 | 1.39 | 1.45 | 1.68 | 1.49 |
| | 1.5 | 0.67 | 0.80 | 0.54 | 0.85 | 0.59 | 0.43 |
| | 2 | 0.29 | 0.37 | 0.36 | 0.22 | 0.29 | 0.33 |
| | 2.5 | 0.09 | 0.12 | 0.11 | 0.11 | 0.08 | 0.13 |

TABLE 18

Pirfenidone Pharmacokinetics and Heart Tissue Distribution - Co-Solvent-Based Formulation Study (Dosing group formulations listed in Table 9)

| Analyte | Time (hr) | Group 1 Mean µg/gram | Group 2 Mean µg/gram | Group 3 Mean µg/gram | Group 4 Mean µg/gram | Group 5 Mean µg/gram | Group 6 Mean µg/gram |
|---|---|---|---|---|---|---|---|
| PIRFENIDONE | 0 | 0.02 | 0.19 | NOT TESTED | | | 0.08 |
| | 0.0667 | 7.90 | 5.92 | | | | 6.32 |
| | 0.167 | 4.91 | 4.10 | | | | 4.95 |
| | 0.333 | 3.85 | 3.13 | | | | 3.43 |
| | 0.667 | 1.80 | 2.19 | | | | 2.22 |
| | 1 | 1.40 | 1.10 | | | | 1.23 |
| | 1.5 | 0.60 | 0.69 | | | | 0.35 |
| | 2.5 | 0.09 | 0.12 | | | | 0.12 |

TABLE 19

Pirfenidone Pharmacokinetics and Kidney Tissue Distribution - Co-Solvent-Based Formulation Study (Dosing group formulations listed in Table 9)

| Analyte | Time (hr) | Group 1 Mean µg/gram | Group 2 Mean µg/gram | Group 3 Mean µg/gram | Group 4 Mean µg/gram | Group 5 Mean µg/gram | Group 6 Mean µg/gram |
|---|---|---|---|---|---|---|---|
| PIRFENIDONE | 0 | 0.01 | 0.47 | NOT TESTED | | | 0.27 |
| | 0.0667 | 9.88 | 10.79 | | | | 12.90 |
| | 0.167 | 6.62 | 8.30 | | | | 6.65 |
| | 0.333 | 4.87 | 7.44 | | | | 4.87 |
| | 0.667 | 2.86 | 3.31 | | | | 3.53 |
| | 1 | 1.93 | 1.75 | | | | 1.71 |
| | 1.5 | 0.95 | 0.96 | | | | 0.57 |
| | 2.5 | 0.21 | 0.18 | | | | 0.20 |

Figure 1:
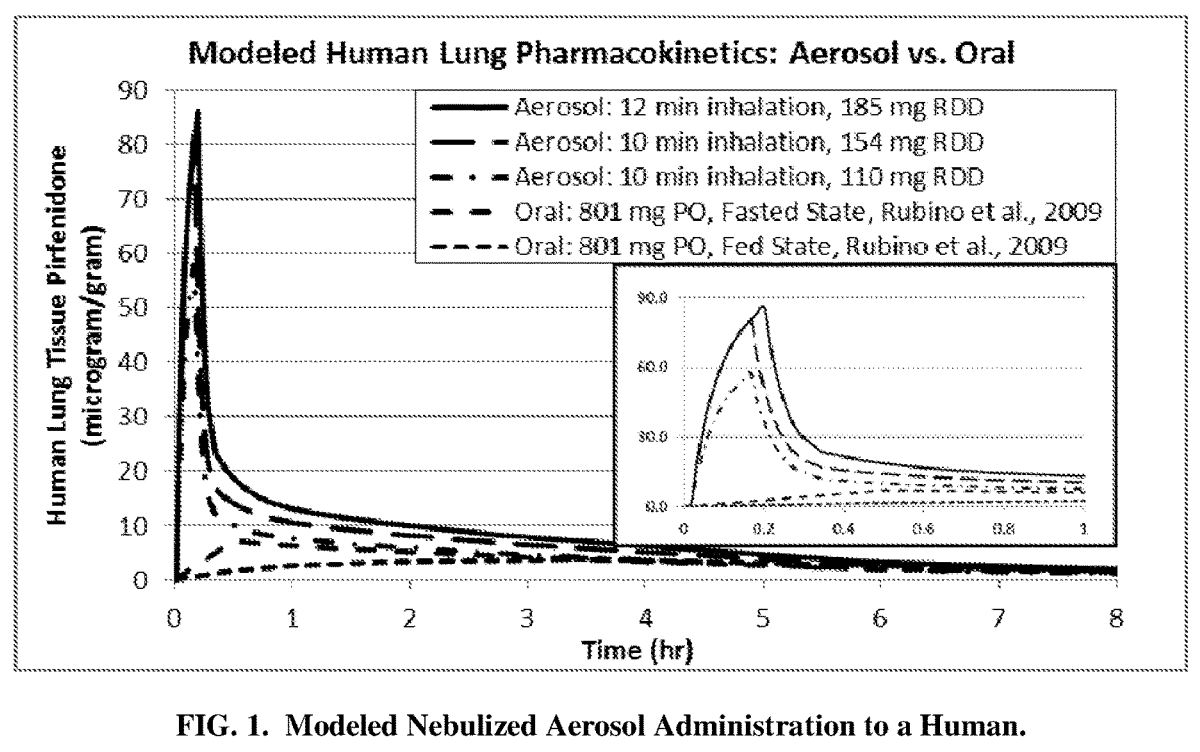

Results from the co-solvent effects tissue distribution studies show that the presence of up to 8% ethanol with 16% propylene glycol to change the tissue or plasma pharmacokinetic profile compared to a 0.4% sodium chloride formulation. Further, these results show a delayed appearance of 5-Carboxy-pirfenidone (the primary pirfenidone liver metabolite). Comparing the initial rapid elimination of pirfenidone from the lung tissue and parallel appearance of pirfenidone in the plasma suggest that direct pulmonary administration may be a good route for systemic administration of pirfenidone. The delayed appearance of 5-Carboxy-pirfenidone metabolite supports this hypothesis in that this metabolite serves as a marker for re-circulation of pirfenidone to the lung and other tissues following direct aerosol administration to the lung. Further, as suggested in Tables 15 and 16 and supported by the modeled data in FIG. 1 and Table 20, re-circulated pirfenidone likely contributes to long-term pirfenidone levels in the lung and other tissues of potential efficacy.

To understand pirfenidone human lung tissue distribution and associated pharmacokinetics following a 10-12 minute aerosol administration from a nebulizer, measured rat pharmacokinetic and lung tissue distribution data following bolus nebulizing catheter administration was scaled. Briefly, using allometric scaling, rat aerosol lung data and plasma delivery was scaled to humans. Rat data was taken from Table 16 and 17. Allometric scaling used parameters established in the US FDA Guidance for Industry—Estimating the Maximum Safe Starting Dose in Initial Clinical Trials for Therapeutics in Adult Healthy Volunteers. July, 2005, and Caldwell et al., European Journal of Drug Metabolism and Pharmacokinetics, 2004, Vol. 29, No. 2, pp. 133-143. For comparative purposes, human plasma pharmacokinetic data resulting from oral administration was taken directly Rubino et al., 2009. For oral data, fed-state human data was used. To model plasma pirfenidone pharmacokinetics where plasma pirfenidone was delivered from aerosol administration, pharmacokinetics data from fasting-state humans was used (Rubino et al., 2009). Inhaled aerosol-derived plasma pirfenidone levels were calculated based upon an assumed 100% bioavailability of inhaled, respirable-deposited pirfenidone to a 5,000 mL total blood volume. The contribution of plasma-derived pirfenidone (whether from oral or aerosol inhalation dosing) to lung tissue distribution and pharmacokinetics assumed at any given time 50% of plasma pirfenidone was delivered to the lung tissue. By example, a plasma level of 10 μg/mL contributed 5 μg/gram pirfenidone to the lung tissue. Results of this analysis are shown in FIG. 1 and Table 20.

Aerosol deliver parameters based on Table 10 formulation characterization in high-efficiency, mesh-based nebulizers (Tables 11-13). Respirable delivered dose (RDD) calculated by the product of fine particle fraction (FPF, %≤5 microns) and inhaled mass. An about 110 mg RDD was calculated from a 5 mL device-loaded dose of a 40 mg/mL pirfenidone formulation (200 mg loaded dose). The FPF and inhaled mass were 85% and 67%, respectively. Inhaled mass was calculated based upon breathing pattern. A 1:1 inhalation: exhalation breathing pattern (e.g. a 2 second inhalation followed by a 2 second exhalation) using the eFlow device and 35-head is predicted to produce an inhaled mass of about 67%. From this, a 2:1 breathing pattern (e.g., a 4 second inhalation followed by a 2 second exhalation) may produce an inhaled mass between about 74% and about 80%. Using the inhaled mass of 74% and the FPF of 85%, a 200 mg device-loaded dose may produce an RDD of about 125 mg. Similarly, the inhaled mass of 80% may produce an RDD of about 136 mg from a 200 mg device-loaded dose. Continuing, a 3:1 breathing pattern (e.g., a 6 second inhalation followed by a 2 second exhalation) may produce an inhaled mass between about 80% and about 87%. Using the inhaled mass of 87% and the FPF of 85%, a 200 mg device-loaded dose may produce an RDD of about 148 mg. In some embodiments, the RDD may be further increased or decreased by additional means: by non-limiting example, changing the device-loaded volume and/or changing the formulation pirfenidone concentration. In some embodiments, increasing the formulation concentration to 50 mg/mL and using the 5 mL device-loaded volume will provide a 250 mg device-loaded dose. Using the FPF of 85% and inhaled mass of about 67%, a 250 mg device-loaded dose may produce an RDD of about 142 mg, a 74% inhaled mass may produce an RDD of about 157 mg, a 80% inhaled mass may produce an RDD of about 170 mg, and a 87% inhaled mass may produce an RDD of about 185 mg. Additional dose escalations are possible with increased co-solvent addition to the pirfenidone formulation. Similarly, dose de-escalations are possible with reduced device-loaded dose (reduced volume and/or reduced pirfenidone formulation concentration) and/or less-efficient breathing pattern. While allometric scaling is an established means to predict pharmacokinetic parameters and dose scaling between animals and humans, precedent exists that supports human-inhaled therapies remaining in the lung significantly longer than the duration predicted by allometric scaling. This possibility may also result in longer lung pirfenidone residence time and may also translate to reduced plasma exposure.

were prepared in 0.45% sodium chloride solution and were administered as described in Table 21.

TABLE 21

Extended-duration intratracheal and oral pharmacokinetic study dose groups

| Group Numbers | Group Designation | Dose Level of Pirfenidone (mg/kg) | Dose Formulation Concentration (mg/mL) | No. of Male Animals |
|---|---|---|---|---|
| 1 | IT - Low Dose | 2.5 | 3.75 | 32 |
| 2 | IT - Mid Dose | 5 | 7.5 | 32 |
| 3 | IT - High Dose | 10 | 15 | 32 |
| 4 | Oral - Low Dose | 10 | 1 | 32 |
| 5 | Oral - Mid Dose | 30 | 3 | 32 |
| 6 | Oral - High Dose | 100 | 10 | 32 |
| 7 | Control | N/A | N/A | 4 |

Plasma samples and entire lungs were taken at pre-dose, 2, 4, 6, 10, 30, 60 and 120 minutes post dosing. Materials were extracted and pirfenidone quantitated as mcg/mL plasma and μg/gram lung tissue. Results from these studies are shown in Table 22. No adverse events were noted in these studies.

TABLE 20

Modeled human pirfenidone pharmacokinetics and tissue distribution.

| | Aerosol (RDD[a]) | | | | | | Oral (801 mg) | | | |
|---|---|---|---|---|---|---|---|---|---|---|
| | 110 mg | | 154 mg | | 185 mg | | Fed-State | | Fasted-State | |
| Parameter | LT | P | LT | P | LT | P | LT | P | LT | P |
| Cmax[b] | 57.5 | 17.7 | 71.2 | 24.8 | 85.8 | 30.0 | 3.9 | 7.9 | 7.1 | 14.2 |
| AUC[c] | 43.4 | 68.9 | 61.0 | 96.8 | 75.1 | 118.3 | 22.1 | 58.9 | 33.9 | 67.7 |
| TOE[d] | 8.7 | — | 9.9 | — | 10.4 | — | 10.4 | — | 10.0 | — |
| $T_{1/2\ alpha}$ (min) | 5 | — | 5 | — | 5 | — | — | — | — | — |
| $T_{1/2\ beta}$ (hr)[e] | 2.5 | 2.5 | 2.5 | 2.5 | 2.5 | 2.5 | 2.4 | 2.4 | 2.5 | 2.5 |
| $T_{1/2\ Absorption}$ (hr)[f] | — | 0.1 | — | 0.1 | — | 0.1 | — | 1.8 | — | 0.4 |

LT = lung tissue;
P = plasma.
[a]RDD: respirable delivered dose = fine particle fraction (FPF; % particles <5 microns) × inhaled mass
[b]Cmax: Lung tissue = microgram/gram; plasma = microgram/mL
[c]AUC: Expressed as AUC over 0-18 hours, Lung tissue in mg · hr/kg and plasma expressed in mg · hr/L.
[d]TOE: Time of exposure measured as minutes over 1 microgram/gram lung tissue
[e]$T_{1/2\ beta}$: Lung tissue pirfenidone levels and associated beta phase lung tissue $T_{1/2}$ derived solely from plasma-pirfenidone and hence, plasma pirfenidone $T_{1/2}$. Aerosol = Rubino et al., 2009 fasted-state; Oral = Rubino et al., 2009
[f]$T_{1/2\ absorption}$: Aerosol = modeled from allometrically-scaled bolus aerosol rat data; Oral = Rubino et al., 2009.

Example 8: Pharmacokinetics and Lung-Tissue Distribution

Previous intratracheal aerosol delivery (see Example 6) was performed as a single bolus instillation just above the first bifurcation of the lung. For in vivo efficacy studies, an attempt was made to mimic tidal inhaled breathing by splitting the dose into equal parts and administering as before, but over a 2 minute period. For this work, Wistar rats (300-500 grams) in groups of four were either administered pirfenidone by bolus aerosol (intratracheal Penn Century MicroSprayer® nebulizing catheter) split into 6 equal administrations of 50 mcL/animal (approximately 20 seconds apart) for a total of 300 mcL/animal over a total of 2 minutes, or by bolus oral gavage (300 mcL/animal). Doses

TABLE 22

Extended-duration intratracheal and oral pharmacokinetic results

| | Intratracheal Aerosol (mg/kg) | | | Oral Gavage (mg/kg) | | |
|---|---|---|---|---|---|---|
| | 2.5 | 5 | 10 | 10 | 30 | 100 |
| | Lung Tissue | | | | | |
| Cmax | 14.4 | 27.9 | 61.1 | 3.5 | 9.8 | 33.6 |
| $AUC_{(0-2\ hr)}$ | 3.5 | 6.6 | 14.5 | 4.9 | 13.5 | 27.9 |

TABLE 22-continued

Extended-duration intratracheal and oral pharmacokinetic results

|  | Intratracheal Aerosol (mg/kg) | | | Oral Gavage (mg/kg) | | |
| --- | --- | --- | --- | --- | --- | --- |
|  | 2.5 | 5 | 10 | 10 | 30 | 100 |
| Plasma | | | | | | |
| Cmax | 3.4 | 8.8 | 22.8 | 3.6 | 9.8 | 26.3 |
| $AUC_{(0-2\ hr)}$ | 3.2 | 5.8 | 14.6 | 4.4 | 12.9 | 24.2 |

Example 9. In Vivo Efficacy—Bleomycin Model of Pulmonary Fibrosis

To compare anti-fibrotic efficacy between extended-duration intratracheal, direct-lung aerosol administration and oral gavage, the bleomycin model of pulmonary fibrosis was performed. Doses for this study were selected based upon pharmacokinetic parameters obtained in Table 22 (from Example 8). Briefly, Wistar rats (175-225 grams) were administered bleomycin by the intratracheal route using a Penn Century MicroSprayer® catheter. On the seventh day following bleomycin exposure, animals initiated treatment with either saline or pirfenidone. Animals were dosed once a day on days 7 through 28, and euthanized on day 29. Pirfenidone was administered either intratracheally using Penn Century MicroSprayer catheter or by oral gavage. Sham and bleomycin control groups received either no treatment or intratracheal saline by Penn Century MicroSprayer catheter. While dosing more frequently (or less frequently) may improve the observed effects, anesthesia required for intratracheal administration reduced animal weight gain (reduced food intake) and, thus limited dosing to once a day for this study. Because anesthesia reduced weight gain, all study animals (intratracheal, oral and control) received once-a-day isoflurane using the same technique and duration. Twelve animals were enrolled into each dosing group. For oral pirfenidone, one group received 30 mg/kg by oral gavage, while the second group received 100 mg/kg. For intratracheal pirfenidone administration, one group received 0.9 mg/kg (targeted to match 30 mg/kg oral lung tissue Cmax), a second group received 3.0 mg/kg (targeted to match 100 mg/kg oral lung tissue Cmax), and a third group received 6.4 mg/kg (targeted to match 30 mg/kg oral plasma AUC). Oral gavage was administered in a single 300 mcL volume. Due to technical restrictions, instead of the mg/kg dose being equally split between six 50 mcL administrations over 2 minutes, intratracheal administration was performed with three equal 50 mcL volumes administered every 40 seconds over the same period. For dose selection, data from Table 22 was extrapolated. On day 29, animals were euthanized. Right lungs were extracted and measured for hydroxyproline content, while left lungs were subjected to histology. Histological sections were stained with picrosirius red and scored for lung tissue fibrosis. Twenty random photographs of each stained lung tissue section were taken, blinded and scored by an independent review panel. Observations were pooled for analysis. Data and results from these studies are shown in Tables 23, 24, 25, 26 and 27, and FIGS. 3 and 4.

TABLE 23

Bleomycin study doses and resultant pharmacokinetic parameters

|  |  | Lung Tissue | | Plasma | |
| --- | --- | --- | --- | --- | --- |
| Group[a] | Pirfenidone (mg/kg) | Cmax (mcg/g) | $AUC_{0-2\ hrs}$ (mcg*hr/g) | Cmax (mcg/mL) | $AUC_{0-2\ hrs}$ (mcg*hr/mL) |
| Bleomycin + PO Pirfenidone | 30 | 11.8 | 18.2 | 10.3 | 16.6 |
| Bleomycin + PO Pirfenidone | 100 | 33.6 | 34.4 | 21.7 | 29.6 |
| Bleomycin + IT Pirfenidone | 0.9 | 11.6 | 2.6 | 2.6 | 3.0 |
| Bleomycin + IT Pirfenidone | 3.0 | 33.5 | 7.3 | 10.9 | 7.7 |
| Bleomycin + IT Pirfenidone | 6.4 | 71.5 | 15.5 | 23.3 | 16.5 |

[a]IT: intratracheal; PO: oral gavage.

TABLE 24

Right lung hydroxyproline content

| Group[a] | Pirfenidone (mg/kg) | Average Hydroxyproline (mg/right lung) | STDV Hydroxyproline (mg/right lung) |
| --- | --- | --- | --- |
| Sham | 0 | 1.87 | 0.11 |
| Sham + IT saline | 0 | 1.90 | 0.13 |
| Bleomycin | 0 | 3.22 | 0.15 |
| Bleomycin + IT saline | 0 | 3.58* | 0.35 |
| Bleomycin + PO Pirfenidone | 30 | 3.65 | 0.67 |
| Bleomycin + PO Pirfenidone | 100 | 3.73 | 0.79 |
| Bleomycin + IT Pirfenidone | 0.9 | 2.88* | 0.68 |
| Bleomycin + IT Pirfenidone | 3.0 | 3.56 | 0.49 |
| Bleomycin + IT Pirfenidone | 6.4 | 3.50 | 0.32 |

[a]IT: intratracheal; PO: oral gavage.
*P-value = 0.041.

TABLE 25

Right lung Hydroxyproline content - Intratracheal aerosol versus oral Gavage

| Group[a] | Pirfenidone mg/kg | Difference from bleomycin control[b] | |
|---|---|---|---|
| | | Average Hydroxyproline (mg/right lung) | STDV Hydroxyproline (mg/right lung) |
| Bleomycin + PO Pirfenidone | 30 | 0.43*,** | 0.67 |
| Bleomycin + PO Pirfenidone | 100 | 0.51*** | 0.79 |
| Bleomycin + IT Pirfenidone | 0.9 | −0.70*,**** | 0.68 |
| Bleomycin + IT Pirfenidone | 3.0 | −0.02**,**** | 0.49 |
| Bleomycin + IT Pirfenidone | 6.4 | −0.08***,**** | 0.32 |

[a]IT: intratracheal, PO: oral gavage;
[b]mg/right lung hydroxyproline sham values were subtracted from treated values. Sham-subtracted treated values were then subtracted from bleomycin control values.
*P-value = 0.012,
**P-value = 0.084,
***P-value = 0.075,
****P-value = 0.049 and 0.053 for IT 0.9 mg/kg to IT 3.0 mg/kg and IT 6.4 mg/kg, respectively.

TABLE 26

Fibrosis Score - Picrosirius Red-Stained Left Lung Sections

| Group[a] | Pirfenidone (mg/kg) | Average Fibrosis Score | STDV FibrosisScore |
|---|---|---|---|
| Sham | 0 | 0.46 | 0.14 |
| Sham + IT saline | 0 | 0.36 | 0.16 |
| Bleomycin | 0 | 2.43 | 0.60 |
| Bleomycin + IT saline | 0 | 3.40 * | 0.69 |
| Bleomycin + PO Pirfenidone | 30 | 3.11 | 0.65 |
| Bleomycin + PO Pirfenidone | 100 | 3.61 | 0.85 |
| Bleomycin + IT Pirfenidone | 0.9 | 2.88 * | 1.00 |
| Bleomycin + IT Pirfenidone | 3.0 | 3.66 | 1.19 |
| Bleomycin + IT Pirfenidone | 6.4 | 3.47 | 1.46 |

[a]IT: intratracheal; PO: oral gavage.
* P-value = 0.144.

TABLE 27

Fibrosis Score - Intratracheal aerosol versus oral Gavage

| Group[a] | Pirfenidone mg/kg | Difference from bleomycin control[b] | |
|---|---|---|---|
| | | Average Fibrosis Score | STDV Fibrosis Score |
| Bleomycin + PO Pirfenidone | 30 | 0.68 *, ** | 0.65 |
| Bleomycin + PO Pirfenidone | 100 | 1.18 *** | 0.85 |
| Bleomycin + IT Pirfenidone | 0.9 | −0.53 *, **** | 1.00 |
| Bleomycin + IT Pirfenidone | 3.0 | 0.26 ***, **** | 1.19 |
| Bleomycin + IT Pirfenidone | 6.4 | 0.07 **, **** | 1.46 |

[a]IT: intratracheal, PO: oral gavage;
[b]fibrosis score sham values were subtracted from treated values. Sham-subtracted treated values were then subtracted from bleomycin control values.
* P-value = 0.007,
** P-value = 0.214,
*** P-value = 0.042,
**** P-value = 0.121 and 0.214 for IT 0.9 mg/kg to IT 3.0 mg/kg and IT 6.4 mg/kg, respectively.

Doses selected for this study targeted critical pharmacokinetic parameters from the comparator oral route (matching lung tissue Cmax or plasma AUC). These targets were selected from a pharmacokinetic study wherein lung tissue and plasma were collected and pirfenidone levels were compared. In these studies, lung tissue Cmax following intratracheal administration was always the first collected time point. It is important to consider that the duration of time required to collect this first lung tissue may not accurately capture the true lung Cmax. In our studies, collection time was about 1 minute. It was this pharmacokinetic point that the above Cmax for dosing was selected. If it was possible to collect lung tissue earlier, the Cmax may be higher. As the Penn Century MicroSprayer catheter delivers nearly the entire loaded dose, the possible delivered Cmax in these studies may be higher. By example, a 250 gram rat lung weighs about 1.5 grams. Delivering a 0.9 mg/kg dose (225 mg) to this animal would result in up to a 150 mcg/gram lung tissue Cmax. In this study, we divided the dose into thirds. Therefore, the possible Cmax was about 50 mcg/gram lung tissue (about 5× that actually delivered by the 30 mg/kg oral dose). To the interpretation that large systemic pirfenidone exposure reduces lung efficacy, a nearly 150 to 200 mg/kg oral dose would be required to achieve a 50 mcg/gram lung tissue Cmax, a dose that the oral safety profile will not permit.

From these results, and other nonclinical and clinical experience with the pirfenidone, it appears lung Cmax is important for anti-fibrotic efficacy. Further, while Cmax is important, high systemic exposure reduces this effect. While oral dosing delivers a very large plasma AUC, only a small lung tissue Cmax is obtained. Comparatively, to achieve a low lung tissue dose, relatively small aerosol doses can be delivered directly to the lung to achieve high lung tissue Cmax levels with lower systemic exposure; an administration profile not possible with oral delivery.

Results from this study show that pirfenidone delivered directly to the lung is more efficacious (less fibrosis and less hydroxyproline). However, large systemic pirfenidone exposure either directly or indirectly reduces this effect. More specifically, the oral route requires a large oral dose to achieve a relatively small lung tissue Cmax. Delivering a similar Cmax without the large systemic dose provides increased efficacy. However, further escalating this direct lung dose, which results in increased systemic exposure, reduces this effect. Coupling these results with other published observations (Swaney et al. Br. J. Pharmacol. 160(7):1699-713, 2010; Tian et al., Chin. Med. Sci. J. 21(3):145-51, 2006; and Trivedi et al., Nanotechnology. 23(50):505101, 2012), it is evident that pirfenidone follows an AUC-dependent, U-shaped dose response. Specifically, a high lung tissue Cmax is important for lung tissue anti-fibrotic efficacy. However, this positive effect appears dependent upon an associated small plasma AUC; the larger the plasma AUC, the lower the efficacy. FIGS. 3 and 4 show the AUC-dependent, U-shaped pirfenidone dose response. In practice, the oral route of administration is not capable of meeting this U-shaped-restricted dose response. Safety and tolerability prevent further dose escalation of the 801 mg/dose oral medicine (Esbriet®). These data and other published studies (Swaney et al., 2010, Tian et al., 2006, and Trivedi et al., 2012) indicate that if oral escalation were possible, the associated increase in plasma AUC may reduce or negate any associated lung tissue Cmax advantage. Comparatively, inhalation of small aerosol pirfenidone doses enable dosing within the confines of the U-shaped dose response; high lung tissue Cmax, low plasma AUC. To illustrate these findings, possible human lung tissue and plasma pharmacokinetics following tidal-breath-inhaled aerosol administration were again modeled (FIG. 5). As mentioned, safety and tolerability restrict further escalation of the 801 mg oral pirfenidone dose (801 mg taken three times a day). These safety and/or tolerability restrictions may be associated with plasma AUC, plasma Cmax, gastrointestinal exposure or a combination of these events. For purposes of the model, the plasma AUC resulting from an 801 mg oral pirfenidone dose was established as the limit for inhaled aerosol pirfenidone administration. However, this limitation could also be set as the plasma Cmax or a combination of these pharmacokinetic parameters.

Aerosol deliver parameters for the FIGS. 2 and 5 models were based on high-efficiency, mesh-based nebulizer characterization (Table 12). The lung half-life following aerosol delivery was scaled from both bolus intratracheal (Examples 6 and 7) and extended-duration, intratracheal pirfenidone pharmacokinetic results (Example 8). Respirable delivered dose (RDD) calculated by the product of fine particle fraction (FPF, %≤5 microns) and inhaled mass. Using a pulmonary half-life obtained from bolus intratracheal pharmacokinetic results, the modeled human pharmacokinetics following about 5 minute tidal inhalation of a 47 mg RDD was calculated from a 3.6 mL device-loaded dose of 25 mg/mL pirfenidone formulation (90 mg loaded dose). For this non-limiting example, a FPF of 78% and inhaled mass of 67% was used. Using these numbers, a 90 mg device-loaded dose may produce an RDD of about 47 mg (Table 26 and FIG. 2). Using a pulmonary half-life obtained from extended-duration, intratracheal pharmacokinetic results the modeled human pharmacokinetics following tidal inhalation of 120 mg, 50 mg and 2.5 mg RDDs were again calculated (FIG. 5). An about 120 mg RDD was calculated from a 3.6 mL device-loaded dose of a 68 mg/mL pirfenidone formulation (230 mg loaded dose). For this non-limiting example, a FPF of 78% and inhaled mass of 67% was used. Using these numbers, a 230 mg device-loaded dose may produce an RDD of about 120 mg. The about 50 mg RDD was calculated from a 3.6 mL device-loaded dose of a 27 mg/mL pirfenidone formulation (96 mg loaded dose). Similarly, the 2.5 mg RDD was calculated from a 0.66 mL device-loaded dose of a 7.2 mg/mL pirfenidone formulation (4.8 mg loaded dose). This later dose was modeled to be delivered in 1 minute. Additional dose escalations are possible with increased co-solvent addition to the pirfenidone formulation. Similarly, dose de-escalations are possible with reduced device-loaded dose (reduced volume and/or reduced pirfenidone formulation concentration) and/or less-efficient breathing pattern. Reductions in pirfenidone formulation concentration below about 20 mg/mL may not require co-solvents, but may include buffer, permeant ion, osmolality-adjusting agent or taste-masking agent. Pulmonary elimination and plasma exposure assume 100% bioavailability following inhaled aerosol administration. Thus, it is possible that actual human plasma pirfenidone exposure may be less following human inhaled administration.

TABLE 28

Modeled human pirfenidone pharmacokinetics and tissue distribution.

| | Tidal-Inhaled Aerosol (47 mg RDD[a]) Alpha $T_{1/2}$ = 3.5 min | | Oral (801 mg)* Fed-State | | Oral (801 mg)* Fasted-State | |
|---|---|---|---|---|---|---|
| Parameter | Lung Tissue | Plasma | Lung Tissue | Plasma | Lung Tissue | Plasma |
| Cmax[b] | 52.2 | 7.8 | 3.9 | 7.9 | 7.1 | 14.2 |
| AUC (0-18 hrs)[c] | 42.3 | 37.2 | 22.1 | 58.9 | 33.9 | 67.7 |
| TOE (hrs > 1 μg/g)[d] | 9.4 | — | 10.4 | — | 10.0 | — |
| $T_{1/2\ alpha}$ (min) | 3.5 | — | — | — | — | — |
| $T_{1/2\ beta}$ (hr)[e] | 2.5 | 2.5 | 2.4 | 2.4 | 2.5 | 2.5 |
| $T_{1/2}$ Absorption (hr)[f] | — | 0.4 | — | 1.8 | — | 0.4 |

[a]RDD: respirable delivered dose = fine particle fraction (FPF; % particles <5 microns) × inhaled mass.

[b]Cmax: Lung tissue = microgram/gram; plasma = microgram/mL.

[c]AUC: Expressed as AUC over 0-18 hours, Lung tissue in mg · hr/kg and plasma expressed in mg · hr/L.

[d]TOE: Time of exposure measured as minutes over 1 microgram/gram lung tissue.

[e]$T_{1/2\ beta}$: Lung tissue pirfenidone levels and associated beta phase lung tissue $T_{1/2}$ derived solely from plasma-pirfenidone and hence, plasma pirfenidone $T_{1/2}$. Aerosol = Rubino et al., 2009 fasted-state; Oral = Rubino et al., 2009.

[f]$T_{1/2\ absorption}$: Aerosol = modeled from allometrically-scaled bolus aerosol rat data; Oral = Rubino et al., 2009.

An additional clinical consideration is the rat plasma AUC showing non-efficacy in the bleomycin model. By non-limiting example, as shown in FIGS. 3 and 4, a 3.0 mg/kg intratracheal, direct lung aerosol rat dose results in a plasma AUC that has no observed pirfenidone efficacy. Only lower delivered doses show anti-fibrotic effect. Plasma AUCs obtained from higher intratracheal or oral doses appears to have similar non-efficacy or enhanced disease. Therefore, it could be argued that inhalation-delivered plasma AUCs less than that obtained from a 3 mg/kg intratracheal dose may be important to permit pirfenidone efficacy. Using allometric scaling (by total body surface area), a 3 mg/kg rat dose scaled to a 60 kg human results in a 29 mg human lung-delivered dose (assuming equal pulmonary elimination rate and 100% bioavailability). From this, a consideration in human doses may be that an RDD equivalent to a 29 mg intratracheal aerosol dose may result in a human plasma AUC representing the upper threshold of the U-shaped pirfenidone dose response curve. Using the extended-duration intratracheal pharmacokinetic data model, the possible achieved human lung tissue Cmax and plasma $AUC_{0\text{-}18\ hrs}$ following a 3 minute tidal-inhaled nebulized dose resulting in a 29 mg RDD is 43.2 mcg/gram lung tissue and 13.4 mcg·hr/mL, respectively.

Example 10: Pirfenidone Formulations for Low Concentration Dosage Forms

TABLE 29

Pirfenidone formulations for low concentration dosage forms

| Phosphate Formulations | Citrate Buffer Formulations | Water Formulations |
|---|---|---|
| 5 mM sodium phosphate, pH 7 (+/−0.5) | 5 mM citrate buffer, pH 5.5 (+/−0.5) | Water |
| 50 mM NaCl | 50 mM NaCl | 50 mM NaCl |
| 16 mg/mL pirfenidone | 16 mg/mL pirfenidone | 16 mg/mL pirfenidone |
| 5 mM sodium phosphate, pH 7 (+/−0.5) | 5 mM citrate buffer, pH 5.5 (+/−0.5) | Water |

TABLE 29-continued

| Pirfenidone formulations for low concentration dosage forms | | |
|---|---|---|
| Phosphate Formulations | Citrate Buffer Formulations | Water Formulations |
| 100 mM NaCl | 100 mM NaCl | 100 mM NaCl |
| 4 mg/mL pirfenidone | 4 mg/mL pirfenidone | 4 mg/mL pirfenidone |
| 5 mM sodium phosphate, pH 7 (+/−0.5) | 5 mM citrate buffer, pH 5.5 (+/−0.5) | Water |
| 43.3 mM MgCl2 | 43.3 mM MgCl2 | 43.3 mM MgCl2 |
| 16 mg/mL pirfenidone | 16 mg/mL pirfenidone | 16 mg/mL pirfenidone |
| 5 mM sodium phosphate, pH 7 (+/−0.5) | 5 mM citrate buffer, pH 5.5 (+/−0.5) | Water |
| 43.3 mM MgCl2 | 43.3 mM MgCl2 | 43.3 mM MgCl2 |
| 50 mM NaCl | 50 mM NaCl | 50 mM NaCl |
| 16 mg/mL pirfenidone | 16 mg/mL pirfenidone | 16 mg/mL pirfenidone |
| 5 mM sodium phosphate, pH 7 (+/−0.5) | 5 mM citrate buffer, pH 5.5 (+/−0.5) | Water |
| 10.8 mM MgCl2 | 10.8 mM MgCl2 | 10.8 mM MgCl2 |
| 4 mg/mL pirfenidone | 4 mg/mL pirfenidone | 4 mg/mL pirfenidone |
| 5 mM sodium phosphate, pH 7 (+/−0.5) | 5 mM citrate buffer, pH 5.5 (+/−0.5) | Water |
| 10.8 mM MgCl2 | 10.8 mM MgCl2 | 10.8 mM MgCl2 |
| 100 mM NaCl | 100 mM NaCl | 100 mM NaCl |
| 4 mg/mL pirfenidone | 4 mg/mL pirfenidone | 4 mg/mL pirfenidone |
| 5 mM sodium phosphate, pH 7 (+/−0.5) | 2% Ethanol | Water |
| 2% Ethanol | 4% Propylene Glycol | 2% Ethanol |
| 4% Propylene Glycol | 22 mg/mL pirfenidone | 4% Propylene Glycol |
| 22 mg/mL pirfenidone | | 22 mg/mL pirfenidone |
| 5 mM sodium phosphate, pH 7 (+/−0.5) | 5 mM citrate buffer, pH 5.5 (+/−0.5) | Water |
| 50 mM NaCl | 50 mM NaCl | 50 mM NaCl |
| 0.1-1.0 mM sodium saccharin | 0.1-1.0 mM sodium saccharin | 0.1-1.0 mM sodium saccharin |
| 16 mg/mL pirfenidone | 16 mg/mL pirfenidone | 16 mg/mL pirfenidone |
| 5 mM sodium phosphate, pH 7 (+/−0.5) | 5 mM citrate buffer, pH 5.5 (+/−0.5) | Water |
| 100 mM NaCl | 100 mM NaCl | 100 mM NaCl |
| 0.1-1.0 mM sodium saccharin | 0.1-1.0 mM sodium saccharin | 0.1-1.0 mM sodium saccharin |
| 4 mg/mL pirfenidone | 4 mg/mL pirfenidone | 4 mg/mL pirfenidone |
| 5 mM sodium phosphate, pH 7 (+/−0.5) | 5 mM citrate buffer, pH 5.5 (+/−0.5) | Water |
| 0.1-1.0 mM sodium saccharin | 0.1-1.0 mM sodium saccharin | 0.1-1.0 mM sodium saccharin |
| 43.3 mM MgCl2 | 43.3 mM MgCl2 | 43.3 mM MgCl2 |
| 16 mg/mL pirfenidone | 16 mg/mL pirfenidone | 16 mg/mL pirfenidone |
| 5 mM sodium phosphate, pH 7 (+/−0.5) | 5 mM citrate buffer, pH 5.5 (+/−0.5) | Water |
| 0.1-1.0 mM sodium saccharin | 0.1-1.0 mM sodium saccharin | 0.1-1.0 mM sodium saccharin |
| 43.3 mM MgCl2 | 43.3 mM MgCl2 | 43.3 mM MgCl2 |
| 50 mM NaCl | 50 mM NaCl | 50 mM NaCl |
| 16 mg/mL pirfenidone | 16 mg/mL pirfenidone | 16 mg/mL pirfenidone |
| 0.1-1.0 mM sodium saccharin | 0.1-1.0 mM sodium saccharin | 0.1-1.0 mM sodium saccharin |
| 5 mM sodium phosphate, pH 7 (+/−0.5) | 5 mM citrate buffer, pH 5.5 (+/−0.5) | Water |
| 10.8 mM MgCl2 | 10.8 mM MgCl2 | 10.8 mM MgCl2 |
| 4 mg/mL pirfenidone | 4 mg/mL pirfenidone | 4 mg/mL pirfenidone |
| 0.1-1.0 mM sodium saccharin | 0.1-1.0 mM sodium saccharin | 0.1-1.0 mM sodium saccharin |
| 5 mM sodium phosphate, pH 7 (+/−0.5) | 5 mM citrate buffer, pH 5.5 (+/−0.5) | Water |
| 10.8 mM MgCl2 | 10.8 mM MgCl2 | 10.8 mM MgCl2 |
| 0.1-1.0 mM sodium saccharin | 0.1-1.0 mM sodium saccharin | 0.1-1.0 mM sodium saccharin |
| 100 mM NaCl | 100 mM NaCl | 100 mM NaCl |
| 4 mg/mL pirfenidone | 4 mg/mL pirfenidone | 4 mg/mL pirfenidone |
| 5 mM sodium phosphate, pH 7 (+/−0.5) | 5 mM citrate buffer, pH 5.5 (+/−0.5) | Water |
| 0.1-1.0 mM sodium saccharin | 0.1-1.0 mM sodium saccharin | 0.1-1.0 mM sodium saccharin |
| 2% Ethanol | 2% Ethanol | 2% Ethanol |
| 4% Propylene Glycol | 4% Propylene Glycol | 4% Propylene Glycol |
| 22 mg/mL pirfenidone | 22 mg/mL pirfenidone | 22 mg/mL pirfenidone |

TABLE 30

Compositions and Additional Aerosol Tolerability Analysis

| Citrate Buffer (mM) | Phosphate Buffer (mM) | Sodium Chloride (mM) | Magnesium Chloride (mM) | Sodium Saccharin (mM) | pH (+/−0.5) | Pirfenidone (mg/mL) | Est. Osmolality (mOsmo/Kg) | Mean Aerosol Particl Size (micron)[a] | Metallic Taste[b] | Throat Irritation[b] | General Taste[b] |
|---|---|---|---|---|---|---|---|---|---|---|---|
| 0 | 5 | 50 | 0 | 0 | 7 | 16 | 200 | 3.7 | 5 | 5 | 3 |
| 0 | 5 | 0 | 43.3 | 0 | 7 | 16 | 210 | 3.7 | 5 | 5 | 3 |
| 0 | 5 | 0 | 43.3 | 0.5 | 7 | 16 | 210 | 3.7 | 5 | 5 | 1 |
| 0 | 5 | 50 | 43.3 | 0 | 7 | 16 | 310 | 3.7 | 5 | 4 | 2 |
| 0 | 5 | 150 | 0 | 0 | 7 | 16 | 400 | 3.7 | 5 | 3 | 2 |
| 5 | 0 | 150 | 0 | 0 | 5.5 | 16 | 400 | 3.7 | 4 | 4 | 2 |
| 5 | 0 | 0 | 130 | 0 | 5.5 | 16 | 490 | 3.7 | 5 | 3 | 2 |
| 5 | 0 | 100 | 43.3 | 0 | 5.5 | 16 | 430 | 3.7 | 4 | 3 | 2 |
| 5 | 0 | 100 | 43.3 | 0.6 | 5.5 | 16 | 430 | 3.7 | 4 | 2 | 1 |
| 5 | 0 | 150 | 0 | 0.5 | 5.5 | 16 | 400 | 3.7 | 2 | 1 | 2 |
| 5 | 0 | 150 | 0 | 0.9 | 5.5 | 16 | 400 | 3.7 | 1 | 1 | 1 |
| 5 | 0 | 0 | 130 | 0.5 | 5.5 | 16 | 490 | 3.7 | 1 | 2 | 2 |
| 5 | 0 | 100 | 0 | 0 | 5.5 | 16 | 400 | 3.7 | 3 | 3 | 2 |
| 5 | 0 | 100 | 0 | 0.7 | 5.5 | 16 | 400 | 3.2 | 2 | 3 | 2 |
| 5 | 0 | 100 | 0 | 0.7 | 5.5 | 16 | 400 | 4.6 | 1 | 1 | 2 |
| 5 | 0 | 100 | 0 | 0 | 5.5 | 16 | 400 | 3.2 | 1 | 2 | 2 |
| 5 | 0 | 100 | 0 | 0 | 5.5 | 16 | 400 | 3.7 | 2 | 3 | 2 |
| 5 | 0 | 100 | 0 | 0.7 | 5.5 | 16 | 400 | 3.7 | 3 | 2 | 2 |
| 5 | 0 | 100 | 0 | 0.9 | 5.5 | 16 | 400 | 3.7 | 2 | 2 | 1 |
| 5 | 0 | 100 | 0 | 0.9 | 5.5 | 16 | 400 | 3.2 | 2 | 1 | 1 |
| 0 | 0 | 150 | 0 | 0 | ND | 16 | 375 | 3.2 | 3 | 5 | 3 |
| 0 | 0 | 150 | 0 | 0.7 | ND | 16 | 375 | 3.2 | 2 | 5 | 2 |
| 5 | 0 | 150 | 0 | 0 | 5.5 | 4 | 330 | 3.2 | 2 | 1 | 2 |
| 5 | 0 | 150 | 0 | 0 | 5.5 | 4 | 330 | 3.7 | 2 | 2 | 2 |
| 5 | 0 | 150 | 0 | 0.2 | 5.5 | 4 | 330 | 3.7 | 2 | 2 | 2 |
| 5 | 0 | 150 | 0 | 0.3 | 5.5 | 4 | 330 | 3.7 | 1 | 1 | 1 |
| 5 | 0 | 100 | 0 | 0 | 5.5 | 4 | 270 | 3.2 | 2 | 2 | 2 |
| 5 | 0 | 100 | 0 | 0.3 | 5.5 | 4 | 270 | 3.7 | 1 | 2 | 2 |

[a]Estimate based upon general device performace with pirfenidone formulations. 3.7 and 3.2 micron particles sizes were delivered by high output device (~0.7 mL/minute). 4.6 micron particle sizes were delivered by a slower output device (~0.5 mL/minute).
[b]Throat irritation: 1 = none, 5 = strong; b. General taste: 1 = good, 3 = bad Table 30 results indicate that slower device outputs (less than or about 0.5 mL/minute) improve tolerability (even with a larger particle size) over smaller particles of greater output (more than or about 0.7 mL/min). This output aerosol tolerability difference can be overcome with inclusion of the following liquid formulation characteristics: 1. that the pH range between 5 and 6 is generally better than the neutral pH; 2. sodium chloride is more well tolerated than magnesium chloride, which tends to carry a stronger metallic flavor; 3. citrate buffer (and associated pH range) is more well tolerated than phosphate buffer; and inclusion of between 0.5 and 0.9 mM sodium saccharin for pirfenidone concentrations about 16 mg/mL and between 0.1 and 0.4 mM sodium saccharin for pirfenidone concentrations about 4 mg/mL (to be titrated for optimal taste and tolerability between these two and various pirfenidone concentrations. In addition to sodium saccharin, 5 mM sodium citrate buffer, pH about 5.5 and about 150 mM sodium chloride are optimal for pirfenidone concentrations below and up to aqueous saturation solubility. Additional observations include maintaining osmolality between about 250 to about 500 mOsmo/kg. The tolerability for formulations with an osmolality outside this range may be adjusted with modifications in the above formulation parameters and device output and aerosol particle size characteristics.

Example 11: Nebulization Device Performance

To evaluate aerosol performance, several formulations (Table 31) were tested in the PARI eFlow device. For these studies the standard eFlow 35L head was used. Particle size distribution was determined using an Insitec Spraytec Laser Particle Sizer. Breath simulation was performed using a Servo 1000i ventilator attached to a respiratory therapy training lung. The European Standard breath pattern (15 breaths per minute, 500 cc tidal volume and 1:1 inhalation-to-exhalation ratio) was used in determinations. Results from these studies are shown in Table 32 and 33. Each result is an average of duplicate trials in each of three devices.

TABLE 31

Device characterization formulations

| Ingredient | Formulation 1 | Formulation 2 |
|---|---|---|
| Pirfenidone (mg/mL) | 15.0 | 4.0 |
| Sodium citrate, dihydrate (mM) | 3.5 | 3.5 |
| Citric acid, monohydrate (mM) | 1.5 | 1.5 |
| Sodium Chloride (mM) | 150.0 | 150.0 |
| Sodium Saccharin (mM) | 0.9 | 0.9 |
| Water (q.s.) | q.s. | q.s. |

TABLE 32

Nebulized aerosol particle sizing

| Formulation (Table 31): | | 1 | 2 |
|---|---|---|---|
| Fill volume: | mL | 3.0 | 3.0 |
| Label claim | mg/mL | 15.0 | 4.0 |
| Dv(90)[a] (stdv) | μm | 6.04 (0.46) | 6.25 (0.34) |
| Dv(50)[a] (stdv) | | 3.72 (0.13) | 3.77 (0.18) |
| DV (10)[a] (stdv) | | 2.21 (0.26) | 1.84 (0.56) |
| Span[b] (stdv) | | 1.03 (0.19) | 1.17 (0.18) |
| RF[c] (stdv) | % <5 μm | 77.93 (4.13) | 75.68 (3.07) |

[a]Dv(X): Maximum particle diameter below which 90%, 50% (median population particle size) and 10% of the sample volume exists.;
[b]Span = [Dv(90) − Dv(10)]/Dv(50);
[c]Respirable fraction (RF) is the percent of nebulized particles <5 μm.

TABLE 33

Nebulized aerosol breath simulation

| Formulation from Table 31: | | 1 | 2 |
|---|---|---|---|
| Fill Volume | mL | 2.0 | 2.0 |
| Lable Claim | mg/mL | 15.0 | 4.0 |
| Inhaled Dose | mg | 19.9 | 5.5 |
| Inhaled Dose | % | 66.3 | 68.8 |
| Residual Dose | mg | 4.5 | 1.1 |
| Recovery | % | 81.4 | 82.2 |
| Nebulization Time | min | 2.9 | 3.1 |
| TOR[a] | mg/min | 6.9 | 1.8 |
| RDD[b] | mg | 15.5 | 4.2 |

[a]Total output rate (TOR);

[b]Respirable delivered dose (RDD) calculated by multiplying the inhaled dose (mg) and respirable fraction (Table 32).

These results show that 2 mL of a 15 mg/mL pirfenidone formulation will be administered in 2.9 minutes and result in a 15.5 mg RDD. These results also show that 2 mL of a 4 mg/mL pirfenidone formulation will be administered in 3.1 minutes and result in a 4.2 mg RDD. Manipulation of the pirfenidone concentration and device fill volume will permit optimization of dose delivery time and lung Cmax/plasma exposure ratio.

Example 12: Pirfenidone Activity and Exposure Requirements—Inflammasome Activation and Fibroblast Differentiation Inflammasome Activation The impact of pirfenidone on inhibiting the initial stage of inflammasome activation was determined in 264.7 macrophages. Briefly, macrophage were plated on a 96 well plate with seeding density of 100 000 cells per well. Cells were then incubated overnight. The next day cells received 200 ng/ml of LPS and various pirfenidone concentrations and incubated for 4 hours in 0% FBS media. To characterize the impact of pirfenidone time of exposure on inhibiting this step, these cultures were either diluted or left untouched. To mimic inhaled pharmacokinetics, cultures were diluted 2-fold at 10, 20, 30, 40, and 120 minutes after LPS/pirfenidone addition. After 240 minutes of incubation supernatants were collected. Diluted cultures did not replace LPS. Separate controls were included for diluted cultures containing LPS or media alone. At the end of the 4 hour incubation, supernatants were removed and 2 mM ATP was added. Cultures were incubated an additional 40 minutes. Supernatants were collected for quantitation of secreted IL-1β. 0% FBS media containing MTS dye was then added to remaining cells for cytotoxicity determination.

The impact of pirfenidone on inhibiting the second stage of inflammasome activation was also determined in 264.7 macrophages. Briefly, macrophage were plated on a 96 well plate with seeding density of 100 000 cells per well. Cells were then incubated overnight. The next day cells received 200 ng/ml of LPS and incubated for 4 hours in 0% FBS media. At the end of the 4 hour incubation, supernatants were removed and two approaches for pirfenidone impact were assessed. First, media containing 0% FBS with or without pirfenidone was added and incubated for 5 minutes. At the end of 5 minutes, supernatants were either removed and media containing 0% FBS and 2 mM ATP were added or a final concentration of 2 mM ATP was added to the pirfenidone-containing culture. Cultures were incubated for an additional 40 minutes. Supernatants were collected for quantitation of secreted IL-1β. 0% FBS media containing MTS dye was then added to remaining cells for cytotoxicity determination. In the second approach, once LPS-containing supernatants were removed, media containing 0% FBS and 2 mM ATP with or without pirfenidone were added. Where cultures were assessed for short-term pirfenidone exposure, media was removed after 10 minutes incubation and replaced with fresh media containing 0% FBS. These cultures were incubated an additional 30 minutes. Both the 10 minute and 40 minute culture supernatants were analyzed for secreted IL-1β. Short-term exposure results are reported for the 10 min sample, 40 min sample and the sum of these results. For longer-term pirfenidone exposure control, cultures maintained pirfenidone throughout the 40 minute ATP incubation period. These supernatants were similarly analyzed for secreted IL-1β. Under both approaches, 0% FBS media containing MTS dye was then added to remaining cells for cytotoxicity determination.

TABLE 34

Impact of pirfenidone and exposure duration on inflammsome first signal activation.

| | | | Pirfenidone Exposure | | | |
|---|---|---|---|---|---|---|
| | | Pirfenidone | Short-term | | Longer-term | |
| LPS | ATP | mcg/mL | IL-1β[a] | SEM | IL-1β[a] | SEM |
| + | + | 0 | 1.00 | 0.04 | 1.00 | 0.08 |
| + | + | 25 | 0.50 | 0.05 | 0.55 | 0.07 |
| + | + | 100 | 0.08 | 0.03 | 0.39 | 0.02 |
| + | + | 400 | 0.04 | 0.03 | 0.07 | 0.01 |
| + | + | 1600 | 0.12 | 0.02 | 0.03 | 0.00 |

[a]Relative

Results from Table 34 show that pirfenidone is dose-responsive in inhibiting first-signal inflammasome activation. The data also show that only short-term pirfenidone exposure is required for this activity with a fifty-percent inhibitory concentration (IC50) of about 25 mcg/mL.

TABLE 35

Impact of pirfenidone and exposure duration on inflammsome second signal activation.

| | | | Pirfenidone Exposure | | | | | | | |
|---|---|---|---|---|---|---|---|---|---|---|
| | | | Short-term | | | | | | Longer-term | |
| | | | 10 min > ATP | | 40 min > ATP | | 10 + 40 min > ATP | | 40 min > ATP | |
| LPS | ATP | Pirfenidone mcg/mL | IL-1β[a] | SEM | IL-1β[a] | SEM | IL-1β[a] | SEM | IL-1β[a] | SEM |
| + | − | 0 | 10.9 | 2.5 | 19.7 | 1.4 | 0.2 | 0.02 | 0.0 | 0.01 |
| + | + | 0 | 58.8 | 5.5 | 94.0 | 5.2 | 1.0 | 0.07 | 1.0 | 0.07 |
| + | + | 5 | 81.5 | 5.7 | 95.8 | 11.8 | 1.1 | 0.09 | 1.4 | 0.15 |
| + | + | 25 | 100.0 | 17.1 | 50.4 | 10.3 | 1.0 | 0.13 | 1.1 | 0.08 |
| + | + | 125 | 118.7 | 5.2 | 36.3 | 3.6 | 1.0 | 0.04 | 0.9 | 0.06 |
| + | + | 625 | 66.3 | 6.2 | 27.3 | 2.5 | 0.6 | 0.05 | 0.4 | 0.04 |

[a]pg/mL;
[b]Relative

Results from Table 35 show that pirfenidone is also dose-responsive in inhibiting second-signal inflammasome activation. Analysis of the 10 and 40 minute sampling points, suggest the kinetics of caspase 1 activation, pro-IL-1β cleavage and/or IL-1β secretion should be considered in the interpretation. The initial 10 minute sampling point suggests pirfenidone may enhance second-signal activation. However, analysis of the 40 minute sampling point shows a return of dose-responsive inhibitory activity. Comparing the sum of the short-term sampling points and the longer-term sampling point, inhibition of second-signal inflammasome activation appears similar between the two exposure periods, albeit weakly dose responsive (IC50 about 625 mcg/mL). However, the IC50 reduces to about 25 mcg/mL when measuring the second sampling point alone. These results suggest pirfenidone activity requires a short-period following initial exposure to achieve optimal inhibitory activity. Further supporting the observation that only short-term pirfenidone exposure is required for this activity.

It has been shown that the unfolded-protein response (UPR) to endoplasmic reticulum stress (ER stress) modulates both first-signal and second-signal inflammasome activation. Central to these data, IRE1α modulates NFκB activation (first-signal event) and NLRP3 activation of the inflammasome (second signal event). Macroscopically, IRE1α induces cytokine production (via NFκB activation), which in turn modulates the pro-fibrotic IL-1β/TGFβ amplification loop (autocrine and paracrine). IRE1α also activates XBP1 (via splicing), which in turn increases protein chaperone production and ER secretory capacity; inhibiting IRE1α blocks the cells ability to transform from a non-secreting cell to a secreting cell. Comparing the Table 34 and Table 35 results, these data suggest that pirfenidone may inhibit this central modulator of the UPR/inflammasome, thereby directly reducing these otherwise pro-fibrotic cellular responses.

Fibroblast Differentiation

The impact of pirfenidone on inhibiting TGFβ1-induced fibroblast differentiation was determined in normal human pulmonary fibroblasts. Briefly, 20 000 cells per well were seeded in black 96 well collagen coated plates and incubate overnight (approximately 24 hours) to allow adherence. Following incubation, media was removed and replaced with media containing 0% FBS and either TGFβ1 alone or TGFβ1 with various pirfenidone concentrations. Cultures were then incubated for 48 hours. To characterize the impact of pirfenidone time of exposure on inhibiting differentiation, cultures were either diluted or left untouched. To mimic inhaled pharmacokinetics (short-term exposure), cultures were diluted 2-fold at 10, 20, 30, 40, 120, 240 and 360 minutes after TGFβ1/pirfenidone addition. Diluted cultures did not replace TGF 1 (long-term exposure). Separate controls were included for diluted cultures containing TGFβ1 or media alone. At the end of incubation, cells were fixed and stained for imaging and fluorescence plate reader quantitation. Parallel cultures were assessed for cytotoxicity using the MTS dye assay.

TABLE 36

Impact of pirfenidone and exposure duration on TGFβ-induced fibroblast differentiation.

| | | | | Pirfenidone Exposure | | | |
|---|---|---|---|---|---|---|---|
| | | | | Short-term | | Long-term | |
| TGFβ | Pirfenidone mcg/mL | αSMA[a] | SEM | αSMA[a] | SEM | αSMA[a] | SEM |
| − | 0 | 2.20 | 0.15 | — | — | — | — |
| + | 0 | 5.70 | 0.92 | — | — | — | — |
| + | 5 | — | — | 6.76 | 1.05 | 4.72 | 0.90 |
| + | 25 | — | — | 5.34 | 0.33 | 4.04 | 0.93 |
| + | 125 | — | — | —[b] | —[b] | 3.15 | 0.51 |
| + | 625 | — | — | 3.57 | 0.79 | 2.47 | 0.32 |

[a]Fluorescence;
[b]Not determined

Results from Table 36 show that pirfenidone is dose-responsive in inhibiting fibroblast differentiation. Similar to that shown in the inflammasome model, these data show that long-term pirfenidone exposure (in this case 48 hours) exhibits an IC50 of about 25 mcg/mL. Interestingly, short-term pirfenidone exposure was about 5-fold less active that longer-term exposure (IC50 about 125 mcg/mL).

TABLE 37

Impact of short-term pirfenidone exposure on TGFβ-induced fibroblast differentiation.

| TGFβ | Pirfenidone mcg/mL | αSMA[a] | SEM | Pirfenidone Exposure Short-term αSMA[a] | SEM |
|---|---|---|---|---|---|
| − | 0 | 1.73 | 0.08 | — | — |
| + | 0 | 6.65 | 0.72 | — | — |
| + | 1 | — | — | 7.65 | 0.82 |
| + | 10 | — | — | 7.75 | 0.70 |
| + | 100 | — | — | 5.61 | 0.55 |
| + | 1000 | — | — | 2.27 | 0.06 |

[a]Fluorescence

To characterize a broader dose-response, the ability of short-term pirfenidone exposure to inhibit fibroblast differentiation was again assessed (Table 37). Similar to that shown in Table 36, these data show that short-term pirfenidone exposure was about 5-fold less active that longer-term exposure. Considering these studies only evaluated a single short-term exposure compared to a constant 48 hour exposure, the actual IC50 values between these two exposure durations may be much closer, providing further support that only short-term pirfenidone exposure is required for activity.

In some embodiments, TGFβ induces ER stress in pulmonary fibroblasts. In some embodiments, this ER stress results in activation of IRE1α and subsequent expression of αSMA and collagen secretion. In further embodiments, inhibiting IRE1α reduces αSMA and collagen secretion. In some embodiments, given these observations and pirfenidone's ability to inhibit the inflammasome and fibroblast differentiation at the same IC50 suggests the mechanism behind these two events may be related.

Example 13: In Vivo Efficacy—LPS-Induced Pulmonary Inflammasome Model

To compare the efficacy of intratracheal, direct-lung aerosol administration and oral gavage, the LPS-induced pulmonary inflammasome model was performed. Briefly, Sprague Dawley rats (200-250 grams) were administered a single dose of LPS by the intratracheal route (IT) using a intubation aerosol delivery device. All IT doses were delivered just above the first pulmonary bifurcation. Sham animals were treated with saline. A single pirfenidone dose was either delivered by gavage (PO; 30 mg/kg in 300 mcL) 2 hours before LPS exposure or IT (0.5 mg/kg in 300 mcL LPS dosing solution) at the same time as LPS. After 24 hours, animals were euthanized. Lungs were lavaged and collected bronchial lavage fluid (BAL) was assessed for total cell count, neutrophils, macrophage, eosinophils and lymphocytes. BAL was also assessed for IL-lb. Data and results from these studies are shown in Tables 38 and 39.

TABLE 38

BAL total cell count and differentials - Intratracheal aerosol versus oral Gavage.

| Group (n = 4) | Pirfenidone (mg/kg) | | Number cells[a] and (%) MP | NP | EO | LM |
|---|---|---|---|---|---|---|
| Sham + IT saline | 0.0 | Average | 6.5 (82.7) | 1.4 (16.3) | 0.0 (0.3) | 0.1 (0.9) |
| | | SEM | 0.7 (3.9) | 0.6 (3.9) | 0.0 (0.2) | 0.0 (0.5) |
| LPS + IT saline | 0.0 | Average | 11.3 (55.8) | 13.0 (42.9) | 0.2 (0.8) | 0.2 (0.6) |
| | | SEM | 4.6 (12.7) | 6.5 (12.5) | 0.1 (0.3) | 0.1 (0.2) |
| LPS + PO pirfenidone | 30.0 | Average | 15.8 (62.2) | 13.2 (36.4) | 0.3 (0.6) | 0.3 (0.9) |
| | | SEM | 5.6 (15.7) | 6.1 (15.8) | 0.2 (0.4) | 0.2 (0.5) |
| LPS + IT pirfenidone | 0.5 | Average | 6.2 (85.4) | 0.7 (13.0) | 0.0 (0.7) | 0.1 (1.0) |
| | | SEM | 1.8 (13.3) | 0.7 (13.0) | 0.0 (0.5) | 0.1 (0.8) |

[a]Number cells in 1 × 10e5. MP: macrophage; NP: neutrophils; EO: eosinophil; LM: lymphocytes.

TABLE 39

BAL IL-1β levels - Intratracheal aerosol versus oral Gavage.

| Group (n = 4) | Pirfenidone (mg/kg) | | BAL IL-1β (pg/mL) | LPS-induced IL-1β (%) |
|---|---|---|---|---|
| Sham + IT saline | 0.0 | Average | 0.7 | NA |
| | | SEM | 0.7 | |
| LPS + IT saline | 0.0 | Average | 94.0 | 100 |
| | | SEM | 35.3 | |
| LPS + PO pirfenidone | 30.0 | Average | 105.9 | 113 |
| | | SEM | 40.9 | |
| LPS + IT pirfenidone | 0.5 | Average | 36.2 | 38 |
| | | SEM | 22.0 | |

Results from Tables 38 and 39 suggest that 0.5 mg/kg given directly to the lung negated LPS-induced inflammatory cell infiltration and reduced LPS-induced BAL IL-1β levels 62%. By comparison, a 60-fold larger oral dose had no effect on either endpoint. From data described herein, it is estimated that the 0.5 mg/kg IT resulted in a lung tissue Cmax~83 mcg/gram, with very low blood levels. By comparison, Table 22 shows that a 30 mg/kg PO dose to a similar size rat results in a lung tissue Cmax~10 mcg/mL, with substantially greater blood levels. Together with Examples 9 and 12, these results further support that only short-term pirfenidone exposure is required for activity and that direct lung administration enables delivery of high lung Cmax levels not possible by oral delivery.

Example 14: Nebulization Device Performance

To evaluate aerosol performance, several formulations (Table 40) were tested in the AKITA JET and AKITA2 APIXNEB Nebulizer System devices. Particle size distribution was determined using an HELOS Particle Sizer. Device input parameters are shown in Table 41. Results from these studies are shown in Tables 42 to 45. Each result is an average of duplicate trials in each of three devices.

TABLE 40

Device characterization formulations

| Ingredient | Formulation 1 | Formulation 2 |
|---|---|---|
| Pirfenidone (mg/mL) | 15.0 | 4.0 |
| Sodium citrate, dihydrate (mM) | 3.5 | 3.5 |
| Citric acid, monohydrate (mM) | 1.5 | 1.5 |
| Sodium Chloride (mM) | 150.0 | 150.0 |
| Sodium Saccharin (mM) | 0.9 | 0.9 |
| Water (q.s.) | q.s. | q.s. |

TABLE 41

Device input parameters

| Device | Inhale volume (mL) | Exhale volume (mL) | Inhale time per breath (sec) | Exhale time per breath (sec) | Nebulization time per breath (sec) | Bolus depth (mL) | Bolus width (mL) | Help Flow rate (L/min) |
|---|---|---|---|---|---|---|---|---|
| AKITA ® Jet | 1600 | 1600 | 8 | 8 | 7 | 1600 | 1400 | 12 |
| AKITA ®2 APIXNEB | 1600 | 1600 | 6.4 | 6.4 | 5.4 | 1600 | 1350 | 15 |

TABLE 42

AKITA ®2 APIXNEB aerosol particle sizing

| Formulation (Table 40): | | 1 | 2 |
|---|---|---|---|
| Fill volume: | mL | 2.0 | 2.0 |
| Label claim | mg/mL | 15.0 | 4.0 |
| VMD (stdv) | μm | 4.14 (0.24) | 4.15 (0.12) |
| GSD (stdv) | | 1.60 (0.04) | 1.59 (0.03) |
| RF[a] (stdv) | % | 65.6 | 66.7 |

[a]Respirable fraction (RF) is the percent of nebulized particles <5 μm.

TABLE 43

AKITA ® Jet aerosol particle sizing

| Formulation (Table 40): | | 1 | 2 |
|---|---|---|---|
| Fill volume: | mL | 2.0 | 2.0 |
| Label claim | mg/mL | 15.0 | 4.0 |
| VMD (stdv) | μm | 3.25 (0.08) | 3.32 (0.11) |
| GSD (stdv) | | 2.04 (0.01) | 1.99 (0.01) |
| RF[a] (stdv) | % | 71.44 | 70.85 |

[a]Respirable fraction (RF) is the percent of nebulized particles <5 μm.

TABLE 44

AKITA ®2 APIXNEB aerosol breath simulation

| Formulation (Table 40): | | 1 | 2 |
|---|---|---|---|
| Fill Volume | mL | 2.0 | 2.0 |
| Label Claim | mg/mL | 15.0 | 4.0 |
| Inhaled Dose | mg | 29.32 | 7.92 |
| Inhaled Dose | % | 97.73 | 98.95 |
| Nebulization Time | min | 4.55 | 5.01 |
| TOR[a] | mg/min | 6.44 | 1.58 |
| RDD[b] | mg | 19.23 | 5.28 |

[a]Total output rate (TOR);
[b]Respirable delivered dose (RDD) calculated by multiplying the inhaled dose (mg) and respirable fraction (Table 42).

TABLE 45

AKITA ® Jet aerosol breath simulation

| Formulation (Table 40): | | 1 | 2 |
|---|---|---|---|
| Fill Volume | mL | 2.0 | 2.0 |
| Label Claim | mg/mL | 15.0 | 4.0 |
| Inhaled Dose | mg | 14.99 | 3.52 |
| Inhaled Dose | % | 50.00 | 44.06 |
| Nebulization Time | min | 6.58 | 6.58 |
| TOR[a] | mg/min | 2.28 | 0.54 |
| RDD[b] | mg | 10.71 | 2.49 |

[a]Total output rate (TOR);
[b]Respirable delivered dose (RDD) calculated by multiplying the inhaled dose (mg) and respirable fraction (Table 43).

These results show that 2 mL of a 15 mg/mL pirfenidone formulation will be administered in 4.55 minutes and 6.58 minutes and result in a 10.71 mg and 2.49 mg RDD for the AKITA®2 APIXNEB and AKITA® Jet Nebulizer System devices, respectively. These results also show that 2 mL of a 4 mg/mL pirfenidone formulation will be administered in 5.01 minutes and 6.58 minutes and result in a 5.28 mg and 2.49 mg RDD for the AKITA®2 APIXNEB and AKITA® Jet Nebulizer System devices, respectively. Manipulation of the pirfenidone concentration and device fill volume will permit optimization of dose delivery time and lung Cmax/plasma exposure ratio.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of decreasing IL-1β levels in the lungs of a mammal diagnosed with pulmonary fibrosis comprising administering by inhalation an aqueous solution of pirfenidone to the mammal diagnosed with pulmonary fibrosis, wherein the pirfenidone has a concentration from about 0.1 mg/mL to about 20 mg/mL; sodium citrate; citric acid; sodium chloride; and sodium saccharin wherein the molar ratio of sodium saccharin to pirfenidone is between 1 to 53.9 and 1 to 215.9; wherein the osmolality of the aqueous solution is from about 200 mOsmol/kg to about 500 mOsmol/kg; and wherein the pH of the solution is about 5 to about 6, and wherein the administration of the aqueous solution to the mammal decreases IL-1β levels in the bronchial lavage fluid (BAL) of the mammal by at least 20%.

2. The method of claim 1, wherein the pulmonary fibrosis is idiopathic pulmonary fibrosis (IPF) or pulmonary fibrosis associated with systemic sclerosis, radiation exposure or transplant.

3. A method for the treatment of lung disease in a mammal comprising:
administering by inhalation a dose of the aqueous solution of pirfenidone to the mammal in need thereof on a continuous dosing schedule, wherein the pirfenidone has a concentration from about 0.1 mg/mL to about 20 mg/mL; sodium citrate; citric acid; sodium chloride; and sodium saccharin wherein the molar ratio of sodium saccharin to pirfenidone is between 1 to 53.9 and 1 to 215.9; wherein the osmolality of the aqueous solution is from about 200 mOsmol/kg to about 500 mOsmol/kg; and wherein the pH of the solution is about 5 to about 6.

4. The method of claim 3, wherein the lung disease is idiopathic pulmonary fibrosis, or pulmonary fibrosis associated with systemic sclerosis, radiation exposure or transplant, lung cancer or pulmonary hypertension.

5. The method of claim 4, wherein the lung disease is lung cancer and the treatment comprises inhibiting, reducing or slowing the growth of lung tumor stroma.

6. The method of claim 3, wherein the aqueous solution is administered by inhalation to the mammal in need thereof with a liquid nebulizer.

7. The method of claim 6, wherein the liquid nebulizer is a jet nebulizer, an ultrasonic nebulizer, a pulsating membrane nebulizer, a nebulizer comprising a vibrating mesh or plate with multiple apertures, a nebulizer comprising a vibration generator and an aqueous chamber, or a nebulizer that uses controlled device features to assist inspiratory flow of the aerosolized aqueous solution to the lungs of the mammal.

8. The method of claim 7, wherein the liquid nebulizer:
(i) after administration of the inhaled dose, achieves lung deposition of at least 7% of the pirfenidone administered to the mammal;
(ii) provides a Geometric Standard Deviation (GSD) of emitted droplet size distribution of the aqueous solution of about 1.0 µm to about 2.5 µm;
(iii) provides droplets of the aqueous solution emitted with the high efficiency liquid with:
   a) a mass median aerodynamic diameter (MMAD) of about 1 µm to about 5 µm;
   b) a volumetric mean diameter (VMD) of about 1 µm to about 5 µm; and/or
   c) a mass median diameter (MMD) of about 1 µm to about 5 µm;
(iv) provides a fine particle fraction (FPF=%≤5 µm) of droplets emitted from the liquid nebulizer of at least about 30%;
(v) provides an output rate of at least 0.1 mL/min; and/or
(vi) provides at least about 25% of the aqueous solution to the mammal.

9. The method of claim 3, wherein the dose of the aqueous solution of pirfenidone is administered at least once a week.

10. The method of claim 3, wherein the dose of the aqueous solution of pirfenidone is administered on a continuous daily dosing schedule.

11. The method of claim 3, wherein the dose of the aqueous solution of pirfenidone is administered once a day, twice a day, three times a day, four times a day, five times a day, or six times a day.

12. The method of claim 3, wherein each dose of the aqueous solution of pirfenidone is administered within 20 minutes.

13. The method of claim 3, wherein the method further comprises administration of one or more additional therapeutic agents to the mammal.

* * * * *